United States Patent
Gupta et al.

(10) Patent No.: US 9,375,423 B2
(45) Date of Patent: *Jun. 28, 2016

(54) USE OF AMINOINDANE COMPOUNDS IN TREATING OVERACTIVE BLADDER AND INTERSTITIAL CYSTITIS

(71) Applicant: Asana Biosciences, LLC, Bridgewater, NJ (US)

(72) Inventors: Sandeep Gupta, Plainsboro, NJ (US); Tony Priestley, West Chester, PA (US); Nicholas James Laping, Malvern, PA (US)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/727,024

(22) Filed: Jun. 1, 2015

(65) Prior Publication Data
US 2015/0290182 A1  Oct. 15, 2015

Related U.S. Application Data

(62) Division of application No. 13/967,389, filed on Aug. 15, 2013, now Pat. No. 9,044,482.

(60) Provisional application No. 61/718,072, filed on Oct. 24, 2012, provisional application No. 61/683,518, filed on Aug. 15, 2012.

(51) Int. Cl.
| | | |
|---|---|---|
| A61K 31/535 | (2006.01) |
| A01N 43/54 | (2006.01) |
| A61K 31/452 | (2006.01) |
| A61K 31/40 | (2006.01) |
| A61K 31/435 | (2006.01) |
| A61K 31/453 | (2006.01) |
| A61K 31/454 | (2006.01) |
| A61K 31/4545 | (2006.01) |
| A61K 31/506 | (2006.01) |
| A61K 31/5386 | (2006.01) |
| C07D 207/09 | (2006.01) |
| C07D 211/26 | (2006.01) |
| C07D 401/12 | (2006.01) |
| C07D 405/12 | (2006.01) |
| C07D 417/12 | (2006.01) |
| C07D 471/10 | (2006.01) |
| C07D 498/10 | (2006.01) |
| A61K 45/06 | (2006.01) |
| A61K 31/015 | (2006.01) |
| A61K 31/438 | (2006.01) |
| A61K 31/4425 | (2006.01) |

(Continued)

(52) U.S. Cl.
CPC ............ *A61K 31/452* (2013.01); *A61K 31/015* (2013.01); *A61K 31/167* (2013.01); *A61K 31/40* (2013.01); *A61K 31/435* (2013.01); *A61K 31/438* (2013.01); *A61K 31/445* (2013.01); *A61K 31/4425* (2013.01); *A61K 31/453* (2013.01); *A61K 31/454* (2013.01); *A61K 31/4545* (2013.01); *A61K 31/506* (2013.01); *A61K 31/5386* (2013.01); *A61K 45/06* (2013.01); *C07D 207/09* (2013.01); *C07D 211/26* (2013.01); *C07D 401/12* (2013.01); *C07D 405/12* (2013.01); *C07D 417/12* (2013.01); *C07D 471/10* (2013.01); *C07D 498/10* (2013.01)

(58) Field of Classification Search
None
See application file for complete search history.

(56) References Cited

U.S. PATENT DOCUMENTS

| | | |
|---|---|---|
| 5,190,956 A | 3/1993 | Afonso et al. |
| 5,344,836 A | 9/1994 | Hamanaka et al. |

(Continued)

FOREIGN PATENT DOCUMENTS

| | | |
|---|---|---|
| AT | 330166 B | 6/1976 |
| CA | 997786 A1 | 9/1976 |

(Continued)

OTHER PUBLICATIONS

Dorland's Medical Dictionary for Health Consumers (Saunder, 2007).*

(Continued)

*Primary Examiner* — Dennis Heyer
*Assistant Examiner* — Daniel M Podgorski
(74) *Attorney, Agent, or Firm* — Lerner, David, Littenberg, Krumholz & Mentlik, LLP

(57) ABSTRACT

The present application provides methods of using the aminoindane compounds of formula (I) or (II) in treating an overactive bladder or interstitial cystitis by administering one or more of the compounds to a patient.

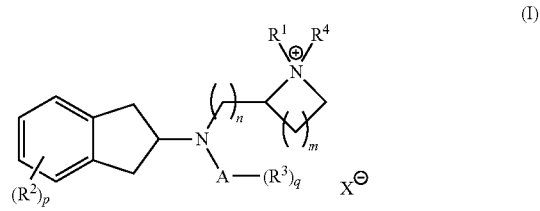

(I)

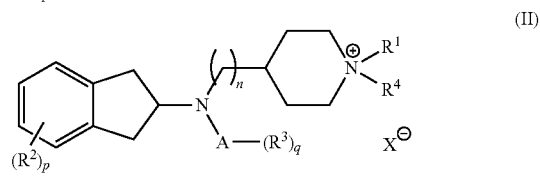

(II)

16 Claims, 4 Drawing Sheets

(51) Int. Cl.
*A61K 31/445* (2006.01)
*A61K 31/167* (2006.01)

(56) References Cited

U.S. PATENT DOCUMENTS

| | | | |
|---|---|---|---|
| 5,854,268 | A | 12/1998 | Baker et al. |
| 5,998,440 | A | 12/1999 | Castro Pineiro et al. |
| 6,127,388 | A | 10/2000 | Bourrain et al. |
| 6,413,987 | B1 | 7/2002 | Aberg et al. |
| 6,630,451 | B1 | 10/2003 | Zhang et al. |
| 6,696,467 | B2 | 2/2004 | Mattei et al. |
| 6,858,577 | B1 | 2/2005 | Zhang et al. |
| 6,921,759 | B2 | 7/2005 | Anthony et al. |
| 6,995,162 | B2 | 2/2006 | Chen et al. |
| 7,049,297 | B2 | 5/2006 | Zhang et al. |
| 7,101,868 | B2 | 9/2006 | Elbaum et al. |
| 7,102,009 | B2 | 9/2006 | Patel et al. |
| 7,399,774 | B2 | 7/2008 | Siegel et al. |
| 7,511,149 | B2 | 3/2009 | Arndt et al. |
| 7,514,564 | B2 | 4/2009 | Chen et al. |
| 7,604,815 | B2 | 10/2009 | Loso et al. |
| 7,709,649 | B2 | 5/2010 | Zhu et al. |
| 7,718,674 | B2 | 5/2010 | Aberg |
| 8,110,575 | B2 | 2/2012 | Gottschling et al. |
| 2002/0147198 | A1 | 10/2002 | Chen et al. |
| 2004/0156869 | A1 | 8/2004 | Bakthavatchalam et al. |
| 2005/0222266 | A1 | 10/2005 | Pietra et al. |
| 2006/0063789 | A1 | 3/2006 | Freyne et al. |
| 2006/0079558 | A1 | 4/2006 | Aberg et al. |
| 2009/0069323 | A1 | 3/2009 | Coulter et al. |
| 2009/0137628 | A1 | 5/2009 | Aberg et al. |
| 2010/0324028 | A1 | 12/2010 | Gottschling et al. |
| 2011/0195954 | A1 | 8/2011 | Gottschling et al. |
| 2012/0214809 | A1* | 8/2012 | Thompson et al. ........ 514/235.5 |
| 2013/0101667 | A1 | 4/2013 | Thompson et al. |

FOREIGN PATENT DOCUMENTS

| | | | |
|---|---|---|---|
| GB | 1321424 | A | 6/1973 |
| WO | 0076510 | A1 | 12/2000 |
| WO | 0105767 | A1 | 1/2001 |
| WO | 0136381 | A1 | 5/2001 |
| WO | 2006036936 | A2 | 4/2006 |
| WO | 2006037047 | A2 | 4/2006 |
| WO | 2006050908 | A1 | 5/2006 |
| WO | 2007002885 | A2 | 1/2007 |
| WO | WO 2007002885 | A2 * | 1/2007 |
| WO | 2007038325 | A2 | 4/2007 |
| WO | 2008063603 | A2 | 5/2008 |
| WO | 2008097235 | A1 | 8/2008 |
| WO | 2008099022 | A1 | 8/2008 |
| WO | 2009065922 | A2 | 5/2009 |
| WO | 2009114139 | A2 | 9/2009 |
| WO | 2010021864 | A1 | 2/2010 |
| WO | 2011006073 | A1 | 1/2011 |
| WO | 2012112969 | A1 | 8/2012 |

OTHER PUBLICATIONS

Dorland's Medical Dictionary for Health Consumers (Saunder 2007).
Roberson "Targeting of sodium channel blockers into nociceptors to produce long duration analgesia: a systematic study and review" British Journal of Pharmacology 164(1):48-58 (Sep. 2011; e-publication: Aug. 5, 2011).
Zuliani "Sodium channel blockers for neuropathic pain" Expert Opinion Therapeutic Patents 20(6):755-779 (Jun. 2010).
Juszczak "Urodynamic effects of the bladder C-fiber afferent activity modulation in chronic model of overactive bladder in rats" Journal of Physiology and Pharmacology 60(4):85-91 (Dec. 2009).
Steer "Pathophysiology of overactive bladder and urge urinary incontinence" Reviews in Urology 4 Suppl4:S7-S18 (2002).
Su "Pharmacologic evaluation of pressor and visceromotor reflex responses to bladder distension" Neurourology & Urodynamics 27(3):249-53 (Mar. 2008; e-publication: Jun. 27, 2007).
International Search Report dated May 25, 2012 and issued in related International Patent Application No. PCT|US2012/025759.
International Search Report dated Oct. 29, 2013 and issued in corresponding International Patent Application No. PCT/US2013/055029.

* cited by examiner

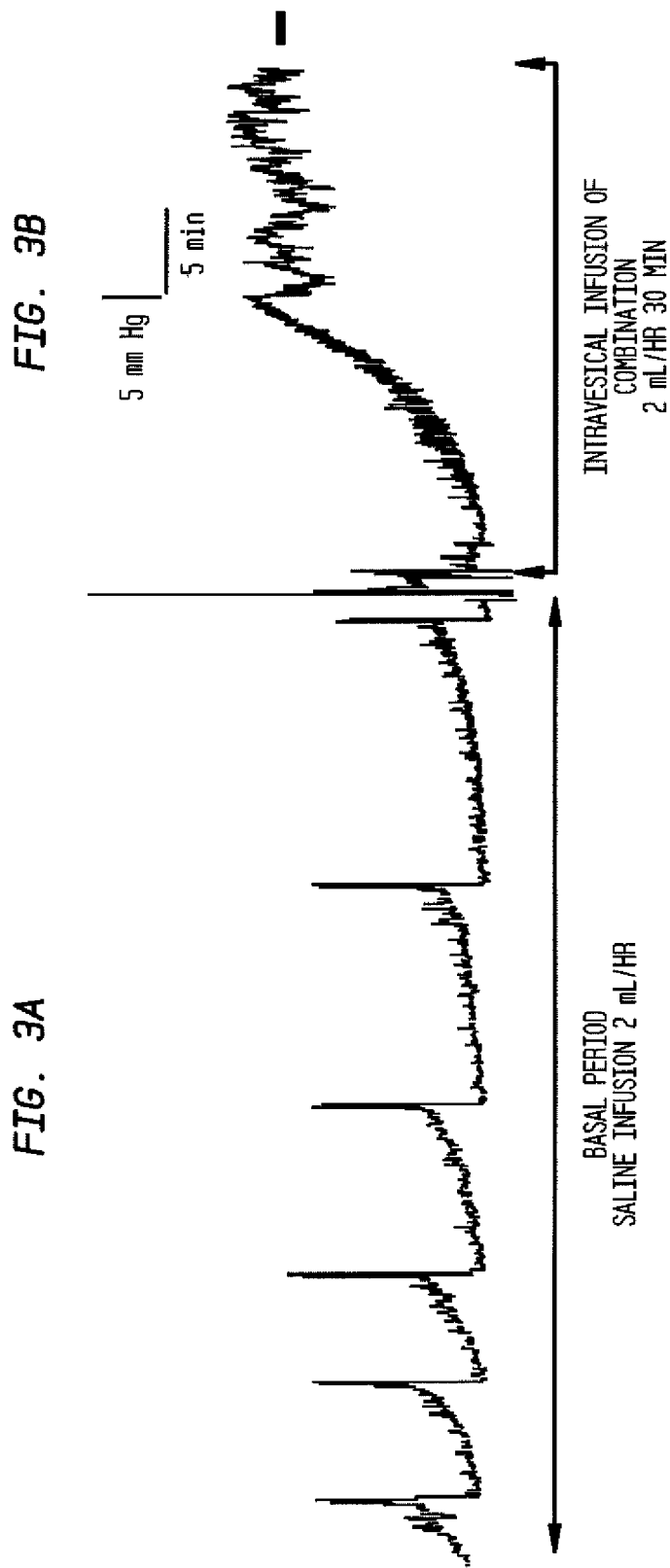

SEQUENCE LISTING

<160> NUMBER OF SEQ ID NOS: 1

<210> SEQ ID NO 1
<211> LENGTH: 839
<212> TYPE: PRT
<213> ORGANISM: human

<400> SEQUENCE: 1

```
Met Lys Lys Trp Ser Ser Thr Asp Leu Gly Ala Ala Asp Pro Leu
1               5                  10                  15

Gln Lys Asp Thr Cys Pro Asp Pro Leu Asp Gly Asp Pro Asn Ser Arg
              20                  25                  30

Pro Pro Pro Ala Lys Pro Gln Leu Ser Thr Ala Lys Ser Arg Thr Arg
             35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                    85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
                115                 120                 125

Asp Leu Glu Ser Leu Leu Leu Phe Leu Gln Lys Ser Lys Lys His Leu
            130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
            195                 200                 205

Ala Ile Glu Arg Arg Asn Met Ala Leu Val Thr Leu Leu Val Glu Asn
210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
    275                 280                 285

Leu His Ala Leu Val Glu Val Ala Asp Asn Thr Ala Asp Asn Thr Lys
            290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
                355                 360                 365
```

```
Lys Phe Thr Glu Trp Ala Tyr Gly Pro Val His Ser Ser Leu Tyr Asp
    370                 375                 380
Leu Ser Cys Ile Asp Thr Cys Glu Lys Asn Ser Val Leu Glu Val Ile
385                 390                 395                 400
Ala Tyr Ser Ser Glu Thr Pro Asn Arg His Asp Met Leu Leu Val
                405                 410                 415
Glu Pro Leu Asn Arg Leu Leu Gln Asp Lys Trp Asp Arg Phe Val Lys
            420                 425                 430
Arg Ile Phe Tyr Phe Asn Phe Leu Val Tyr Cys Leu Tyr Met Ile Ile
        435                 440                 445
Phe Thr Met Ala Ala Tyr Tyr Arg Pro Val Asp Gly Leu Pro Pro Phe
    450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
                485                 490                 495
Leu Gln Arg Arg Pro Ser Met Lys Thr Leu Phe Val Asp Ser Tyr Ser
            500                 505                 510
Glu Met Leu Phe Phe Leu Gln Ser Leu Phe Met Leu Ala Thr Val Val
        515                 520                 525
Leu Tyr Phe Ser His Leu Lys Glu Tyr Val Ala Ser Met Val Phe Ser
    530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
            580                 585                 590
Thr Ala Val Val Thr Leu Ile Glu Asp Gly Lys Asn Asp Ser Leu Pro
        595                 600                 605
Ser Glu Ser Thr Ser His Arg Trp Arg Gly Pro Ala Cys Arg Pro Pro
    610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
            660                 665                 670
Ile Leu Leu Leu Asn Met Leu Ile Ala Leu Met Gly Glu Thr Val Asn
        675                 680                 685
Lys Ile Ala Gln Glu Ser Lys Asn Ile Trp Lys Leu Gln Arg Ala Ile
    690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Ser Arg Val Ser
    770                 775                 780
Gly Arg His Trp Lys Asn Phe Ala Leu Val Pro Leu Leu Arg Glu Ala
```

```
785                 790                 795                 800
Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
                820                 825                 830

Pro Ala Ala Ser Gly Glu Lys
                835
```

USE OF AMINOINDANE COMPOUNDS IN TREATING OVERACTIVE BLADDER AND INTERSTITIAL CYSTITIS

CROSS-REFERENCE TO RELATED APPLICATIONS

The present application is a divisional of U.S. patent application Ser. No. 13/967,389, filed Aug. 15, 2013, which is now U.S. Pat. No. 9,044,482, which claims priority from Provisional Applications 61/718,072, filed Oct. 24, 2012, and 61/683,518, filed Aug. 15, 2012, the disclosures of which are incorporated herein by reference.

BACKGROUND

Pathological symptoms of bladder storage such as urgency, frequency and nocturia are characterized as overactive bladder (OAB). Interstitial cystitis (IC) on the other hand transcends mere urgency to include symptoms of bladder pain along with increased urinary frequency. Overactive bladder presents as an increased voiding frequency and may be the result of infection or injury to the bladder tissue itself, e.g., interstitial cystitis, or may arise as a comorbid association to conditions such as stress, anxiety disorder, endometriosis, vulvodynia, chronic fatigue syndrome, or fibromyalgia, among other conditions.

In both IC and OAB, increased afferent signals are conducted by myelinated Aδ-fibers and the unmyelinated C-fibers. Typically the C-fibers mediate painful mechanical, thermal and chemical sensations and this signaling requires action potentials that are initiated and maintained via activated sodium channels. Therefore, targeting the sodium channel mediated conduction of action potentials in bladder C-fiber afferent nerves may be a therapeutic approach for the treatment of OAB and IC (Steers, 2002, Rev. Urol., 4 Suppl 4:S7-S18). In an animal model of IC and OAB, blocking the conduction of afferent signals with the sodium channel blocker lidocaine, normalizes the micturition pattern as determined by cystometry (Juszczak, 2009, J. Physiol. Pharmacol. Dec, 60(4):85-91). Similarly, mexilitine prevents the painful sensation of noxious urinary bladder distention (Su, 2008, Neurourol. Urodyn., 27(3):249-53). Unfortunately neither lidocaine nor mexilitine offer therapeutically tractable options for patients with these bladder conditions due to the fact that their beneficial effects are short-lived.

There remains a need in the art for compounds which are useful in treating painful bladder conditions such as interstitial cystitis and overactive bladder.

SUMMARY OF THE INVENTION

In one aspect, methods for treating overactive bladder are provided and include administering a compound of formula (I) and/or (II) to a patient in need thereof.

In another aspect, methods for treating interstitial cystitis are provided and include administering a compound of formula (I) and/or (II) to a patient in need thereof.

Other aspects and advantages of the invention will be readily apparent from the following detailed description of the invention.

BRIEF DESCRIPTION OF THE DRAWINGS

FIGS. 3A and 3B are graphs measuring cystometric bladder pressure. FIG. 3A represents measurements taken during saline infusion into the bladder. FIG. 3B represents measurements of 30 minutes of infusing a combined solution of 0.3% of the compound of example 43 with 2% lidocaine which followed the saline infusion.

DETAILED DESCRIPTION OF THE INVENTION

Figure 1A:
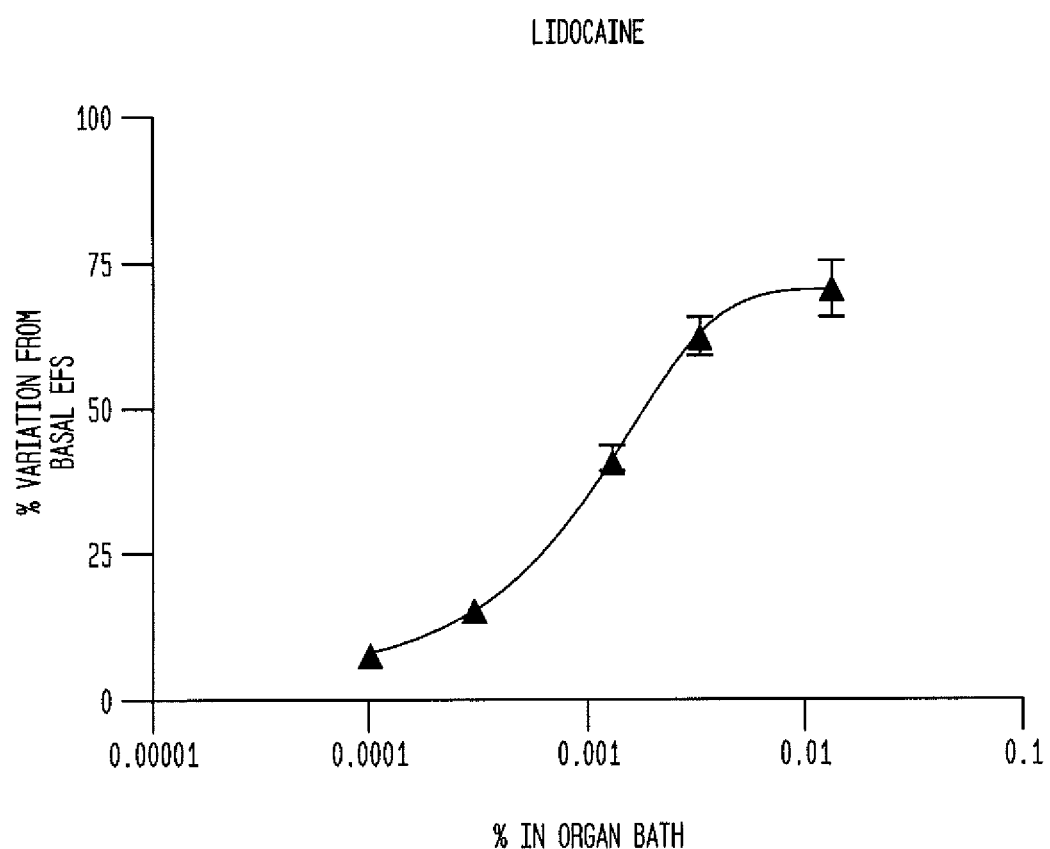
FIGS. 1A and 1B are line graphs illustrating the effects of lidocaine alone and the compound of Example 43, i.e., (R)-1,1-dimethyl-2-[2-((indan-2-yl)(2-methylphenyl)amino) ethyl]piperidinium iodide alone, respectively, on the contractile response of isolated detrusor bladder muscle. The test drugs were introduced into the organ bath at varying concentrations in order to construct cumulative concentration-response relationships for the inhibition of EFS-induced contractions.

The present invention provides methods of treating painful bladder conditions such as interstitial cystitis or overactive bladder using the compounds discussed herein, optionally in combination with a TRPV1 agonist. These novel compounds are permanently charged by virtue of the presence of quaternary nitrogen-atom contained within the nitrogen-containing ring rendering them highly soluble. These compounds are quaternary ammonium salts, where the counter-anion is a halogen anion, i.e., chloride, bromide, or iodide ion; or trifluoroacetate, sulfate, phosphate, acetate, fumarate, maleate, citrate, pyruvate, succinate, oxalate, a sulfonate, e.g., methanesulfonate, trifluoromethanesulfonate, toluenesulfonate such as p-toluenesulfonate, benzenesulfonate, ethanesulfonate, camphorsulfonate, 2-mesitylenesulfonate, or naphthalenesulfonate such as 2-naphthalenesulfonate, bisulfate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), D-mandelate, L-mandelate, propionate, phthalate, hydrochlorate, hydrobromate or nitrate.

The novel charged compounds disclosed herein are incapable of passing through the cell membrane. However, it is believed that they will penetrate into the cell, in therapeutically effective amounts, when access is afforded via open TRPV1 channels. This is one advantage of the charged compounds of the invention as compared to their corresponding neutral molecules that are believed to freely penetrate all cell membranes.

In one aspect, the methods discussed herein may be performed using a compound of formula (I) or (II).

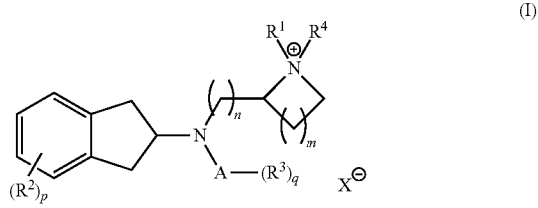

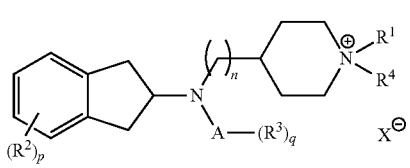

(II)

In these compounds, n is 1 to 3; m is 1 to 4; p is 0 to 2; and q is 0 to 4. In one embodiment, n is 1. In another embodiment, n is 2. In yet another embodiment, n is 3. In a further embodiment, p is 0. In yet another embodiment, p is 1. In another embodiment, p is 2. In still another embodiment, q is 0. In yet a further embodiment, q is 1. In still a further embodiment, q is 2. In yet another embodiment, q is 3. In yet a further embodiment, q is 4. In still a further embodiment, m is 2 and n is 1. In another embodiment, m is 2 and n is 2. In a further embodiment, m is 3 and n is 2. In a further embodiment, m is 3 and n is 1. In still a further embodiment, m is 4 and n is 2. In another embodiment, m is 4 and n is 3. In yet another embodiment, m is 2. In a still further embodiment, m is 3.

A is phenyl or heteroaryl.

$R^1$ and $R^4$ are, independently, $C_1$ to $C_6$ alkyl, or $CH_2CH_2OH$. Alternatively, $R^1$ and $R^4$ are joined together to form a 4- to 6-membered carbocyclic or heterocyclic ring. In one embodiment, $R^1$ and $R^4$ are joined to form an optionally substituted carbocyclic ring such as cyclobutane, cyclopentane, cyclohexane, cycloheptane, and cyclooctane. In another embodiment, $R^1$ and $R^4$ are joined to form an optionally substituted heterocyclic ring such as a cyclic ether, amine, or sulfide. In a further embodiment, $R^1$ and $R^4$ are joined to form a cyclic ether.

$R^2$ is H, halogen, $NO_2$, OH, or $C_1$ to $C_6$ alkoxy. In one embodiment, $R^1$ and $R^4$ are the same. In another embodiment, $R^1$ and $R^4$ differ. In a further embodiment, $R^1$ and/or $R^4$ are methyl, ethyl, propyl(n-propyl or i-propyl), butyl, pentyl, hexyl, or the like.

$R^3$ is hydrogen, halogen, CN, $NO_2$, $NH_2$, optionally substituted $C_1$ to $C_6$ alkyl, $C_2$ to $C_6$ alkenyl, $C_2$ to $C_6$ alkynyl, OH, $CF_3$, $OCF_3$, $SCF_3$, optionally substituted $C_1$ to $C_6$ alkoxy, $C_2$ to $C_6$ alkynyloxy, heterocyclyloxy, heteroaryloxy, optionally substituted $C_1$ to $C_6$ alkylthio, heteroarylthio, $C(O)O(C_1$ to $C_6$ alkyl), $C(O)(C_1$ to $C_6$ alkyl), $C(O)$(aryl), $C(O)$(heterocycle), $C(O)NH_2$, $C(O)NH(C_1$ to $C_6$ alkyl), $C(O)NH$(aryl), $C(O)NH$(heterocycle), $C(O)NH$(heteroaryl), $C(O)N(C_1$ to $C_6$ alkyl)$(C_1$ to $C_6$ alkyl), $C(O)N$(aryl)$(C_1$ to $C_6$ alkyl), $C(S)NH_2$, optionally substituted aryl, heteroaryl, heterocycle, $NHC(O)$ $(C_1$ to $C_6$ alkyl), $NHC(O)$(aryl), $NHC(O)$(heteroaryl), $NHC$ $(O)O(C_1$ to $C_6$ alkyl), $N(C_1$ to $C_6$ alkyl)$C(O)(C_1$ to $C_6$ alkyl), $N(C_1$ to $C_6$ alkyl)$C(O)O(C_1$ to $C_6$ alkyl), $NHC(O)NH_2$, $NHC$ $(O)NH(C_1$ to $C_6$ alkyl), $NHC(O)NH$(heteroaryl), $NHSO_2(C_1$ to $C_6$ alkyl), $SO_2(C_1$ to $C_6$ alkyl), $SO_2NH_2$, $SO_2NH(C_1$ to $C_6$ alkyl), $SO_2NH(C_2$ to $C_6$ alkynyl), $SO_2N(C_1$ to $C_6$ alkyl)$(C_1$ to $C_6$ alkyl), $SO_2NH$(heteroaryl), $NH(C_1$ to $C_6$ alkyl), $N(C_1$ to $C_6$ alkyl)$(C_1$ to $C_6$ alkyl), $N(C_1$ to $C_6$ alkyl)$(C_2$ to $C_6$ alkenyl), or $N(C_1$ to $C_6$ alkyl)(heterocycle). Alternatively, two $R^3$ groups are joined to form an optionally substituted 6-membered aryl, optionally substituted 5- or 6-membered carbocyclic ring, or optionally substituted 5- or 6-membered heterocycle or heteroaryl containing 1 to 3 oxygen, nitrogen, or sulfur atoms and 4 or 5 carbon atoms. In one embodiment, $R^3$ is halogen. In another embodiment, $R^3$ is chlorine or fluorine. In a further embodiment, $R^3$ is CN. In yet another embodiment, $R^3$ is $C(O)OCH_3$. In still a further embodiment, $R^3$ is $C(O)NH_2$. In yet a further embodiment, $R^3$ is $SO_2CH_3$. In another embodiment, $R^3$ is $CH_3$.

$X^-$ is halogen anion, trifluoroacetate, sulfate, phosphate, acetate, fumarate, maleate, citrate, pyruvate, succinate, oxalate, a sulfonate, e.g., methanesulfonate, trifluoromethanesulfonate, toluenesulfonate such as p-toluenesulfonate, benzenesulfonate, ethanesulfonate, camphorsulfonate, 2-mesitylenesulfonate, or naphthalenesulfonate such as 2-naphthalenesulfonate, bisulfate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isethionate (2-hydroxyethylsulfonate), D-mandelate, L-mandelate, propionate, tartarate, phthalate, hydrochlorate, hydrobromate, and nitrate. In one embodiment, X is halogen. In another embodiment, X is chlorine, bromine or iodine. In another embodiment, X is iodine.

Also contemplated by the present invention is the one embodiment that two hydrogen atoms attached to a carbon atom, i.e., $CH_2$, can be replaced with a double bond to an oxygen atom or sulfur atom to form a carbonyl, i.e., C(O), or thiocarbonyl, i.e., C(S), respectively.

In another embodiment, the methods may be performed using the compounds of formula (I-A), (I-AA), or (II-A), wherein $R^1$, $R^3$, $R^4$, A, X, m, n, and q are defined herein. In one example, m is 2 or 3.

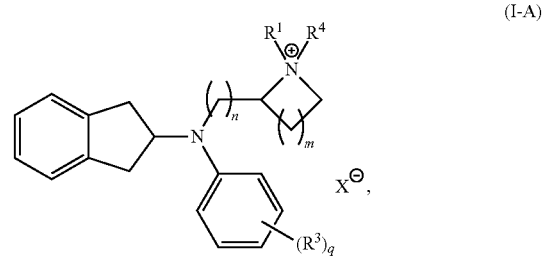

(I-A)

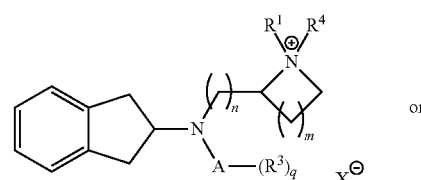

(I-AA)

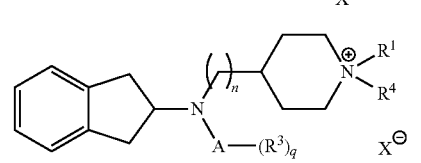

(II-A)

In a further embodiment, the methods may be performed using the compounds of formula (I-B), (I-BB), or (II-B) wherein $R^1$, $R^2$, $R^4$, A, X, m, n, and p are defined herein. In one example, m is 2 or 3.

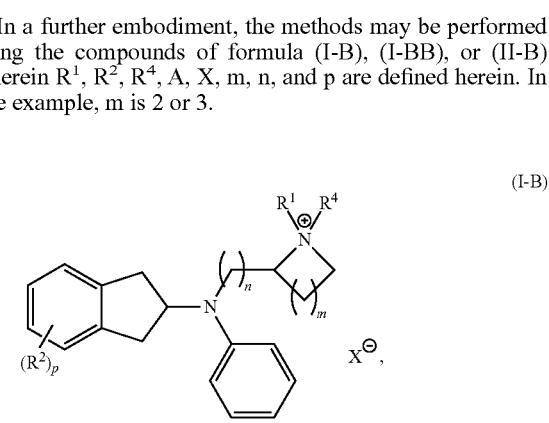

(I-B)

(I-BB)
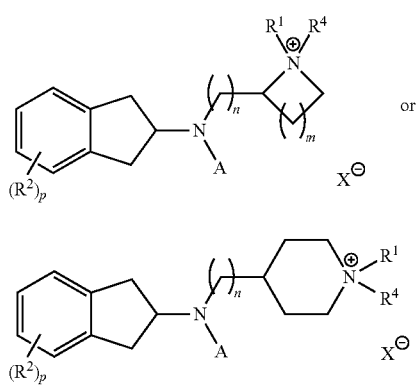
or
(II-B)
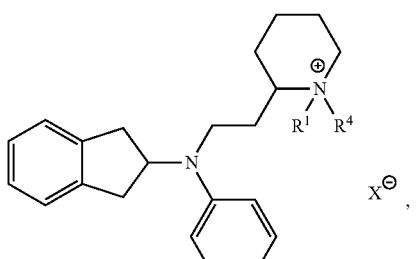
In yet another embodiment, the methods may be performed using the compounds of formula (I-C), (I-CC), or (II-C) wherein R¹, R⁴, A, and X are defined herein.
(I-C)
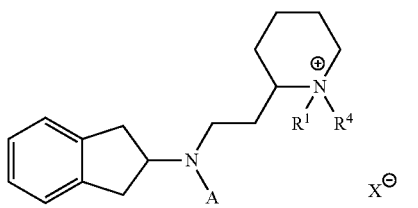
(I-CC)
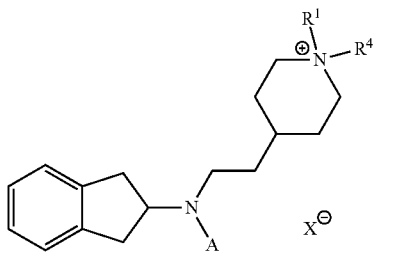
or
(II-C)
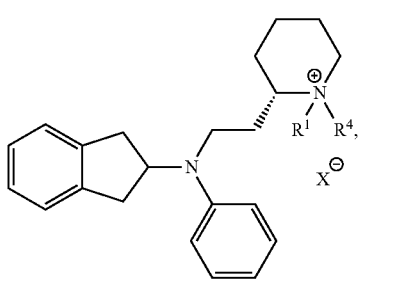
In still a further embodiment, the methods may be performed using the compounds of formula (I-D) or (I-DD), wherein R¹, R⁴, and X are defined herein.
(I-D)
(I-DD)
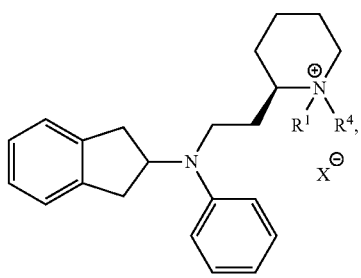
(I-DDD)
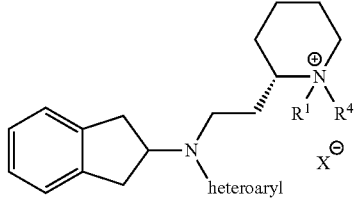
(I-DDDD)
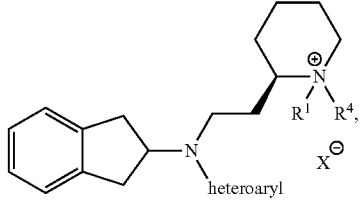
(II-D)
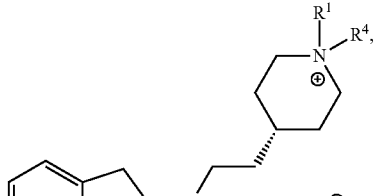
(II-DD)
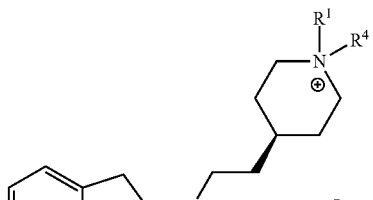
(II-DDD)
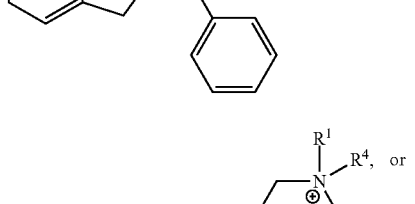

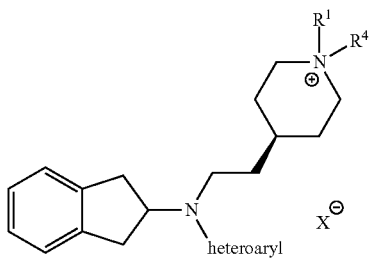
(II-DDDD)

In another embodiment, the methods may be performed using the compounds of formula (I-E), wherein $R^1$, $R^4$, and X are defined herein.

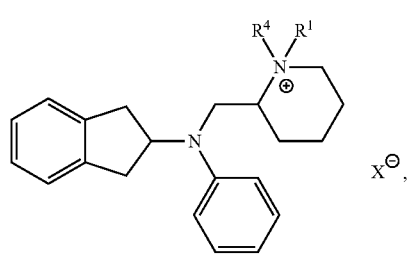
(I-E)

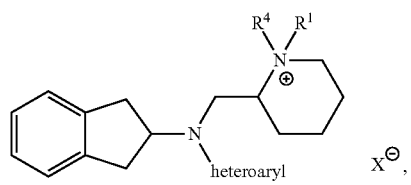
(I-EE)

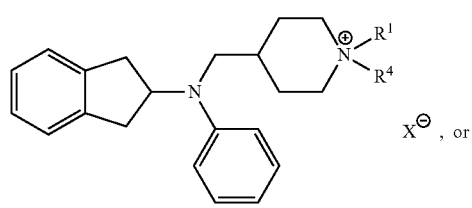
(I-EEE)

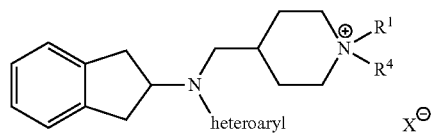
(I-EEEE)

In yet another embodiment, the methods may be performed using the compounds of formula (I-F)-(I-FFFF) or (II-F)-(II-FFFF), wherein $R^1$, $R^4$, and X are defined herein.

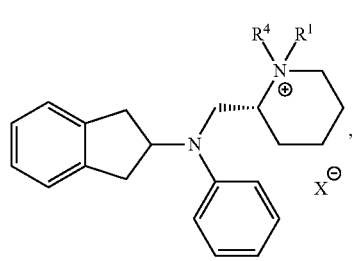
(I-F)

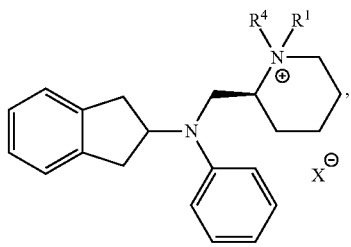
(I-FF)

(I-FFF)

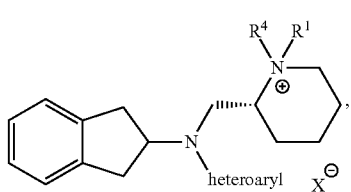
(I-FFFF)

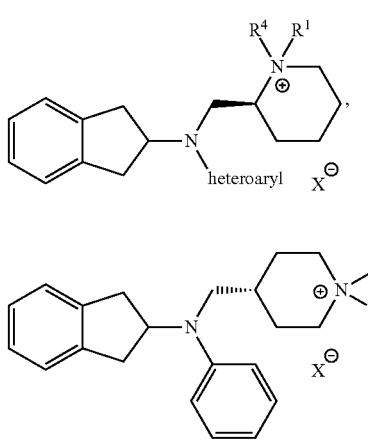
(II-F)

(II-FF)

(II-FFF)

(II-FFFF)

In still a further embodiment, the methods may be performed using the compounds of formula (I-G), (I-GG), or (II-G), wherein $R^1$, $R^4$, A, X, m, and n are defined herein. In one example, m is 2 or 3.

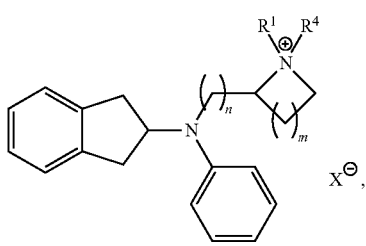
(I-G)

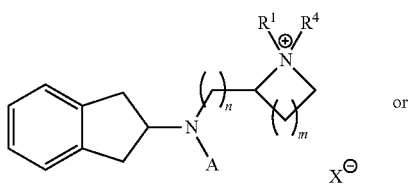
(I-GG)

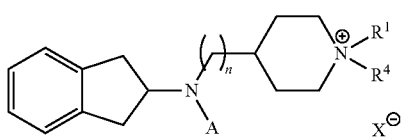
(II-G)

In another embodiment, the methods may be performed using the compounds of formula (I-H), wherein $R^1$, $R^4$, X, m, and n are defined herein. In one example, m is 2 or 3.

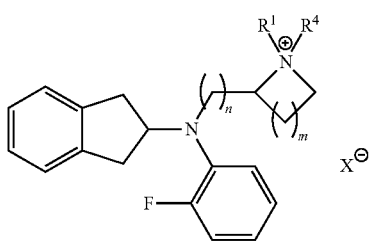
(I-H)

In still a further embodiment, the methods may be performed using the compounds of formula (I-J), wherein $R^1$, $R^4$, X, m, and n are defined herein. In one example, m is 2 or 3.

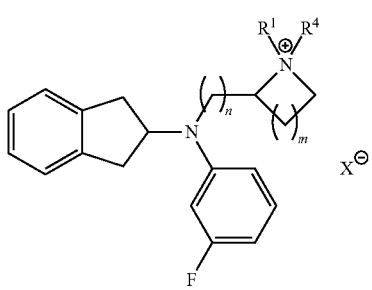
(I-J)

In still a further embodiment, the methods may be performed using the compounds of formula (I-K), wherein $R^1$, $R^4$, X, m, and n are defined herein. In one example, m is 2 or 3.

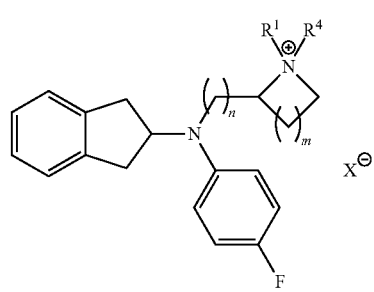
(I-K)

In yet another embodiment, the methods may be performed using the compounds of formula (I-L) or (II-L), wherein $R^1$, $R^4$, X, m, and n are defined herein. In one example, m is 2 or 3.

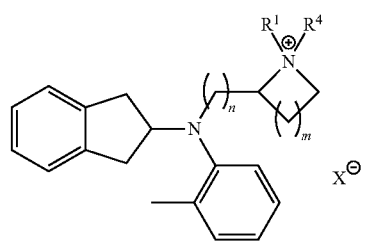
(I-L)

or

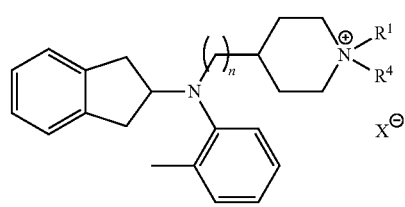
(II-L)

In a further embodiment, the methods may be performed using the compounds of formula (I-M) or (II-M), wherein $R^1$, $R^4$, X, m, and n are defined herein. In one example, m is 2 or 3.

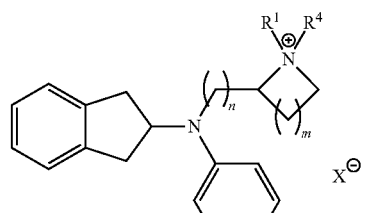
(I-M)

or

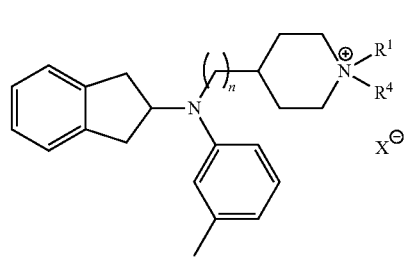
(II-M)

In yet a further embodiment, the methods may be performed using the compounds of formula (I-N) or (II-N) wherein $R^1$, $R^4$, X, m, and n are defined herein. In one example, m is 2 or 3.

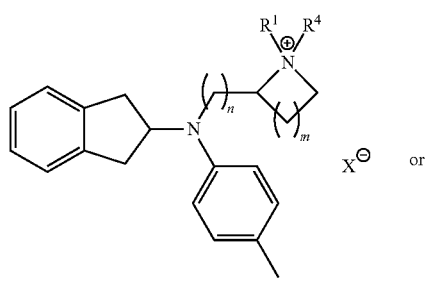
(I-N)

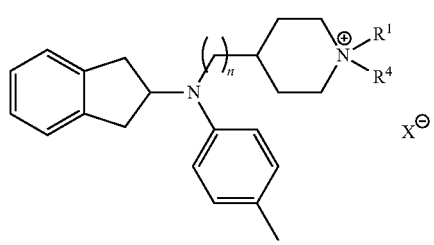
(II-N)

In another embodiment, the methods may be performed using the compounds of formula (I-O), (I-OO), (II-O), or (II-OO), wherein $R^1$, $R^4$, X, m, and n are defined herein. In one example, m is 2 or 3.

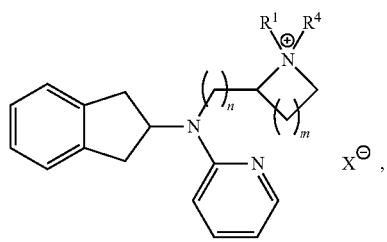
(I-O)

(II-O)

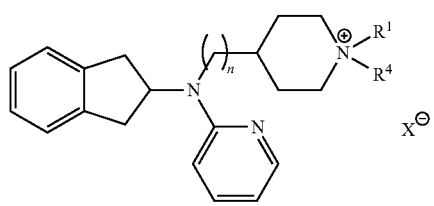

(I-OO)

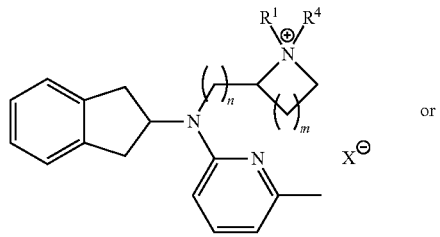

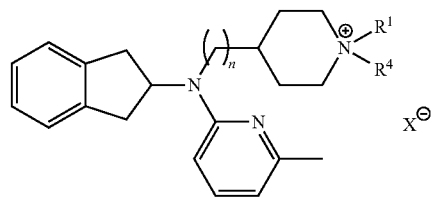
(II-OO)

In still a further embodiment, the methods may be performed using the compounds of formula (I-P) or (II-P) wherein $R^1$, $R^4$, X, m, and n are defined herein. In one example, m is 2 or 3.

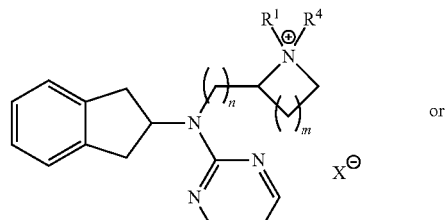
(I-P)

(II-P)

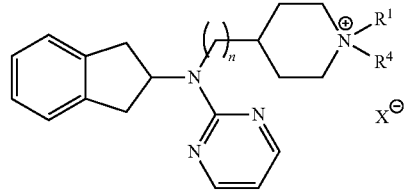

In yet another embodiment, the methods may be performed using the compounds of formula (I-Q) or (II-Q) wherein $R^1$, $R^4$, X, m, and n are defined herein. In one example, m is 2 or 3.

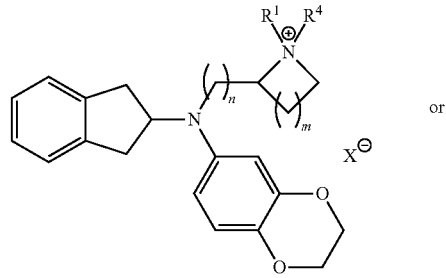
(I-Q)

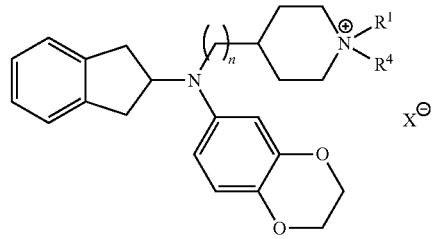
(II-Q)

In a further embodiment, the methods may be performed using the compounds of formula (I-R) or (II-R) wherein $R^1$, $R^4$, X, m, and n are defined herein. In one example, m is 2 or 3.

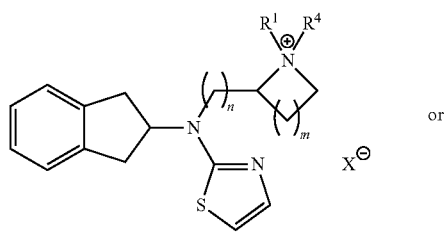

(I-R)

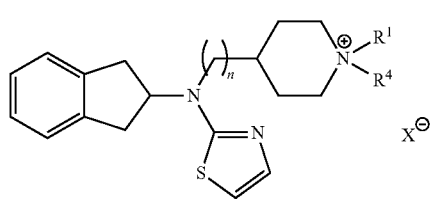

(II-R)

In still a further embodiment, the methods may be performed using the compounds of formula (I-S) or (II-S) wherein $R^1$, $R^4$, X, m, and n are defined herein. In one example, m is 2 or 3.

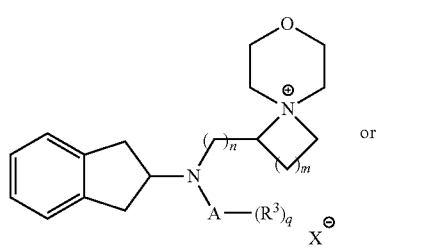

(I-S)

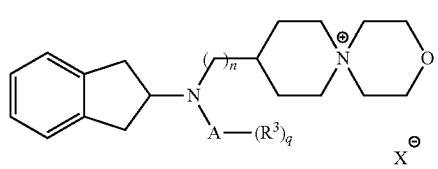

(II-S)

In yet another embodiment, the methods may be performed using the compounds of formula (I-T) or (II-T) wherein $R^1$, $R^4$, X, m, and n are defined herein. In one example, m is 2 or 3.

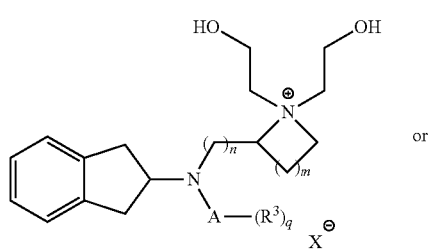

(I-T)

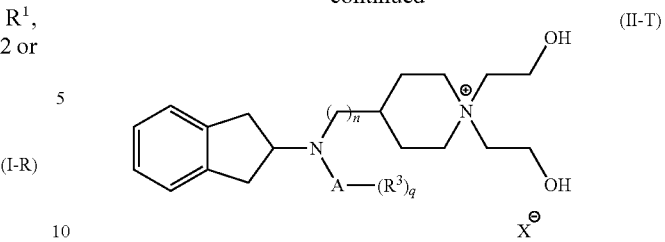

(II-T)

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

"Alkyl" refers to a hydrocarbon chain that may be straight or branched. In one embodiment, an alkyl contains 1 to 6 (inclusive) carbon atoms. In another embodiment, an alkyl contains 1 to 5 (inclusive) carbon atoms. In a further embodiment, an alkyl contains 1 to 4 (inclusive) carbon atoms. In yet another embodiment, an alkyl contains 1 to 3 (inclusive) carbon atoms. In still a further embodiment, an alkyl contains 1 or 2 carbon atoms. Examples of alkyl groups that are hydrocarbon chains include, but are not limited to, methyl, ethyl, propyl, butyl, pentyl, and hexyl, where all isomers of these examples are contemplated.

Alkyl groups may also consist of or contain a cyclic alkyl radical, i.e., "carbocyclic ring". Examples of carbocyclic rings include, but are not limited to, cyclopropyl, cyclobutyl, cyclopentyl, cyclohexyl, and the like. In one embodiment, the carbocyclic ring is 3- to 6-membered. In a further embodiment, the carbocyclic ring is 3- to 5-membered. In still a further embodiment, the carbocyclic ring is 4- to 6-membered. In another embodiment, the carbocyclic ring is 3- or 4-membered, i.e., cyclopropyl or cyclobutyl. Unless specifically noted, the alkyl groups are unsubstituted, i.e., they contain carbon and hydrogen atoms only. However, when the alkyl group or carbocyclic ring is substituted, it is prefaced with the term "optionally substituted" or "substituted". The optional substituents of the alkyl groups or carbocyclic rings include, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkyl-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH ($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl), or NHC(O)$NH_2$.

"Alkenyl" refers to hydrocarbon chain which is straight or branched and contains at least one degree of unsaturation (i.e., with one or more carbon-carbon double bonds), or to a hydrocarbon group that consists of or contains a cyclic alkenyl radical. Each alkenyl double bond may exist in the E or Z conformation. In one embodiment, an alkenyl contains 2 to about 6 (inclusive) carbon atoms or integers or ranges there between. In another embodiment, an alkenyl contains 2 to 5 (inclusive) carbon atoms. In a further embodiment, an alkenyl contains 2 to 4 (inclusive) carbon atoms. In yet another embodiment, an alkenyl contains 2 or 3 carbon atoms. An alkenyl contains at least 1 double bond. In one embodiment, the alkenyl may contain 1 to 3 double bonds, or integers there between. Examples of alkenyl hydrocarbon chain include, but are not limited to, ethene, propene, butene, pentene and hexene. Examples of alkenyl that consist of or contain a cyclic alkenyl radical include, but are not limited to, cyclopentene, and cyclohexene. An alkenyl can be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Alkynyl" refers to a hydrocarbon chain which is straight or branched chain and contains at least one degree of unsaturation, i.e., with one or more carbon-carbon triple bond. In one embodiment, an alkynyl contains 2 to about 6 (inclusive) carbon atoms or integers or ranges there between. In another embodiment, an alkynyl contains 2 to 5 (inclusive) carbon atoms. In a further embodiment, an alkynyl contains 2 to 4 (inclusive) carbon atoms. In yet another embodiment, an alkynyl contains 2 or 3 carbon atoms. An alkynyl contains at least 1 triple bond. In one embodiment, the alkynyl may contain 1 to 3 triple bonds, or integers there between. Examples of alkynyl include, but are not limited to, ethyne, propyne, butyne, pentyne, and hexyne. An alkynyl can be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH ($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Alkoxy" refers to ∼O(alkyl), where the alkyl is optionally substituted and is defined above. In one embodiment, an alkoxy contains 1 to 6 (inclusive) carbon atoms or integers or ranges there between. In another embodiment, an alkoxy contains 1 to 5 (inclusive) carbon atoms or ranges there between. In a further embodiment, an alkoxy contains 1 to 4 (inclusive) carbon atoms. In yet another embodiment, an alkoxy contains 1 to 3 (inclusive) carbon atoms. In still a further embodiment, an alkoxy contains 1 or 2 carbon atoms. Examples of alkoxy include, but are not limited to, methoxy, ethoxy, propoxy, and butoxy. The alkyl radical of an alkoxy group can be unsubstituted or substituted as defined above for "alkyl".

"Alkynyloxy" refers to ∼O(alkynyl), where the alkynyl is optionally substituted and is defined above. Examples of alkynyloxy include, but are not limited to, propynyloxy, butynyloxy, pentynyloxy, and hexynyloxy.

"Heterocyclyloxy" refers to ∼O(heterocycle), where the heterocycle is optionally substituted and is defined below.

"Heteroaryloxy" refers to ∼(heteroaryl), where the heteroaryl is optionally substituted and is defined below.

"Aryl" refers to an aromatic hydrocarbon group containing carbon atoms. In one embodiment, the aryl contains 6 to 10 carbon atoms, i.e., 6-, 7-, 8-, 9- or 10-membered. In another embodiment, aryl is an aromatic or partly aromatic bicyclic group. In a further embodiment, the aryl is a phenyl group. In another embodiment, the aryl is naphthyl (such as α-naphthyl or β-naphthyl), 1,2,3,4-tetrahydronaphthyl, or indanyl. An aryl group can be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O) ($C_1$ to $C_6$ alkyl), $NHSO_2$($C_1$ to $C_6$ alkyl), N($C_1$ to $C_6$ alkyl) $SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Halogen" refers to F, Cl, Br and I.

The term "heteroatom" refers to a sulfur, nitrogen, or oxygen atom.

"Heteroaryl" refers to a monocyclic aromatic 5- or 6-membered ring containing at least one ring heteroatom. In one embodiment, the heteroaryl contains 1 to 5 carbon atoms (inclusive) or integers or ranges there between. In a further embodiment, the heteroaryl contains 2 to 5 carbon atoms (inclusive). In another embodiment, the heteroaryl contains 3 to 5 carbon atoms (inclusive). In still a further embodiment, the heteroaryl contains 4 or 5 carbon atoms. "Heteroaryl" also refers to bicyclic aromatic ring systems wherein a heteroaryl group as just described is fused to at least one other cyclic moiety. In one embodiment, a phenyl radical is fused to a 5- or 6-membered monocyclic heteroaryl to form the bicyclic heteroaryl. In another embodiment, a cyclic alkyl is fused to a monocyclic heteroaryl to form the bicyclic heteroaryl. In yet a further embodiment, the bicyclic heteroaryl is a pyridine fused to a 5- or 6-membered monocyclic heteroaryl. In still another embodiment, the heteroaryl ring has 1 or 2 nitrogen atoms in the ring. In a further embodiment, the heteroaryl ring has 1 nitrogen atom and 1 oxygen atom. In yet another embodiment, the heteroaryl ring has 1 nitrogen atom and 1 sulfur atom. Examples of heteroaryl groups include, without limitation, furan, thiophene, indole, azaindole, oxazole, thiazole, isoxazole, isothiazole, imidazole, pyridine, pyrimidine, pyrazine, pyridazine, pyrrole, pyrazole, 1,3,4-oxadiazole, 1,2,4-triazole, tetrazole, benzoxazole, benzothiazole, benzofuran, benzisoxazole, benzimidazole, azabenzimidazole, indazole, quinazoline, quinoline, and isoquinoline. A heteroaryl may be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Heterocycle" refers to a monocyclic or bicyclic group in which at least 1 ring atom is a heteroatom. A heterocycle may be saturated or partially saturated. In one embodiment, the heterocycle contains 3 to 7 carbon atoms (inclusive) or integers or ranges there between. In a further embodiment, the heterocycle contains 4 to 7 carbon atoms (inclusive). In another embodiment, the heterocycle contains 4 to 6 carbon atoms (inclusive). In still a further embodiment, the heterocycle contains 5 or 6 carbon atoms (inclusive). Examples of heterocycles include, but are not limited, to aziridine, oxirane, thiirane, morpholine, thiomorpholine, pyrroline, pyrrolidine, azepane, dihydrofuran, tetrahydrofuran, dihydrothiophene, tetrahydrothiophene, dithiolane, piperidine, 1,2,3,6-tetrahydropyridine-1-yl, tetrahydropyran, pyran, thiane, thiine, piperazine, homopiperazine, oxazine, azecane, tetrahydroquinoline, perhydroisoquinoline, 5,6-dihydro-4H-1,3-oxazin-2-yl, 2,5-diazabicyclo[2.2.1]heptane, 2,5-diazabicyclo[2.2.2]octane, 3,6-diazabicyclo[3.1.1]heptane, 3,8-diazabicyclo[3.2.1]octane, 6-oxa-3,8-diazabicyclo[3.2.1]octane, 7-oxa-2,5-diazabicyclo[2.2.2]octane, 2,7-dioxa-5-azabicyclo[2.2.2]octane, 2-oxa-5-azabicyclo[2.2.1]heptane-5-yl, 2-oxa-5-azabicyclo[2.2.2]octane, 3,6-dioxa-8-azabicyclo[3.2.1]octane, 3-oxa-6-azabicyclo[3.1.1]heptane, 3-oxa-8-azabicyclo[3.2.1]octan-8-yl, 5,7-dioxa-2-azabicyclo[2.2.2]octane, 6,8-dioxa-3-azabicyclo[3.2.1]octane, 6-oxa-3-azabicyclo[3.1.1]heptane, 8-oxa-3-azabicyclo[3.2.1]octan-3-yl, 2,5-diazabicyclo[2.2.1]heptane-5-yl, 6-azabicyclo[3.2.1]oct-6-yl, 8-azabicyclo[3.2.1]octan-8-yl, 3-oxa-7,9-diazabicyclo[3.3.1]nonan-9-yl, 9-oxa-3-azabicyclo[3.3.1]nonan-3-yl, 3-oxa-9-azabicyclo[3.3.1]nonan-9-yl, 3,7-dioxa-9-azabicyclo[3.3.1]nonan-9-yl, 3,4-dihydro-2H-1,4-benzoxazin-7-yl, thiazine, dithiane, and dioxane. In another embodiment, the heterocycle contains 1 or 2 nitrogen atoms. In a further embodiment, the heterocycle contains 1 or 2 nitrogen atoms and 3 to 6 carbon atoms. In yet another embodiment, the heterocycle contains 1 or 2 nitrogen atoms, 3 to 6 carbon atoms, and 1 oxygen atom. In a further embodiment, the heterocycle is 5- to 8-membered. In another embodiment, the heterocycle is 5-membered. In still a further embodiment, the heterocycle is 6-membered. In yet another embodiment, the heterocycle is 8-membered. A heterocycle may be unsubstituted or substituted with one or more groups including, without limitation, halogen, CN, $NO_2$, $C_1$ to $C_6$ alkyl, OH, $C_1$ to $C_6$ alkoxy, $C_1$ to $C_6$ alkoxy-$C_1$ to $C_6$ alkoxy, $C_1$ to $C_6$ alkoxy-$C_1$ to $C_6$ alkoxy-$C_1$ to $C_6$ alkoxy, heterocyclyloxy, $C_1$ to $C_6$ alkylthio, aryl, heterocycle, heteroaryl, C(O)($C_1$ to $C_6$ alkyl), C(O)(heterocycle), C(O)O($C_1$ to $C_6$ alkyl), C(O)$NH_2$, C(O)NH($C_1$ to $C_6$ alkyl), C(O)N($C_1$ to $C_6$ alkyl)($C_1$ to $C_6$ alkyl), $SO_2$($C_1$ to $C_6$ alkyl), $SO_2$($C_2$ to $C_6$ alkynyl), $SO_2$NH($C_1$ to $C_6$ alkyl), $SO_2$(heterocycle), NHC(O)($C_1$ to $C_6$ alkyl), $NHSO_2$($C_1$ to $C_6$ alkyl), N($C_1$ to $C_6$ alkyl)$SO_2$($C_1$ to $C_6$ alkyl), $NH_2$, NH(aryl), N($C_1$ to $C_6$ alkyl)($C_1$ to $C_6$ alkyl) or NHC(O)$NH_2$.

"Alkylthio" refers to ⁓S(alkyl) where the alkyl is optionally substituted and is defined above. In one embodiment, an alkylthio contains 1 to 6 (inclusive) carbon atoms or integers or ranges therebetween. Examples of alkylthio include, but are not limited to, $SCH_2CH_3$, $SCH_2CH_2CH_3$, $SCH_2CH_2CH_3$, $SCH_2CH_2CH_2CH_3$, $SCH_2CH_2CH_2CH_3$ and $SCH_2CH_2CH_2CH_3$.

"Heteroarylthio" refers to ⁓S(heteroaryl) where the heteroaryl is optionally substituted and is defined below.

"Alkylsulfonyl" refers to ⁓$SO_2$(alkyl) where the alkyl is optionally substituted and defined above. Examples of alkylsulfonyl include, but are not limited to, $CH_3SO_2$, $CH_3CH_2CH_2SO_2$, $CH_3CH(CH_3)SO_2$, $CH_3CH_2CH_2CH_2SO_2$, $CH_3CH(CH_3)CH_2SO_2$, $(CH_3)_3CSO_2$, and the like.

"Alkynylsulfonyl" refers to ⁓$SO_2$(alkynyl) where the alkynyl is optionally substituted and defined above. Examples of alkynylsulfonyl include, but are not limited to, CH≡$CSO_2$, CH≡$CHCH_2SO_2$, and the like.

"Heterocyclesulfonyl" refers to ⁓$SO_2$(heterocycle) where the heterocycle is optionally substituted and defined above.

"Alkylamino" refers to an NH or N group, the nitrogen atom of the group being attached to 1 or 2 alkyl substituents, respectively, wherein the alkyl is optionally substituted and defined above. The alkylamino is bound through the nitrogen atom of the group. In one embodiment, alkylamino refers to ⁓NH(alkyl). In another embodiment, alkylamino refers to ⁓N(alkyl)(alkyl), i.e., a "dialkylamino". In a further embodiment, alkylamino refers to ⁓N($C_1$ to $C_6$ alkyl)($C_1$ to $C_6$ alkyl). In yet another embodiment, alkylamino refers to ⁓N(alkyl)(heterocycle). In still a further embodiment, alkylamino refers to ⁓N(alkyl)(aryl). In another embodiment, alkylamino refers to ⁓N(alkyl)(heteroaryl). In yet a further embodiment, alkylamino refers to ⁓N(alkyl)(alkenyl). When the nitrogen atom is bound to two alkyl groups, each alkyl group may be independently selected. In another embodiment, two alkyl groups on the nitrogen atom may be taken together with the nitrogen to which they are attached to form a 3- to 4-membered nitrogen-containing heterocycle where up to two of the carbon atoms of the heterocycle can be replaced with N(H), N($C_1$ to $C_6$ alkyl), N(aryl), N(heteroaryl), O, S(O), or $S(O)_2$. Examples of alkylamino include, but are not limited to $N(CH_3)_2$, $N(CH_2CH_3)(CH_3)$, $N(CH_2CH_3)_2$, $N(CH_2CH_2CH_3)_2$, $N(CH_2CH_2CH_2CH_3)_2$, $N(CH(CH_3)_2)(CH_3)$, and the like.

"Arylamino" refers to an NH or N group, the nitrogen atom of the group being attached to 1 or 2 aryl substituents, respectively, wherein the aryl is optionally substituted and defined above. The arylamino is bound through the nitrogen atom of the group. In one embodiment, arylamino refers to ⁓NH(aryl). In another embodiment, arylamino refers to ⁓N(aryl)(aryl), i.e., a "diarylamino". When the nitrogen atom is bound to two aryl groups, each aryl may be independently selected.

"Alkylcarbonylamino" refers to ⁓NHC(O)(alkyl) or ⁓N(alkyl)C(O)(alkyl) where the alkyl groups are independently defined and independently optionally substituted as described above. Examples of alkylcarbonylamino include, but are not limited to, $CH_3$CONH, $CH_3CH_2$CONH, $CH_3CH_2CH_2$CONH, $CH_3CH(CH_3)$CONH, and the like.

"Arylcarbonylamino" refers to ⁓NHC(O)(aryl) where the aryl group is defined and optionally substituted as described above.

"Heteroarylcarbonylamino" refers to ⁓NHC(O)(heteroaryl) where the heteroaryl group is defined and optionally substituted as described above.

"Alkylsulfonylamino" refers to ⁓$NHSO_2$(alkyl) where the alkyl group is defined and optionally substituted as described above. Examples of alkylsulfonylamino include, but are not limited to $CH_3SO_2NH$, $CH_3CH_2SO_2NH$, $CH_3CH_2CH_2SO_2NH$, $CH_3CH(CH_3)SO_2NH$, and the like.

"Ester" refers to ⁓C(O)O(alkyl), which is bound through the carbon atom. The alkyl group is defined and optionally substituted as described above. Examples of ester include, without limitation, C(O)OCH₃, C(O)O(CH₂CH₃), C(O)O(CH₂CH₂CH₃), C(O)(O)(CH₂CH₂CH₂CH₃), and the like.

"Carbamate" refers to ⌇NHC(O)O(alkyl) or ⌇N(alkyl)C(O)O(alkyl) where the alkyl groups are independently defined and independently optionally substituted as described above. Examples of carbamate include, but are not limited to, NHC(O)OCH₃, NHC(O)OCH₂CH₃, NHC(O)OCH₂CH₂CH₃, NHC(O)OCH₂CH₂CH₂CH₃, and the like.

"Urea" refers to a group having a ⌇NHC(O)NH⌇ where one of the nitrogen atoms is bound to an alkyl or heteroaryl group. The alkyl or heteroaryl groups are defined and optionally substituted as described above. Examples of urea include, without limitation, NHC(O)NHCH₃, NHC(O)NHCH₂CH₃, NHC(O)NHCH₂CH₂CH₃, NHC(O)NHCH₂CH₂CH₂CH₃, and the like.

"Alkylaminocarbonyl" refers to ⌇C(O)NH(alkyl) or ⌇C(O)N(alkyl)(alkyl) where the alkyl groups are independently defined and independently optionally substituted as described above. Examples of alkylaminocarbonyl include, but are not limited to, CH₃NHCO, CH₃CH₂NHCO, CH₃CH₂CH₂NHCO, CH₃CH(CH₃)NHCO, and the like.

"Arylaminocarbonyl" refers to ⌇C(O)NH(aryl) or ⌇C(O)N(aryl)(aryl) where the aryl groups are independently defined and independently optionally substituted as described above.

"Heteroarylaminocarbonyl" refers to ⌇C(O)NH(heteroaryl) or ⌇C(O)N(heteroaryl)(heteroaryl) where the heteroaryl groups are independently defined and independently optionally substituted as described above.

"Heterocycleaminocarbonyl" refers to ⌇C(O)NH(heterocycle) or ⌇C(O)N(heterocycle)(heterocycle) where the heterocycle groups are independently defined and independently optionally substituted as described above.

"Alkylaminosulfonyl" refers to ⌇SO₂NH(alkyl) or ⌇SO₂N(alkyl)₂ where the alkyl groups are independently defined and independently optionally substituted as described above. Examples of alkylaminosulfonyl include, but are not limited to, SO₂NHCH₃, SO₂NHCH₂CH₃, SO₂NHCH₂CH₂CH₃, SONHC(CH₃)CH₃, SO₂N(CH₃)₂, SO₂NH(CH₃)(CH₂CH₃), and the like.

"Alkynylaminosulfonyl" refers to ⌇SO₂NH(alkynyl) where the alkynyl group is defined and optionally substituted as described above. Examples of alkynylaminosulfonyl include, but are not limited to, CH≡CNHSO₂, CH≡CCH₂NHSO₂, and the like.

"Heteroarylaminosulfonyl" refers to ⌇SO₂NH(heteroaryl) or ⌇SO₂N(heteroaryl)₂ where the heteroaryl groups are independently defined and independently optionally substituted as described above.

A "patient" or "subject" is a mammal, e.g., a human or a veterinary patient or subject, e.g., mouse, rat, guinea pig, dog, cat, horse, cow, pig, or non-human primate, such as a monkey, chimpanzee, baboon or gorilla.

The term % enantiomeric excess (% ee) as used herein is recognized by those skilled in the art to refer to the enantiomeric purity of the sample, i.e., the percentage of one enantiomer over other enantiomers in the sample. In one embodiment, a "high" % ee of at least 90, at least 91, at least 92, at least 93, at least 94, at least 95, at least 96, at least 97, at least 98, or 100% may be obtained.

The terms "comprise", "comprises", and "comprising" are to be interpreted inclusively rather than exclusively. The terms "consist", "consisting", and its variants, are to be interpreted exclusively, rather than inclusively.

As used herein, the term "about" means a variability of 10% from the reference given, unless otherwise specified.

Methods useful for making the compounds of formulae (I) and (II) are set forth in the Examples below and generalized in Schemes 1-27. One of skill in the art will recognize that Schemes 1-27 can be adapted to produce the other compounds of formulae (I) and (II) according to the present invention.

The following methods outline the synthesis of the compounds of formulae (I) and (II). The following examples are presented to illustrate certain embodiments of the present invention, but should not be construed as limiting the scope of this invention.

Scheme 1

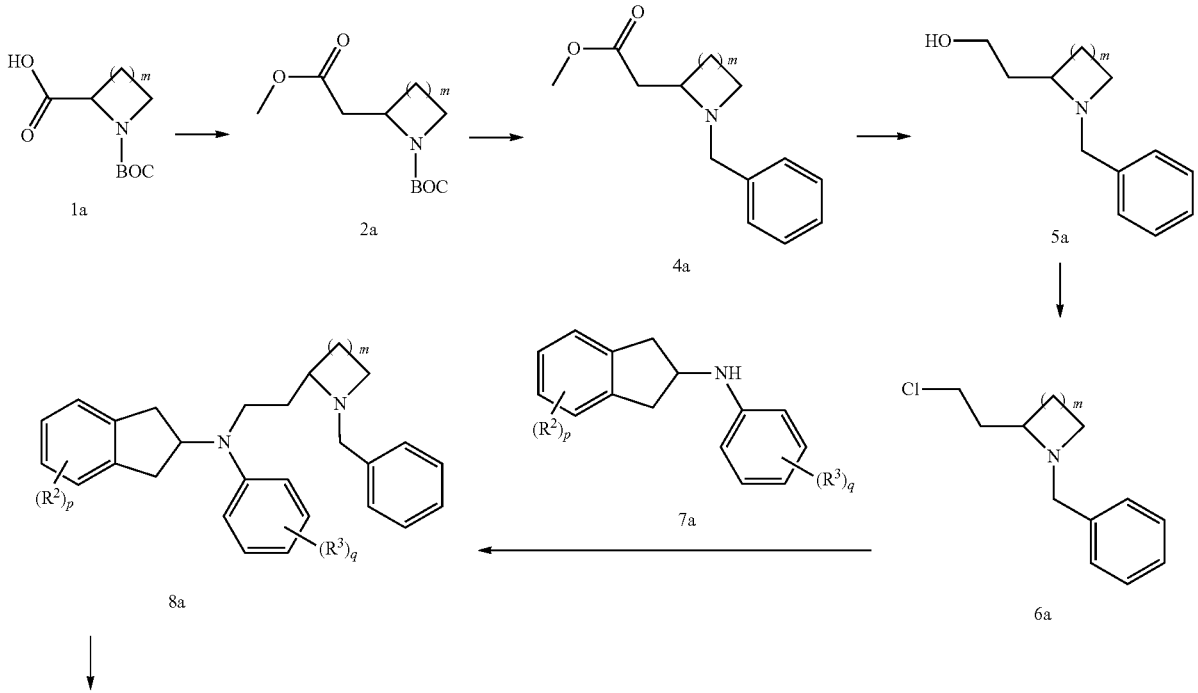

-continued

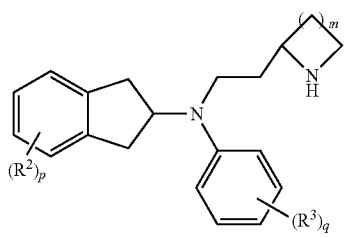

9a

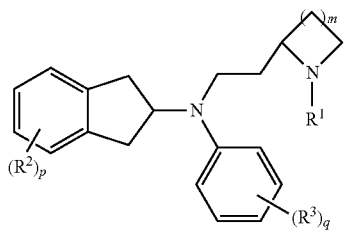

11a

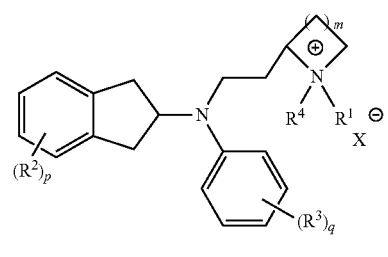

(I-OO)

In one aspect, compounds of formula (I-OO) are prepared using the synthetic steps provided in Scheme 1, wherein $R^1$-$R^4$, X, m, q, and p are defined herein. In this scheme, an acid 1a bearing a protecting group such as a butoxycarbonyl (BOC) group, is converted to the corresponding ester 2a. In one embodiment, ester 2a is formed using isobutyl chloroformate, diazomethane, and silver benzoate or silver oxide. In another embodiment, protected acid 1a is N-Boc-azetidine-2-carboxylic acid (BOC Sciences, Shirley, N.Y.), Boc-pyrrolidine-2-carboxylic acid, Boc-L-pipecolic acid, or N-Boc-azepane-2-carboxylic acid (AstaTech, Inc., Bristol, Pa.). Ester 2a is then converted to benzylamine 4a. In one embodiment, the conversion is performed using trifluoroacetic acid, followed by benzyl bromide. Compound 4a is then reduced to the corresponding alcohol 5a. In one embodiment, the reduction is performed using diisobutyl aluminum hydride (DIBAL-H) or lithium aluminum hydride (LAH). Alcohol 5a is then converted to the corresponding chloride 6a using a suitable chlorinating agent. In one embodiment, the chlorinating agent is thionyl chloride, phosphorus oxychloride, phosphorus pentachloride, or a combination of carbontetrachloride and triphenylphosphine. Chloride 6a is then coupled with substituted aminoindane 7a to provide compound 8a. In one embodiment, chloride 6a is coupled with aminoindane 7a in the presence of $NaNH_2$, potassium t-butoxide, sodium t-butoxide, or butyl lithium, among others. The benzyl group of compound 8a is then removed via hydrogenation to provide compound 9a. In one embodiment, the hydrogenation is performed using ammonium formate, hydrogen gas and Pd/C, or $Pd(OH)_2$. The N-atom of the heterocyclic ring of compound 9a is then substituted to provide compound 11a. In one embodiment, the N-atom of the heterocyclic ring of compound 9a is substituted with an $R^1$ group. In another embodiment, the substitution is an alkylation. In a further embodiment, the alkylation is performed using an aldehyde such as propanaldehyde, acetaldehyde, or formaldehyde, and $NaCNBH_3$. The same N-atom is further substituted with a $R^4$ group to provide a compound of formula (I-OO). In one embodiment, the further substitution is an alkylation. In another embodiment, the further substitution is performed using an alkyl halide, alkyl triflate, or alkyl besylate. In a further embodiment, the further substitution is performed using 1-iodopropane, ethyl iodide, methyl iodide, methyl triflate, ethyl triflate, propyl triflate, or methyl besylate, among others.

Scheme 2

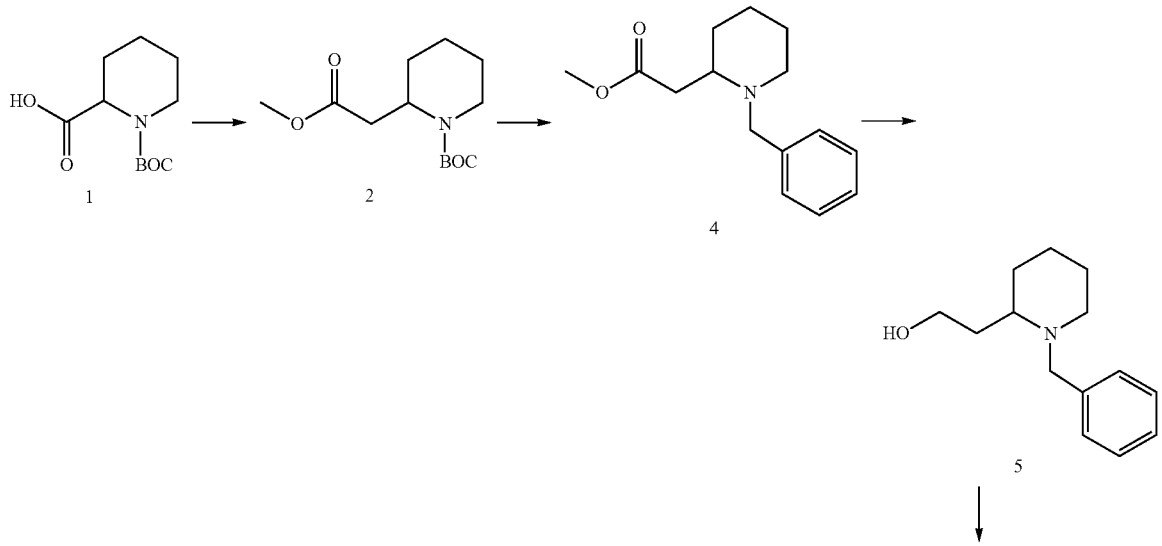

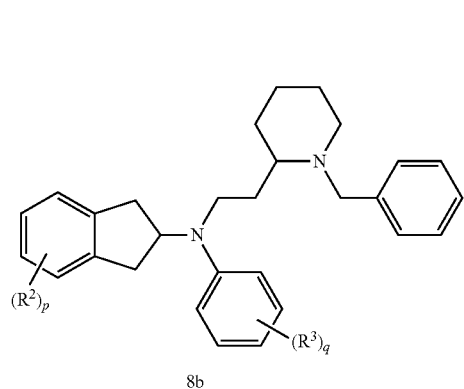
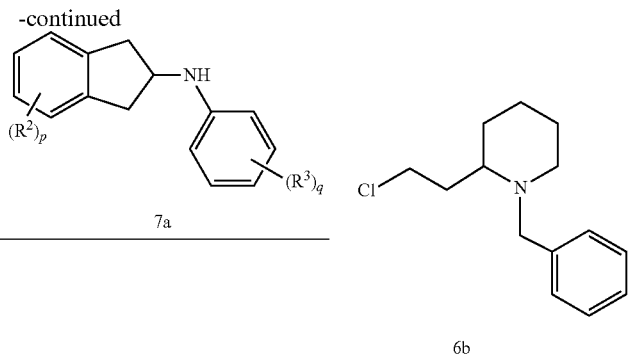
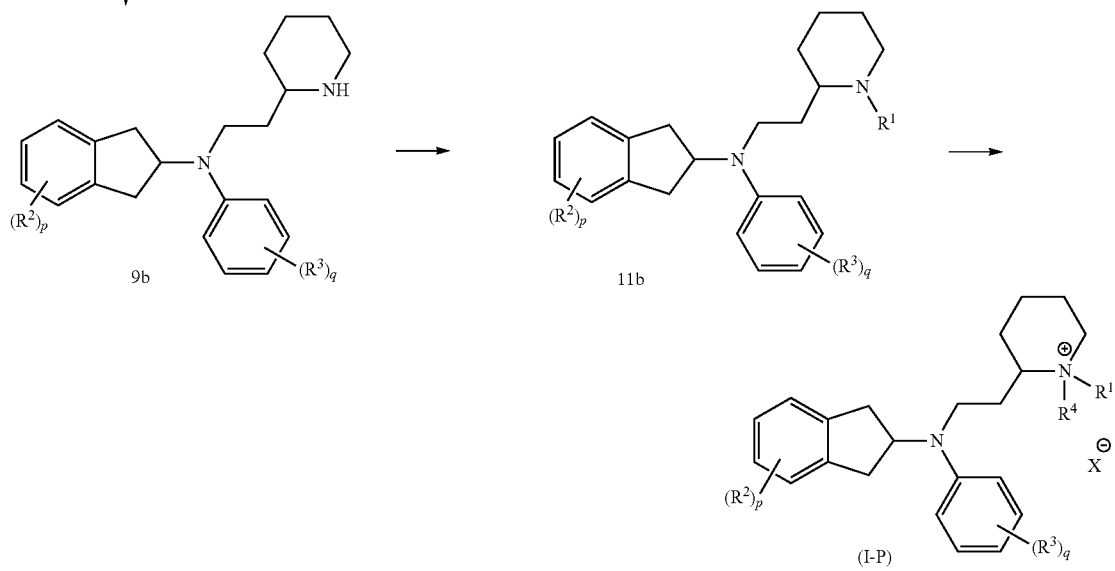

Scheme 2, wherein $R^1$-$R^4$, X, q, and p are defined herein, depicts the synthesis of compounds of formula (I-P). In this scheme, Boc-L-pipecolic acid 1 is converted to corresponding ester compound 2, i.e., (S)-2-(methoxycarbonylmethyl) piperidine-1-carboxylic acid tert-butyl ester. In one embodiment, (S)-2-(Methoxycarbonylmethyl)piperidine-1-carboxylic acid tert-butyl ester is formed using isobutyl chloroformate, diazomethane, and silver benzoate. (S)-2-(Methoxycarbonylmethyl)piperidine-1-carboxylic acid tert-butyl ester is then converted to benzylamine 4, i.e., (S)-2-(1-benzyl-piperidin-2-yl)acetic acid methyl ester. In one embodiment, the conversion is performed using trifluoroacetic acid, followed by treatment with benzyl bromide. Compound 4 is then reduced to the corresponding alcohol 5, i.e., (S)-2-(1-benzyl-piperidin-2-yl)-ethanol. In one embodiment, the reduction is performed using diisobutyl aluminum hydride (DIBAL-H). Alcohol 5 is then converted to the corresponding chloride 6, i.e., (S)-1-benzyl-2-(2-chloroethyl)-piperidine, using thionyl chloride. Chloride 6 is then coupled with aminoindane 7a to provide compound 8b. In one embodiment, chloride 6a is coupled with aminoindane 7a in the presence of $NaNH_2$. The benzyl group of compound 8b is then removed via hydrogenation to provide compound 9b. In one embodiment, the hydrogenation is performed using ammonium formate and Pd/C. The N-atom of the heterocyclic ring of compound 9b is then substituted to provide compound 11b. In one embodiment, the N-atom of the heterocyclic ring of compound 9b is substituted with an $R^1$ group. In another embodiment, the substitution is an alkylation. In a further embodiment, the alkylation is performed using propanaldehyde and $NaCNBH_3$. The same N-atom of compound 11b is further substituted with a $R^4$ group to provide a compound of formula (I-P). In one embodiment, the further substitution is an alkylation. In another embodiment, the further substitution is performed using an alkyl halide. In a further embodiment, the further substitution is performed using 1-iodopropane.

Scheme 3

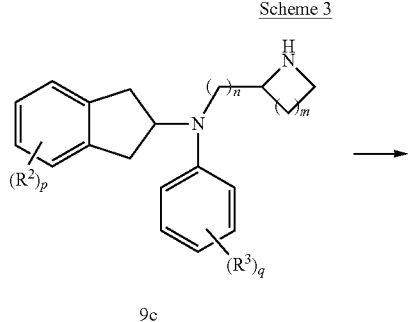

9c

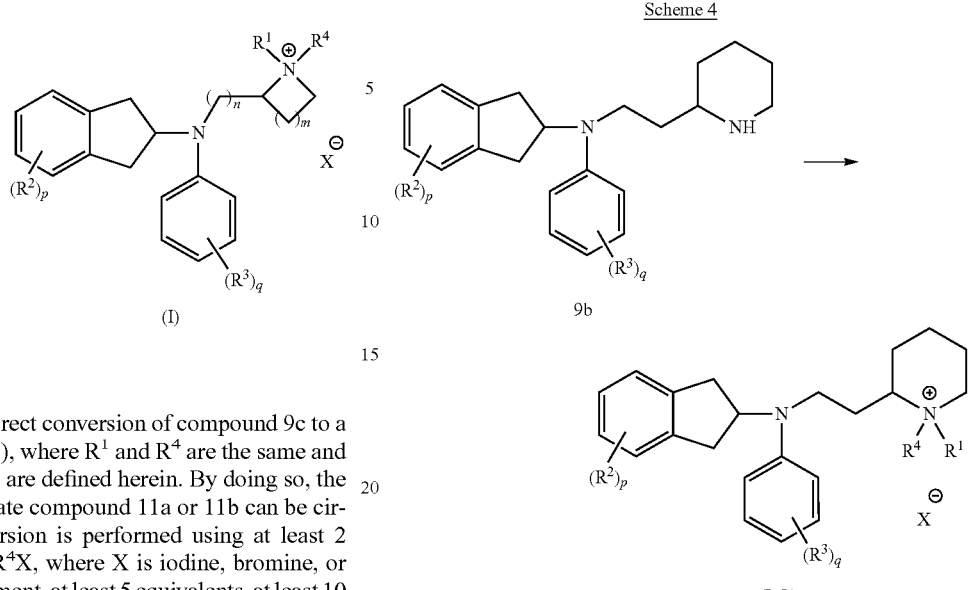

Scheme 3 depicts a direct conversion of compound 9c to a compound of formula (I), where $R^1$ and $R^4$ are the same and $R^1$-$R^4$, m, n, p, q, and X are defined herein. By doing so, the generation of intermediate compound 11a or 11b can be circumvented. This conversion is performed using at least 2 equivalents of $R^1X$ or $R^4X$, where X is iodine, bromine, or chlorine. In one embodiment, at least 5 equivalents, at least 10 equivalents, at least 20 equivalents, at least 30 equivalents, at least 40 equivalents, at least 50 equivalents, at least 60 equivalents, at least 70 equivalents, at least 80 equivalents, at least 90 equivalents, and at least 100 equivalents of $R^1X$ or $R^4X$ are utilized. In another embodiment, the conversion is performed using an alkylating agent. In a further embodiment, the conversion is performed using methyl iodide, ethyl iodide, propyl iodide, benzyl iodide, methyl triflate, ethyl triflate, propyl triflate, or methyl besylate.

Similarly, scheme 4 depicts a direct conversion of compound 9b to a compound of formula (I-Q), where $R^1$ and $R^4$ are the same and $R^1$-$R^4$, p, q, and X are defined herein. This conversion is performed using at least 2 equivalents of $R^1X$ or $R^4X$, where X is iodine, bromine, or chlorine. In one embodiment, the conversion is performed using an alkylating agent. In a further embodiment, the conversion is performed using methyl iodide, ethyl iodide or propyl iodide.

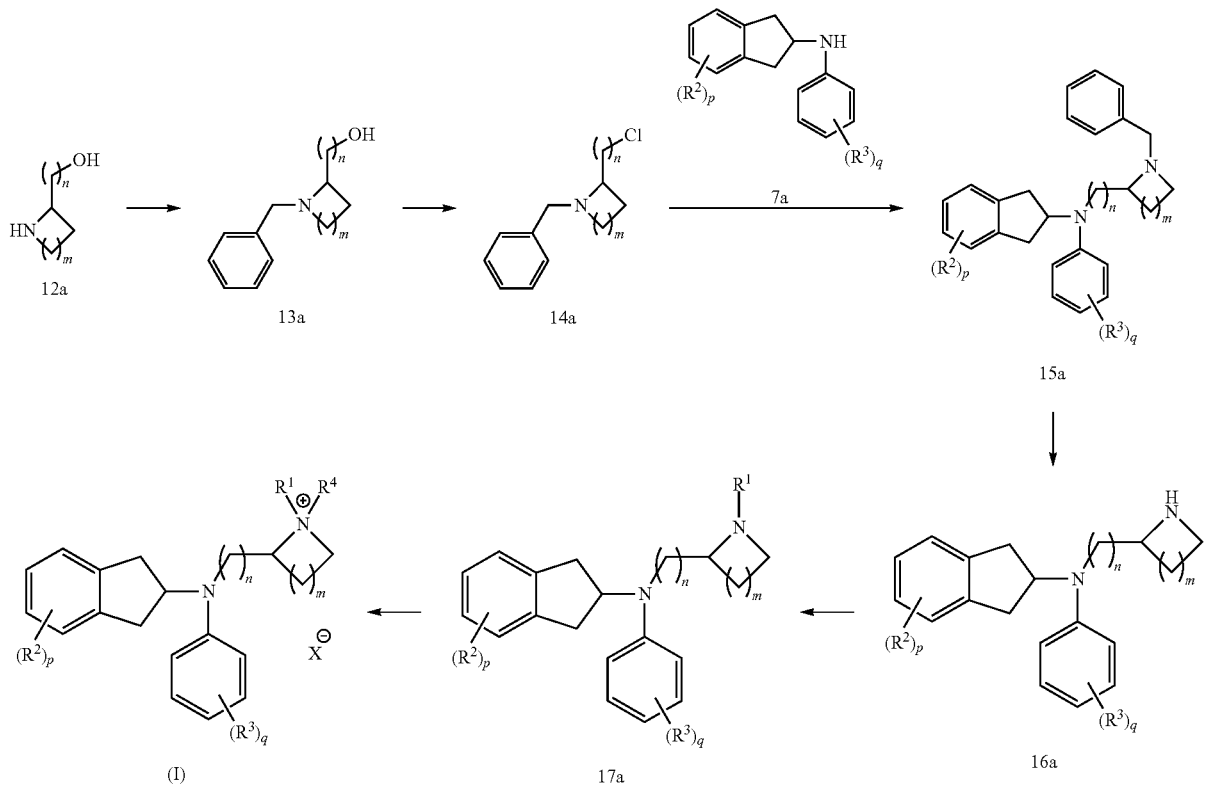

Compounds of formula (I), wherein $R^1$-$R^4$, m, n, p, q, and X are defined herein, may also be prepared according to the transformations noted in Scheme 5. The initial step of this scheme entails protecting the N-atom of a compound 12a to form protected compound 13a. In one embodiment, the N-atom of compound 12a is protected using an optionally performed using an alkyl halide, alkyl triflate, or alkyl besylate, such as $R^4X$, where X is halogen, such as iodine, chlorine, or bromine, triflate, or besylate. In a further embodiment, the further substitution is performed using 1-iodopropane, ethyl iodide, methyl iodide, methyl triflate, ethyl triflate, propyl triflate, or methyl besylate.

Scheme 6

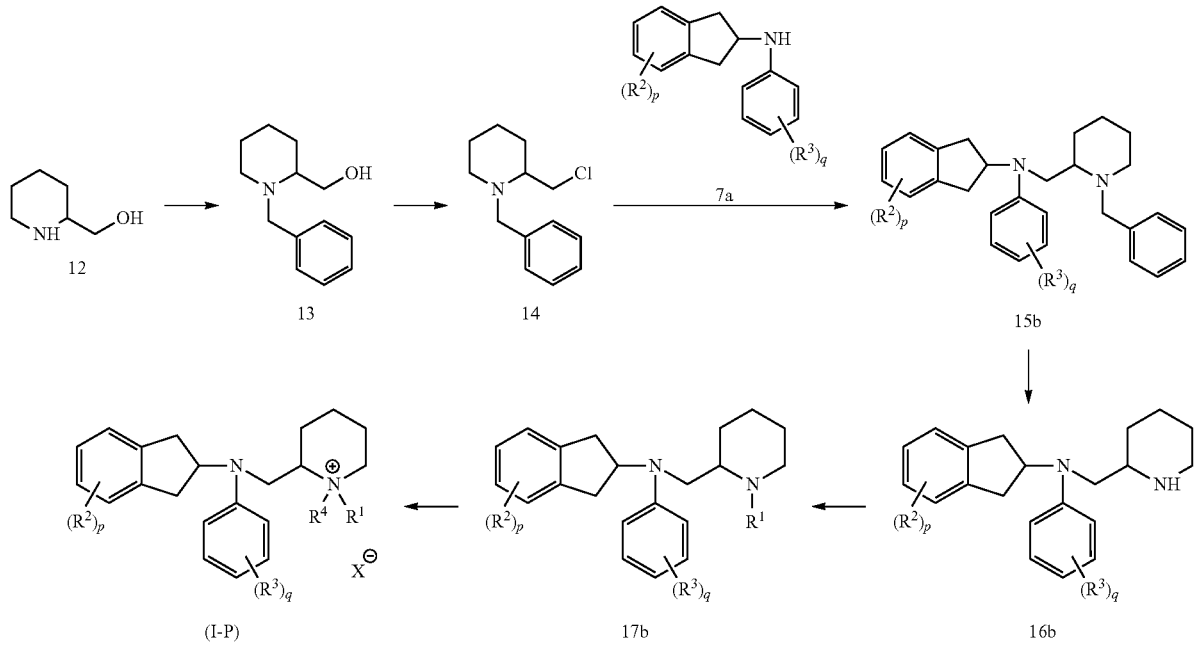

substituted benzyl or carbamate group. In another embodiment, the N-atom of compound 12a is protected with a benzyl, p-methoxy benzyl, or BOC. In a further embodiment, the N-atom of compound 12a is protected using a benzyl halide such as benzyl bromide, p-methoxy benzyl bromide, or boc-anhydride. Compound 13a is then converted to chloride 14a using reagents and techniques known in the art. In one embodiment, compound 13a is chlorinated using thionyl chloride, phosphorus oxychloride, phosphorus pentachloride, or a combination of carbon tetrachloride, and triphenylphosphine. Compound 14a is then coupled with an aminoindane to form compound 15a. In one embodiment, compound 14a is coupled with aminoindane compound 7a to provide compound 15a. The N-atom of compound 15a is then deprotected using reagents and techniques standard in the art. In one embodiment, the N-atom is deprotected using ammonium formate, hydrogen gas in the presence of a catalyst such as Pd—C, Pd(OH)$_2$, trifluoroacetic acid, or dioxane-HCl. Desirably, the deprotection is performed at elevated temperatures to provide compound 16a. The N-atom of compound 16a may then be $R^1$ substituted using reagents and techniques known by those of skill in the art to provide compound 17a. In one embodiment, the N-atom of compound 16a is $R^1$ substituted using an appropriately substituted aldehyde or alkyl halide to provide compound 17a. In one embodiment, the N-atom of compound 16a may be $R^1$ substituted using formaldehyde and NaCNBH$_3$. Compound 17a may then be further substituted at the N-atom with $R^4$ to provide a compound of formula (I). In one embodiment, the further substitution is an alkylation. In another embodiment, the further substitution is In a similar fashion, compounds of formula (I-P), wherein $R^1$-$R^4$, p, q, and X are defined herein, may be prepared according to the transformations noted in Scheme 6. The initial step includes protecting the N-atom of piperidine-2-methanol (12) to form protected (1-benzylpiperidin-2-yl)-methanol (13). In one embodiment, the N-atom of piperidine-2-methanol is protected using an optionally substituted benzyl group. In another embodiment, the N-atom of piperidine-2-methanol is protected with a benzyl group. In a further embodiment, the N-atom of piperidine-2-methanol is protected using a benzyl halide such as benzyl bromide. (1-Benzylpiperidin-2-yl)-methanol is then converted to 1-benzyl-2-(chloromethyl)piperidine (14) using reagents and techniques known in the art. In one embodiment, (1-benzylpiperidin-2-yl)-methanol is chlorinated using thionyl chloride. Compound 14 is then coupled with an aminoindane to form compound 15b. In one embodiment, compound 14 is coupled with aminoindane 7a to provide compound 15b. The N-atom of compound 15b is then deprotected using reagents and techniques standard in the art. In one embodiment, the N-atom is deprotected using ammonium formate in the presence of a catalyst such as Pd—C. Desirably, the deprotection is performed at elevated temperatures to provide compound 16b. The N-atom of compound 16b may then be $R^1$ substituted using reagents and techniques known by those of skill in the art to provide compound 17b. In one embodiment, the N-atom of compound 16b is $R^1$ substituted using an appropriately substituted aldehyde to provide compound 17b. In one embodiment, the N-atom of compound 16b may be $R^1$ substituted using formaldehyde. Compound 17b may then be further substituted at the N-atom with $R^4$ to provide a compound of formula (I-P). In one embodiment, the further substitution is an alkylation. In another embodiment, the further substitution is performed using an alkyl halide such as R⁴X, where X is iodine, chlorine, or bromine. In a further embodiment, the further substitution is performed using 1-iodopropane.

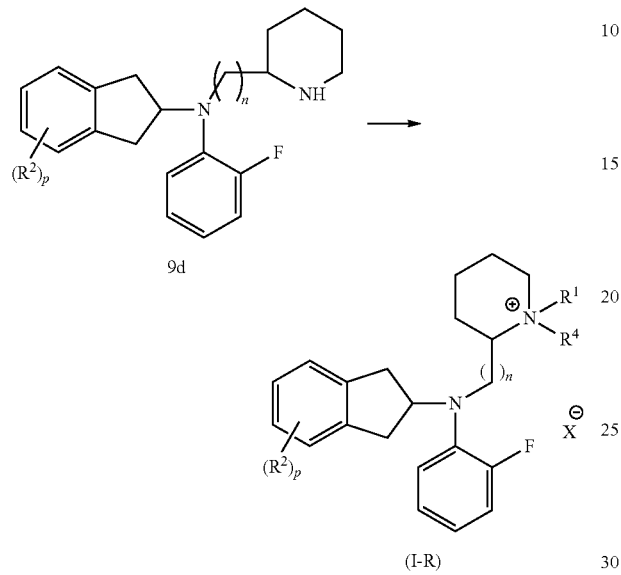

Scheme 7 illustrates the embodiment whereby a compound of formula (I-R) is formed from compound 9d, i.e., a compound of formula (I) when $R^3$ is F, p is 1, and $R^1$ and $R^4$ are the same and $R^1$, $R^2$, $R^4$, n, p, and X are defined herein. In this scheme, compound 9d is $R^1$ or $R^4$ substituted at the N-atom. In one embodiment, at least 2 equivalents of $R^1X$ or $R^4X$, where X is a leaving group such as iodine, chlorine, bromine, triflate, or besylate, are reacted with compound 9d. In another embodiment, at least 2 equivalents of an alkyl halide are reacted with compound 9d. In a further embodiment, at least 2 equivalents of methyl iodide, ethyl iodide, propyl iodide, methyl triflate, ethyl triflate, or propyl triflate are reacted with compound 9d.

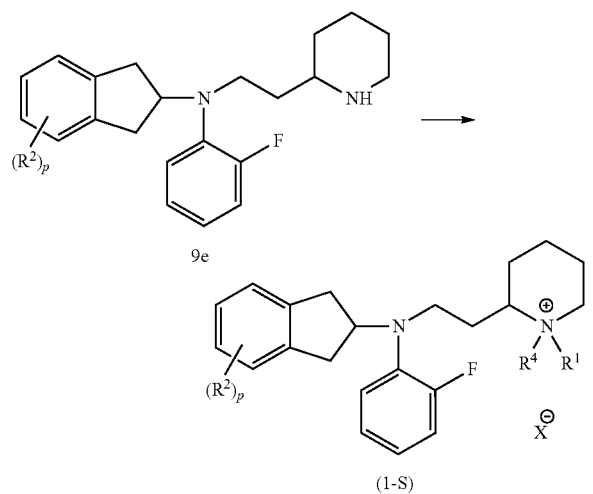

Scheme 8 provides a summary of the preparation of a compound of formula (I-S), wherein $R^1$, $R^2$, $R^4$, p, and X are defined herein from compound 9e. In this scheme, compound 9e is $R^1$ or $R^4$ substituted at the N-atom. In one embodiment, at least 2 equivalents of $R^1X$ or $R^4X$, where X is a leaving group such as iodine, chlorine, or bromine, are reacted with compound 9e. In another embodiment, at least 2 equivalents of an alkyl halide are reacted with compound 9e. In a further embodiment, at least 2 equivalents of methyl iodide, ethyl iodide, or propyl iodide are reacted with compound 9e.

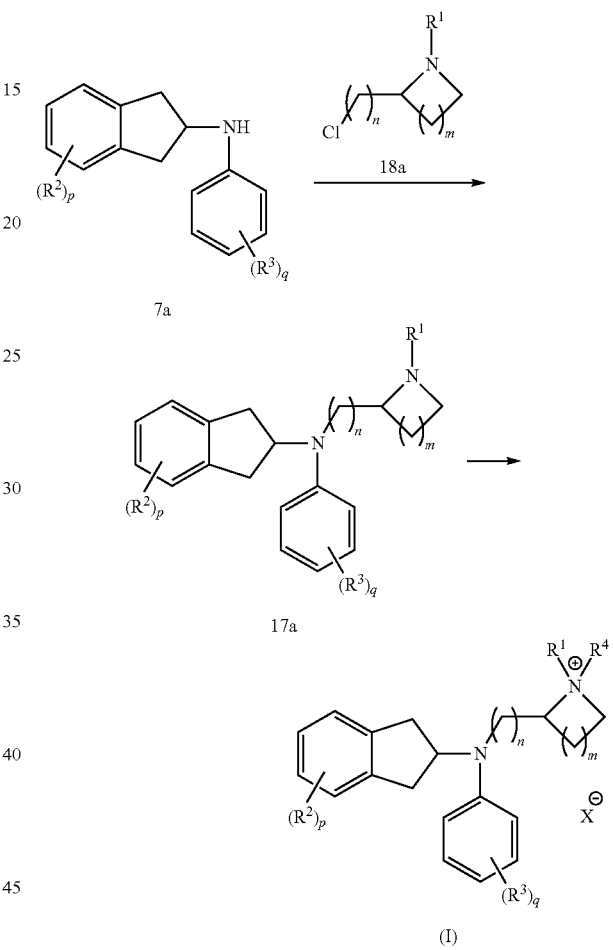

Scheme 9 provides an alternate route to a compound of formula (I), where $R^1$ and $R^4$ are the same or different and $R^1$-$R^4$, m, n, p, q, and X are defined herein, via the use of reagent 18a. Specifically, compound 7a is reacted with compound 18a to provide compound 17a. In one embodiment, the reaction between compounds 7a and 18a is performed in the presence of sodamide, potassium t-butoxide, sodium t-butoxide, or butyl lithium. $R^4$ substitution of the N-atom may then be performed to provide a compound of formula (I). In one embodiment, the $R^4$ substitution is an alkylation at the N-atom. In another embodiment, the $R^4$ substitution is performed using $R^4X$, wherein X is a leaving group such as iodine, chlorine, or bromine. In a further embodiment, the $R^4$ substitution is performed using an alkyl halide such as methyl iodide, ethyl iodide, or propyl iodide. Doing so provides the compound of formula (I).

Scheme 10

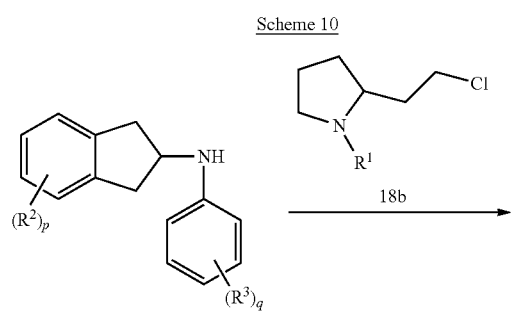

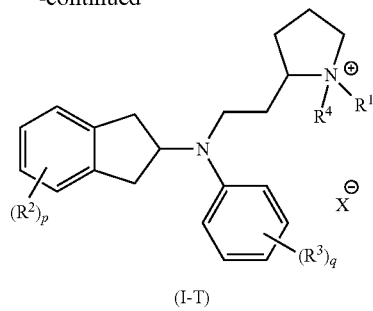

Scheme 10 provides an alternate route to a compound of formula (I-T), where $R^1$ and $R^4$ are the same or different and $R^1$-$R^4$, p, q, and X are defined herein, via the use of reagent 18b. Specifically, compound 7a is reacted with compound 18b to provide compound 17c. In one embodiment, the reaction between compounds 7a and 18b is performed in the presence of sodamide. $R^4$ substitution of the N-atom may then be performed to provide a compound of formula (I-T). In one embodiment, the $R^4$ substitution is an alkylation at the N-atom. In another embodiment, the $R^4$ substitution is performed using $R^4X$, wherein X is a leaving group such as iodine, bromine, or chlorine. In a further embodiment, the $R^4$ substitution is performed using an alkyl halide such as methyl iodide, ethyl iodide, or propyl iodide. Doing so provides the compound of formula (I-T).

Scheme 11

Scheme 11 provides the preparation of a compound of formula (I-U), where $R^1$ and are the same and $R^2$, $R^3$, X, n, p, and q are defined herein, via the use of reagent 20a. Specifically, compound 20a is reduced in the presence of an acid to form compound 21a. In one embodiment, the reduction is performed using standard reagents and conditions such as hydrogen gas in the presence of a catalyst. In one embodiment, the catalyst is $PtO_2$. Compound 20a is then protected using a suitable protecting group to provide compound 22a. In one embodiment, the protecting group is a benzyl group. In another embodiment, compound 22a is prepared using a benzyl halide such as benzyl bromide, or p-methoxy benzyl bromide. Compound 22a is then oxidized to form the corresponding aldehyde 23a. This oxidation is performed using reagents and conditions known to those of skill in the art. In one embodiment, the oxidation is performed using oxalyl chloride, dimethylsulfoxide (DMSO) and triethylamine. Compound 23a is then coupled with aminoindane 7b to provide compound 24a. This reaction is typically performed in the presence of sodium triacetoxy borohydride. The nitrogen-atom of the aminoindane is then substituted with a $R^3$-substituted phenyl group. In one embodiment, the substitution is performed using bromobenzene. In another embodiment, the substitution is performed in the presence of catalytic reagents such as a t-butoxide, such as potassium, sodium, or lithium t-butoxide, a phosphate agent such as 2-dicyclohexylphosphino-2'-(N,N-dimethylamino)biphenyl (DavePhos), and a palladium reagent such as $Pd_2(dba)_3$. The benzyl group of compound 25a is then removed using standard deprotection reagents. In one embodiment, compound 25a is converted to compound 26a using ammonium formate and a palladium catalyst such as Pd/C or $Pd(OH)_2$. Compound 26a is then $R^1/R^4$ substituted using an alkylating agent to provide compound (I-U). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

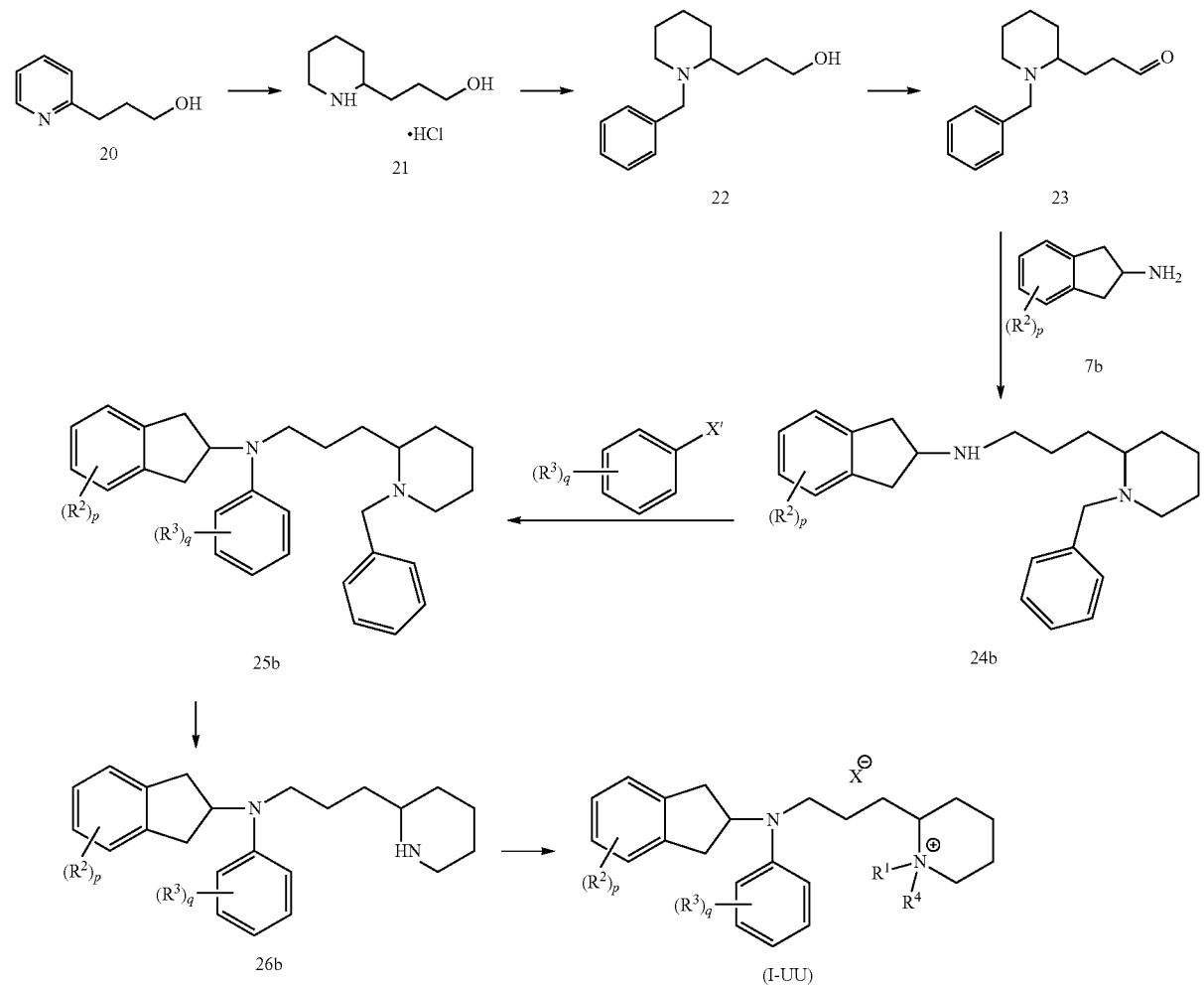

Scheme 12

Scheme 12 provides the synthesis to compound (I-UU), wherein $R^1$-$R^4$, X, p, and q are defined herein, starting with pyridine-2-propanol (20). Specifically, compound 20 is reduced using hydrogen gas in the presence of $PtO_2$ and hydrochloric acid to provide 3-cyclohexyl-propan-1-ol hydrochloride (21). Compound 21 is then protected with a benzyl group using benzyl bromide to provide 3-(1-benzyl-piperidin-2-yl)-propan-1-ol (22). Compound 22 is thereby oxidized to form the corresponding 3-(1-benzyl-piperidin-2- yl)-propionaldehyde (23) using oxalyl chloride, DMSO and triethylamine. Compound 23 is then coupled with aminoindane 7b to provide compound 24b, which reaction is performed in the presence of sodium triacetoxy borohydride. The nitrogen-atom of the aminoindane moiety is then substituted with a phenyl group using bromobenzene, potassium t-butoxide, DavePhos, and $Pd_2(dba)_3$ to provide compound 25b. The benzyl group of compound 25a is then removed using standard deprotection reagents such as ammonium formate to provide compound 26a. Compound 26a is alkylated to provide compound (I-UU). In one embodiment, the alkylating agent is an alkyl halide, alkyl triflate, or alkyl besylate such as 1-iodopropane, ethyl iodide, methyl iodide, methyl triflate, ethyl triflate, propyl triflate, or methyl besylate, among others.

methyl triflate, or methyl besylate, among others. Ester 2a is then converted to benzylamine 4a. In one embodiment, the conversion is performed using trifluoroacetic acid, followed by benzyl bromide. Compound 4a is then reduced to the corresponding alcohol 5a. In one embodiment, the reduction is performed using DIBAL-H or LAH. Alcohol 5a is then converted to the corresponding aldehyde 23a using an oxidizing agent. In one embodiment, the oxidizing agent is oxalyl chloride, DMSO and triethylamine. Compound 23a is then coupled with substituted aminoindane 7b to provide compound 24c. In one embodiment, compound 23a is coupled with aminoindane 7b in the presence of sodium triacetoxy borohydride. The N-atom of compound 24c is then substituted with an optionally substituted phenyl group to provide compound 8c. In one embodiment, the N-atom of compound

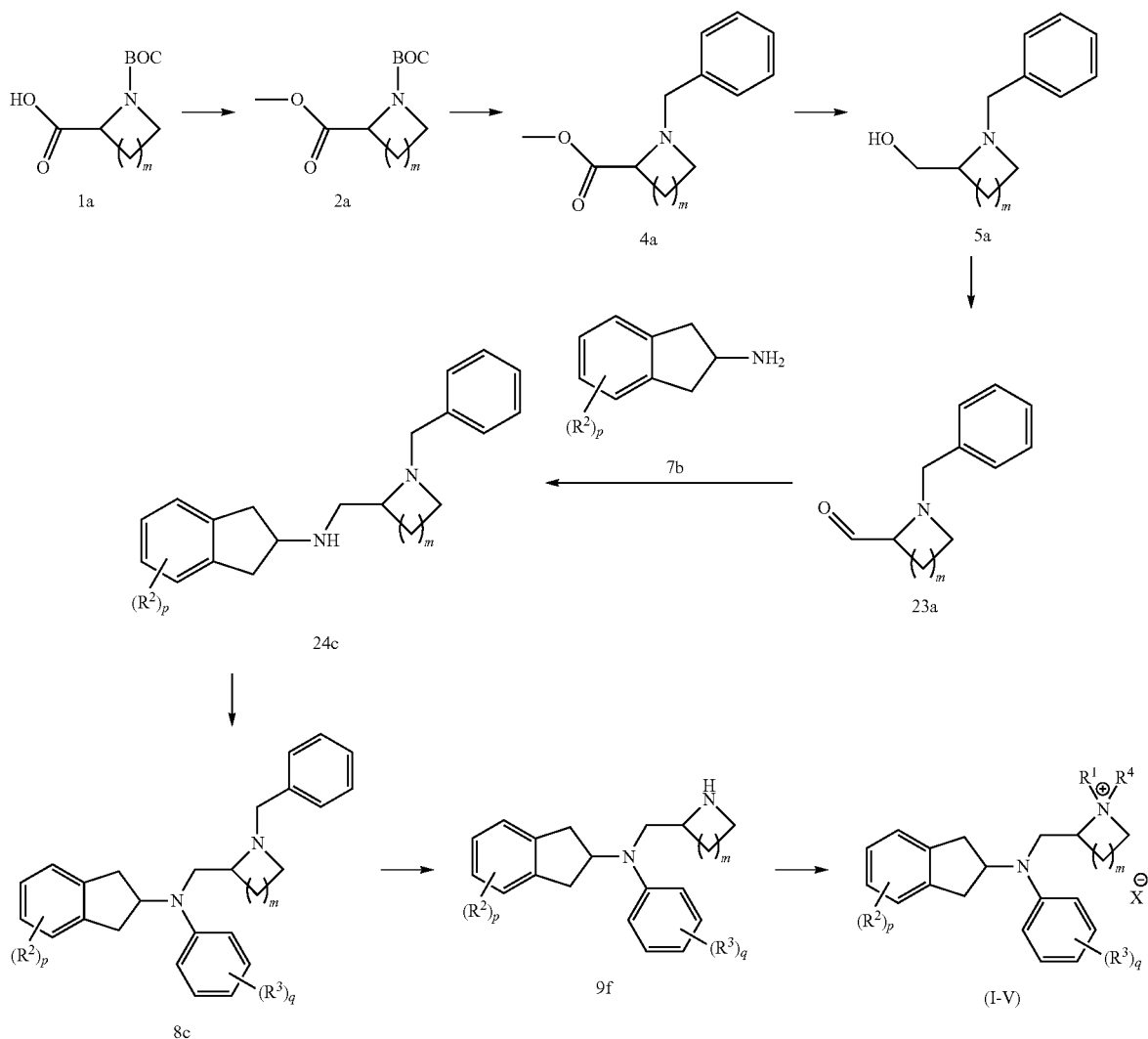

Scheme 13

Scheme 13 depicts the preparation of the compound of formula (I-V), where $R^1$ and $R^4$ are the same and $R^1$-$R^4$, X, p, and q are defined herein. In this scheme, a Boc protected acid 1a is converted to corresponding ester 2a via methylation of the acid moiety. In one embodiment, compound 1a is reacted with a methylating agent to provide compound 2a. In another embodiment, compound 1a is reacted with methyl iodide, 8c is substituted with bromobenzene. The benzyl group of compound 8c is then removed via hydrogenation to provide compound 9f. In one embodiment, the hydrogenation is performed using ammonium formate, hydrogen gas and Pd/C, or $Pd(OH)_2$. The N-atom of the heterocyclic ring of compound 9f is then substituted to provide compound (I-V). In one embodiment, the substitution is performed using an alkylating agent. In a further embodiment, the substitution is performed using an alkyl halide, alkyl triflate, or alkyl besylate. In yet a further embodiment, the substitution is performed using 1-iodopropane, ethyl iodide, methyl iodide, methyl triflate, ethyl triflate, propyl triflate, or methyl besylate, among others. In still another embodiment, the substitution is performed using at least 2 equivalents of the alkylating agent.

ment, the oxidizing agent is oxalyl chloride, DMSO and triethylamine. Compound 23b is then coupled with substituted aminoindane 7b to provide compound 24d. In one embodiment, compound 23b is coupled with aminoindane 7b in the presence of sodium triacetoxy borohydride. The N-atom of compound 24d is then substituted with a phenyl group to provide compound 8d. In one embodiment, substi-

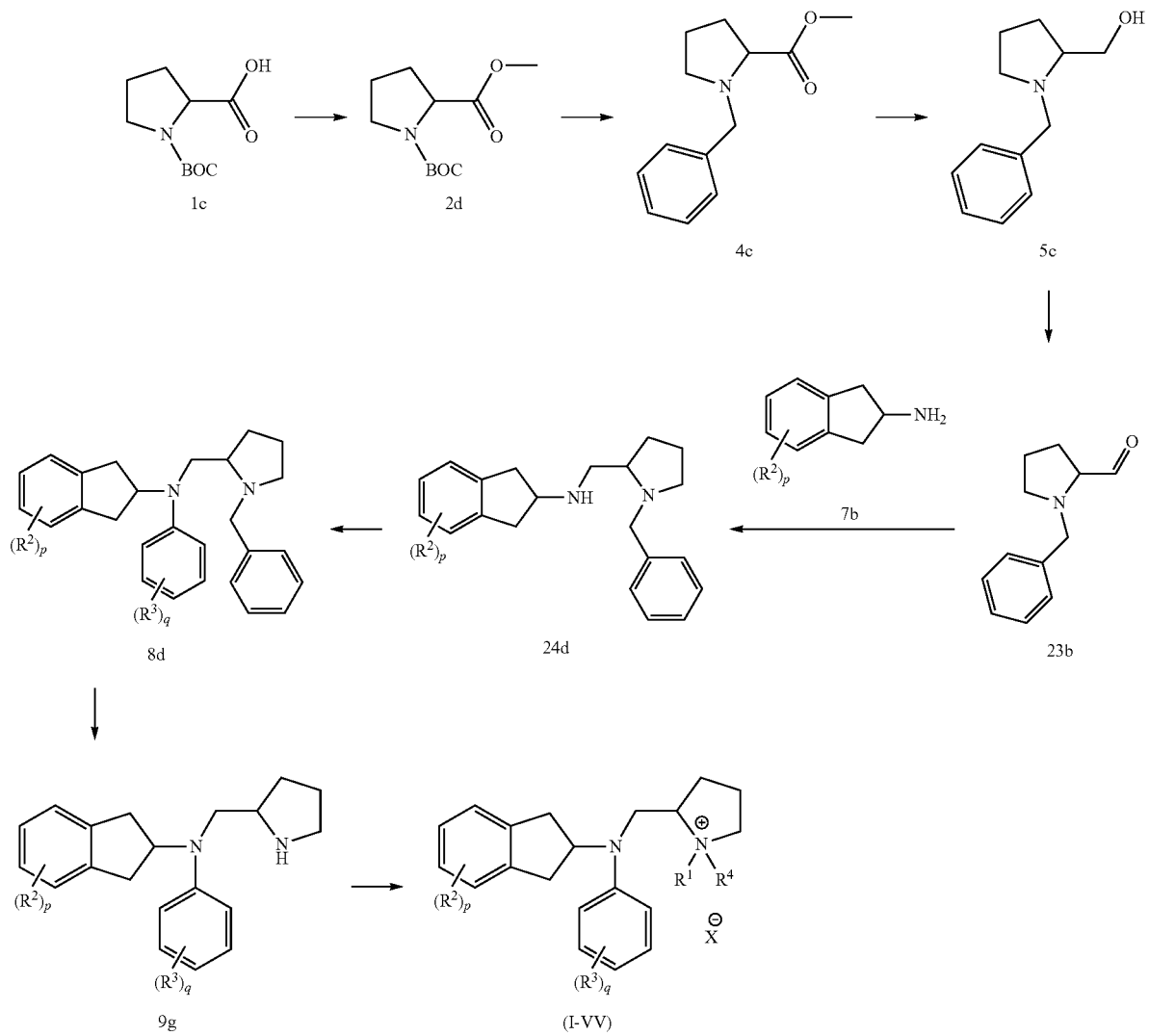

Scheme 14

Scheme 14 provides the synthesis of a compound of formula (I-VV), wherein $R^1$-$R^4$, X, p, and q are defined herein. In this scheme, Boc-pyrrolidine-2-carboxylic acid (1c) is converted to pyrrolidine-1,2-dicarboxylic acid 1-tert-butyl ester 2-methyl ester (2d) via methylation of the acid moiety using methyl iodide, methyl triflate, or methyl besylate, among others. Ester 2d is then converted to 1-benzyl-pyrrolidine-2-carboxylic acid methyl ester (4c) using trifluoroacetic acid, followed by benzyl bromide. Compound 4c is then reduced to the corresponding (1-benzyl-pyrrolidin-2-yl)-methanol (5c) using DIBAL-H or LAH. Alcohol 5c is then converted to the corresponding 1-benzyl-pyrrolidine-2-carbaldehyde (23b) using an oxidizing agent. In one emboditution of the N-atom of compound 24d is accomplished using bromobenzene. The benzyl group of compound 8d is then removed via hydrogenation to provide compound 9g. In one embodiment, the hydrogenation is performed using ammonium formate, hydrogen gas and Pd/C, or Pd(OH)$_2$. The N-atom of the heterocyclic ring of compound 9g is then alkylated using an alkyl halide, alkyl triflate, or alkyl besylate to provide the compound of formula (I-VV). In one embodiment, the substitution is performed using 1-iodopropane, ethyl iodide, methyl iodide, methyl triflate, ethyl triflate, propyl triflate, or methyl besylate, among others. In still another embodiment, the substitution is performed using at least 2 equivalents of the alkylating agent.

Scheme 15

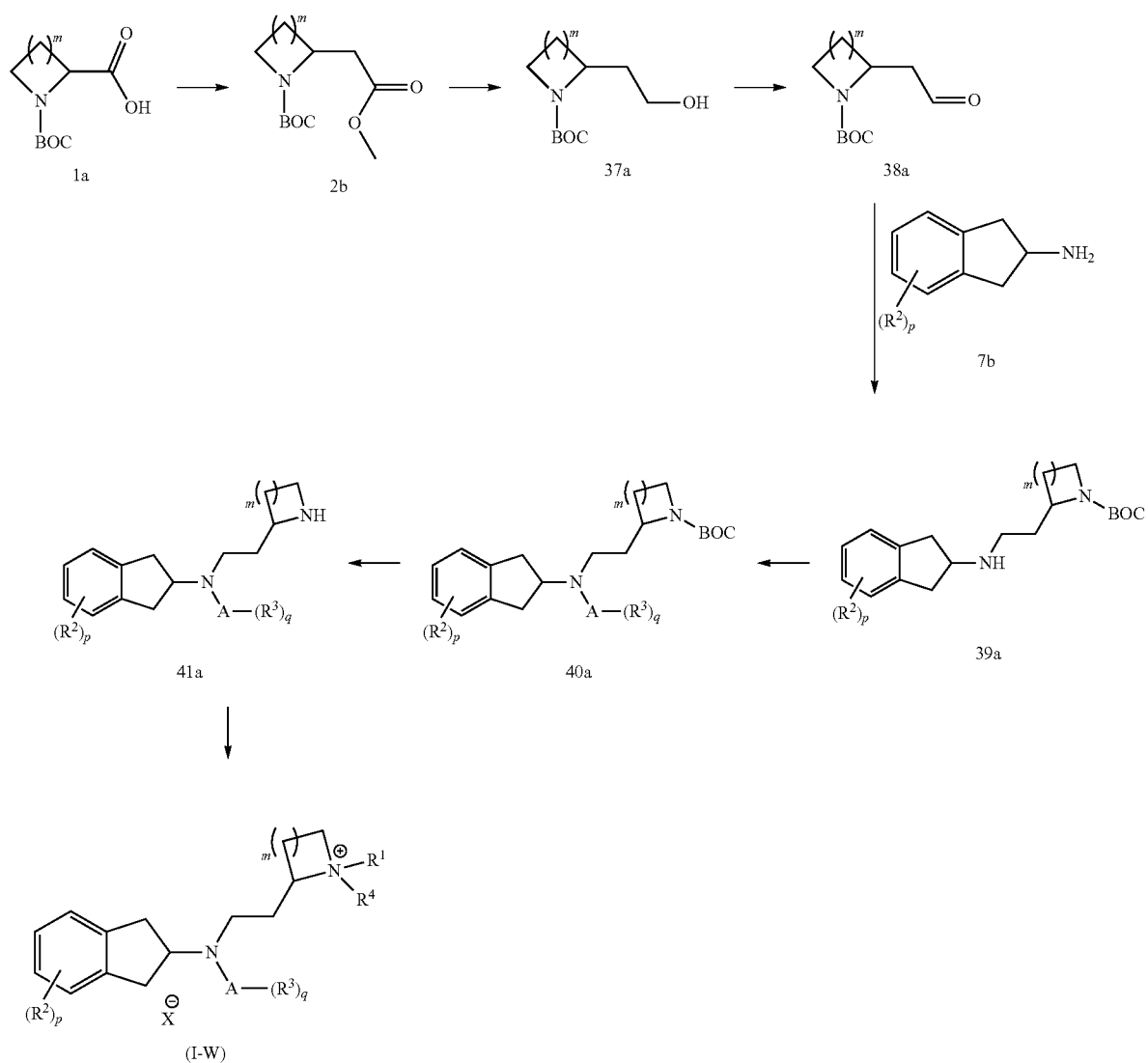

In another aspect, compounds of formula (I-W) are prepared, wherein $R^1$-$R^4$, A, X, m, q, and p are defined herein. In this scheme, acid 1a is converted to the corresponding ester 2b as described in Scheme 1. Ester 2b is then reduced to corresponding alcohol 37a using a suitable reducing agent. In one embodiment, the reducing agent is a hydride agent such as lithium aluminum hydride or DIBAL-H. Alcohol 37a is then oxidized to form aldehyde 38a. This oxidation may be performed using reagents and conditions known to those of skill in the art. In one embodiment, the oxidation is performed using oxalyl chloride, DMSO and triethylamine. Compound 38a is then coupled with aminoindane 7b to provide compound 39a. This reaction may be performed in the presence of a mild reducing agent such as sodium triacetoxy borohydride. The nitrogen-atom of compound 39a is then substituted with an A-$(R^3)_q$ group to provide compound 40a. In one embodiment, compound 39a is substituted with an optionally substituted phenyl group. In another embodiment, compound 39a is substituted with an optionally substituted heteroaryl. In a further embodiment, the substitution is performed using bromobenzene. In another embodiment, the substitution is performed in the presence of catalytic reagents such as a t-butoxide, such as potassium, sodium, or lithium t-butoxide, a phosphate agent such as DavePhos, and a palladium reagent such as $Pd_2(dba)_3$. The t-butoxycarbonyl group of compound 40a is then removed using standard deprotection reagents. In one embodiment, compound 40a is converted to compound 41a using an acidic medium such as dioxane-HCl or trifluoroacetic acid. Compound 41a is then $R^1$/$R^4$ substituted, where $R^1$ and $R^4$ are the same, using an alkylating agent to provide compound (I-W) as described for Scheme 1.

Scheme 16

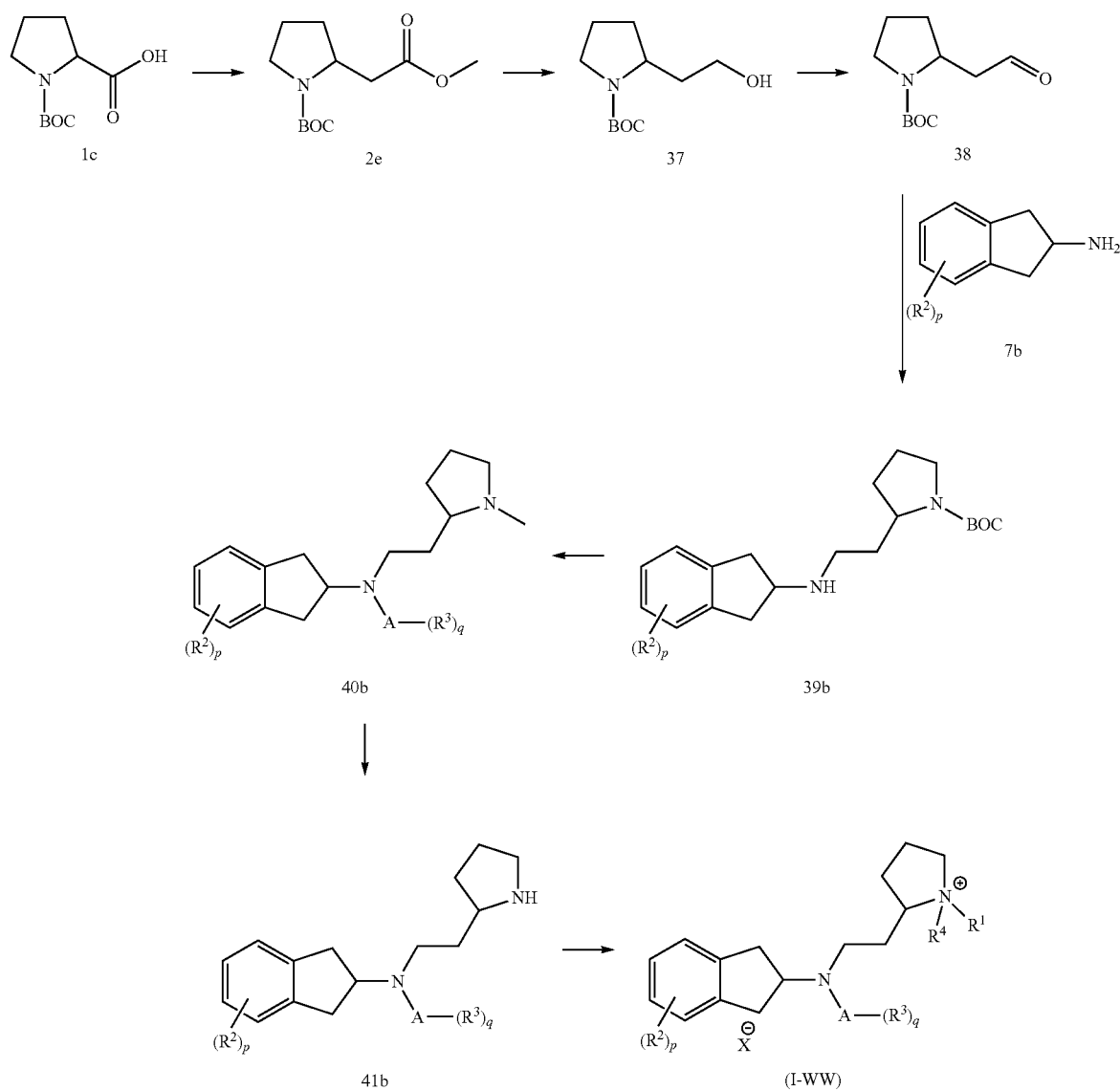

Scheme 16 provides the preparation of compounds of formula (I-WW), wherein $R^1$-$R^4$, A, p, q, and X are defined herein. In this scheme, pyrrolidine-1,2-dicarboxylic acid 1-tert-butyl ester (1c) is converted to corresponding 2-methoxycarbonylmethylpyrrolidine-1-carboxylic acid tert-butyl ester (2e). In one embodiment, 2-methoxycarbonylmethylpyrrolidine-1-carboxylic acid tert-butyl ester is formed using isobutyl chloroformate, diazomethane, and silver benzoate. 2-Methoxycarbonylmethylpyrrolidine-1-carboxylic acid tert-butyl ester (2e) is then reduced to 2-(2-hydroxyethyl)pyrrolidine-1-carboxylic acid tert-butyl ester (37) using a reducing agent. In one embodiment, the reducing agent is a hydride agent such as lithium aluminum hydride. Compound 37 is then oxidized to form 2-(2-oxoethyl)pyrrolidine-1-carboxylic acid tert-butyl ester (38). This oxidation is performed using oxalyl chloride, DMSO and triethylamine. Compound 38 is then coupled with aminoindane 7b to provide compound 39b. This reaction may be performed in the presence of sodium triacetoxy borohydride. The nitrogen-atom of compound 39b is then substituted with an A-$(R^3)_q$ group to provide compound 40b. In one embodiment, the substitution is performed using bromobenzene optionally in the presence of catalytic reagents such as a t-butoxide, such as potassium, sodium, or lithium t-butoxide, a phosphate agent such as DavePhos, and a palladium reagent such as $Pd_2(dba)_3$. The t-butoxycarbonyl group of compound 40b is then removed using dioxane-HCl or trifluoroacetic acid to provide compound 41b. Compound 41b is then $R^1$/$R^4$ substituted using an alkylating agent such as an alkyl halide, to provide compound (I-WW).

Scheme 17

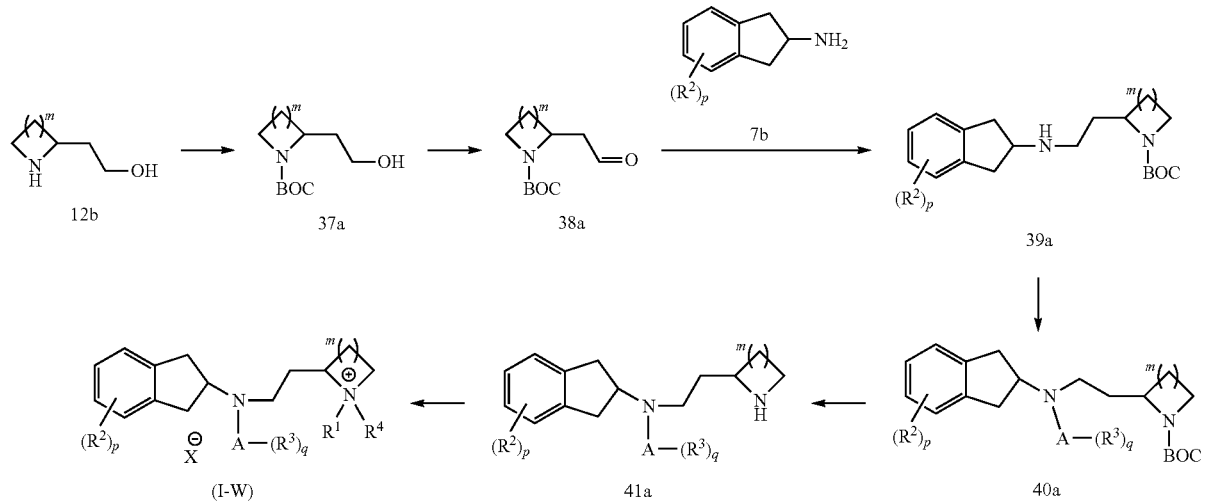

Scheme 17 provides a second route to prepare a compound of formula (I-W), where $R^1$ and $R^4$ are the same and $R^1$-$R^4$, A, m, p, q, and X are defined herein. Specifically, the nitrogen atom of compound 12b is protected to provide compound 37a. In one embodiment, the nitrogen atom is protected with a protecting group such as a t-butoxycarbonyl group. Compound 37a is then oxidized to form the corresponding aldehyde 38a. This oxidation is performed using reagents and conditions known to those of skill in the art. In one embodiment, the oxidation is performed using oxalyl chloride, DMSO and triethylamine. Compound 38a is then coupled with aminoindane 7b to provide compound 39a. This reaction may be typically performed in the presence of a mild reducing agent such as sodium triacetoxy borohydride. The nitrogen-atom of compound 39a is then substituted with an A-$(R^3)_q$ group to provide compound 40a. In one embodiment, compound 39a is substituted with an optionally substituted phenyl group. In another embodiment, compound 39a is substituted with an optionally substituted heteroaryl. In a further embodiment, the substitution is performed using bromobenzene or bromopyridine such as 2-bromo-pyridine, 3-bromo-pyridine, or 4-bromo-pyridine. In another embodiment, the substitution is performed in the presence of catalytic reagents such as a t-butoxide, such as potassium, sodium, or lithium t-butoxide, a phosphine catalyst such as P(i-BuNCH$_2$CH$_2$)$_3$N, and a palladium reagent such as Pd$_2$(dba)$_3$. The protecting group, i.e., the t-butoxycarbonyl group, of compound 40a is then removed using standard deprotection reagents to provide compound 41a. In one embodiment, the deprotection is performed using an acidic medium such as dioxane-HCl or trifluoroacetic acid. Compound 26a is then $R^1/R^4$ substituted, where $R^1$ and $R^4$ are the same, using an alkylating agent to provide compound (I-W). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

Scheme 18

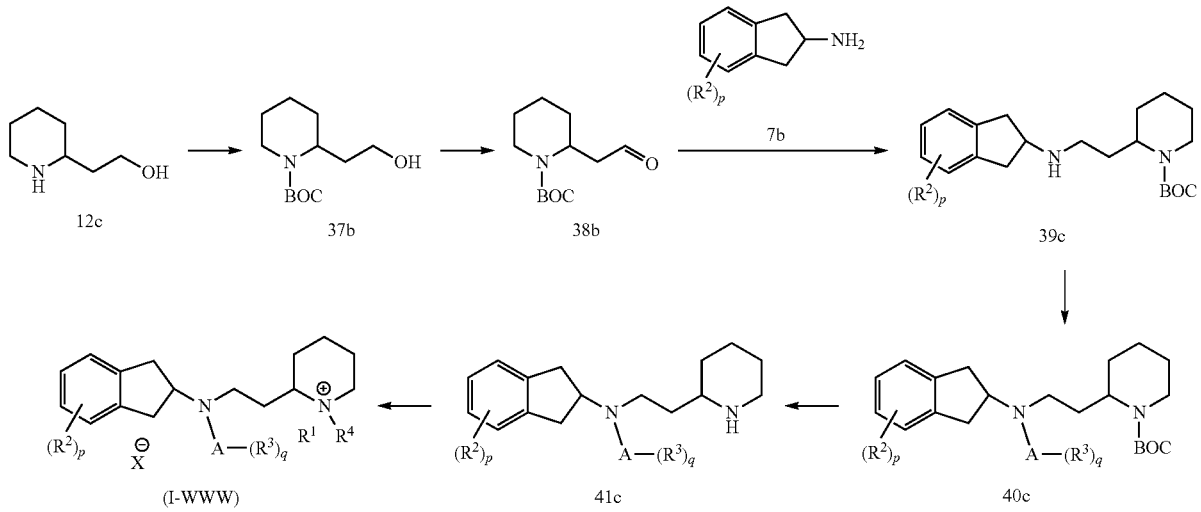

Scheme 18 provides the preparation of a compound of formula (I-WWW), where $R^1$ and $R^4$ are the same and $R^1$-$R^4$, A, p, q, and X are defined herein. Specifically, the nitrogen atom of piperidine-2-ethanol (12c) is protected with a t-butoxycarbonyl group to provide 2-(2-hydroxyethyl)piperidine-1-carboxylic acid tert-butyl ester (37b). Compound 37b is then oxidized to form 2-(2-oxoethyl)piperidine-1-carboxylic acid tert-butyl ester (38b). In one embodiment, the oxidation is performed using oxalyl chloride, DMSO and triethylamine. Compound 38b is then coupled with aminoindane 7b to provide compound 39c. This reaction is typically performed in the presence of sodium triacetoxy borohydride. The nitrogen-atom of compound 39c is then substituted with an A-$(R^3)_q$ group to provide compound 40c. In one embodiment, the substitution is performed using an optionally substituted phenyl. In another embodiment, the substitution is performed using an optionally substituted heteroaryl. In a further embodiment, the substitution is performed using bromobenzene or bromopyridine such as 2-bromo-pyridine, 3-bromo-pyridine, or 4-bromo-pyridine. In another embodiment, the substitution is performed in the presence of catalytic reagents such as a t-butoxide, such as potassium, sodium, or lithium t-butoxide, a phosphine catalyst such as P(i-BuNCH$_2$CH$_2$)$_3$N, and a palladium reagent such as Pd$_2$(dba)$_3$. The protecting group, i.e., the t-butoxycarbonyl group, of compound 40c is then removed using standard deprotection reagents to provide compound 41c. In one embodiment, the deprotection is performed using an acidic medium such as dioxane-HCl or trifluoroacetic acid. Compound 41c is then $R^1/R^4$ substituted, where $R^1$ and $R^4$ are the same, using an alkylating agent to provide compound (I-WWW). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

Scheme 19 provides a third route in the preparation of compound (I-W), wherein $R^1$-$R^4$, A, m, p, q, and X are defined herein, via compound 39a, which may be prepared as described herein. The nitrogen atom of compound 39a is A-$(R^3)_q$ substituted to provide compound 40a. In one embodiment, compound 39a is substituted with an optionally substituted phenyl. In another embodiment, compound 39a is substituted with an optionally substituted heteroaryl. In a further embodiment, the substitution is performed using bromobenzene, bromopyridine, or bromopyrimidine. In another embodiment, the substitution is performed in the presence of catalytic reagents such as a t-butoxide, such as potassium, sodium, or lithium t-butoxide, a phosphine catalyst such as P(i-BuNCH$_2$CH$_2$)$_3$N, or a strong base such as Verkade's super base, and a palladium reagent such as Pd$_2$(dba)$_3$. The protecting group, i.e., the t-butoxycarbonyl group, of compound 40a is then removed using standard deprotection reagents to provide compound 41a. In one embodiment, the deprotection is performed using an acidic medium such as dioxane-HCl or trifluoroacetic acid. Compound 41a is then $R^1/R^4$ substituted, where $R^1$ and $R^4$ are the same, using an alkylating agent to provide compound (I-W). In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

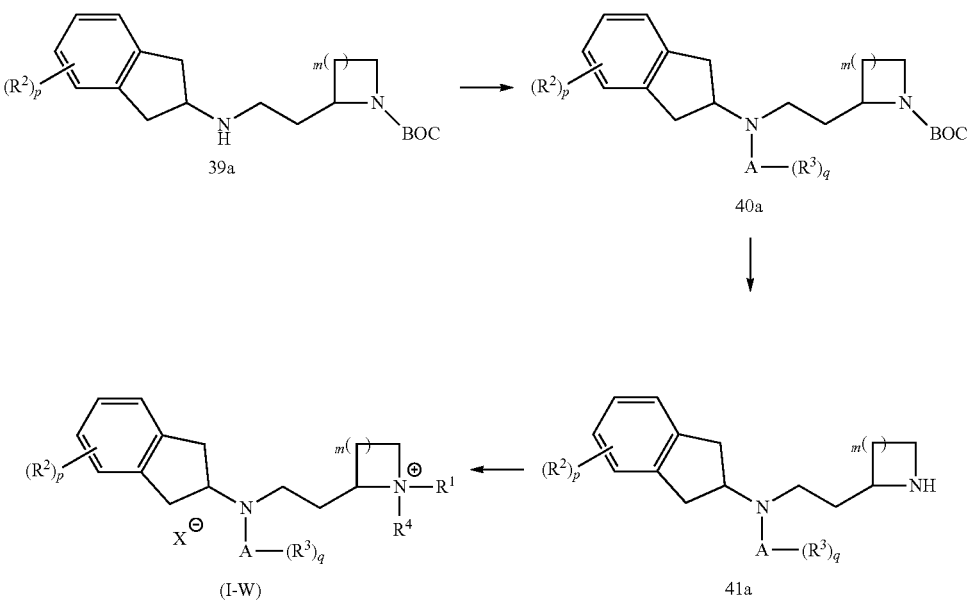

Scheme 19

Scheme 20

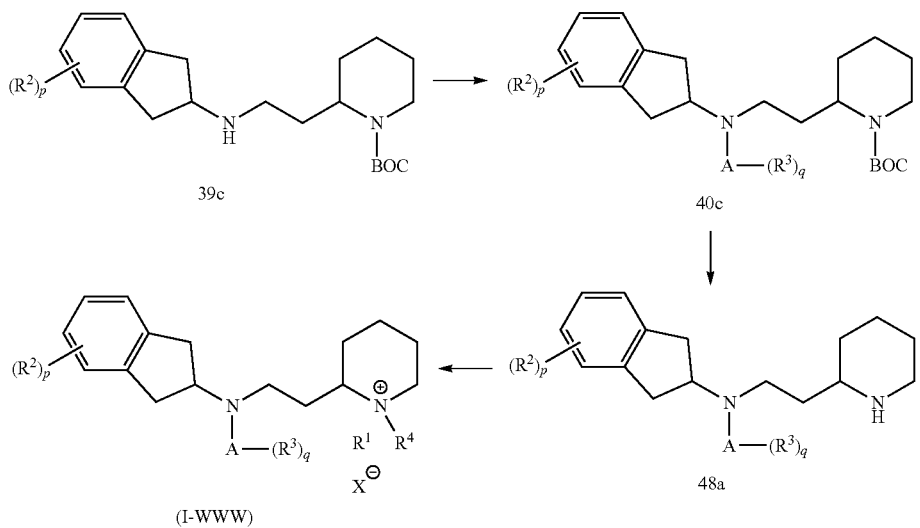

Scheme 20 provides another preparation of compound (I-WWW), wherein $R^1$-$R^4$, A, p, q, and X are defined herein, via compound 39c where the nitrogen atom of compound 39c is A-$(R^3)_q$ substituted to provide compound 40c. In one embodiment, the substitution is performed using bromobenzene, bromopyridine, or bromopyrimidine. In another embodiment, the substitution is performed in the presence of sodium t-butoxide, P(i-BuNCH$_2$CH$_2$)$_3$N, and Pd$_2$(dba)$_3$. The protecting group, i.e., the t-butoxycarbonyl group, of compound 40c is then removed using standard deprotection reagents to provide compound 48a. In one embodiment, the deprotection is performed using dioxane-HCl or trifluoroacetic acid. Compound 48a is then $R^1$/$R^4$ substituted, where $R^1$ and $R^4$ are the same, using an alkylating agent to provide compound (I-WWW). In one embodiment, the alkylating agent is an alkyl halide such as 1-iodopropane, ethyl iodide, methyl iodide, methyl triflate, ethyl triflate, propyl triflate, or methyl besylate, among others.

Scheme 21

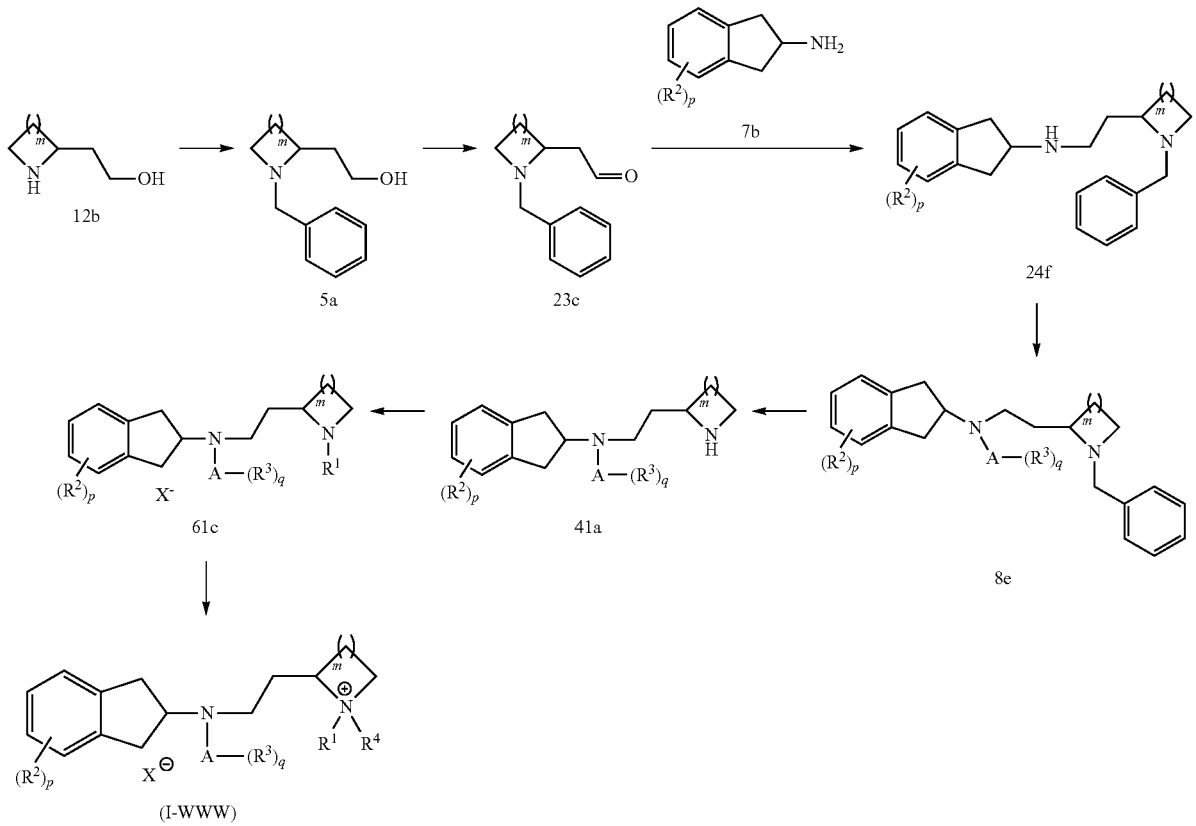

Scheme 21 provides a further preparation of compound (I-WWW), wherein $R^1$-$R^4$, A, m, p, q, and X are defined herein. Specifically, the nitrogen atom of compound 12b is protected to provide compound 5a. In one embodiment, the nitrogen atom is protected with a protecting group such as a benzyl group using a reagent such as benzyl bromide. Compound 5a is then oxidized to form the corresponding aldehyde 23c. This oxidation is performed using reagents and conditions known to those of skill in the art. In one embodiment, the oxidation is performed using an oxidizing agent such as oxalyl chloride/DMSO, and a strong base such as triethylamine. Compound 23c is then coupled with aminoindane 7b deprotection is performed using isobutyl chloroformate. Compound 41a is then $R^1$ substituted to provide compound 61c. In one embodiment, the $R^1$ substitution is an alkylation. In another embodiment, the alkylation is performed using an aldehyde such as propanaldehyde, acetaldehyde, or formaldehyde. Compound 61c is then $R^4$ substituted using an alkylating agent. In one embodiment, the alkylating agent is an alkyl halide, alkyl triflate, or alkyl besylate. In a further embodiment, the alkylating agent is 1-iodopropane, ethyl iodide, methyl iodide, methyl triflate, ethyl triflate, propyl triflate, or methyl besylate, among others.

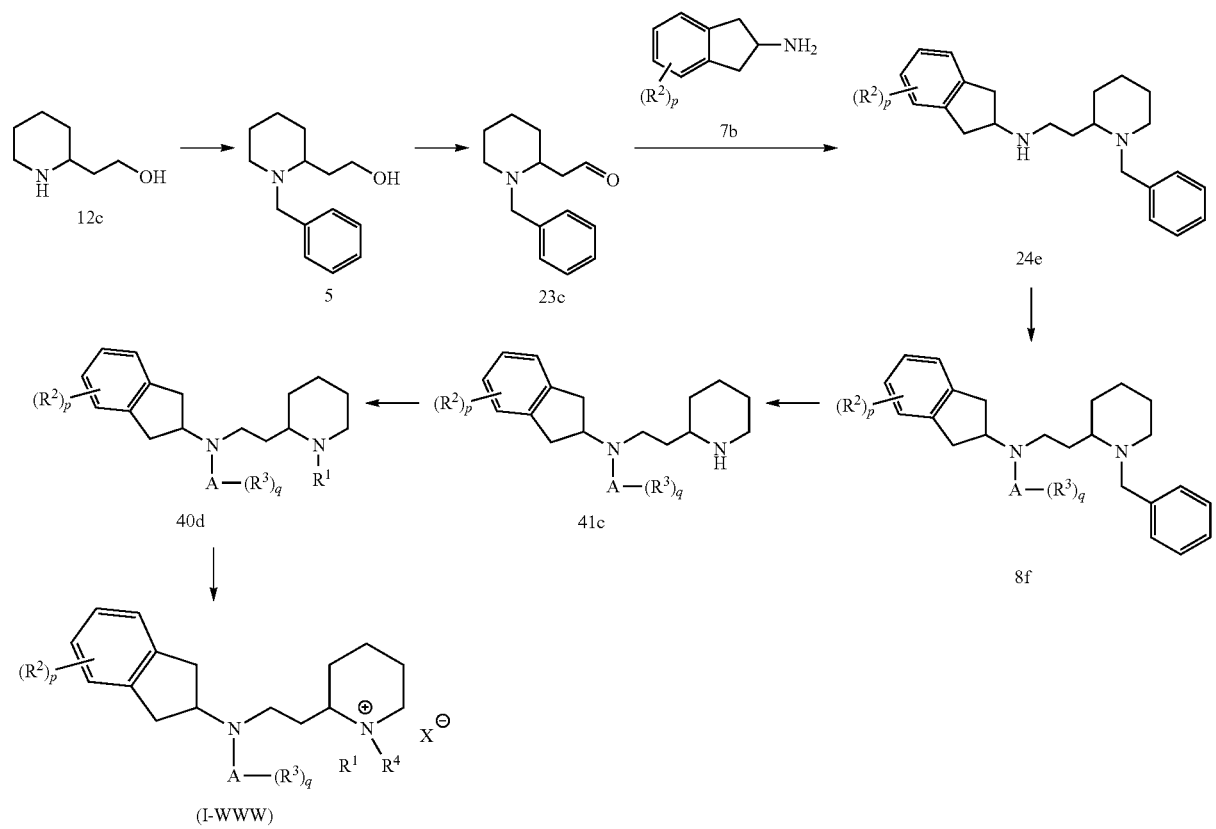

Scheme 22 to provide compound 24f. This reaction is typically performed in the presence of a mild reducing agent such as sodium triacetoxy borohydride. The nitrogen-atom of compound 24f is then substituted with an A-$(R^3)_q$ group to provide compound 8e. In one embodiment, the compound 24f is substituted with an optionally substituted phenyl. In another embodiment, compound 24f is substituted with an optionally substituted heteroaryl. In a further embodiment, the substitution is performed using a bromo-aryl or bromo-heterocyclic group. In another embodiment, the substitution is performed using bromobenzene, bromopyridine, or bromothioazole. In another embodiment, the substitution is performed in the presence of catalytic reagents such as a t-butoxide, such as potassium, sodium, or lithium t-butoxide, a base such as Verkade's super base, and a palladium reagent such as $Pd_2(dba)_3$. The protecting group, i.e., the benzyl group, of compound 8e is then removed using standard deprotection reagents to provide compound 41a. In one embodiment, the Scheme 22 provides yet another preparation of compound (I-WWW), wherein $R^1$-$R^4$, A, X, p, and q are defined herein. Specifically, the nitrogen atom of piperidine-2-ethanol (12c) is protected to provide 2-(1-benzylpiperidin-2-yl)ethanol (5). In one embodiment, the nitrogen atom is protected with a benzyl group using benzyl bromide. 2-(1-Benzylpiperidin-2-yl)ethanol is then oxidized to form (1-benzylpiperidin-2-yl)acetaldehyde (23c). In one embodiment, the oxidation is performed using oxalyl chloride, DMSO and triethylamine. (1-Benzylpiperidin-2-yl)acetaldehyde is then coupled with aminoindane 7b to provide compound 24e. In one embodiment, the reaction is performed in the presence of sodium triacetoxy borohydride. The nitrogen-atom of compound 24e is then substituted with a A-$(R^3)_q$ group to provide compound 8f. In one embodiment, the substitution is performed using bromobenzene, bromopyridine, or bromothioazole, a catalytic reagent such as a t-butoxide, such as potassium, sodium, or lithium t-butoxide, a base such as Verkade's super base, and a palladium reagent such as $Pd_2(dba)_3$. The protecting group, i.e., the benzyl group, of compound 8f is then removed using isobutyl chlorformate. Compound 41c is then $R^1$ substituted to provide compound 61d. In one embodiment, the $R^1$ substitution is performed using an aldehyde such as propionaldehyde, acetaldehyde, or formaldehyde. Compound 61d is then $R^4$ substituted using an alkylating agent such as an alkyl halide, alkyl triflate, or alkyl besylate to provide compound (I-WWW).

Scheme 23 form a cyclic ether. In still a further embodiment, substitution of the nitrogen atom is performed using a 1-halo-2-(2-chloro-alkoxy)-alkane such as 1-chloro-2-(2-chloro-ethoxy)-ethane.

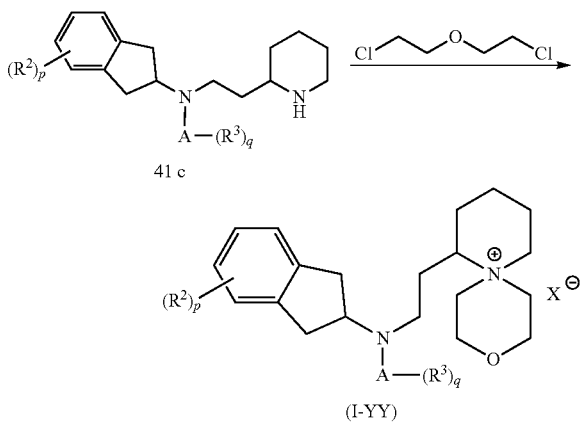

Scheme 24

Scheme 24 provides a synthesis of a compound, i.e., compound (I-YY), whereby $R^1$ and $R^4$ are joined to form a heterocyclic ring and $R^2$, $R^3$, A, p, q, and X are defined herein. In one embodiment, $R^1$ and $R^4$ are joined to form a cyclic ether. In a further embodiment, alkylation of the nitrogen atom is performed using a 1-halo-2-(2-chloro-alkoxy)-alkane such as 1-chloro-2-(2-chloro-ethoxy)-ethane.

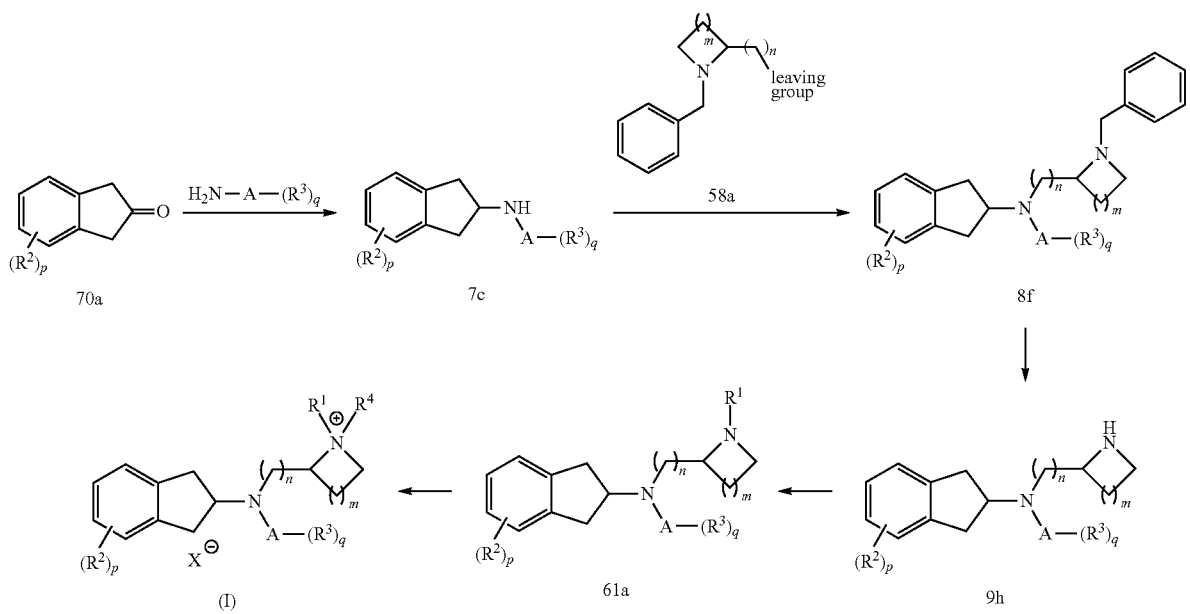

Scheme 25

Scheme 23 provides a synthesis of a compound whereby $R^1$ and $R^4$ are joined and $R^2$, $R^3$, A, m, p, q, Y, and X are defined herein, i.e., compound (I-Y). Specifically, the nitrogen atom of compound 41a may be substituted with an optionally substituted —CH$_2$YCH$_2$— group to form a compound of formula (I-Y). In one embodiment, $R^1$ and $R^4$ are joined to form a carbocyclic, i.e., where Y is a carbon atom. In another embodiment, $R^1$ and $R^4$ are joined to form a heterocyclic ring. In a further embodiment, $R^1$ and $R^4$ are joined to Scheme 25 provides the preparation of compounds of formula (I), wherein $R^1$-$R^4$, A, m, n, p, q, and X are defined herein. These compounds are prepared by first aminating ketone 70a to provide compound 7c. In one embodiment, ketone 70a is aminated using a primary amine. In another embodiment, ketone 70a is aminated using H$_2$N-A-(R$^3$)$_q$. This transformation is performed in the presence of a mild reducing agent such as Na(OAc)$_3$BH. Compound 7c is then coupled with amine 58a to provide compound 8f. The leaving group of amine 58a may be selected by one of skill in the art. In one embodiment, the leaving group is a halogen, mesylate, tosylate, or triflate. In another embodiment, coupling of compounds 7c and 58a is performed using an alkoxide, such as those described above. Compound 8f is then deprotected by removal of the benzyl group using techniques and reagents known in the art to provide compound 9h. In one embodiment, the deprotection is performed via a hydrogenation. In another embodiment, the hydrogenation is performed using ammonium formate, hydrogen gas and Pd/C, or Pd(OH)$_2$. The nitrogen-ring atom is then successively $R^1$ and then $R^4$ substituted using the reagents and conditions described above, e.g., the descriptions for Schemes 1-24, to provide compounds 61a and (I), respectively.

Scheme 26 provides the preparation of compounds of formula (I-WWWW), wherein $R^1$-$R^4$, p, q, and X is defined herein. These compounds are prepared by aminating ketone 70a to provide compound 7d. In one embodiment, ketone 70a is aminated using primary amine 71a in the presence of a mild reducing agent such as Na(OAc)$_3$BH. Compound 7d is then coupled with amine 58 in the presence of an alkoxide to provide compound 8e. Compound 8e is then deprotected via hydrogenation to provide compound 9i. The nitrogen-ring atom of compound 9i is then successively $R^1$ and then $R^4$ substituted using the reagents and conditions described above, to provide compounds 61b and (I-WWWW), respectively.

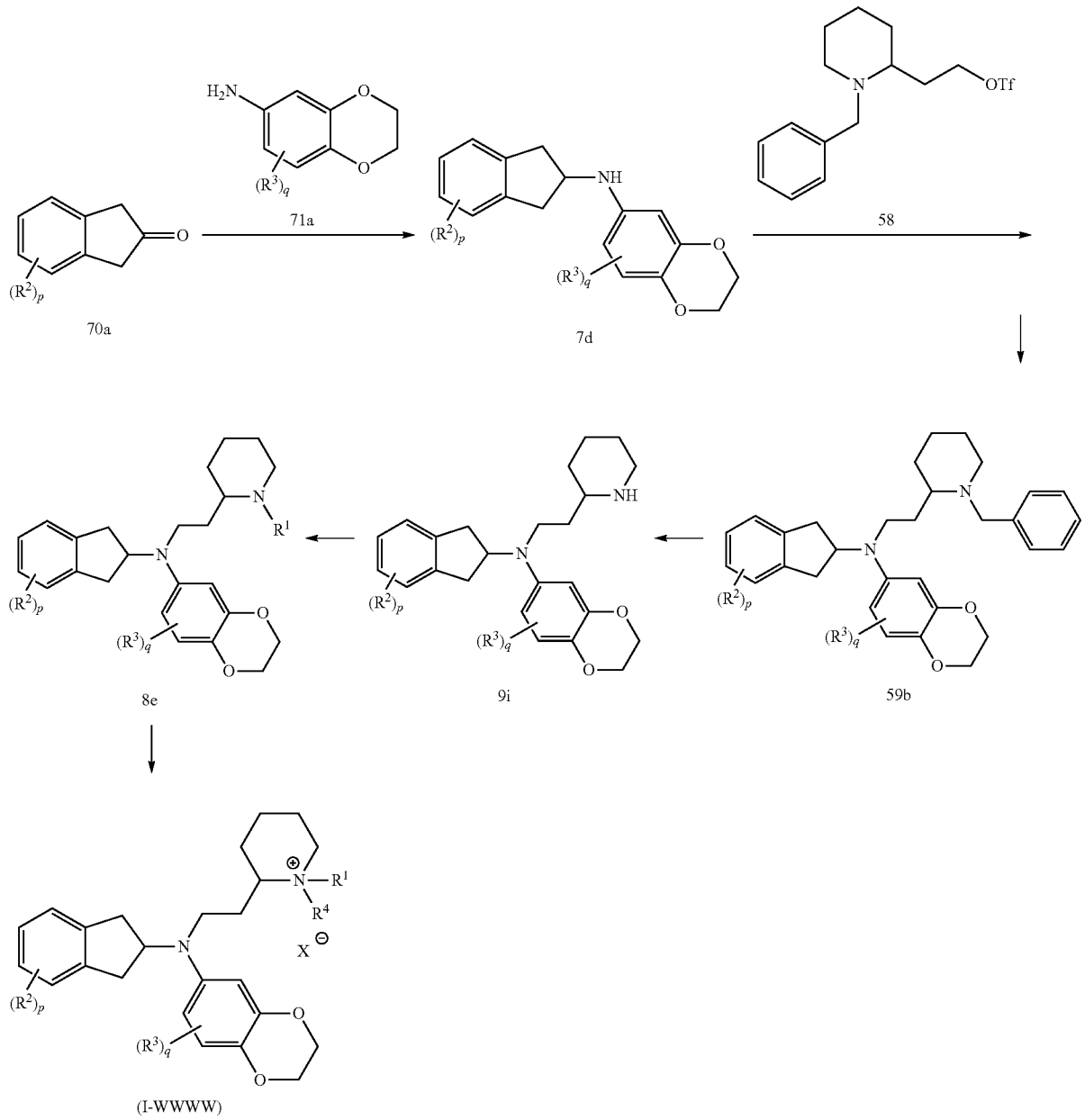

Scheme 27

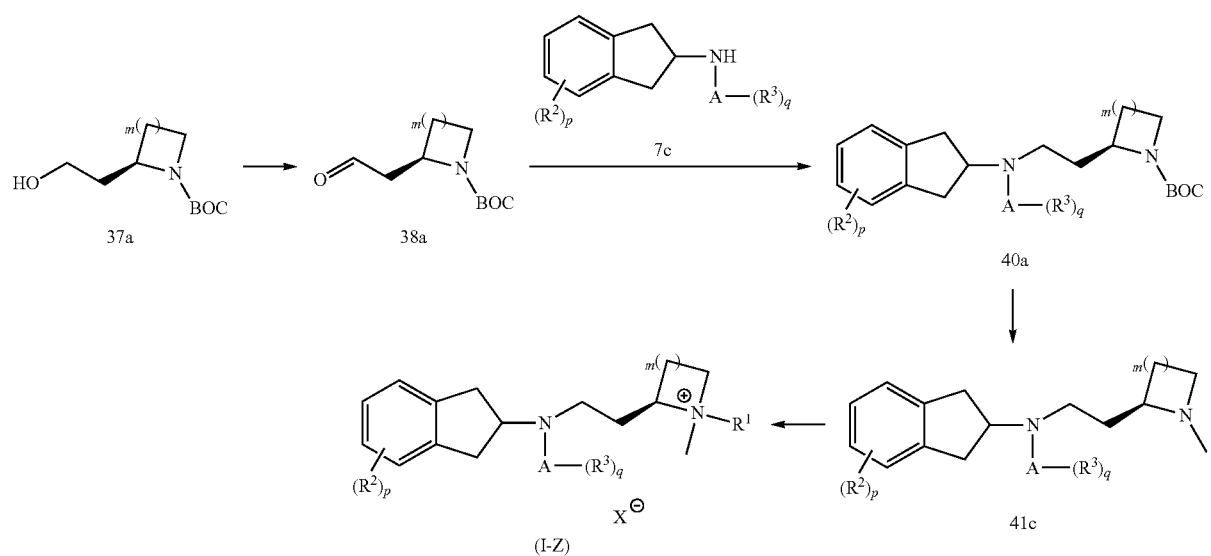

Scheme 27 provides an alternate route to compound (I-Z), wherein $R^1$-$R^3$, A, m, p, q, and X are defined herein, via compound 40a. Compound 37a may be prepared as discussed in Tetrahedran, 2007, 63:3000-3005, which is hereby incorporated by reference, and is then oxidized to form compound 38a. The oxidation may be performed using an oxidizing agent such as sodium hypochlorite and 2,2,6,6-tetramethylpiperidin-1-yl)oxidanyl (TEMPO) catalyst. Compound 40a is then prepared by adding compound 38a to a solution of compound 7c and Na(OAc)$_3$BH. The inventors found that this order of addition afforded the production of compound 40a in a high enantiomeric excess (ee). Compound 40a is then deprotected by reduction of the BOC group using standard reducing agents to form diamine 41c. In one embodiment, the BOC group is reduced to a methyl group using lithium aluminum hydride. The nitrogen atom of compound 41c is then $R^1$-substituted as discussed above for other $R^1$/$R^4$ substitutions to provide a compound of formula (I-Z). In one embodiment, the alkylation is performed using an alkyl halide such as methyl bromide or methyl iodide in a solvent such as dichloroethane or methyl t-butyl ether. This route may also be used to prepare the (S)-enantiomer of compound (I-Z).

In one embodiment, a method for preparing the compound of formula (I), wherein A is phenyl, is provided and includes (i) converting

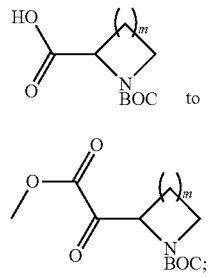

to

2a (ii) converting compound 2a to

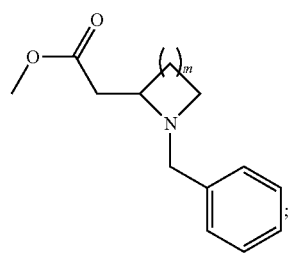

4a (iii) reducing compound 4a to

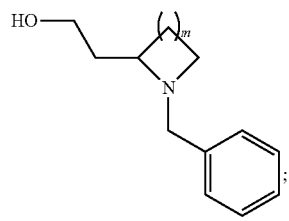

5a (iv) chlorinating compound 5a to form

6a (v) coupling compound 6a with

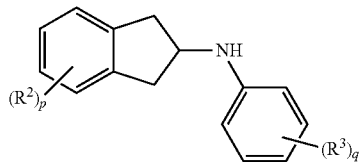

to form

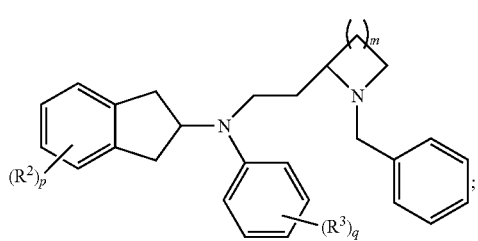

(vi) removing the benzyl group of compound 8a via hydrogenation to form

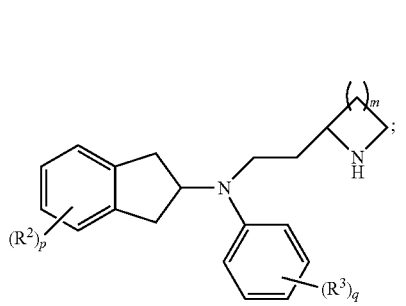

(vii) R¹ substituting compound 9a to form

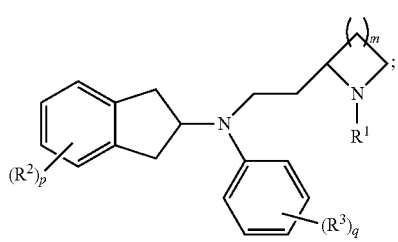

and (viii) R⁴ substituting compound 11a.

In another embodiment, a method for preparing the compound of the invention, wherein A is phenyl, is provided and includes (i) converting

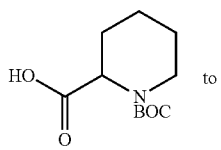  to

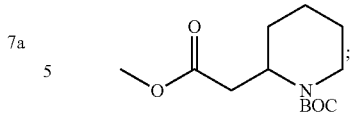

(ii) converting compound 2a to

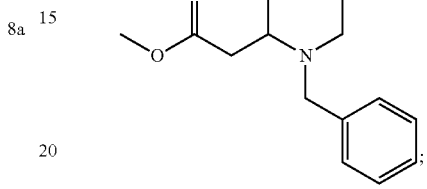

(iii) reducing compound 4a

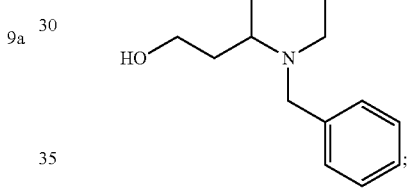

to (iv) chlorinating compound 5a to form

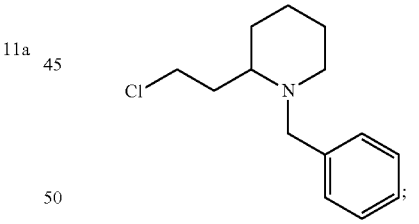

(v) coupling compound 6a with

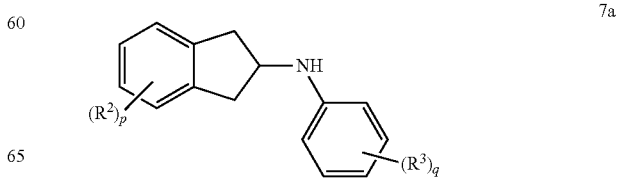

to form

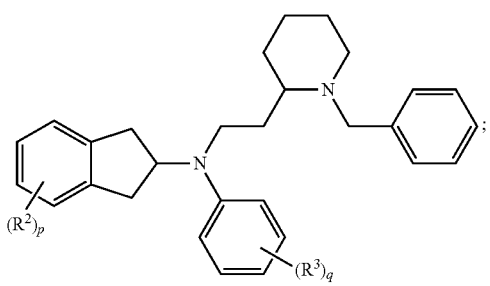
8a (vi) removing the benzyl group of compound 8a via hydrogenation to form

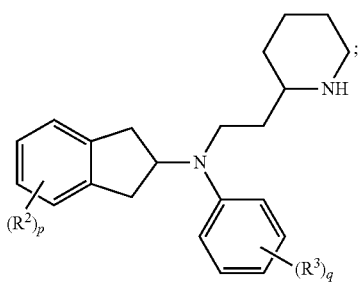
9a (vii) R¹ substituting compound 9a to form

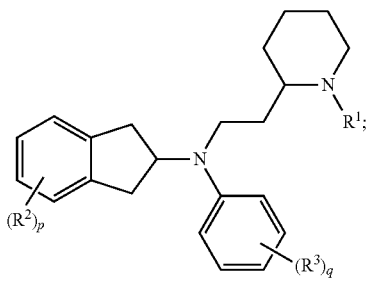
11a and (viii) R⁴ substituting compound 11a.

In a further embodiment, a method for preparing a compound of the invention, wherein A is phenyl and the method includes R¹ and R⁴ substituting

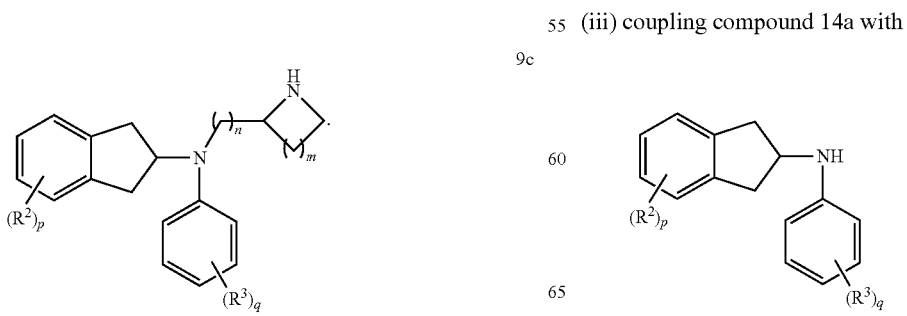
9c

In one aspect, compound 9c

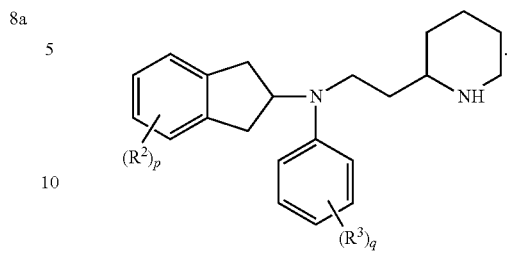

In yet another embodiment, a method for preparing a compound of the invention wherein A is phenyl, is provided and includes (i) protecting the nitrogen atom of

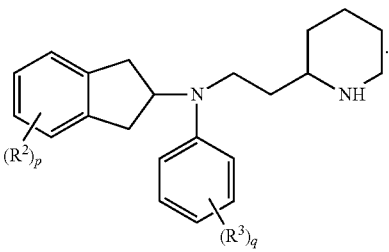

to form

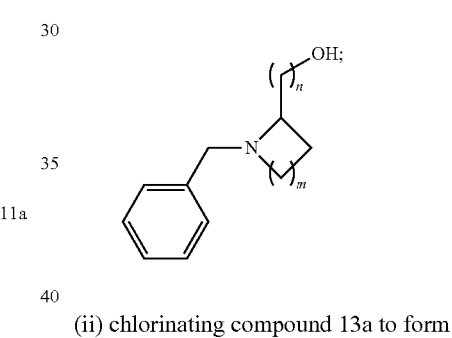
13a (ii) chlorinating compound 13a to form

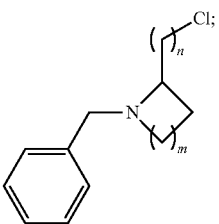
14a (iii) coupling compound 14a with

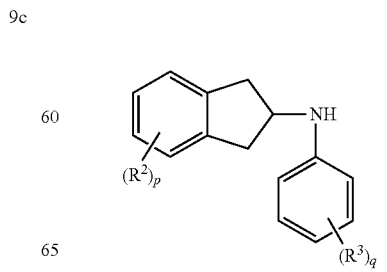
7a to form

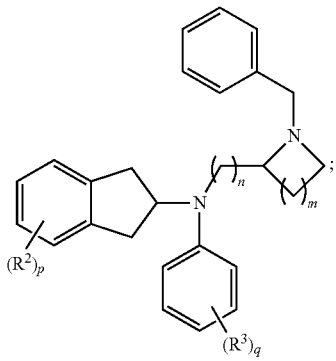
15a (iv) deprotecting compound 15a to form

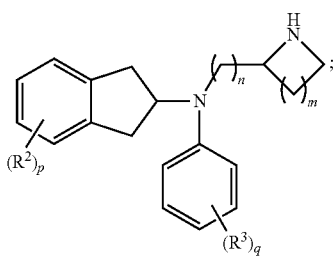
16a (v) R¹ substituting compound 16a to form

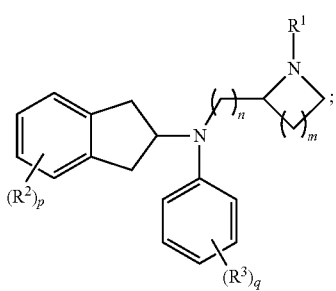
17a and (vi) R⁴ substituting compound 17a.

In still a further embodiment, a method for preparing a compound of the invention, wherein A is phenyl, is provided and includes (i) protecting the nitrogen atom of piperidine-2-methanol to form

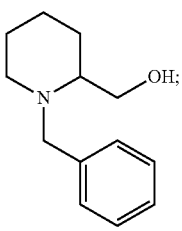
13a (ii) chlorinating compound 13a to form

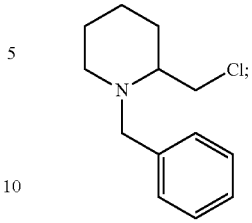
14a (iii) coupling compound 14a with

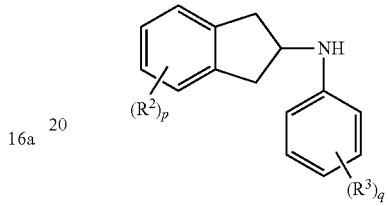
7a to form

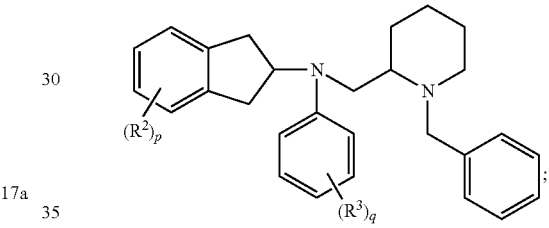
15a (iv) deprotecting compound 15a to form

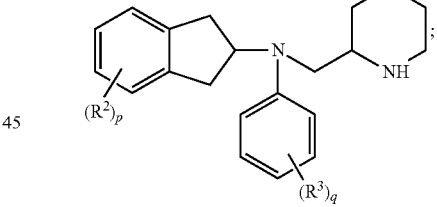
16a (v) R¹ substituting compound 16a to form

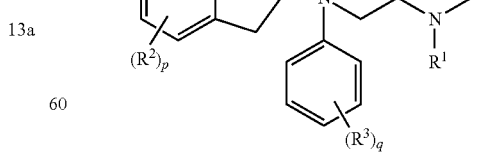
17a and (vi) R⁴ substituting compound 17a.

In yet another embodiment, a method for preparing a compound of the invention, wherein A is phenyl, R³ is 2-F, m is 2, and q is 1, is provided and includes R¹ and R⁴ substituting

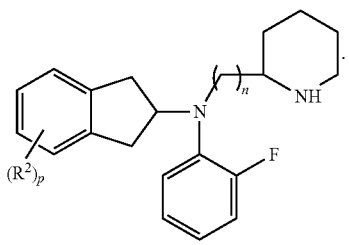

In one aspect, compound 9d is

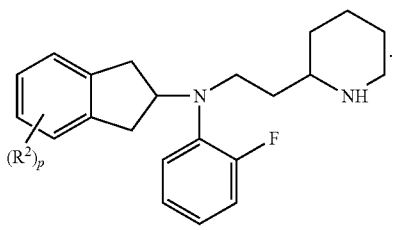

In yet a further embodiment, a method for preparing a compound of the invention, wherein A is phenyl, is provided and includes (i) coupling

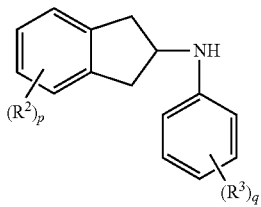 and 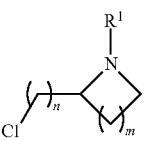

to form

17a

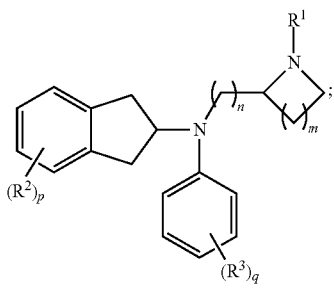

and (ii) R⁴ substituting compound 17a.

In still another embodiment, a method for preparing a compound of the invention, wherein A is phenyl, is provided and includes (i) coupling

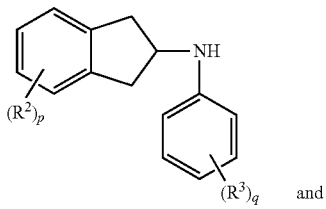 and

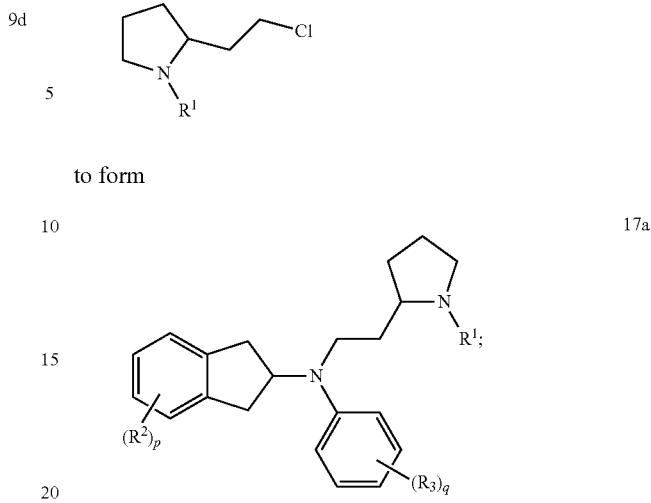

to form

17a and (ii) R⁴ substituting compound 17a.

In a further embodiment, a method for preparing a compound of the invention, wherein m is 3, is provided and includes (i) reducing

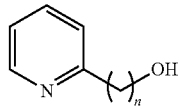

using an acid to form

21a

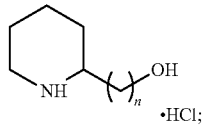

protecting compound 21a with a benzyl group to provide

22a

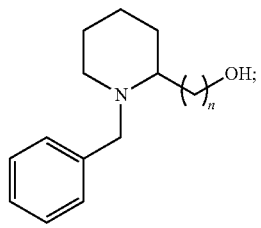

(iii) oxidizing compound 22a to provide

23a

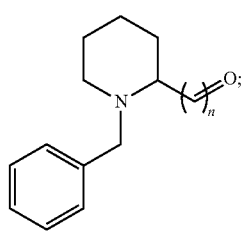

(iv) coupling compound 23a with

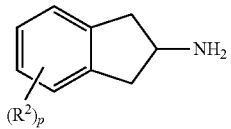
7b to provide

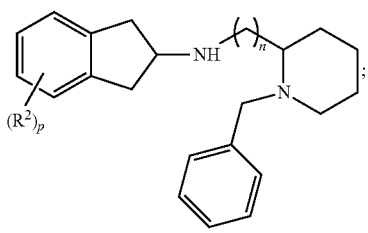
24a (v) substituting the nitrogen atom of compound 24a with a $R^3$-substituted phenyl group to form

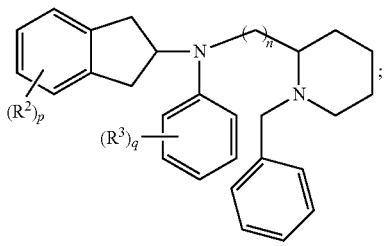
25a (vi) deprotecting compound 25a to provide

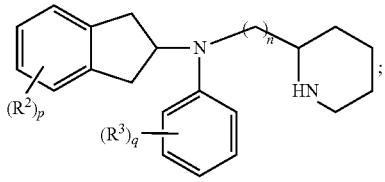
26a and (v) $R^1$ and $R^4$ substituting compound 26a.

In yet a further embodiment, a method for preparing a compound of the invention, wherein m is 3, is provided and includes (i) reducing

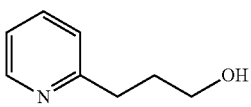

using an acid to form

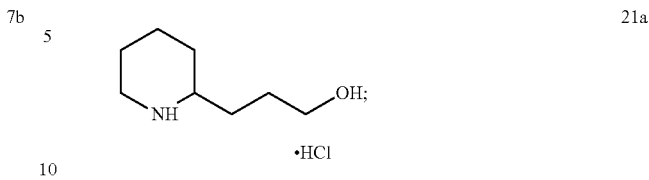
21a (ii) protecting compound 21a with a benzyl group to provide

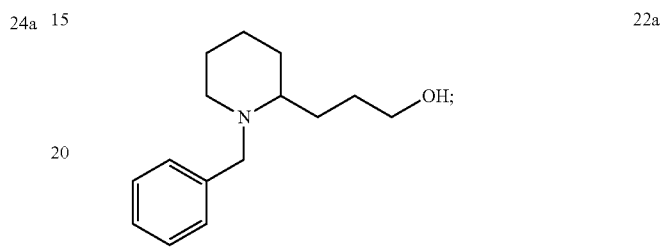
22a (iii) oxidizing compound 22a to provide

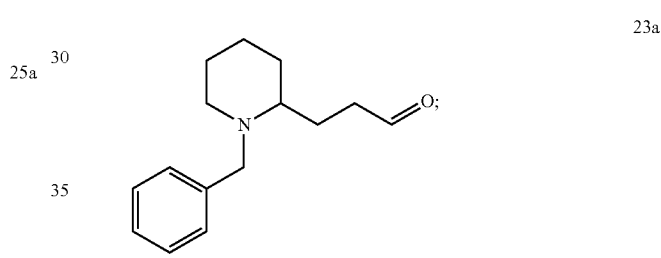
23a (iv) coupling compound 23a with

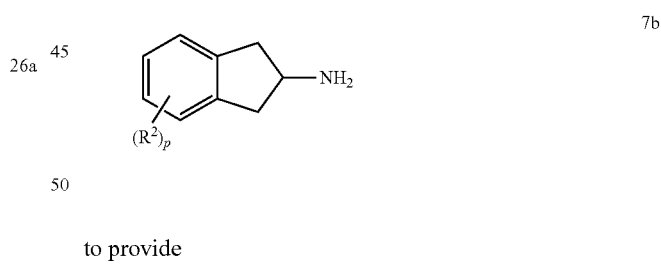
7b to provide

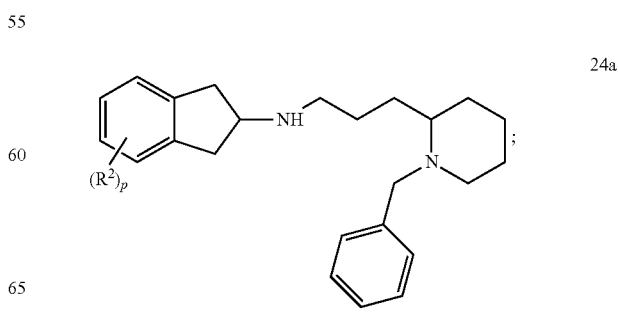
24a (v) substituting the nitrogen atom of compound 24a with a R³-substituted phenyl group to form

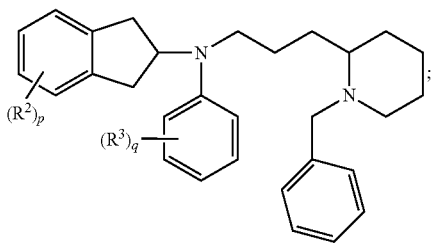
25a (vi) deprotecting compound 25a to provide

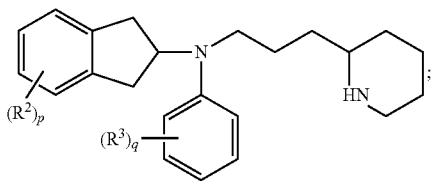
26a and (v) R¹ and R⁴ substituting compound 26a.

In another embodiment, a method for preparing a compound of the invention, wherein A is phenyl, is provided and includes (i) converting

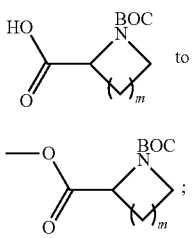

to

2a (ii) converting compound 2a to

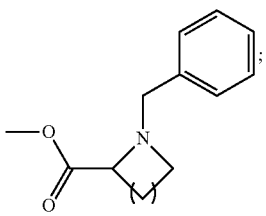
4a (iii) reducing compound 4a to

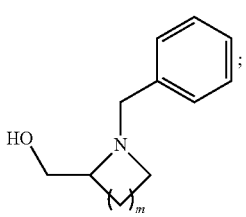
5a (iv) oxidizing compound 5a to provide

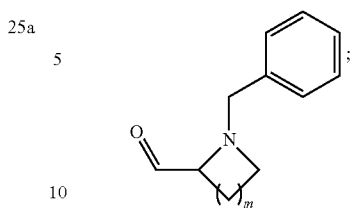
23a (v) coupling compound 23a with

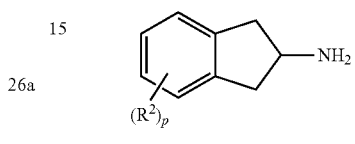
7b to provide

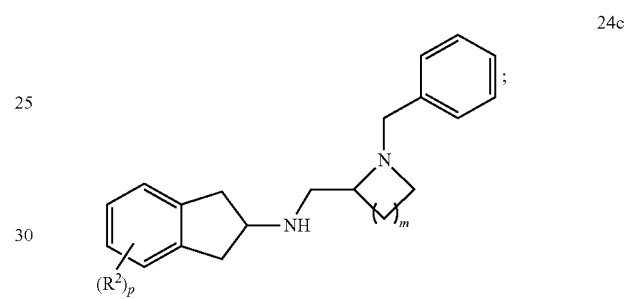
24c (v) substituting the nitrogen atom of compound 24c with an R³-substituted phenyl group to provide

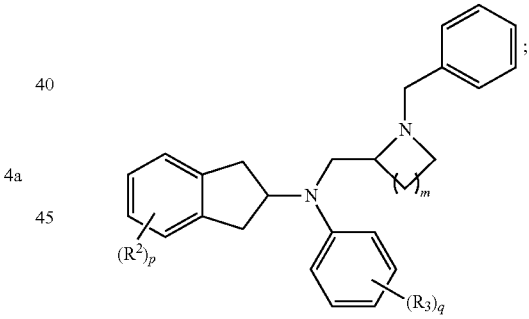
8c (vi) deprotecting compound 8c to form

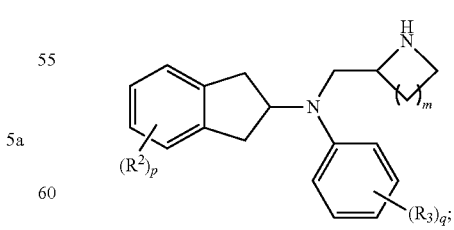
9f and (vii) R¹ and R⁴ substituting the nitrogen ring.

In still another embodiment, a method for preparing a compound of the invention, wherein A is phenyl, is provided and includes (i) converting

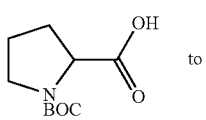

to

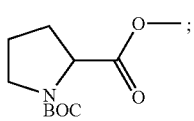

(ii) converting compound 2c to

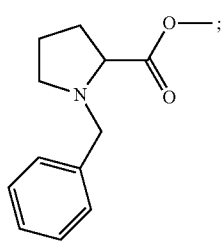

4c (iii) reducing compound 4c to

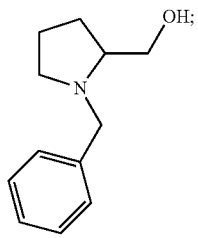

(iv) oxidizing compound 5c to provide

23a

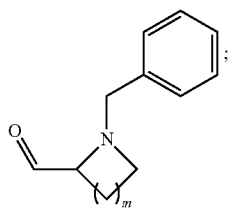

(v) coupling compound 23a with

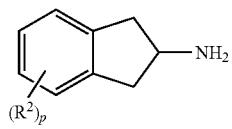

to provide

24c (v) substituting the nitrogen atom of compound 24c with an $R^3$-substituted phenyl group to provide

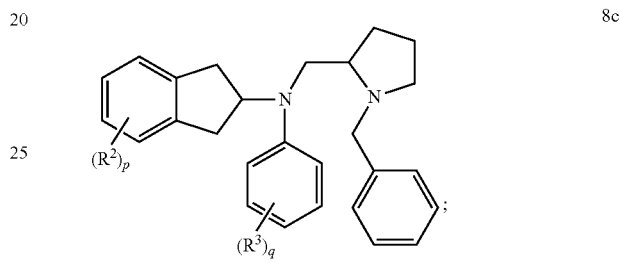

8c (vi) deprotecting compound 8c to form

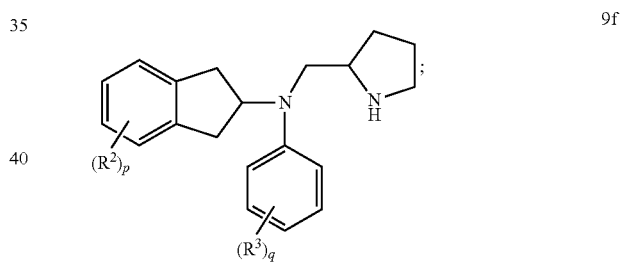

9f and (vii) $R^1$ and $R^4$ substituting the nitrogen ring.

In still a further embodiment, a method for preparing a compound of the invention is provided and includes (i) converting

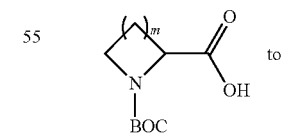

7b to

2b (ii) reducing compound 2b to

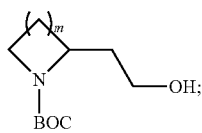

(iii) oxidizing compound 37a to

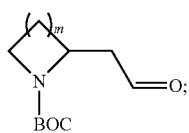

(iv) coupling compound 38a with

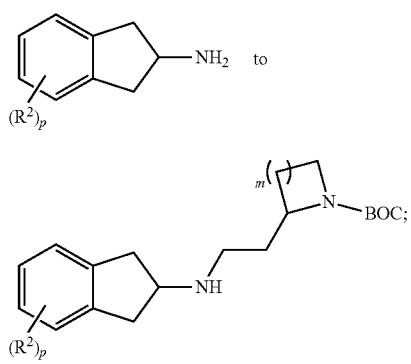

(v) coupling compound 39a with an A-(R³)q group to form

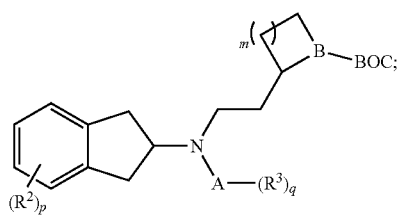

(vi) deprotecting compound 40a to form

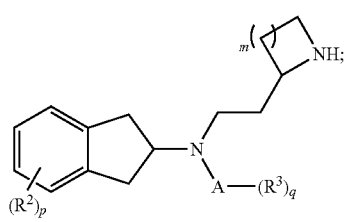

and (vii) $R^1$ and $R^4$ substituting compound 41a.

In yet a further embodiment, a method for preparing a compound of the invention is provided and includes (i) converting

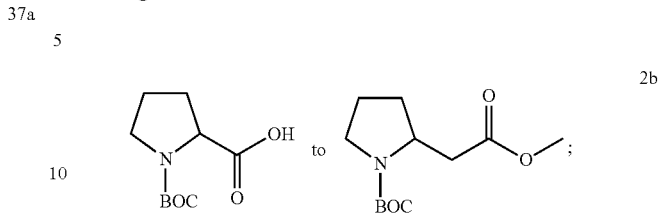

(ii) reducing compound 2b to

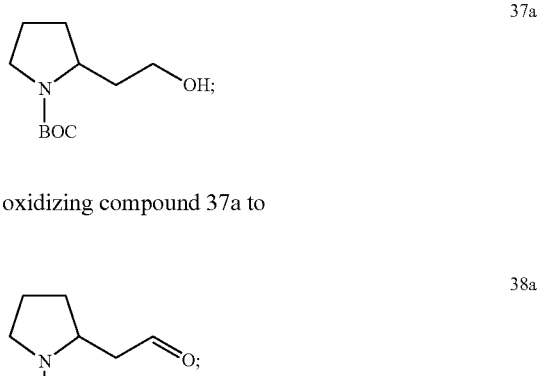

(iii) oxidizing compound 37a to

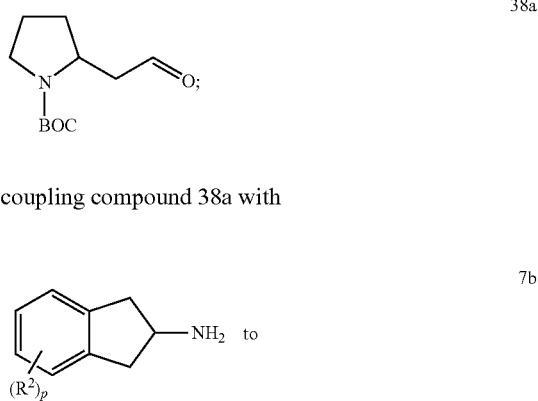

(iv) coupling compound 38a with

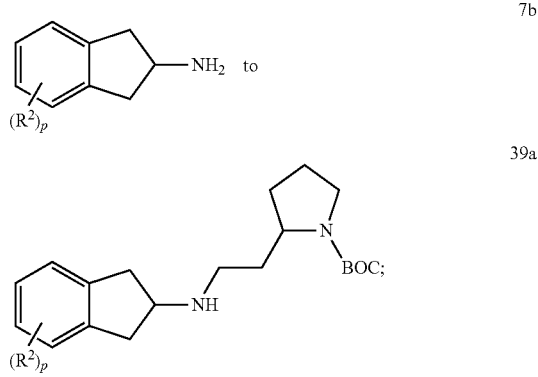

(v) coupling compound 39a with an A-(R³)q group to form

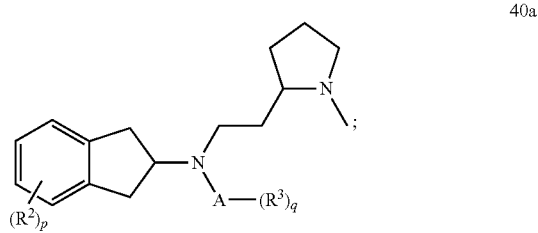

(vi) deprotecting compound 40a to form

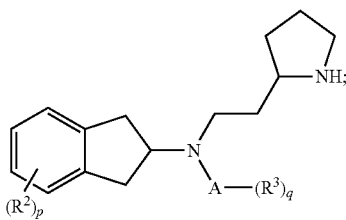
41a and (vii) $R^1$ and $R^4$ substituting compound 41a.

In another embodiment, a method for preparing a compound of the invention is provided and includes (i) BOC protecting

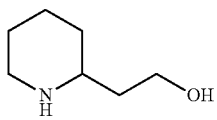

to form

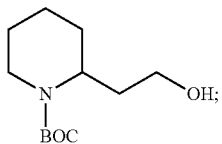
37a (ii) oxidizing compound 37a to form

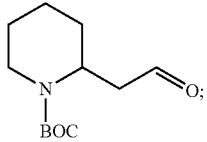
38a (iii) coupling compound 38a with

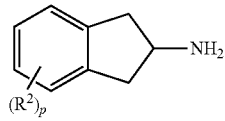
7b to form

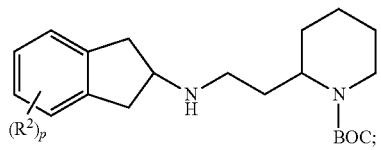
39a (iv) substituting compound 39a with A-$(R^3)_q$ to form

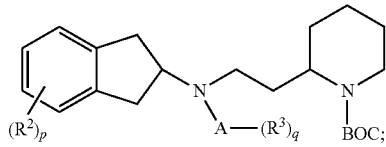
40a (v) deprotecting compound 40a to form

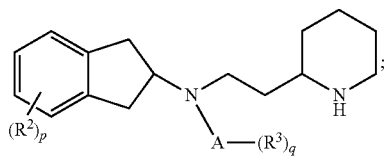
41a and (vi) $R^1$ and $R^4$ substituting compound 41a.

In yet another embodiment, a method for preparing a compound of the invention is provided, wherein n is 2, and includes (i) substituting

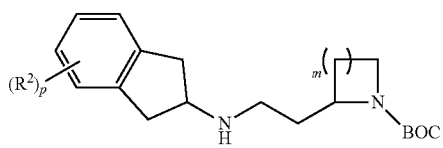
39a with A-$(R^3)_q$ to form

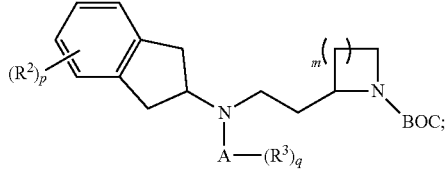
40a (ii) deprotecting compound 40a to form

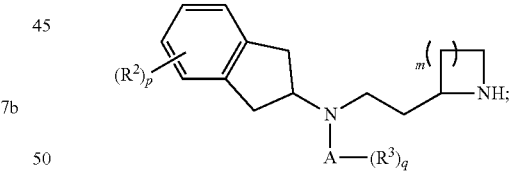
41a and (iii) $R^1$ and $R^4$ substituting compound 41a.

In still another embodiment, a method for preparing a compound of the invention is provided, wherein n is 2, and includes (i) substituting

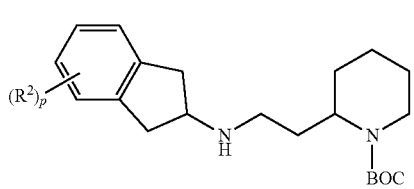
39a with A-(R³)_q to form

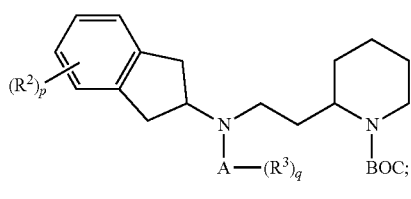
40a (ii) deprotecting compound 40a to form

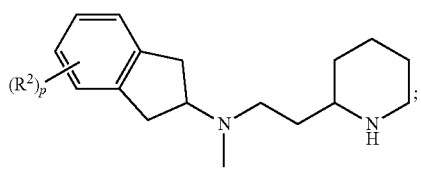
41a and (iii) R¹ and R⁴ substituting compound 41a.

In a further embodiment, a method for preparing a compound of the invention is provided and includes (i) protecting

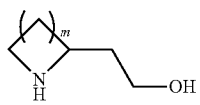
12b to form

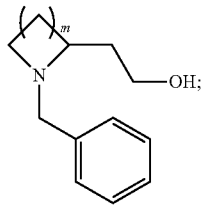
5a (ii) oxidizing compound 5a to form

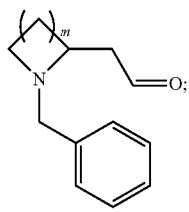
23c (iii) coupling compound 23a with

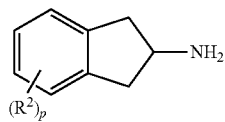
7b to form

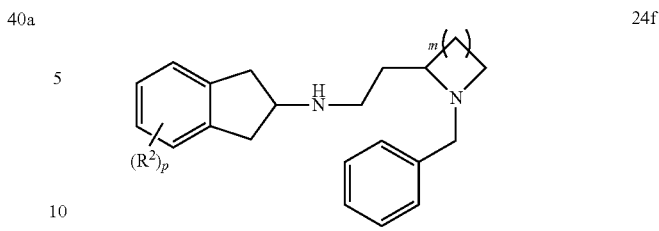
24f (iv) substituting compound 24f with A-(R³)_q to form

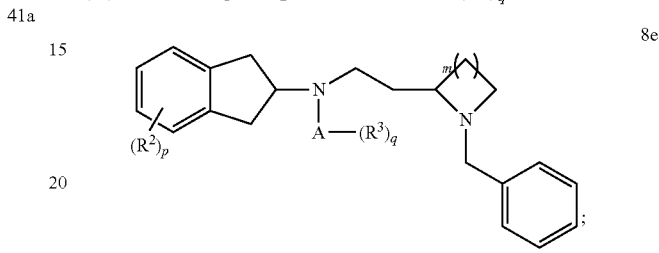
8e (v) deprotecting compound 8e to form

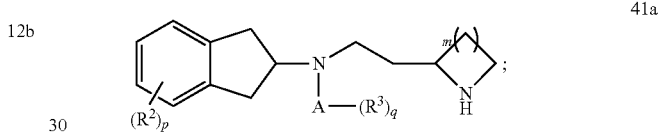
41a (vi) R¹ substituting compound 41a to form

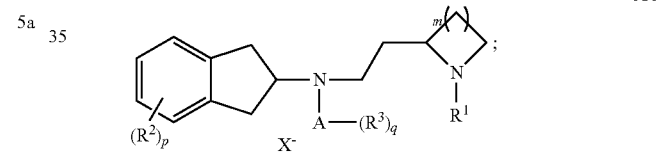
61c and (vii) R⁴ substituting compound 61c.

In a further embodiment, a method for preparing a compound of the invention is provided, wherein n is 2, and includes (i) substituting

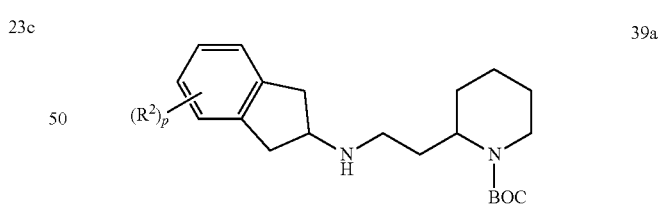
39a with A-(R³)_q to form

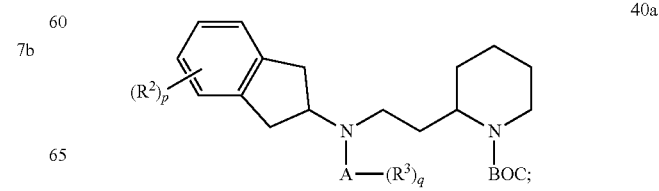
40a (ii) deprotecting compound 40a to form

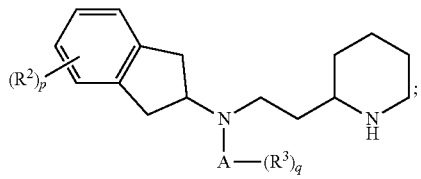
41a and (iii) R¹ and R⁴ substituting compound 41a.

In a further embodiment, a method for preparing a compound of the invention is provided and includes (i) protecting

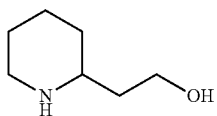

to form

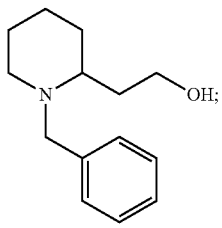
5a (ii) oxidizing compound 5a to form

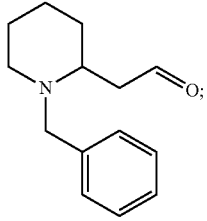
23c (iii) coupling compound 23a with

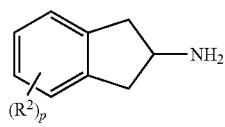
7b to form

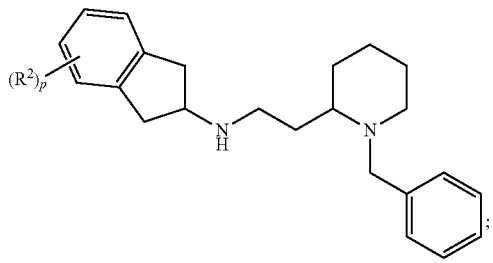
24f (iv) substituting compound 24f with A-(R³)$_q$ to form

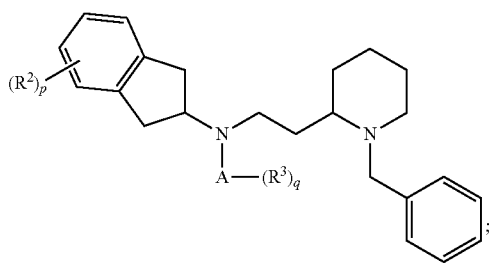
8e (v) deprotecting compound 8e to form

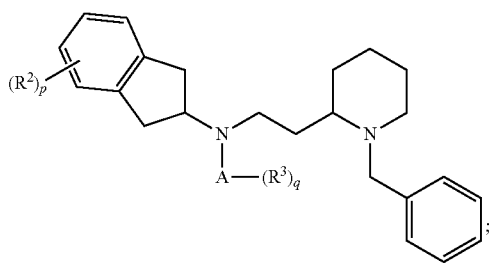
41a (vi) R¹ substituting compound 41a to form

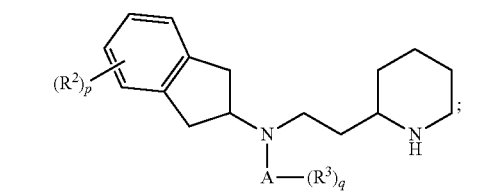
61c and (vii) R⁴ substituting compound 61c.

In another embodiment, a method for preparing a compound of the invention is provided and includes reacting

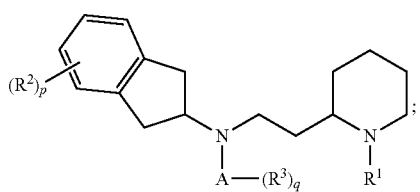
41a with X''—(CH$_2$)$_r$—Y—(CH$_2$)$_s$—X'', wherein r is 1 to 4; s is 1 to 4; Y is CH$_2$, O, or S; and X'' is a leaving group.

In still another embodiment, a method for preparing a compound of the invention is provided and includes reacting

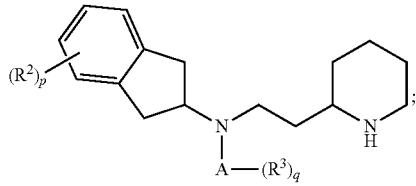

with ClCH$_2$CH$_2$OCH$_2$CH$_2$Cl.

In a further embodiment, a method for preparing a compound of the invention is provided and includes (i) reacting

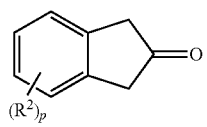

70a with H$_2$N-A-(R$^3$)$_q$ to form

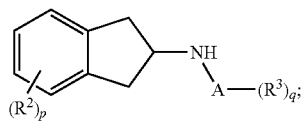

7c (ii) coupling compound 7c with

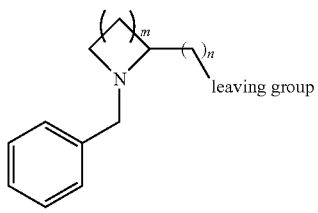

58a to form

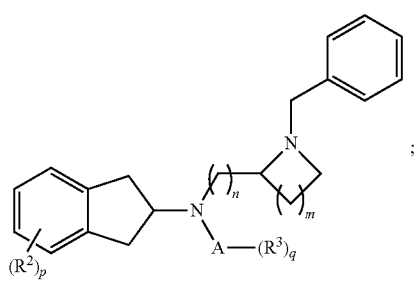

8f (iii) deprotecting compound 8f to form

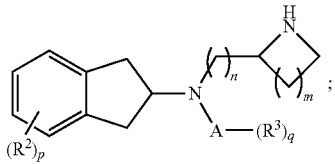

9h (iv) R$^1$ substituting compound 9h to form

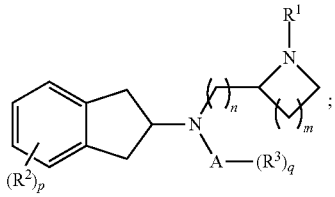

61a and (v) R$^4$ substituting compound 61a.

In yet a further embodiment, a method for preparing a compound of the invention is provided and includes (i) reacting

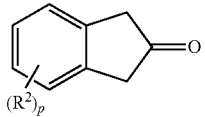

70a with

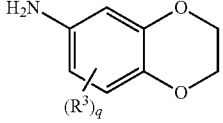

to form

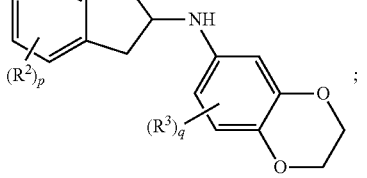

7c (ii) coupling compound 7c with

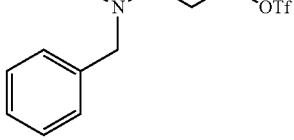

58a to form

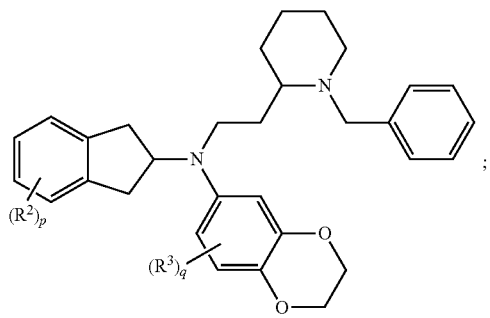
8f (iii) deprotecting compound 8f to form

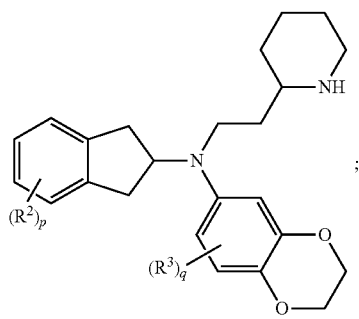
9h (iv) R¹ substituting compound 9h to form

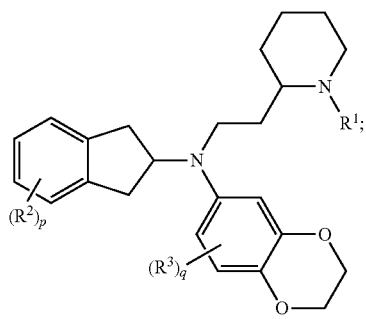
61a and (v) R⁴ substituting compound 61a.

In still another embodiment, a method for preparing a compound of the invention is provided, wherein R⁴ is CH₃, and includes (i) oxidizing

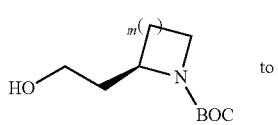
37a to

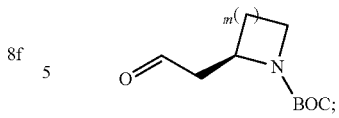
38a (ii) coupling compound 38a with

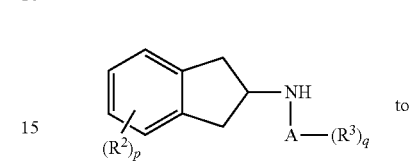
7c to

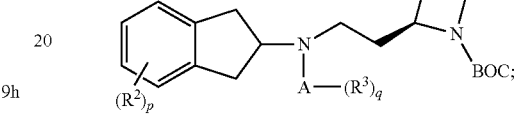
40a (iii) reducing compound 40a to

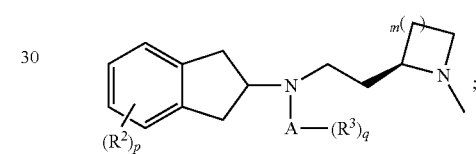
41c and (iv) R¹ substituting compound 41c. In one aspect, compound 40a is prepared by adding compound 38a to a solution containing compound 7c and a mild reducing agent. In another aspect, the mild reducing agent is Na(OAc)₃BH. In a further aspect, the % ee of compound 40a is at least about 97% ee.

Pharmaceutical compositions of the invention comprise a compound of formula (I) and/or (II) optionally with other pharmaceutically inert or inactive ingredients. In one embodiment, the pharmaceutically inert or inactive ingredient is one or more pharmaceutically acceptable carrier or excipient. The present invention also contemplates combining the compound of formula (I) and/or (II) with one or more therapeutic agents, i.e., active ingredients, as described below. In a further embodiment, a compound of formula (I) and/or (II) is combined with one or more inert/inactive ingredients and one or more therapeutic agents.

The pharmaceutical compositions of the invention contain an amount of a compound of formula (I) and/or (II) that is effective for treating interstitial cystitis or overactive bladder in a subject. Specifically, the dosage of the compound of formula (I) and/or (II) to achieve a therapeutic effect will depend on factors such as the formulation, pharmacological potency of the drug, age, weight and sex of the patient, condition being treated, severity of the patient's symptoms, specific compound of formula (I) and/or (II), route of delivery, and response pattern of the patient. It is also contemplated that the treatment and dosage of the compound of formula (I) and/or (II) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. Further, one of skill in the art would be able to calculate any changes in effective amounts of any one of the compounds of the compositions due to changes in the composition components or dilutions. In one embodiment, the compositions may be diluted 2-fold. In another embodiment, the compositions may be diluted 4-fold. In a further embodiment, the compositions may be diluted 8-fold.

In one embodiment, the therapeutically effective amount is about 0.0001% to about 25% w/v. In another embodiment, the therapeutically effective amount is less than about 20% w/v, about 15% w/v, about 10% w/v, about 5% w/v, or about 1% w/v. In another embodiment, the therapeutically effective amount is about 0.0001% to about 10% w/v. In a further embodiment, the therapeutically effective amount is about 0.005 to about 5% w/v. In yet another embodiment, the therapeutically effective amount is about 0.01 to about 5% w/v. In still a further embodiment, the therapeutically effective amount is about 0.01% w/v, about 0.05% w/v, about 0.1% w/v, about 0.2% w/v, about 0.3% w/v, about 0.4% w/v, about 0.5% w/v, about 0.6% w/v, about 0.7% w/v, about 0.8% w/v, about 0.9% w/v, about 1% w/v, about 2% w/v, about 3% w/v, about 4% w/v, or about 5% w/v. In one embodiment, the therapeutically effective amount of the compound of formula (I) and/or (II) is about 0.2% w/v. In another embodiment, the therapeutically effective amount is about 0.5% w/v.

The therapeutically effect amount of the compound of formula (I) and/or (II) may, therefore, be about 1 mg to about 1000 mg per dose based on a 70 kg mammalian subject. In another embodiment, the therapeutically effective amount is about 2 mg to about 250 mg per dose. In a further embodiment, the therapeutically effective amount is about 5 mg to about 100 mg. In yet a further embodiment, the therapeutically effective amount is about 25 mg to 50 mg, about 20 mg, about 15 mg, about 10 mg, about 5 mg, about 1 mg, about 0.1 mg, about 0.01 mg, about 0.001 mg.

The therapeutically effective amounts may be provided on regular schedule, i.e., on a daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of therapy will be determined according to the judgment of a health-care practitioner. The therapeutically effective amounts described herein refer to total amounts administered for a given time period; that is, if more than one compound of formula (I) and/or (II) is administered, the therapeutically effective amounts correspond to the total amount administered.

The compound of formula (I) and/or (II) may be administered by any route, taking into consideration the specific condition for which it has been selected. The compounds of formula (I) and/or (II) may be delivered orally, by injection, inhalation (including orally, intranasally and intratracheally), ocularly, transdermally, transdermally (via simple passive diffusion formulations or via facilitated delivery using, for example, iontophoresis, microporation with microneedles, radio-frequency ablation or the like), intravascularly, cutaneously, subcutaneously, intramuscularly, sublingually, intracranially, epidurally, rectally, intravesically, and vaginally, among others.

In one embodiment, the compound of formula (I) and/or (II) may be administered by injection, including microinjection, transdermally or topically. In one embodiment, the amount of the compound of formula (I) and/or (II) is about 0.05% w/w to about 10% w/w of the preparation depending on the route of administration. In one embodiment, the compound of formula (I) and/or (II) is present in a concentration of about 0.1% w/w to about 3% w/w. These compositions may also contain stabilizing agents, antibacterial agents, buffers and may be manufactured in different dosage unit ampoules or bottles. When for ocular use, the amount of the compound of formula (I) and/or (II) can be about 0.05% w/w to about 2.5% w/w. Compositions for injection or infusion may be prepared as an aqueous suspension or solution.

When used for dermal anesthesia, the amount of the compound of formula (I) and/or (II) can be about 0.1% w/w to about 10% w/w. When used for non-ocular, topical (e.g., oral, nasal, rectal, urethral, vaginal) administration the amount of the compound of formula (I) and/or (II) can be about 0.5% w/w to about 5% w/w. When used as in an injection, the amount of the compound of formula (I) and/or (II) can be about 0.25% w/w to about 3% w/w for injections. When used for infusions (e.g., for epidural, spinal or regional anesthesia), the amount of the compound of formula (I) and/or (II) can be about 0.1% w/w to about 3% w/w.

In one embodiment, the compound of formula (I) and/or (II) may be administered topically to the eye, e.g., as solutions, suspensions or ointments. Examples of ophthalmically compatible carriers which may be used include, without limitation, an aqueous solution, such as saline solution, oil solution or ointments containing ophthalmically compatible preservatives, surfactants, buffers, and viscosity regulators. These compositions may also contain stabilizing agents, antibacterial agents, and may be manufactured in different dosage units, suitable for ocular administration. Drug inserts, either soluble or insoluble, may also be used.

In another embodiment, the compound of formula (I) and/or (II) may be administered by injection. Solutions for injection or infusion may be prepared as aqueous solutions. Desirably, the compound of formula (I) and/or (II) is present in a concentration of about 0.1% w/w to about 3% w/w. These solutions may also contain stabilizing agents, antibacterial agents, buffers and may be manufactured in different dosage unit ampoules or bottles.

In a further embodiment, the compound of formula (I) and/or (II) may be administered rectally. Dosage units for rectal administration may be prepared in the form of ointments or suppositories, which contain the compound of formula (I) and/or (II) in a mixture with a neutral fat base, or they may be prepared in the form of gelatin-rectal capsules that contain the compound of formula (I) and/or (II) in a mixture with, e.g., a vegetable oil or paraffin oil. Ointments, suppositories or creams containing at least one compound of formula (I) and/or (II) are useful for the treatment of hemorrhoids.

In still another embodiment, the compound of formula (I) and/or (II) may be administered transdermally. A variety of transdermal delivery systems are known. For use in these systems, a compound of formula (I) and/or (II) may be admixed with a variety of excipients which may include, e.g., pH adjusters, preservatives, and/or penetration enhancers in order to form a solution, ointment, cream, lotion, or gel. Such a composition may form a constituent of a transdermal delivery system ("patch" etc.).

A transdermal delivery system may be selected which permits or assists a compound of the invention in passing though the dermal layer and to the targeted area, such as muscular tissues or a perineural space. Such systems may include formulation with skin penetration enhancers. Examples of skin penetration enhancers include physical enhancers (ultrasound, iontophoresis, electroporation, magnetophoresis, microneedle), vesicles, particulate systems (liposome, niosome, transfersome, microemulsion, solid lipid nanoparticle), and chemical enhancers (sulphoxides, azones, glycols, alkanols, terpenes, etc.). Further examples of chemical enhancers include, e.g., propylene glycol, polyethylene glycol, isopropanol, ethanol, oleic acid, N-methylpyrrolidone, which increase the permeability of the skin to the compounds, and permit the compounds to penetrate through the skin to deeper tissues. See, Sagie & Kohane, "Prolonged Sensory-Selective Nerve Blockade", PNAS, 2010(8): 3740-3745, 2010, which is herein incorporated by reference, for additional examples of chemical enhancers.

As a further embodiment, the compound of formula (I) and/or (II) may be instilled via direct instillation into the bladder and/or urothelium. In one example, a pharmaceutical composition containing a compound of formula (I) and/or (II) and one or more carriers or excipients is formulated for instillation. For example, the compound of formula (I) and/or (II) may be instilled as a solution. In a further example, the compound instilled may be placed into said bladder or urothelium as an extended-release formulation. A variety of extended-release formulations may be utilized for this purpose and include, without limitation, solution, suspension, gel or other solid dosage form containing reservoirs, a drug coated material, a drug impregnated material, a liposomal-drug formulation, among others.

The pharmaceutical compositions containing a compound of formula (I) and/or (II) may be formulated neat or with one or more pharmaceutical carriers and/or excipients for administration. The amount of the pharmaceutical carrier(s) is determined by the solubility and chemical nature of the compound of formula (I) and/or (II), chosen route of administration and standard pharmacological practice. The pharmaceutical carrier(s) may be solid or liquid and may incorporate both solid and liquid carriers/matrices. A variety of suitable liquid carriers is known and may be readily selected by one of skill in the art. Such carriers may include, e.g., dimethylsulfoxide (DMSO), saline, buffered saline, cyclodextrin, hydroxypropylcyclodextrin (HPβCD), n-dodecyl-β-D-maltoside (DDM) and mixtures thereof. Similarly, a variety of solid (rigid or flexible) carriers and excipients are known to those of skill in the art. Such carriers may also be designed so as to undergo a state transition when injected into the bladder (e.g., liquid to gel, liquid to solid, gel to solid); such materials are known to those skilled in the art. Such carriers may also comprise a membrane, for example comprising a thermoelastic polymer, which defines a reservoir containing a solid or liquid composition. Such carriers may also comprise a thermoelastic polymer matrix, in which a composition which contains a compound of formula (I) and/or (II) is embedded.

The compounds of formula (I) and/or (II) can also be administered together with other-membrane stabilizers (local anesthetics), for example to form eutectic mixtures.

Although the compound of formula (I) and/or (II) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized, they are desirably sterile liquids. Liquid carriers are typically utilized in preparing solutions, suspensions, emulsions, syrups and elixirs. In one embodiment, the compound of formula (I) and/or (II) is dissolved a liquid carrier. In another embodiment, the compound of formula (I) and/or (II) is suspended in a liquid carrier. One of skill in the art of formulations would be able to select a suitable liquid carrier, depending on the route of administration. The compound of formula (I) and/or (II) may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, a solid carrier may also act as a flavoring agent, lubricant, solubilizer, suspending agent, filler, glidant, compression aid, binder, disintegrant, or encapsulating material. In one embodiment, a solid carrier acts as a lubricant, solubilizer, suspending agent, binder, disintegrant, or encapsulating material. In another embodiment, the carrier comprises a thermoelastic polymer defining a reservoir containing at a minimum, at least one compound of formula (I) and/or (II) as a solid or liquid composition. In a further embodiment, such carriers comprise a thermoelastic polymer matrix, in which a composition described herein is embedded.

The composition may also be sub-divided to contain appropriate quantities of the compound of formula (I) and/or (II). For example, the unit dosage can be packaged compositions, e.g., packeted powders, vials, ampoules, prefilled syringes or sachets containing liquids.

In one embodiment, compositions described herein optionally contain one or more carriers and/or excipients, and one or more compounds of formula (I) and/or (II), optionally with a TRPV1 receptor activator. Examples of suitable excipients include without limitation, surfactants, adjuvants, antioxidants, binders, buffers, coatings, coloring agents, compression aids, diluents, disintegrants, emulsifiers (e g., polyoxyethylene fatty acid esters), emollients, encapsulating materials, fillers, flavoring agents, glidants, granulating agents, lubricants, metal chelators, osmo-regulators, pH adjustors (e.g., sodium hydroxide), preservatives, solubilizers, sorbents, stabilizing agents, sweeteners (such as saccharin), surfactants, suspending agents, syrups, thickening agents (e.g., carboxypolymethylene or hydroxypropylmethylcellulose), penetration enhancers (e.g., hydroxypolyethoxydodecane, DMSO, DMAC, DDM, etc) or viscosity regulators (such as polymers to increase viscosity). See, for example, the excipients described in the "Handbook of Pharmaceutical Excipients", $5^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a modified-release delivery device. "Modified-release" as used herein refers to delivery of a compound of formula (I) and/or (II) which is controlled, for example over a period of at least about 8 hours (e.g., extended delivery) to at least about 12 hours (e.g., sustained delivery). Such devices may also permit immediate release (e.g., therapeutic levels achieved in under about 1 hour, or in less than about 2 hours). Those of skill in the art know suitable modified-release delivery devices. For use in such modified-release delivery devices, the compound of formula (I) and/or (II) is formulated as described herein.

Suitable modified release delivery devices include drug-eluting implants. Such implants can comprise a thermoelastic polymer matrix, such as a silicon or ethylene vinyl acetate matrix, wherein one or more compounds of formula (I) and/or (II), optionally with one or more excipients, is embedded. See, e.g., U.S. Pat. No. 7,736,665 and US Patent Publication No. US-2011/0280922, the disclosures of which are herein incorporated by reference. Other drug-eluting implants can comprise an "osmotic pump" or other mechanism by which a solution comprising one or more compounds of formula (I) and/or (II) (optionally with one or more excipients) contained within the device is forced out, for example through the implant walls or through one or more apertures, by osmotic pressure which builds within the device once it is implanted into a subject. See, e.g., U.S. Pat. Nos. 5,035,891 and 6,464,688, the disclosures of which are herein incorporated by reference. Still other drug-eluting implants can comprise a hydrogel such as a polymethacrylate-based polymer (see, e.g., U.S. Pat. Nos. 5,292,515 and 5,266,325, the disclosures of which are herein incorporated by reference), or a thermoelastic polymer, such as a polyurethane (see, e.g., U.S. Pat. Nos. 7,858,110 and 7,842,303, the disclosures of which are herein incorporated by reference), which define a reservoir containing a solid or liquid composition comprising one or more compounds of formula (I) and/or (II) optionally with one or more excipients. Still other drug-eluting implants can comprise a bio-degradable or bio-erodable polymer and at least one or more compounds of formula (I) and/or (II), optionally with one or more excipients. See, e.g., U.S. Pat. Nos. 4,906,474 and 5,633,002, the disclosures of which are herein incorporated by reference.

Modified release of the compounds of formula (I) and/or (II) may also be achieved by injecting a composition comprising one or more of these compounds into the bladder tissue (e.g., into the urothelium or muscularis propria) with a device that can be employed via an endoscope inserted into the bladder or percutaneously. For example, one or more compounds of formula (I) and/or (II) can be injected into the bladder tissue via a needle, or a needleless device as described in US Patent Publication No. US-2011/0046600, the disclosure of which is incorporated by reference. A suitable needleless injection device includes the JetTouch™ platform (American Medical Systems; Minnetonka, Minn.). The injected compounds can form a depot, and in certain embodiments, the one or more compounds of formula (I) and/or (II) can be encapsulated in a bio-degradable or bio-erodable polymer, for example as described in U.S. Pat. Nos. 5,480,656 and 6,036,976, the disclosures of which are incorporated by reference.

Modified release of the compounds of formula (I) and/or (II) may also be achieved by instilling a composition comprising one or more compounds of formula (I) and/or (II) and a material which solidifies or gels, for example once instilled into the bladder or upon contact with the bladder urothelium, to coat at least a portion of the bladder wall. The one or more compounds of formula (I) and/or (II) can then elute from the solidified or gelled material. See, e.g., U.S. Pat. Nos. 6,894,071; 5,575,815 and 6,039,967, the disclosures of which are incorporated by reference.

In still a further embodiment, the compositions may be administered transdermally, i.e., via the use of a drug-eluting patch. In one embodiment, the patch is an "iontophoretic" transdermal patch in which one or more medication(s) is delivered using a simple or more sophisticated (e.g., microprocessor-controlled) electrical current using, for example, an on-board battery. In still a further embodiment, the patch is a "microneedle" transdermal patch which contains microneedles coated with or containing (in dissolvable or non-dissolvable form) a pharmaceutical composition of the invention. See, e.g., U.S. Pat. Nos. 7,798,987 and 7,537,795, the disclosures of which are herein incorporated by reference. The microneedles can themselves be dissolvable or non-dissolvable; see, for example, the "microneedle" technology described in Sullivan et al., "Dissolving Polymer Microneedle Patches for Influenza Vaccination", Nature Medicine, 16:915-920 (Jul. 18, 2010 online publication) and Lee et al., "Dissolving Microneedle Patch for Transdermal Delivery of Human Growth Hormone", Small, Jan. 4, 2011 online publication, which are herein incorporated by reference. Other suitable transdermal delivery systems include the radio-frequency ablations systems described in Sintov et al., "Radiofrequency-Driven Skin Microchanneling as a New Way for Electrically Assisted Transdermal Delivery of Hydrophilic Drugs", Controlled Release 89: 311-320 (2003), and U.S. Pat. No. 7,558,625, the disclosures of which are herein incorporated by reference.

Further examples of transdermal patches useful for administration of the compounds of formula (I) and/or (II) include those described in U.S. Pat. Nos. 5,411,738 and 5,827,528 and Prausnitz and Langer, "Transdermal drug delivery", Nature Biotechnology, 26(11):1261-1268, November 2006, which are herein incorporated by reference. Desirably, a patch is applied via a suitable adhesive on the skin, where it remains in place for at least one hour. In one embodiment, the patch remains in place for about 1 hour and is replaced weekly, for a total of about 2 or about 3 hours wear time. In another embodiment, the patch remains in place for about 2 hours. In a further embodiment, the patch remains in place for about 3 hours. In still another embodiment, the patch remains in place for about 4 hours. In yet another embodiment, the patch remains in place for longer or shorter periods of time.

Also contemplated is the administration of the compounds of formula (I) and/or (II) with other medication(s) or therapeutic agent(s). In one embodiment, the compounds of formula (I) and/or (II) are combined with other medications or therapeutic agents in a single composition. However, the present invention is not so limited. In other embodiments, the compounds of formula (I) and/or (II) may be administered in one or more separate formulations from other compounds of formula (I) and/or (II), or other medications or therapeutic agents as described below.

In one embodiment, the compounds of the invention may be utilized for treating interstitial cystitis or overactive bladder when combined a TRPV1 receptor activator. The term "TRPV1 receptor activator" as used herein refers to any agent or stimulus that activates TRPV1 receptors on nociceptors or pruriceptors and allows for entry of at least one inhibitor of voltage-gated ion (e.g., sodium or calcium) channels. In one embodiment, the TRPV1 receptor activator includes, but is not limited to, capsaicin, dihydrocapsaicin and nordihydrocapsaicin, lidocaine, articaine, procaine, tetracaine, mepivicaine, bupivicaine, eugenol, camphor, clotrimazole, arvanil (N-arachidonoylvanillamine), anandamide, 2-aminoethoxydiphenyl borate (2APB), AM404, resiniferatoxin, phorbol 12-phenylacetate 13-acetate 20-homovanillate (PPAHV), olvanil (NE 19550), OLDA (N-oleoyldopamine), N-arachidonyldopamine (NADA), 6'-iodoresiniferatoxin (6'-IRTX), C1 8 N-acylethanolamines, lipoxygenase derivatives (such as 12-hydroperoxyeicosatetraenoic acid), inhibitor cysteine knot (ICK) peptides (vanillotoxins), MSK1 95 (N-[2-(3,4-dimethylbenzyl)-3-(pivaloyloxy)propyl]-2-[4-(2-aminoethoxy)-3-methoxyphenyl]acetamide), JYL79 (N-[2-(3,4-dimethylbenzyl)-3-(pivaloyloxy)propyl]-N'-(4-hydroxy-3-methoxybenzyl)thiourea), hydroxy-α-sanshool, 2-aminoethoxydiphenyl borate, 10-shogaol, oleylgingerol, oleylshogaol, SU200 (N-(4-tert-butylbenzyl)-N'-(4-hydroxy-3-methoxybenzyl)thiourea)nonivamide, and fatty acyl amides of tetrahydroisoquinolines. In another embodiment, the TRPV1 receptor activator is lidocaine, aprindine, benzocaine, butacaine, cocaine, dibucaine, encainide, mexiletine, oxetacaine (oxethazaine), prilocaine, proparacaine, procainamide, n-acetylprocainamide, chloroprocaine (nesacaine, nescaine), dyclonine, etidocaine, levobupivacaine, ropivacaine, cyclomethycaine, dimethocaine (larocaine), propoxycaine, trimecaine, and sympocaine. In a further embodiment, the TRPV1 receptor activator is lidocaine. In another embodiment, the TRPV1 activator may be a detergent or a surfactant, examples of which may be found in commonly-used hygiene products such as soaps and shampoos (e.g., sodium lauryl sulfate). See, Lilja et al. "Surfactant-Induced TRPV1 activity—A Novel Mechanism for Eye Irritation?" Technological Sciences, 99(1):174-180, 2007, which is incorporated herein by reference. In another embodiment, the TRPV1 receptor activator is heat or inflammation.

In one embodiment, the therapeutically effective amount of the TRPV1 receptor activator is about 0.0001% to about 10% w/v. One of skill in the art would readily understand that the recited therapeutically effective amount is based on the free base of the TRPV1 receptor activator. By using this information and skill in the art, one would be able to determine the amount of the corresponding TRPV1 receptor activator salt for use in the compositions and methods described herein. In another embodiment, the therapeutically effective amount is less than about 10% w/v, about 9% w/v, about 8% w/v, about 7% w/v, about 6% w/v, about 5% w/v, about 4% w/v, about 3% w/v, about 2% w/v, or about 1% w/v. In another embodiment, the therapeutically effective amount is about 0.1% to about 5% w/v. In a further embodiment, the therapeutically effective amount is about 0.5 to about 3% w/v. In yet another embodiment, the therapeutically effective amount is about 0.5 to about 2% w/v. In another embodiment, the therapeutically effective amount of a TRPV1 receptor activator is about 2% w/v. In another embodiment, the therapeutically effective amount is about 1% w/v. In a further embodiment, the therapeutically effective amount is about 0.5% w/v.

The therapeutically effect amount of the TRPV1 receptor activator may, therefore, be about 0.001 mg to about 100 mg per dose based on a 70 kg mammalian subject. In another embodiment, the therapeutically effective amount is about 0.1 mg to about 25 mg per dose. In a further embodiment, the therapeutically effective amount is about 1 mg to about 5 mg. In yet a further embodiment, the therapeutically effective amount is about 0.1 mg, about 0.5 mg, about 1 mg, about 2 mg, about 3 mg, about 4 mg, about 5 mg, about 6 mg, about 7 mg, or about 8 mg.

The present invention, therefore, provides a composition containing a compound of formula (I) and/or (II) and lidocaine. In one embodiment, the composition contains about 0.01% to about 1% w/v of a compound of formula (I) and/or (II) and about 0.1% to about 5% w/v of lidocaine. In another embodiment, the composition contains about 0.1% to about 0.7% w/v of a compound of formula (I) and/or (II) and about 1% to about 3% w/v of lidocaine. In a further embodiment, the composition contains about 0.2% to about 0.5% w/v of a compound of formula (I) and/or (II) and about 1% to about 3% w/v of lidocaine. In yet another embodiment, the composition contains about 0.2% to about 0.5% w/v of a compound of formula (I) and/or (II) and about 2% w/v of lidocaine. In still another embodiment, the composition contains about 0.2% w/v of a compound of formula (I) and/or (II) and about 2% w/v of lidocaine. In another embodiment, the composition contains about 0.5% w/v of a compound of formula (I) and/or (II) and about 2% w/v of lidocaine. As discussed above, these compositions may be further diluted. In one embodiment, these compositions may be diluted 2-fold. In another embodiment, these compositions may be diluted 4-fold.

Also contemplated for use in the pharmaceutical combinations and methods described below are inhibitors of voltage-gated ion channels. In one embodiment, the voltage-gated ion channels are sodium or calcium ion channels. In a further embodiment, the voltage-gated sodium channel inhibitor includes, without limitation, QX-314, N-methyl-procaine (QX-222), N-octyl-guanidine, 9-aminoacridine, and pancuronium. In another embodiment, the inhibitor of voltage-gated calcium channels includes, but is not limited to, D-890 (quaternary methoxyverapamil) and CERM 1 1888 (quaternary bepridil). In a further embodiment, voltage-gated ion channel inhibitors such as riluzole, mexilitine, phenytoin, carbamazepine, procaine, tocainide, prilocaine, diisopyramide, bencyclane, quinidine, bretylium, lifarizine, lamotrigine, flunarizine, articaine, bupivicaine, mepivicaine, fluspirilene, orphenadrine, phenbenzamine, bepridil, pimozide, penfluridol, fluspirilene, propiverine, disopyramide, methadone, tolterodine, tridihexethyl salts, tripelennamine, mepyramine, brompheniramine, chlorpheniramine, dexchlorpheniramine, carbinoxamine, levomethadyl acetate, gallopamil, verapamil, devapamil, tiapamil, emopamil, dyclonine, pramoxine, lamotrigine, mibefradil, gabapentin, amiloride, diltiazem, nifedipine, nimodipine, nitrendipine, cocaine, mexiletine, propafenone, quinidine, oxethazaine, articaine, riluzole, bencyclane, lifarizine, and strychnine may be combined with the compound of formula (I) and/or (II).

Membrane permeable inhibitors of voltage-gated ion channels may also be utilized in combination with the compound of formula (I) and/or (II) in the compositions, combinations, or methods described herein. In one embodiment, the membrane permeable inhibitor of voltage-gated ion channels includes, but is not limited to, cocaine, carbamazepine, disopyramide, lamotrigine, procainamide, phenytoin, oxcarbazepine, topiramate, zonisamide, tetracaine, ethyl aminobenzoate, prilocaine, disopyramide phosphate, flecainide acetate, mexiletine, propafenone, quinidine gluconate, quinidine polygalacturonate, chloroprocaine, dibucaine, dyclonine, mepivacaine, pramoxine, procaine, tetracaine, oxethazaine, propitocaine, levobupivacaine, bupivacaine, lidocaine, moricizine, tocainide, proparacaine, ropivacaine, quinidine sulfate, encainide, ropivacaine, etidocaine, moricizine, quinidine, encainide, flecainide, tocainide, fosphenytoin, chloroprocaine, dyclonine, L-(−)-1-butyl-2',6'-pipecoloxylidide, and pramoxine.

Additionally, one or more agents typically used to treat pain, i.e., analgesics, may be used in conjunction with a combination of the invention in the methods, compositions, and kits described herein. Such agents include, but are not limited to, non-steroidal anti-inflammatory drugs (NSAIDs), opioids, tricyclic antidepressants, amine transporter inhibitors, and anticonvulsants (such as gabapentinoids).

The compound of formula (I) and/or (II) may be administered together with a vasoconstrictor (e.g., epinephrine or vasopressin) when utilized in injectable solutions.

The compound of formula (I) and/or (II) may be combined with glucose or dextrose when utilized for infusion or as a regional analgesic or anti-pruritic.

Further, the compound of formula (I) and/or (II) may be combined with thickening agents to form a jelly, or may also contain penetration enhancers, for use in topical or dermal applications such as for urogenital topical procedures.

Sprays for topical anesthesia of the mouth and oropharynx may contain the compound of formula (I) and/or (II), saccharin and/or alcohol.

Finally, the compound of formula (I) and/or (II) may be formulated as an ointment for administration to accessible mucous membranes.

One or more additional agents typically used to treat itch may be used in conjunction with a combination of the invention in the methods, compositions, and kits described herein. Such agents include topical or oral steroids and antihistamines.

Additionally, one or more agents typically used to treat interstitial cystitis or overactive bladder may be used in conjunction with a combination of the invention in the methods, compositions, and kits described herein. In one embodiment, the additional agent utilized to treat overactive bladder may be an anticholinergic, e.g., Darifenacin (Enablex® drug), Fesoterodine (Toviaz® drug), Oxybutynin (Ditropan®, Ditropan XL®, Oxytrol®, Gelnique® drugs), Solifenacin (Vesicare® drug), Tolterodine (Detrol® and Detrol® LA drugs), and/or Trospium (Sanctura® drug), an antidepressant, e.g., the tricyclic antidepressant imipramine hydrochloride (Tofranil® drug), botulinum toxin, more commonly known for removing wrinkles, estrogen, an α-blocker, capsaicin, and/or resiniferatoxin.

In another embodiment, the additional agent utilized to treat interstitial cystitis may be a non-steroidal anti-inflammatory drug, e.g., ibuprofen (Advil® or Motrin® drugs), naproxen (Aleve® or Anaprox® drugs), an antidepressant such as a tricyclic antidepressant, e.g., amitriptyline or imipramine (Tofranil® drug), an antihistamine, e.g., diphenhydramine (Benadryl® drug) and loratadine (Claritin® drug), pentosan (Elmiron® drug), among others. The additional agent may, alternatively, be selected from among DMSO (Rimso-50® drug), lidocaine, sodium bicarbonate, pentosan, heparin, hyaluronan, chondroitin sulfate and oxybutynin, or combinations thereof.

Also provided herein are regimens, kits or packages of pharmaceutical formulations containing the compounds of formula (I) and/or (II) or compositions described herein. The kits may be organized to indicate a single formulation or combination of formulations to be taken at each desired time.

Suitably, the kit contains packaging or a container with the compound of formula (I) and/or (II) formulated for the desired delivery route. Suitably, the kit contains instructions on dosing and an insert regarding the compound of formula (I) and/or (II). Optionally, the kit may further contain instructions for monitoring local or circulating levels of product and materials for performing such assays including, e.g., reagents, well plates, containers, markers or labels, and the like. Such kits are readily packaged in a manner suitable for treatment of a desired indication. For example, the kit may also contain instructions for use of a patch, spray pump or other delivery device. Other suitable components to include in such kits will be readily apparent to one of skill in the art, taking into consideration the desired indication and the delivery route and may contain lubricants, antiseptic solutions and local anesthetic agents to facilitate the placement of the delivery device.

The compounds of formula (I) and/or (II) or compositions described herein can be a single dose or for continuous or periodic discontinuous administration. For continuous administration, a package or kit can include the compound of formula (I) and/or (II) in each dosage unit (e.g., solution, lotion, tablet, pill, drug-eluting unit/patch or other unit described above or utilized in drug delivery), and optionally instructions for administering the doses less-than-daily, daily, weekly, or monthly, for a predetermined length of time or as prescribed. When the compound of formula (I) and/or (II) is to be delivered periodically in a discontinuous fashion, a package or kit can include placebos during periods when the compound of formula (I) and/or (II) is not delivered. When varying concentrations of a composition, of the components of the composition, or the relative ratios of the compounds of formula (I) and/or (II) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a foil or blister package, labeled ampoule, vial or bottle.

The packaging means of a kit may itself be geared for administration, such as an inhaler, syringe, pipette, eye dropper, catheter, cytoscope, trocar, cannula, pressure ejection device, or other such apparatus, from which the formulation may be applied to an affected area of the body, such as the lungs, injected into a subject, delivered to bladder tissue or even applied to and mixed with the other components of the kit.

One or more components of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials or other suitable packaging means in close confinement for commercial sale such as, e.g., injection or blow-molded plastic containers into which the desired vials are retained. Irrespective of the number or type of packages and as discussed above, the kits also may include, or be packaged with a separate instrument for assisting with the injection/administration or placement of the composition within the body of an animal. Such an instrument may be an inhaler, syringe, pipette, forceps, measuring spoon, eye dropper, catheter, cytoscope, trocar, cannula, pressure-delivery device or any such medically approved delivery means.

In one embodiment, a kit is provided and contains a compound of formula (I) and/or (II). The compound of formula (I) and/or (II) may be in the presence or absence of one or more of the carriers or excipients described above. The kit may optionally contain instructions for administering the compound of formula (I) and/or (II) to a subject having interstitial cystitis or overactive bladder.

In a further embodiment, a kit is provided and contains a compound of formula (I) and/or (II) in a second dosage unit, and one or more of the carriers or excipients described above in a third dosage unit. The kit may optionally contain instructions for administering the compound of formula (I) and/or (II) to a subject having interstitial cystitis or overactive bladder.

When utilized as described herein, the TRPV1 receptor activator may be utilized in amounts greater or less than the compound of formula (I) and/or (II). In one embodiment, the ratio of the compound of formula (I) and/or (II) to the TRPV1 receptor activator may be determined by the attending physician. In one embodiment, an about 1:1 ratio of the compound of formula (I) and/or (II) to the TRPV1 receptor activator is utilized. In another embodiment, greater than or least about a 1:1 ratio of the compound of formula (I) and/or (II) to the TRPV1 receptor activator is utilized. In a further embodiment, less than a 1:1 ratio of the compound of formula (I) and/or (II) to the TRPV1 receptor activator is utilized. In still a further embodiment, the ratio of the compound of formula (I) and/or (II) to the TRPV1 receptor activator is about 1:0.5. In yet another embodiment, the ratio of the compound of formula (I) and/or (II) to the TRPV1 receptor activator is at least about 1:2. In still another embodiment, the ratio of the compound of formula (I) and/or (II) to the TRPV1 receptor activator is about 1:2. In yet a further embodiment, the ratio of the compound of formula (I) and/or (II) to the TRPV1 receptor activator is about 1:3. In another embodiment, the ratio of the compound of formula (I) and/or (II) to the TRPV1 receptor activator is about 1:4. In yet another embodiment, the ratio of the compound of formula (I) and/or (II) to the TRPV1 receptor activator is about 1:5. In a further embodiment, the ratio of the compound of formula (I) and/or (II) to the TRPV1 receptor activator is about 1:7. In yet another embodiment, the ratio of the compound of formula (I) and/or (II) to the TRPV1 receptor activator is about 1:10. In another embodiment, the ratio of the compound of formula (I) and/or (II) to the TRPV1 receptor activator is about 1:25 or lower. In still a further embodiment, the ratio of the compound of formula (I) and/or (II) to the TRPV1 receptor activator is about 1:0.5 to about 1:25.

The compound of formula (I) and/or (II) may also be administered in prior to, concurrently with, or subsequent to non-medication related therapies. In one embodiment, the compounds of formula (I) and/or (II) may be administered in conjunction with nerve stimulation, e.g., transcutaneous electrical nerve stimulation (TENS) or sacral nerve stimulation.

In a further embodiment, the compounds described herein may be used for the manufacture of a medicament for treating overactive bladder and/or interstitial cystitis.

As discussed above, the methods, compositions, and kits of the invention can be used to treat interstitial cystitis or overactive bladder resulting from a number of conditions.

The term "treat", "treating", or any variation thereof is meant to include therapy utilized to remedy a health problem or condition in a patient or subject. In one embodiment, the health problem or condition may be eliminated permanently or for a short period of time. In another embodiment, the severity of the health problem or condition, or of one or more symptoms characteristic of the health problem or condition, may be lessened permanently, or for a short period of time. The effectiveness of a treatment of interstitial cystitis or overactive bladder can be determined using any standard index, such as those described herein, or can be determined based on the patient's subjective assessment. A patient is considered "treated" if there is a reported reduction in symptoms related to overactive bladder activity or interstitial cystitis. In one embodiment, the compounds of formula (I) and/or (II) are useful for treating interstitial cystitis or overactive bladder, as these compounds may selectively modulate the nervous system affecting sensory aspects of OAB and IC without affecting or negatively impacting motor neuron function associated with bladder and sphincter control.

In order to measure the efficacy of any of the methods, compositions, or kits described herein, a measurement index may be used. Indices that are useful for the measurement of overactive bladder are known in the art and include patient-reported outcome devices or notebooks and urodynamic measurements of urinary incontinence such as the measurement of micturition volume using condom catheters and other physical collection devices.

Indices that are useful of the measurement of the pain associated with interstitial cystitis include the interstitial cystitis symptom index (ICSI), the interstitial cystitis problem index (ICPI), the pain-urgency-frequency score (PUF), the Wisconsin Symptom Instrument (UWI) and a visual analog scale (VAS) such as the Likert scale and other categorical pain scales.

A visual analog scale (VAS) provides a measure of a one-dimensional quantity. A VAS generally utilizes a representation of distance, such as a picture of a line with hash marks drawn at regular distance intervals, e.g., ten 1-cm intervals. For example, a patient can be asked to rank a sensation of pain or itch by choosing the spot on the line that best corresponds to the sensation of pain or itch, where one end of the line corresponds to "no pain" (score of 0 cm) or "no itch" and the other end of the line corresponds to "unbearable pain" or "unbearable itch" (score of 10 cm). This procedure provides a simple and rapid approach to obtaining quantitative information about how the patient is experiencing pain or itch. VAS scales and their use are described, e.g., U.S. Pat. Nos. 6,709,406 and 6,432,937, the relevant disclosures of which are herein incorporated by reference.

A Likert scale similarly provides a measure of a one-dimensional quantity. Generally, a Likert scale has discrete integer values ranging from a low value (e.g., 0, meaning no pain) to a high value (e.g., 7, meaning extreme pain). A patient experiencing pain is asked to choose a number between the low value and the high value to represent the degree of pain experienced. Likert scales and their use are described, e.g., U.S. Pat. Nos. 6,623,040 and 6,766,319, the relevant disclosures of which are herein incorporated by reference.

The O'Leary-Sant score and IC Problem Index are self-administered indices for measuring lower urinary tract symptoms.

The Pain-Urgency-Frequency symptom scale is balanced assessment of urinary dysfunction, pelvic pain and symptoms associated with sexual intercourse and frequently used in conjunction with intravesical potassium chloride administration.

The UWI utilizes seven IC-related questions about frequency, urgency, noctuira and pain.

In one embodiment, the treatment methods described herein include administering a compound of formulae (I) and/or (II) to a patient. Additional, optional agents, such as those described above for use in the combination, may be administered to the patient prior to, concurrently with, or subsequent to the compound of formulae (I) and/or (II).

In another embodiment, the methods described herein thereby include administering a compound of formulae (I) and/or (II) and with/without a TRPV1 receptor activator to a patient. In one embodiment, the compound of formulae (I) and/or (II) is administered to the patient prior to the TRPV1 receptor activator. In another embodiment, the TRPV1 receptor activator is administered to the patient prior to the compound of formulae (I) and/or (II). In a further embodiment, the compound of formulae (I) and/or (II) and TRPV1 receptor activator are administered to the patient concurrently.

In a further embodiment, the compounds described herein may be used for the manufacture of a medicament for treating overactive bladder and/or interstitial cystitis.

Also contemplated by the present invention is administration of a compound of formulae (I) and/or (II) after the TRPV1 receptor has been activated. Specifically, this method is performed after the TRPV1 receptor is activated. Such activation may result from administration of an exogenous activating compound or stimulus, or may arise as a result of endogenous activation induced by a pathophysiological state, such as inflammation, that activates TRPV1 receptors.

A variety of in vivo assays and animal models are useful for assessing the ability of compounds to inhibit pain via internal sodium channel inhibition. These models may or may not involve opening (activation) of TRPV1 channels via inducing pain through physical, mechanical, or chemical (e.g., capsaicin) means. Examples of suitable models include, e.g., the use of isolated bladder detrusor muscle preparations (Witte, Naunyn-Schmeideberg's Arch. Pharmacol. 2011, 384:555-563), measurement of voiding frequency and volume in freely moving animals (Clouse, 2012, Urology 79:1410e1-1410e6), measurement of bladder urodynamics using cystometry in anesthetized animals (Shimizu, 2000, British Journal of Pharmacology 131:610-616), which are incorporated by reference herein. However, for a variety of reasons which will be readily apparent to those of ordinary skill in the art, it is desirable to provide in vitro assays which allow for the identification of compounds with the desired properties. Described herein are two such in vitro assays.

In one embodiment, a modified FLIPR® (Fluorometric Imaging Plate Reader) based assay system was developed which is capable of discriminating between non-specific versus hTRPV1-mediated entry of test compounds. Advantageously, the assay system utilizes heat activated opening of hTRPV1 channels followed by an assessment of internal sodium channel block. The assay allows a permanently charged compound to selectively enter through opened hTRPV1 channels and that compound's potency in inhibiting sodium channels from the cytoplasm side of the same cell can be assessed and quantified.

The modified FLIPR® assay utilizes cells which functionally express hTRPV1.

As used herein, the term "functionally express" includes those cells which express the human TRPV1 protein and which respond to stimuli which naturally open this channel, including, e.g., the thermal (e.g., heat) or chemical (e.g., capsaicin, lidocaine) means described herein. Suitable assays may include the calcium or membrane potential assays described herein. However, other functional assays are known in the art (e.g., voltage-clamp electrophysiology such as used by Binshtok, Nature, 449(4) 607-610, 2007)

A suitable cell may be selected for expression of TRPV1 in cis or in trans and constructed using known techniques. In one embodiment, a neuroblastoma cell line such as N1E115 [CRL-2263] or ND7/23 [ECACC catalog code: 92090903] is selected for expression of the hTRPV1. However, another neuroblastoma cell line may be selected, e.g., such as IMR-32 [CRL-127]; Neuro-2a [CRL-131]; NB41A3 [CRL-147]; B104-1-1 [CRL-1887]; SK-N-AS [CRL-2137]; SK-N-F1 [CRL-2142]; SK-N-DZ [CRL-2149]; SH-SY5Y [CRL-2266]; BE(2)-M17 [CRL-2267]; BE(2)-C [CRL-2268]; MC-IXC [CRL-2270]; SK-N-BE(2) (CRL-2271); CHP-212 (CRL-2273]; B35 [CRL-2754], which are available from the American Type Culture Collection, Manassas, Va. (US). Still other cell lines may be selected.

For a generation description of how the cells are produced, see generally, e.g., Sambrook, Molecular Cloning: A Laboratory Manual, Cold Spring Harbor Press, Cold Spring Harbor, N.Y. (US) 2001. In one embodiment, a stable cell line may be prepared using the techniques in Sambrook, using wild-type (wt) or recombinant hTRPV1 coding sequences. For example, preparation of one such cell line is described in detail herein. Preparation of another cell line is described in International Patent Publication No. WO-2007/0066068; the Lipofectamine® method may be employed for transfection of TRPV1 and hTRPV1 into Human Embryonic Kidney cells (HEK293) according to the manufacturer's protocol (Gibco). To create a permanently expressing cell line, wt-TRPV1 transfected HEK cells can be subcloned in geneticin (0.6 mg/mL) containing medium (DMEM containing 10% FCS, 100 U/mL penicillin, 100 μg/mL streptomycin, and 250 ng/mL amphotericin B) and propagated for two weeks to allow selection. To obtain a TRPV1 permanently expressing single cell line, transfected cells can be plated in 96 well plates (1 cell per well) and colonies grown from single cells were subsequently tested for capsaicin responsiveness by measuring increases in intracellular calcium. The final clones selected, are taken through three further rounds of single cell cloning to ensure the cell lines are derived from a single cell. Variations on this methodology will be readily apparent to one of skill in the art. In another embodiment, a cells may be selected from a stable cell line to express the hTRPV1, in trans, e.g., from a viral vector or another suitable genetic element.

In one embodiment, the hTRPV1 protein is selected which has the sequence of SEQ ID NO:1 [NCBI Accession Number NM_080706.3].

```
  1 MKKWSSTDLG AAADPLQKDT CPDPLDGDPN SRPPPAKPQL STAKSRTRLF GKGDSEEAFP

61 VDCPHEEGEL DSCPTITVSP VITIQRPGDG PTGARLLSQD SVAASTEKTL RLYDRRSIFE

121 AVAQNNCQDL ESLLLFLQKS KKHLTDNEFK DPETGKTCLL KAMLNLHDGQ NTTIPLLLEI

181 ARQTDSLKEL VNASYTDSYY KGQTALHIAI ERRNMALVTL LVENGADVQA AAHGDFFKKT

241 KGRPGFYFGE LPLSLAACTN QLGIVKFLLQ NSWQTADISA RDSVGNTVLH ALVEVADNTA

301 DNTKFVTSMY NEILMLGAKL HPTLKLEELT NKKGMTPLAL AAGTGKIGVL AYILQREIQE

361 PECRHLSRKF TEWAYGPVHS SLYDLSCIDT CEKNSVLEVI AYSSSETPNR HDMLLVEPLN

421 RLLQDKWDRF VKRIFYFNFL VYCLYMIIFT MAAYYRPVDG LPPFKMEKTG DYFRVTGEIL

481 SVLGGVYFFF RGIQYFLQRR PSMKTLFVDS YSEMLFFLQS LFMLATVVLY FSHLKEYVAS

541 MVFSLALGWT NMLYYTRGFQ QMGIYAVMIE KMILRDLCRF MFVYIVFLFG FSTAVVTLIE
```

```
601 DGKNDSLPSE STSHRWRGPA CRPPDSSYNS LYSTCLELFK FTIGMGDLEF TENYDFKAVF

661 IILLLAYVIL TYILLLNMLI ALMGETVNKI AQESKNIWKL QRAITILDTE KSFLKCMRKA

721 FRSGKLLQVG YTPDGKDDYR WCFRVDEVNW TTWNTNVGII NEDPGNCEGV KRTLSFSLRS

781 SRVSGRHWKN FALVPLLREA SARDRQSAQP EEVYLRQFSG SLKPEDAEVF KSPAASGEK
```

However, one of skill in the art that minor modifications may be made to this sequence while retaining the desired functionality of the protein. Alternatively, one could select another TRPV1 protein (e.g., from a guinea pig, mouse, or other species) and modify that sequence for use in the present invention. Such modifications may be made for a variety of reasons, including, e.g., to improve yield or purification.

In order to prepare an hTRPV1-expressing cell, a construct containing the coding sequence for the above-identified hTRVP1 sequence is selected. In one embodiment, the coding sequence is any sequence which encodes the above-identified protein. In another embodiment, the coding sequence is selected from one of the four transcript variants reported in NCBI for human TRPV1 (hTRPV1), (NM_018727.5, NM_080704.3, NM_080705.3, and NM_080706.3). The functional protein coding sequence (ORF—Open Reading Frame) for all the four transcripts is same. In one embodiment, the construct contains the functional protein coding sequence only. However, in another embodiment, another variant, including the longest variant (variant 3, NCBI Accession No: NM_080706.3) may also be used. In still another embodiment, another ORF, or another sequence containing the ORF, is selected. In one embodiment, the sequence is cloned from an existing construct such as described herein. In another embodiment, a recombinant sequence is used.

While the use of cells which are infected or transfected such that they express hTRPV1 in trans is possible, the use of a cell line which stably expresses the hTRPV1 channel is desirable. Such cell lines can be generated by one of skill in the art utilizing the information available herein and known in the art.

In one embodiment, in order to prepare the cell line, hTRPV1 is amplified by PCR from IMR322 cDNA (a neuroblastoma cell line). The PCR product obtained containing the protein coding sequence of hTRPV1 is cloned into a production vector under the control of a strong promoter. As illustrated below, the human cytomegalovirus promoter was used. However, another promoter with strong constitutive expression in mammalian host cells may also be used. Optionally, the sequence may be verified by PCR. The cells which are to be transduced (e.g., the N1E115 cells) are prepared using Lipofectamine™ 2000 reagent (Invitrogen, Catalog No. 11668-019), as described herein. The transduced cells are passaged using conventional methods and standard transfection techniques where utilized. By the end of second week, transfected stable colonies appear, which are then expanded and tested functionally. Final clonal candidate for the study was selected based on the functional assay data. These assays assess the ability of the cell to express hTRPV1 in a functional manner, i.e., such that upon being contacted with at least one of stimuli to which wt hTRPV1 respond, the hTRPV1 channel opens. For example, a cell expressing a functional hTRPV1 may respond to capsaicin, or to heat, or to other chemical, mechanical or physical stimuli characteristic of hTRPV1 in its natural setting. Examples of suitable assays include the membrane potential and calcium assays. Other suitable assays include standard single-cell voltage-clamp electrophysiology approaches such as used by Binshtok, Nature, 449(4):607-610, 2007. The TRPV1 assay is performed using a FLIPR®-384 fluorescence measurement platform (Molecular Devices, Inc.) operating in a membrane potential assay mode, or another suitable system, using hTRPV1-expressing cells as described herein. FLIPR® Membrane Potential Assay Kits (both blue and red) are available from Molecular Devices, Inc. (Sunnyvale, Calif., USA), which provides many of the dyes and materials used in the following assay. However, similar materials may be obtained from other sources as needed or desired.

The assay described herein used a method of activation for the TRPV1 channel which differs from that typically described in the literature and the art (i.e., capsaicin). The use of capsaicin to open the hTRPV1 channel in the cells proved to be unsuitable since it eroded the signal-to-noise window of the subsequent sodium channel response component of the assay in the hTRPV1-N1E115 cell line. Alternatively, it is anticipated that another cell line prepared as described herein could be substituted for this cell line. Therefore, another method to open the channel had to be developed. The heat activation method used herein has been found to yield robust and reproducible performance.

The assay is readily performed in multi-well assay plates into which cells in growth media are added and incubated under conditions which permit the formation of a confluent monolayer over a period of hours prior to the start of the assay. Conventional culture media and conditions may be utilized. Duplicate cell assay plates are prepared for each experiment.

The spent media from the cell seeded plates is removed on the day of the assay and replaced with Membrane potential Dye-Blue (Molecular Devices, Inc.). The dye was prepared in assay buffer following manufacturer's instructions. The dye-loaded plate is incubated at room temperature (about 25° C.) for about 30 minutes in order to pre-load the cells with dye. Optionally, the cells may be loaded with the dye simultaneously with adding the test compounds.

An illustrative assay buffer is prepared using purified, deionized water according to Table 1. While the precise components may be varied, the ionic nature of the assay buffer is desirable for use in the assay. The pH is adjusted to 7.4 using potassium hydroxide and the volume is made up with Milli-Q® water (Millipore) up to 500 mL. Unless otherwise mentioned, all the dilutions were done in Assay Buffer.

TABLE 1

| Salt | Concentration (mM) |
| --- | --- |
| NaCl | 150 |
| KCl | 3.25 |
| $CaCl_2 2H_2O$ | 2 |
| $MgCl_2 6H_2O$ | 3 |
| HEPES | 10 |
| Glucose | 11 (198 mg/100 mL) |

The test compounds are diluted in the Assay Buffer and added to each well of a specific 384-well 'compound plate', which serves as a source plate for compound addition using the FLIPR® platform. The concentration of compounds in the compound-plate was adjusted to achieve the desired final concentration when added to the cells in the 'cell-plate'. After completion of the dye incubation period, the dye loaded cell-plates and the compound source plates are inserted into the FLIPR® Tetra device with a 384 FLIPR® tip box (Molecular Devices, Inc.) according to manufacturer's instructions. The compounds are robotically added to the dye loaded cell-plates using software integral to the FLIPR® Tetra instrument.

Immediately following compound addition, hTRPV1 is activated, in one of the duplicate cell plates, by heating. Specifically, entire multi-well plate containing the compound-cells mixture is incubated at 47° C. for 10 minutes, after which they are returned to room temperature (about 25° C.) for a further 30 minutes. Heat activation of hTRPV1 was omitted from the replicate cell plate which was simply maintained at room temperature for the entire 40 minutes.

A membrane potential response is elicited in the dye- and compound-loaded cells by the addition of veratridine which is a known sodium channel 'agonist'. As illustrated herein, an agonist plate containing veratridine (Sigma) is prepared in advance and is inserted into suitable devices such as, e.g., the FLIPR® TETRA device for a "$2^{nd}$ addition" as instructed by the manufacturer. The concentration of veratridine in the 'agonist plate' was adjusted to achieve a final concentration of 100 μM when added to the cells in the cell-plate. Final concentrations of veratridine greater or lesser than 100 μM may also be used but the signal measured by the FLIPR® Tetra device or another suitable device may vary accordingly.

The exposure of the cells in the cell-plate to veratridine induces sodium channels in the cells to open and the resulting ion flux produces a membrane potential depolarization that is detected as a fluorescence signal by the FLIPR® Tetra Device. The activity of test compounds is determined by their ability to attenuate the veratridine-induced fluorescence signal, the most promising compounds are those that show an enhanced activity in the heat-activated cell plate over the non-heat-activated cell plate. This differential activity reflects enhanced compound uptake via the heat activated and open hTRPV1 channels and rests on the fact that sodium channel block requires test compounds to act from the cytoplasmic side of the cell membrane.

Once assessed using these screening assays, compounds may be selected for study in animal models.

The following examples are illustrative only and are not intended to limit the present invention.

EXAMPLES

Unless otherwise stated, all the raw materials are purchased from commercially available common suppliers. $^1$H-NMR spectra were recorded using trimethylsilane (TMS) as the internal reference for CDCl$_3$ dissolved compounds. For DMSO-d$_6$, MeOD and D$_2$O dissolved compounds the instrument was calibrated at δ 2.5, 3.3 and 4.82 ppm respectively. The chemical shift values are quoted in δ (parts per million).

For LCMS analysis LCMS/MS API 2000 (Applied Biosystem) instrument was used. The columns included:
  Column V: Zorbax® C18 column, 4.6×50 mm, 5μ
  Column W: Zorbax® Extend C18 column, 4.6×50 mm, 5μ
  Column X: Gemini® NX C18 column, 4.6×50 mm, 5μ
  Column Y: Xbridge® C18 column, 4.6×50 mm, 5μ
  Column Z: Reprosil® column, 4.6×50 mm, 5μ

The eluent (solvent) typically included (acidic or basic buffer as aqueous phase):
  A channel: (i) 0.05% formic acid in water;
    (ii) 10 mM ammonium acetate in water; or
    (iii) 0.05% TFA in water.
  B channel: acetonitrile (organic phase).

The detector was UV measured at dual wavelengths: 220 and 260 nm.

The LCMS gradients were one of the following:
1. LCMS reaction monitoring and final compound analysis method (for general polarity compounds)
  Gradient condition: 5 minutes run time
  Time Programs: P1: 10 mM ammonium acetate in water/acetonitrile
    Q1: 0.05% TFA in water/acetonitrile,
    R1: 0.05% formic acid in water/acetonitrile.
  The gradient varied acetonitrile from 10% to 90% to 10%.
  Flow rate: 1.2 mL/minute
2. LCMS reaction monitoring and final compound analysis method in 12 minutes run (for close eluting compounds):
  Gradient condition: 12 minutes run time
  Time Programs: P2: 10 mM ammonium acetate in water/acetonitrile
    Q2: 0.05% TFA in water/acetonitrile
    R2: 0.05% formic acid in water/acetonitrile
  The gradient varied acetonitrile from 5% to 90% to 5%
  Flow rate: 1.0 mL/minute
3. LCMS after method development in HPLC—gradient conditions are as per HPLC.

Mass spectral data was obtained using the following:
  Ionization technique: ESI (Electron Spray Ionization) using API
    (Atmospheric pressure Ionization) source
  Declustering Potential: 10-70 V depending on the ionization of
    compound
  Mass range: 100-800 amu
  Scan type: Q1
  Polarity: +/−ve
  Ion Source: Turbo spray
  Ion spray voltage: +5500 for +ve mode and −4500 for −ve mode
  Mass Source temperature: 200° C.

HPLC analysis was carried out using the Shimadzu® LC-2010, the Agilent® 1200 series, and Waters® Alliance® HT instruments. The columns included:
  (i) Zorbax® SB C18 column (50×4.6 mm) 1.8μ
  (ii) Atlantis® dC18 column (150×4.6 mm) 5μ
  (iii) Gemini® NX C18 column (50×4.6 mm) 3μ
  (iv) XBridge® C18 column (50×4.6 mm) 3μ
  (v) XBridge® C18 column (50×4.6 mm) 5μ
  (vi) XTerra® C18 column (250×4.6 mm) 5μ
  (vii) Gemini® C18 column (50×4.6 mm) 5μ
  (viii) Zorbax® SB-C18 column (4.6×50 mm) 5μ
  (ix) Sunfire®-C18 column (150×4.6 mm) 5μ.

The mobile phases included the following and the mobile phase gradients were changed from A. 90% to 10% to 90%. Flow rate was 1 mL/minute.
  A. 0.05% TFA in water, 0.05% HCOOH in water, 0.05% Acetic acid in water, 10 mM ammonium acetate in water (acidic or basic buffer); and
  B. acetonitrile or methanol (organic phase).

Ultra Performance Liquid Chromatography (UPLC) analysis was carried out using Agilent® 1100 series and 1200 series instruments. The columns included:
  (i) Zorbax® SB C18 column (50×4.6 mm) 1.8μ
  (ii) Zorbax® XDB C18 column (50×4.6 mm) 1.8μ
  (iii) Gemini® NX C18 column (50×4.6 mm) 3μ
  (iv) XBridge® C18 column (50×4.6 mm) 3μ
operating at ambient temperature. The mobile phase included the following and mobile phase gradients were changed from A. 95% to 5% to 95%. Flow rate varied from 0.8 to 1 mL/minute.
  A. 0.05% TFA in water, 0.05% HCOOH in water
  B. Acetonitrile

Example 1

General Procedure A1

Preparation of (S)-1,1,-dipropyl-2-[2-((indan-2-yl)(phenyl)amino)ethyl]piperidinium iodide

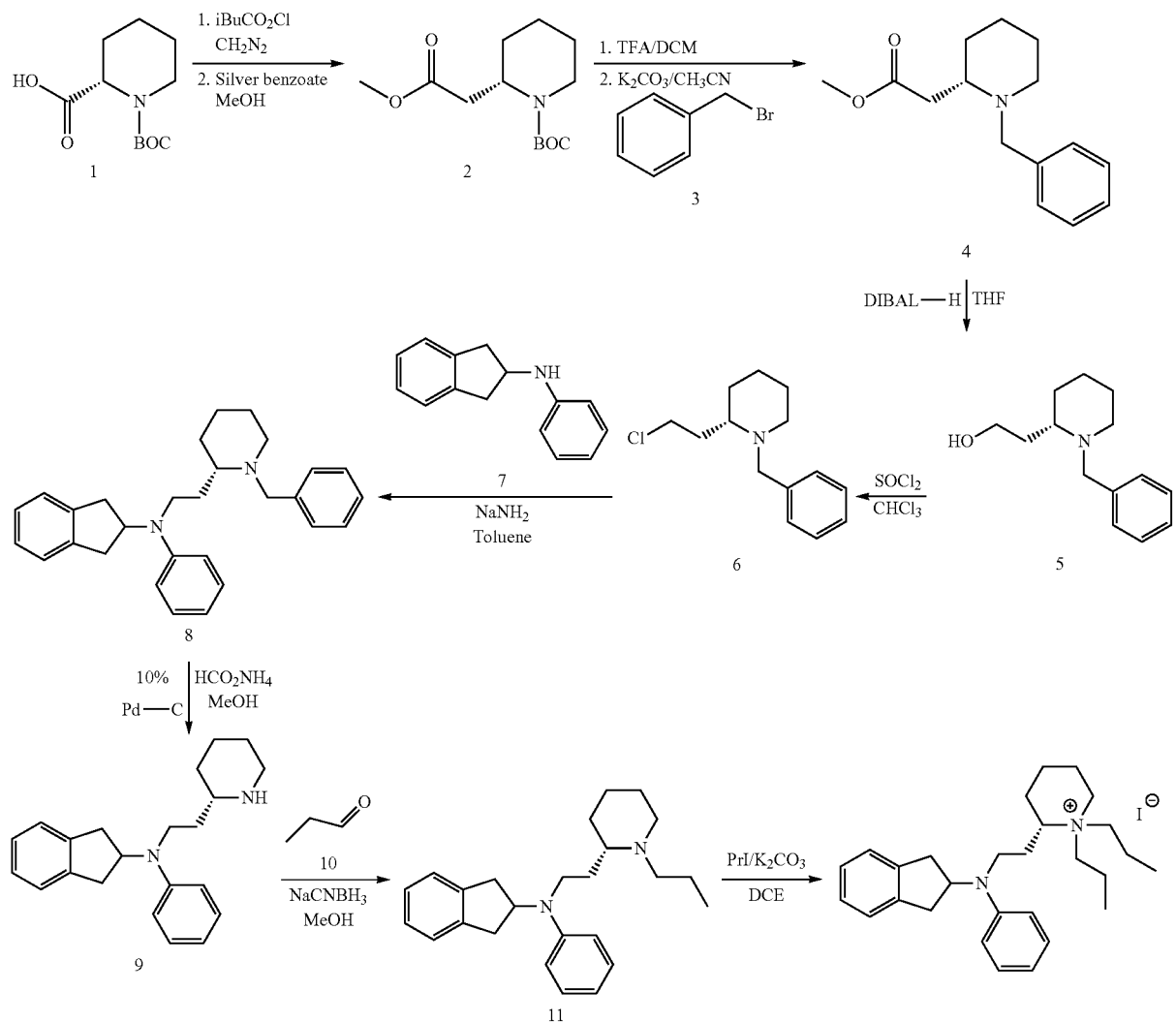

A. (S)-2-(Methoxycarbonylmethyl)piperidine-1-carboxylic acid tert-butyl ester (Compound 2)

To a stirred solution of boc-L-pipecolic acid (1; 15 g, 68.10 mmol) in tetrahydrofuran (THF; 175 mL) was added N-methyl morpholine (9.4 mL, 85.12 mmol) at −30° C., followed by the addition of isobutyl chloroformate (9.8 mL, 74.90 mmol) dropwise at −30° C. The resulting mixture was stirred at that temperature for 1 hour. A solution of diazomethane in diethyl ether was then added to the reaction mixture and the mixture was stirred at room temperature (rt) for 16 hours. The reaction mixture was quenched by adding glacial acetic acid (10 mL) and was then concentrated. The residue was dissolved in diethyl ether (500 mL), washed with water (100 mL) and brine (25 mL). The combined organic layers were dried, filtered and concentrated.

The crude material was dissolved in methanol (130 mL), silver benzoate (4 g) was added portion-wise at ice cold conditions and the mixture was stirred at rt for 16 hours. Brine solution (50 mL) was added to the reaction mixture and filtered through the Celite® reagent and washed with methanol. The organic layer was evaporated in vacuo, the residue was diluted with ethyl acetate (EtOAc, 470 mL) and washed with water (50 mL) and brine (20 mL). The organic layer was dried, filtered and concentrated. The crude material was purified by chromatography using 230-400 mesh silica gel eluting with 3% EtOAc in hexane to provide compound 2 as a liquid. Yield: 10.2 g (58.28%);

$^1$H-NMR (400 MHz, DMSO-$d_6$): δ 4.51 (s, 1H), 3.81 (d, J=11 Hz, 1H), 3.57 (s, 3H), 2.77-2.74 (m, 1H), 2.55 (d, J=7 Hz, 2H), 1.58-1.52 (m, 6H), 1.37 (s, 9H);

LCMS: [M+H]=258.2, RT=3.55 minutes, (Program R1, Column X).

B. (S)-2-(1-Benzyl-piperidin-2-yl)acetic acid methyl ester (Compound 4)

To a stirred solution of compound 2 (10 g, 38.91 mmol) in dichloromethane (DCM; 70 mL) was added trifluoroacetic acid (TFA; 20 mL) dropwise at ice cold conditions and the reaction mixture was stirred at rt for 4 hours. The solvent of the reaction mixture was evaporated in vacuo. The crude material was dissolved in acetonitrile (130 mL), K$_2$CO$_3$ (27 g, 194.55 mmol) was added portion-wise at ice cold conditions, and the reaction mixture was stirred for 15 minutes. Benzyl bromide (3; 7 mL, 58.37 mmol) was then added dropwise and the resulting mixture was heated at 100° C. for 16 hours. The mixture was filtered and washed with EtOAc. The organic layer was washed with water (75 mL) and brine (30 mL). The combined organic layers were dried, filtered and concentrated. The crude material was purified by Combiflash® chromatography eluting with 4.5% EtOAc-hexane to provide compound 4 as a liquid.

Yield: 6.1 g (63.47%);
$^1$H-NMR (400 MHz, DMSO-$d_6$): δ 7.32-7.21 (m, 5H), 3.75 (d, J=14 Hz, 1H), 3.58 (s, 3H), 3.30 (d, J=14 Hz, 1H), 2.87-2.84 (m, 1H), 2.69 (dd, J=15, 5 Hz, 1H), 2.56-2.52 (m, 1H), 2.47-2.41 (m, 1H), 2.15-2.10 (m, 1H), 1.64-1.52 (m, 2H), 1.44-1.32 (m, 4H);
LCMS: [M+H]=248.0, RT=3.61 minutes (Program P1, Column Y).

C. (S)-2-(1-Benzyl-piperidin-2-yl)ethanol (Compound 5)

To a stirred solution of compound 4 (6 g, 24.29 mmol) in dry THF (200 mL) was added diisobutylaluminum hydride (DIBAL-H; 1.2 M in toluene, 81 mL, 97.16 mmol) drop-wise at −30° C. The reaction mixture was then stirred at 0-5° C. for 4 hours. The reaction mixture was quenched by adding saturated NH$_4$Cl solution (15 mL) at −50° C. The reaction mixture was concentrated and diluted with EtOAc. The organic layer was washed with water and brine, dried over Na$_2$SO$_4$, filtered and concentrated to provide compound 5.

Yield: 5.1 g (95.87%);
$^1$H-NMR (400 MHz, DMSO-$d_6$): δ 7.30-7.18 (m, 5H), 4.40 (s, 1H), 3.87 (d, J=14 Hz, 1H), 3.51-3.44 (m, 2H), 3.23 (d, J=14 Hz, 1H), 2.62-2.58 (m, 1H), 2.44-2.42 (m, 1H), 2.05-2.00 (m, 1H), 1.82-1.77 (m, 1H), 1.66-1.59 (m, 3H), 1.40-1.23 (m, 5H);
LCMS: [M+H]=220.5, RT=1.78 minutes (Program P1, Column Y).

D. (S)-1-Benzyl-2-(2-chloroethyl)piperidine (Compound 6)

A solution of compound 5 (3.5 g, 15.98 mmol), thionyl chloride (6 mL) and four drops of concentrated HCl in chloroform (40 mL) was heated at 75° C. for 16 hours. The reaction mixture was concentrated, saturated sodium bicarbonate solution (50 mL) was added, and the product extracted with EtOAc. The organic layer was separated and washed with water and brine, dried over Na$_2$SO$_4$, filtered and concentrated. The crude material was purified by Combiflash® chromatography eluting with 3.5% EtOAc in hexane to provide compound 6 as a liquid.

Yield: 3.1 g (81.85%);
$^1$H-NMR (400 MHz, DMSO-$d_6$): δ 7.30-7.22 (m, 5H), 3.82 (d, J=14 Hz, 1H), 3.72-3.62 (m, 2H), 3.32-3.30 (m, 1H), 2.63-2.55 (m, 2H), 2.12-2.04 (m, 2H), 1.99-1.89 (m, 1H), 1.66-1.59 (m, 2H), 1.42-1.32 (m, 4H);
LCMS: [M+H]=237.8, RT=3.78 minutes (Program P1, Column Y).

E. (S)—N-[2-(1-Benzyl-piperidin-2-yl)ethyl]-N-phenylindan-2-yl-amine (Compound 8)

To a stirred solution of NaNH$_2$ (0.74 g, 18.99 mmol) in toluene (80 mL) was added a solution of compound 7 (2.91 g, 13.92 mmol) in toluene (10 mL) dropwise at ice cold conditions and the mixture was stirred at rt for 3 hours. A solution of compound 6 (3 g, 12.66 mmol) in toluene (10 mL) was then added to the reaction mixture dropwise at ice cold conditions and the mixture was heated at 110° C. for 16 hours. This reaction mixture was diluted with EtOAc (70 mL) and washed with water and brine. The organic layer was dried over Na$_2$SO$_4$, filtered and concentrated. The crude material was purified by Combiflash® chromatography eluting with 11.2% EtOAc in hexane to provide compound 8, which was isolated as a sticky solid.

Yield: 1.5 g (28.90%);
$^1$H-NMR (400 MHz, DMSO-$d_6$): δ 7.30-7.10 (m, 11H), 6.79 (d, J=8 Hz, 2H), 6.64 (t, J=7 Hz, 1H), 4.64-4.61 (m, 1H), 3.67 (d, J=14 Hz, 1H), 3.23-3.15 (m, 5H), 2.95-2.90 (m, 2H), 2.53-2.50 (m, 1H), 2.31 (brs, 1H), 2.02-1.98 (m, 1H), 1.67-1.60 (m, 2H), 1.51-1.49 (m, 2H), 1.35-1.17 (m, 4H);
LCMS: [M+H]=411.0, RT=3.20 minutes (Program P1, Column Y).

F. (S)-2-N-Phenyl-N-[2-(piperidin-2-yl)ethyl]indan-2-yl-amine (Compound 9)

A stirred solution of compound 8 (0.55 g, 1.34 mmol) and ammonium formate (0.85 g, 13.41 mmol) in methanol (30 mL) was purged with N$_2$ for 30 minutes. Ten percent Pd—C (0.07 g) was added and purging was continued for 5 additional minutes. The resulting mixture was heated at 100° C. for 3 hours. The reaction mixture was filtered through the Celite® reagent and washed with methanol. The filtrate was concentrated and the crude material was dissolved in 50% acetonitrile-water mixture and lyophilized to provide compound 9.

Yield: 0.4 g (93.14%);
$^1$H-NMR (DMSO-$d_6$): δ 7.24-7.10 (m, 6H), 6.81 (d, J=8 Hz, 2H), 6.63 (t, J=7 Hz, 1H), 4.68-4.60 (m, 1H), 3.38-3.36 (m, 1H), 3.24-3.11 (m, 3H), 2.96 (dd, J=16, 8 Hz, 2H), 2.93-2.88 (m, 1H), 2.45-2.35 (m, 2H), 1.66-1.65 (m, 1H), 1.47-1.45 (m, 4H), 1.27-1.23 (m, 2H), 0.96-0.93 (m, 1H);
LCMS: [M+H]=320.8, RT=3.03 minutes (Program P1, Column Y).

G. (S)—N-Phenyl-N-[2-(1-propyl-piperidin-2-yl)ethyl]indan-2-yl-amine (Compound 11)

To a stirred solution of compound 9 (0.35 g, 1.09 mmol) in methanol (15 mL) was added NaCNBH$_3$ (0.082 g, 1.2 mmol) at ice cold conditions and the mixture was then stirred at rt for 30 minutes. Propanaldehyde (10; 0.1 mL, 1.37 mmol) was added to the reaction mixture drop-wise at ice cold conditions and the mixture was stirred at rt for 16 hours. The reaction mixture was concentrated using a rotavapour. The crude material was purified by Combiflash® chromatography eluting with 4.6% MeOH in DCM to provide compound 11.

Yield: 0.37 g (93.59%);
$^1$H-NMR (400 MHz, DMSO-$d_6$): δ 7.22-7.15 (m, 6H), 6.89-6.87 (m, 2H), 6.73-6.70 (m, 1H), 4.63-4.61 (m, 1H), 3.33-3.31 (m, 1H), 3.23-3.16 (m, 6H), 2.99-2.94 (m, 4H), 1.99-1.97 (m, 1H), 1.72-1.53 (m, 10H), 0.85-0.82 (m, 6H);
LCMS: [M+H]=363.0, RT=3.44 minutes (Program P1, Column Y).

H. (S)-1,1-Dipropyl-2-[2-((indan-2-yl)(phenyl)amino)ethyl]piperidinium iodide To a stirred solution of compound 11 (0.25 g, 0.69 mmol) in dichloroethane (DCE, 5 mL) were added K$_2$CO$_3$ (1.15 g, 8.29 mmol) and 1-iodopropane (3 mL) in a sealed tube and the mixture was heated at 65° C. for 16 hours. The reaction mixture was filtered and washed with DCM. The organic layer was concentrated using a rotavapour. The crude material was purified by Combiflash® chromatography eluting with 5.3% methanol (MeOH) in DCM to provide (S)-1,1-dipropyl-2-[2-((indan-2-yl)(phenyl)amino)ethyl]piperidinium iodide.

Yield: 0.12 g (31.32%);

$^1$H-NMR (400 MHz, DMSO-$d_6$): δ 7.25-7.16 (m, 6H), 6.87 (d, J=8 Hz, 2H), 6.73 (t, J=7 Hz, 1H), 4.67-4.64 (m, 1H), 3.40-3.35 (m, 2H), 3.27-3.13 (m, 8H), 3.01-2.95 (m, 3H), 1.95-1.82 (m, 2H), 1.70-1.50 (m, 10H), 0.87 (t, J=7 Hz, 3H), 0.80 (t, J=7 Hz, 3H);

LCMS: [M$^+$]=405.4, RT=3.49 minutes;

UPLC: 98.00%, RT=4.03 minutes, $\lambda_{200\,nm}$, Mobile Phase (i) 0.05% TFA in water, (ii) acetonitrile; Column: Zorbax® SB 1.8μ.

Alternatively, the compound of Example 1 may be prepared by the method described in Scheme 27.

Example 2

General Procedure A2

Preparation of (S)-1,1-diethyl-2-[2-((indan-2-yl)(phenyl)amino)ethyl]piperidinium iodide

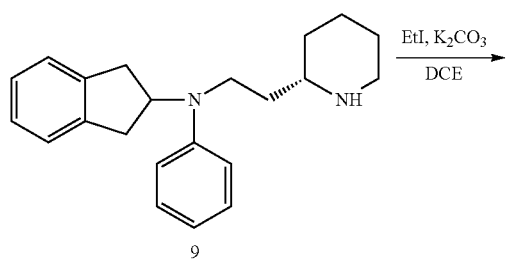

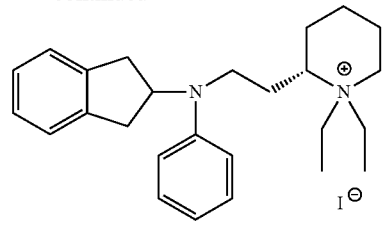

To a stirred mixture of compound 9 (0.15 g, 0.47 mmol) and K$_2$CO$_3$ (0.78 g, 5.63 mmol) in DCE (2 mL) was added ethyl iodide (2 mL) and heated at 65° C. in a sealed tube for 16 hours. The reaction mixture was filtered, washed with MeOH-DCM and concentrated using a rotavapour. The brownish solid crude material was purified using a 230-400 mesh silica gel column chromatograph eluting with 4% MeOH in DCM. The solid material was triturated with etherhexane to provide (S)-1,1-diethyl-2-[2-((indan-2-yl)(phenyl)amino)-ethyl]piperidinium iodide.

Yield: 0.17 g (71.62%);

$^1$H-NMR (400 MHz, DMSO-$d_6$): δ 7.26-7.16 (m, 6H), 6.87 (d, J=8 Hz, 2H), 6.72 (t, J=7 Hz, 1H), 4.68-4.61 (m, 1H), 3.52-3.47 (m, 1H), 3.39-3.16 (m, 9H), 3.04-2.92 (m, 3H), 1.88-1.85 (m, 2H), 1.66-1.47 (m, 6H), 1.19-1.08 (m, 6H);

LCMS: [M$^+$]=377.8, RT=3.33 minutes;

HPLC: 97.43%, RT=2.73 minutes, $\lambda_{200\,nm}$, Mobile Phase (i) 0.05% HCOOH in water, (ii) acetonitrile; Column: Zorbax® SB-C18 (4.6×50 mm) 1.8μ.

Alternatively, the compound of Example 2 may be prepared by the method described in Scheme 27.

Example 3

Procedure B1

Preparation of 1,1-dimethyl-2-[((indan-2-yl)(phenyl)amino)methyl]piperidinium iodide

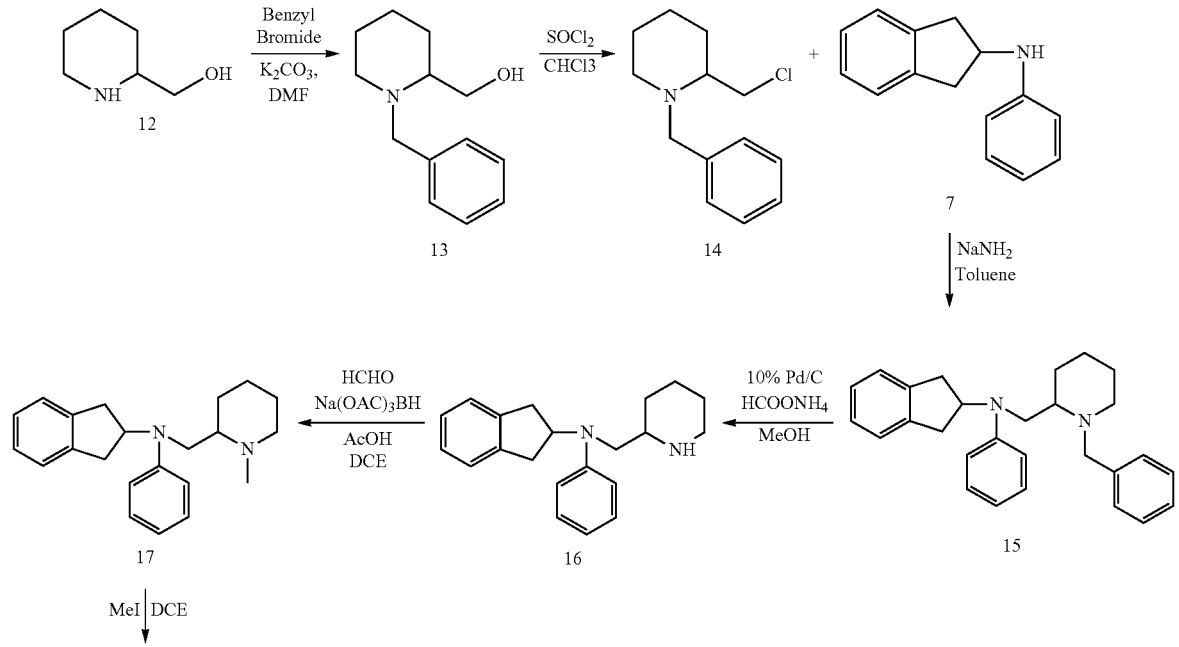

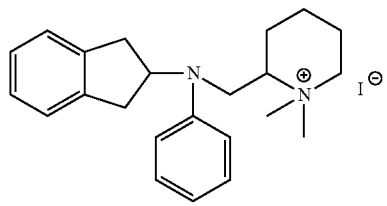

A. (1-Benzylpiperidin-2-yl)methanol (Compound 13)

To a stirred solution of piperidine-2-methanol (12; 6 g, 52.09 mmol) in dimethylformamide (DMF, 50 mL) were added successively $K_2CO_3$ (10.78 g, 78.14 mmol) and benzyl bromide (6.85 mL, 57.30 mmol) at 0° C. and the mixture stirred at rt for 16 hours. The reaction mixture was then filtered and the filtrate was concentrated. The residue was dissolved in EtOAc and the organic layer was washed with water and brine solution. The organic layer was dried over $Na_2SO_4$, filtered and concentrated. The crude material was purified by chromatography on 230-400 mesh silica gel eluting with 30% EtOAc-hexane to provide compound 13.

Yield: 6.0 g (56.6%);
$^1$H-NMR (400 MHz, $CDCl_3$): δ 7.37-7.21 (m, 5H), 4.05 (d, J=13 Hz, 1H), 3.85 (dd, J=11, 4 Hz, 1H), 3.50 (dd, J=11, 4 Hz, 1H), 3.30 (d, J=13 Hz, 1H), 2.88-2.83 (m, 1H), 2.69 (brs, 1H), 2.47-2.43 (m, 1H), 2.17-2.11 (m, 1H), 1.70-1.54 (m, 4H), 1.40-1.33 (m, 2H).

B. 1-Benzyl-2-(chloromethyl)piperidine (Compound 14)

To a stirred solution of compound 13 (3.6 g, 15.00 mmol) in chloroform (50 mL) was added thionyl chloride (1.34 mL) at 0° C. The reaction mixture was heated at reflux for 2 hours and then concentrated. The residue was dissolved in EtOAc and washed with saturated sodium bicarbonate solution, water and brine. The organic layer was dried over $Na_2SO_4$, filtered and concentrated. The crude material was purified by chromatography on 230-400 mesh silica gel eluting with 10% EtOAc-hexane to provide compound 14 as an oil.

Yield: 3.2 g (82.0%);
$^1$H-NMR (400 MHz, $CDCl_3$): δ 7.37-7.28 (m, 4H), 7.23-7.21 (m, 1H), 4.01-3.96 (m, 1H), 3.79-3.66 (m, 2H), 3.32 (d, J=13 Hz, 1H), 2.76-2.72 (m, 1H), 2.61 (brs, 1H), 2.13-2.11 (m, 1H), 1.73-1.50 (m, 5H), 1.42-1.33 (m, 1H);
LCMS: [M+H]=224.2, RT=3.77 minutes (Program P1, Column Y).

C. N-[(1-Benzyl-piperidin-2-yl)methyl]-N-phenylindan-2-yl-amine (Compound 15)

To a stirred suspension of sodamide (706 mg, 18.1 mmol) in toluene (10 mL) was added a solution of compound 7 (2.76 g, 13.2 mmol) in toluene (10 mL) at 0° C. The reaction mixture was stirred at rt for 3 hours. A solution of compound 14 (2.69 g, 12.1 mmol) in toluene was added to the reaction mixture and the resulting mixture was heated at reflux for 16 hours. The reaction mixture was diluted with EtOAc and washed with water and brine. The organic layer was dried over $Na_2SO_4$, filtered and concentrated. The crude material was purified by chromatography on 230-400 mesh silica gel eluting with 15% EtOAc-hexane to provide compound 15.

Yield: 1.5 g (31.9%);
$^1$H-NMR (400 MHz, $CDCl_3$): δ 7.32-7.27 (m, 4H), 7.23-7.13 (m, 7H), 6.89 (d, J=8 Hz, 2H), 6.80 (d, J=7 Hz, 1H), 4.54-4.50 (m, 1H), 4.11 (d, J=14 Hz, 1H), 3.57 (dd, J=14, 4 Hz, 1H), 3.32 (d, J=14 Hz, 1H) 3.24-3.04 (m, 5H), 2.76-2.71 (m, 1H), 2.64-2.62 (m, 1H), 2.16-2.10 (m, 1H), 1.82-1.76 (m, 1H), 1.63-1.61 (m, 1H), 1.48-1.31 (m, 4H).

D. N-Phenyl-N-(piperidin-2-ylmethyl)indan-2-yl-amine (Compound 16)

A solution of compound 15 (1.5 g, 3.79 mmol) in methanol (50 mL) was purged with argon for 20 minutes. Ammonium formate (2.33 g, 37.87 mmol) was then added and the solution was purged for another 10 minutes. Pd—C (10%; 216 mg) was added and the reaction mixture was heated at reflux for 3 hours. The reaction mixture was filtered through the Celite® reagent and washed with methanol. The filtrate was concentrated and the crude material was purified by chromatography on 230-400 mesh silica gel eluting with 2% methanol-DCM to provide compound 16.

Yield: 1.06 g (92.1%);
$^1$H-NMR (400 MHz, DMSO-$d_6$): δ 7.21-7.13 (m, 6H), 6.95 (d, J=8 Hz, 2H), 6.73 (t, J=7 Hz, 1H), 4.67-4.63 (m, 1H), 3.15-2.93 (m, 7H), 2.68-2.66 (m, 1H), 2.45-2.42 (m, 1H), 1.70-1.60 (m, 2H), 1.51-1.48 (m, 1H), 1.33-1.19 (m, 2H), 1.06-1.00 (m, 1H).

E. N-[(1-Methyl-piperidin-2-yl)methyl]-N-phenylindan-2-yl-amine (Compound 17)

To a stirred solution of compound 16 (0.2 g, 0.65 mmol) in DCE (10 mL) were added successively formaldehyde (35% in $H_2O$, 0.08 mL, 0.98 mmol), $Na(OAc)_3BH$ (0.415 g, 1.95 mmol) and acetic acid (AcOH, 0.1 mL) at ice-cold conditions. The resulting mixture was allowed to stir at rt for 16 hours. The reaction mixture was diluted with DCM and basified with NaOH (1N). The organic layer was separated and washed with water and brine, dried over $Na_2SO_4$, filtered and concentrated. The crude material was purified by chromatography on 230-400 mesh silica gel eluting with 5% methanol-DCM to provide compound 17.

Yield: 0.12 g (57.4%);
$^1$H-NMR (400 MHz, DMSO-$d_6$): δ 7.22-7.13 (m, 6H), 6.88 (d, J=8 Hz, 2H), 6.70 (t, J=7 Hz, 1H), 4.61-4.56 (m, 1H), 3.54 (dd, J=14, 4 Hz, 1H), 3.15-2.96 (m, 5H), 2.71-2.66 (m, 1H), 2.21 (s, 3H), 2.11-2.03 (m, 1H), 2.00-1.91 (m, 1H), 1.70-1.59 (m, 2H), 1.47-1.35 (m, 2H), 1.13-1.06 (m, 2H);
LCMS: [M+H]=321.0, RT=3.32 minutes (Program P1, Column Y).

F. 1,1-Dimethyl-2-[((indan-2-yl)(phenyl)amino)methyl]piperidinium iodide

To a stirred solution of compound 17 (0.1 g, 0.31 mmol) in DCE (5 mL) was added methyl iodide (0.058 mL, 0.94 mmol) and the resulting mixture was stirred at rt for 16 hours. The reaction mixture was concentrated under reduced pressure and the crude material was purified by crystallization from methanol-ether to provide 1,1-dimethyl-2-[((indan-2-yl)(phenyl)amino)methyl]piperidinium iodide.

Yield: 0.06 g (41.62%).

$^1$H-NMR (400 MHz, DMSO-d$_6$): δ 7.27 (t, J=7.76 Hz, 2H), 7.22-7.19 (m, 2H), 7.15-7.13 (m, 2H), 7.04 (d, J=7.96 Hz, 2H), 6.90 (t, J=7 Hz, 1H), 4.50-4.46 (m, 1H), 3.83 (d, J=12 Hz, 1H), 3.41-3.35 (m, 4H), 3.19 (s, 3H), 3.06 (d, J=8 Hz, 2H), 3.00-2.98 (m, 5H), 1.95-1.92 (m, 1H), 1.79-1.64 (m, 4H), 1.33-1.30 (m, 1H);

LCMS: [M$^+$]=335.0, RT=3.26 minutes;

UPLC: 99.72%, RT=3.92 minutes, λ$_{200\ nm}$, Mobile Phase (i) 0.05% TFA in water, (i) acetonitrile; Column: Zorbax® SB-C18 (4.6×50 mm) 1.8μ.

Example 4

General Procedure B2

Preparation of 1,1-dimethyl-2-[2-((2-fluorophenyl)(indan-2-yl)amino)ethyl]piperidinium iodide

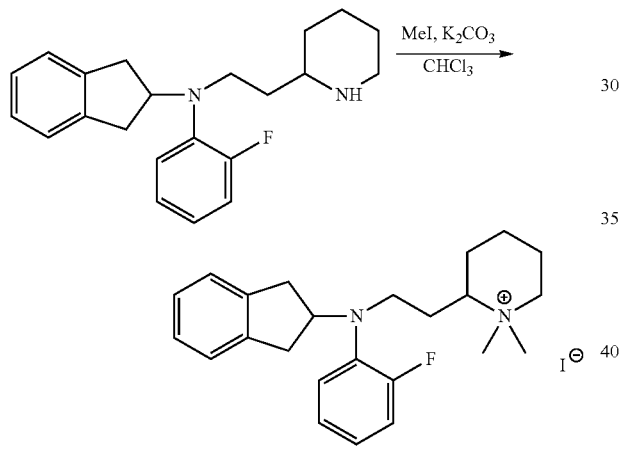

To a stirred solution of (2-fluoro-phenyl)-indan-2-yl-(2-piperidin-2-yl-ethyl)-amine (100 mg, 0.30 mmol) in CHCl$_3$ (3 mL) in a sealed tube were added methyl iodide (97 μL, 1.48 mmol) and potassium carbonate (204 mg, 1.48 mmol) and the reaction mixture was stirred at 50° C. for 16 hours. The reaction mixture was then filtered through a sintered funnel. The filtrate was concentrated in vacuo and purified by 230-400 silica gel column chromatography using MeOH-DCM (1-5%) as the eluent. The solid was lyophilized to provide 1,1-dimethyl-2-[2((2-fluorophenyl)(indan-2-yl)amino)-ethyl]piperidinium iodide.

Yield: 84 mg (57.47%);

$^1$H-NMR (400 MHz, DMSO-d$_6$): δ 7.33 (t, J=15 Hz, 1H), 7.22-7.11 (m, 7H), 4.23-4.19 (m, 1H), 3.42 (d, J=13 Hz, 1H), 3.31-3.22 (m, 2H), 3.10-3.07 (m, 1H), 3.05-3.03 (m, 1H), 3.01-2.99 (m, 1H), 2.91 (s, 3H), 2.88-2.85 (m, 2H), 2.80 (s, 3H), 2.01-1.97 (m, 1H), 1.86-1.76 (m, 2H), 1.69-1.66 (m, 2H), 1.56-1.53 (m, 2H), 1.41-1.34 (m, 3H);

LC-MS: [M$^+$]=367, RT=2.64 minutes;

UPLC: 98.63%, RT=3.96 minutes, λ$_{200\ nm}$, Mobile phase: (i) 0.05% TFA in water, (ii) acetonitrile; Column: Zorbax® SB C18 (50×4.6 mm) 1.8μ)

Example 5

General Procedure C

Preparation of 1,1-dimethyl-2-[2-((indan-2-yl)(phenyl)amino)ethyl]pyrrolidinium iodide

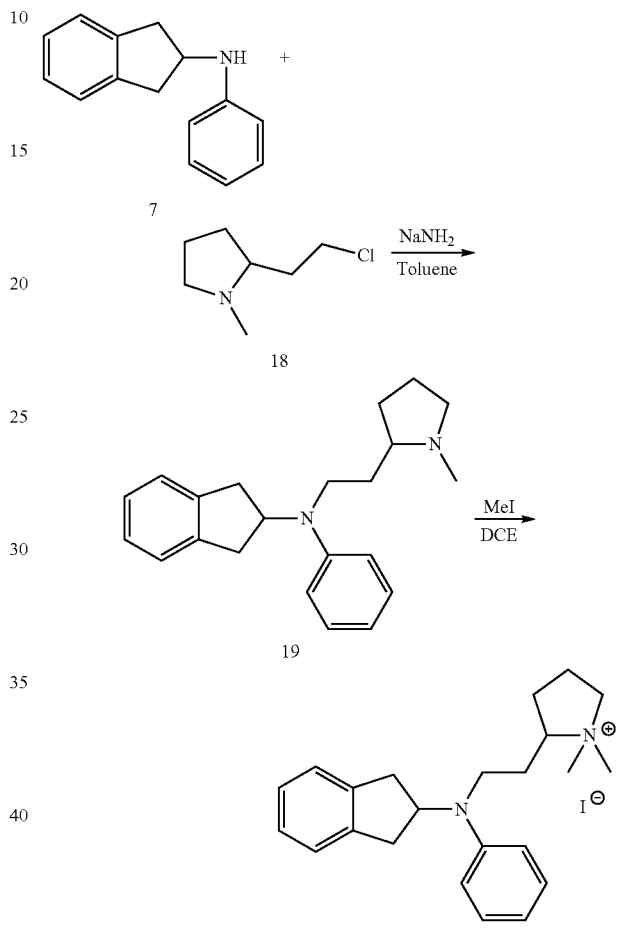

A. Indan-2-yl-[2-(1-methyl-pyrrolidin-2-yl)-ethyl]phenylamine (Compound 19)

To a stirred suspension of sodamide (256 mg, 6.58 mmol) in toluene (10 mL) was added a solution of indan-2-yl-phenyl-amine (7; 1.0 g, 4.78 mmol) in toluene (5 mL) at 0° C. The reaction mixture was stirred at rt for 3 hours. A solution of 2-(2-chloroethyl)-1-methyl-pyrrolidine hydrochloride (18; 0.808 g, 4.39 mmol) in toluene (5 mL) was added to the reaction mixture and the resulting mixture was refluxed for 16 hours. The reaction mixture was diluted with EtOAc and washed with water and brine. The organic layer was dried over Na$_2$SO$_4$, filtered and concentrated. The crude material was purified by column chromatography on neutral alumina eluting with 0.8% methanol-DCM to provide compound 19.

Yield: 0.1 g (7.1%);

$^1$H-NMR (400 MHz, DMSO-d$_6$): δ 7.26-7.14 (m, 6H), 6.81 (d, J=8 Hz, 2H), 6.65 (t, J=7 Hz, 1H), 4.65-4.62 (m, 1H), 3.22-3.14 (m, 4H), 2.97-2.88 (m, 3H), 2.10 (s, 3H), 1.94-1.91 (m, 2H), 1.77-1.68 (m, 2H), 1.57-1.53 (m, 2H), 1.29-1.23 (m, 2H);

LCMS: [M+H]=321.0, RT=3.22 minutes (Program P1, Column Y).

B. 1,1-Dimethyl-2-[2-((indan-2-yl)(phenyl)amino)ethyl]pyrrolidinium iodide

To a stirred solution of compound 19 (0.1 g, 0.31 mmol) in DCE (3 mL) was added methyl iodide (0.058 mL, 0.94 mmol) and the resulting mixture was stirred at rt for 16 hours. The reaction mixture was concentrated under reduced pressures and the crude material was purified by column chromatography on neutral alumina eluting with 1% methanol-DCM to provide 1,1-dimethyl-2-[2-((indan-2-yl)(phenyl)amino)ethyl]pyrrolidinium iodide.

Yield: 0.06 g (41.8%);

$^1$H-NMR (400 MHz, DMSO-$d_6$): δ 7.24-7.15 (m, 6H), 6.90 (d, J=8 Hz, 2H), 6.74 (t, J=7 Hz, 1H), 4.65-4.61 (m, 1H), 3.59-3.55 (m, 1H), 3.45-3.39 (m, 6H), 3.24-3.13 (m, 4H), 2.98-2.94 (m, 5H), 2.74 (s, 3H), 2.30-2.21 (m, 1H), 2.02-1.94 (m, 3H), 1.67-1.62 (m, 1H), 1.54-1.50 (m, 1H);

LCMS: [M$^+$]=335.4, RT=3.65 minutes;

UPLC: 97.93%, RT=3.37 minutes, $\lambda_{200\ nm}$, Mobile Phase (i) 0.05% TFA in water, (ii) acetonitrile; Column: Zorbax® SB-C18 (4.6×50 mm) 1.8μ.

Example 6

General Procedure for Preparation of N-(indan-2-yl)phenylamine (Compound 7)

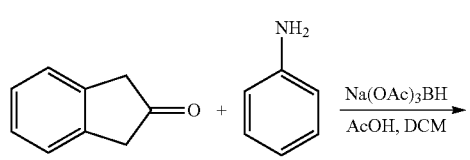

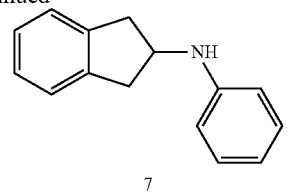

To a stirred solution of 2-indanone (5 g, 37.83 mmol) in DCM (135 mL) were successively added aniline (3.4 mL, 37.83 mmol), AcOH (2.16 mL, 37.83 mmol) and Na(OAc)$_3$BH (11.22 g, 52.96 mmol) portion-wise at ice cold conditions. The reaction mixture was stirred at rt for 16 hours. The reaction mixture was then diluted with EtOAc (450 mL) and washed with water (150 mL) and brine (50 mL). The organic layer was dried over Na$_2$SO$_4$, filtered and concentrated. The crude material was purified by Combiflash® chromatography and eluted with 1.7% EtOAc in hexane to obtain compound 7.

Yield: 7.1 g (89.80%);

$^1$H-NMR (400 MHz, DMSO-$d_6$): δ 7.24-7.21 (m, 2H), 7.15-7.13 (m, 2H), 7.08 (t, J=8 Hz, 2H), 6.61 (d, J=8 Hz, 2H), 6.53 (t, J=7 Hz, 1H), 5.83 (d, J=7 Hz, 1H), 4.24-4.16 (m, 1H), 3.28 (dd, J=16, 7 Hz, 2H), 2.79 (dd, J=16, 7 Hz, 2H);

LCMS: [M+H]=210.2, RT=3.72 minutes (Program P1, Column Y).

Example 7

General Procedure D

Preparation of 1,1-dimethyl-2-[3-((indan-2-yl)phenyl)amino)propyl]piperidinium iodide

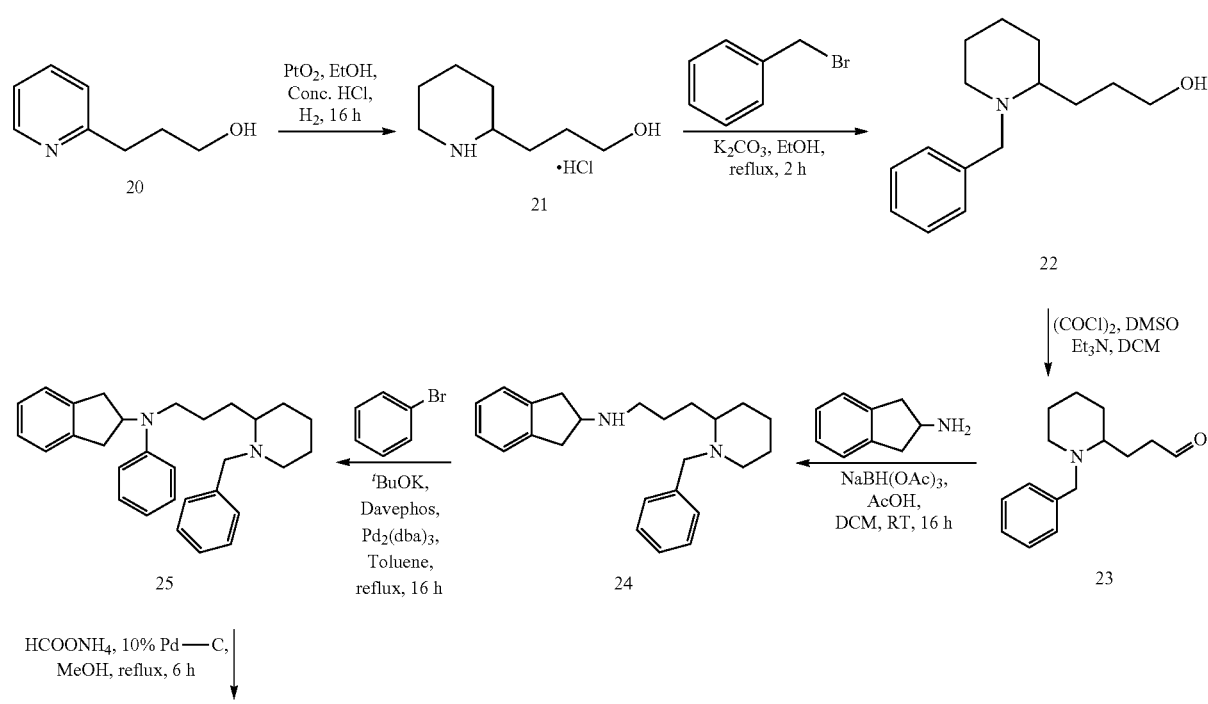

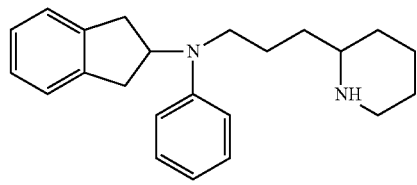 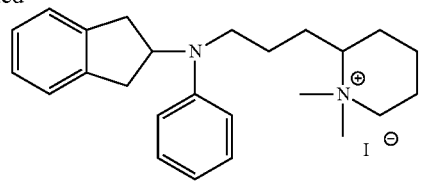

26

A: 3-(Piperidin-2-yl)propan-1-ol hydrochloride (Compound 21)

To a stirred solution of compound 20 (5 g, 36.4 mmol) in ethanol (32 mL) was added concentrated HCl (3.2 mL) and the reaction mixture was degassed with $N_2$ for 15 minutes. Platinum oxide ($PtO_2$; 1 g) was then added and degassed for 5 minutes. Finally, the reaction mixture was hydrogenated at rt in a Parr apparatus for 16 hours under 45 psi $H_2$ pressure. The reaction mixture was filtered through the Celite® reagent, and was washed with ethanol. The filtrate was concentrated to yield the crude product 21 which was used as such for the next step.

Yield: 6.2 g (94.8%);
$^1$H-NMR (400 MHz, DMSO-$d_6$): δ 8.88 (brs, 1H), 8.71 (brs, 1H), 4.57 (s, 1H), 3.40 (d, J=4 Hz, 2H), 3.17 (d, J=12 Hz, 1H), 2.96 (brs, 1H), 2.81-2.79 (m, 1H), 1.84 (d, J=13 Hz, 1H), 1.71-1.65 (m, 3H), 1.62-1.58 (m, 1H), 1.56-1.43 (m, 3H), 1.40-1.38 (m, 1H).

B: 3-(1-Benzyl-piperidin-2-yl)propan-1-ol (Compound 22)

To a stirred solution of compound 21 (3 g, 16.71 mmol) in ethanol (23 mL) was added $K_2CO_3$ (11.5 g, 83.55 mmol) portion-wise at ice cold conditions. Benzyl bromide (2 mL, 16.71 mmol) was then added and the reaction mixture was heated at reflux for 2 hours. The reaction mixture was filtered, and washed with EtOAc. The filtrate was concentrated, the residue was dissolved in EtOAc, washed with saturated $NaHCO_3$ solution and brine, dried over $Na_2SO_4$, filtered and concentrated. The crude material was purified by 230-400 silica gel column chromatography using 1-3% MeOH-DCM as eluent to yield compound 22.

Yield: 2.6 g (66.7%);
$^1$H-NMR (400 MHz, DMSO-$d_6$): δ 7.30-7.29 (m, 4H), 7.23-7.21 (m, 1H), 4.40 (s, 1H), 3.91 (d, J=14 Hz, 1H), 3.37 (s, 2H), 3.16 (d, J=14 Hz, 1H), 2.62 (d, J=12 Hz, 1H), 2.28 (s, 1H), 1.99-1.94 (m, 1H), 1.60-1.48 (m, 4H), 1.43-1.24 (m, 4H);
LCMS [M+H]: 234.2, RT=2.07 minutes, (Program P1, Column Y).

C: 3-(1-Benzyl-piperidin-2-yl)propionaldehyde (Compound 23)

Oxalyl chloride (0.55 mL, 6.44 mmol) was added to a stirred solution of DMSO (0.92 mL, 12.87 mmol) in dry DCM (40 mL) at −78° C. and the reaction mixture was stirred for 15 minutes. Compound 22 (1 g, 4.29 mmol) dissolved in DCM (15 mL) was the added drop-wise and the reaction mixture was stirred at −78° C. for 1 hour. The reaction mixture was then quenched by adding $Et_3N$ (2.9 mL, 21.45 mmol) drop-wise and the solution was stirred at rt for 15 minutes. Water was then added to the solution and the reaction mixture was extracted with DCM. The organic layer was dried over $Na_2SO_4$, filtered and concentrated to yield crude compound 23 which was used as such for the next step.

Yield: 820 mg (83%);
$^1$H-NMR (400 MHz, DMSO-$d_6$): δ 9.68 (s, 1H), 7.52-7.31 (m, 5H), 3.88-3.84 (m, 1H), 3.55-3.47 (m, 1H), 3.20-3.16 (m, 1H), 2.67 (brs, 1H), 2.33 (brs, 1H), 2.10-2.01 (m, 1H), 1.88-1.76 (m, 2H), 1.72-1.61 (m, 3H), 1.45-1.21 (m, 4H).

D: [3-(1-Benzyl-piperidin-2-yl)-propyl]indan-2-yl-amine (Compound 24)

To a stirred solution of compound 23 (820 mg, 3.55 mmol) in DCM (15 mL) was added 2-amino-indane (472 mg, 3.55 mmol) drop-wise at ice cold conditions. Acetic acid (0.2 mL) was added to the reaction mixture, followed by sodium triacetoxy borohydride (2.2 g, 10.65 mmol) portion-wise at ice cold conditions. The reaction mixture was stirred at rt for 16 hours. The reaction mixture was diluted with DCM, washed with saturated $NaHCO_3$ solution and brine. The organic layer was dried over $Na_2SO_4$, filtered and concentrated. The crude material was purified by 230-400 silica gel column chromatography using 1-3% MeOH-DCM as eluent to yield compound 24.

Yield: 500 mg (40.5%);
$^1$H-NMR (400 MHz, DMSO-$d_6$): δ 7.29 (d, J=4 Hz, 4H), 7.22-7.17 (m, 3H), 7.12-7.11 (m, 2H), 3.91 (d, J=14 Hz, 1H), 3.59 (t, J=7 Hz, 1H), 3.18 (d, J=13 Hz, 1H), 3.11-3.05 (dd, J=7, 16 Hz, 2H), 2.75-2.70 (dd, J=6, 16 Hz, 2H), 2.63 (brs, 3H), 2.29 (brs, 1H), 2.04-1.97 (m, 1H), 1.58 (brs, 4H), 1.45-1.28 (m, 5H), 1.23 (s, 1H);
LCMS [M+H]=349.2, RT=2.89 minutes, (Program P1, Column Y)

E: [3-(1-Benzyl-piperidin-2-yl)-propyl]indan-2-yl-phenylamine (Compound 25)

To a stirred solution of compound 24 (400 mg, 1.15 mmol) in dry toluene (12 mL) was added bromo-benzene (0.12 mL, 1.15 mmol) and potassium tertiary butoxide (322 mg, 2.87 mmol) The reaction mixture was purged with nitrogen for 30 minutes. Finally, DavePhos (90 mg, 0.23 mmol) and $Pd_2(dba)_3$ (136 mg, 0.15 mmol) were added and the reaction mixture was heated to 110° C. for 16 hour. Thin layer chromatography (TLC) showed that the reaction was completed. The reaction mixture was then diluted with ethyl acetate, washed with water and brine, dried over $Na_2SO_4$ and concentrated. The crude reaction mixture was purified by 230-400 silica gel column chromatography using 5-20% EtOAc-hexane as eluent yield compound 25.

Yield: 290 mg (59.5%);
$^1$H-NMR (400 MHz, DMSO-$d_6$): δ 7.29-7.21 (m, 6H), 7.16-7.12 (m, 5H), 6.79 (d, J=8 Hz, 2H), 6.63 (t, J=7 Hz, 1H), 3.86 (d, J=14 Hz, 1H), 3.17-3.07 (m, 5H), 2.96-2.90 (dd, J=6, 16 Hz, 2H), 2.60-2.58 (m, 1H), 2.20 (brs, 1H), 1.98-1.89 (m, 1H), 1.56 (brs, 2H), 1.48-1.40 (m, 5H), 1.30-1.23 (m, 3H);
LCMS [M+H]=424.8, RT=3.14 minutes, (Program P1, Column Y).

F: Indan-2-yl-phenyl-(3-piperidin-2-yl-propyl)amine (Compound 26)

Compound 25 (340 mg, 0.80 mmol) and ammonium formate (506 mg, 8.02 mmol) in methanol (20 mL) was purged with N₂ for 15 minutes, 10% Pd—C catalyst (68 mg) was added, purging was continued for another 5 minutes and the mixture was heated at 110° C. for 6 hours. The reaction mixture was filtered through the Celite® reagent and washed with methanol. The combined organic layer was concentrated in rotavapour. A small amount of water was added to the residue and the product was extracted with EtOAc. The organic layer was dried, filtered and concentrated to yield compound 26.

Yield: 248 mg (92.6%);
¹H-NMR (400 MHz, DMSO-d₆): δ 7.24-7.23 (m, 2H), 7.19-7.15 (m, 4H), 6.81 (d, J=8 Hz, 2H), 6.66 (t, J=7 Hz, 1H), 4.64 (t, J=7 Hz, 1H), 3.16-3.13 (m, 4H), 3.06 (d, J=13 Hz, 1H), 2.99-2.93 (dd, J=7, 16 Hz, 2H), 2.67-2.61 (m, 2H), 1.70-1.58 (m, 3H), 1.51-1.45 (m, 2H), 1.42-1.27 (m, 4H), 1.14-1.09 (m, 1H);
LCMS [M+H]=335.2, RT=3.73 minutes, (Program P1, Column Z).

G: 1,1-Dimethyl-2-[3-(indan-2-yl)phenyl)amino) propyl]piperidinium iodide

To a stirred solution of compound 26 (100 mg, 0.30 mmol) in CHCl₃ (3 mL) in a sealed tube were added methyl iodide (97 μL, 1.50 mmol) and potassium carbonate (207 mg, 1.50 mmol) and the reaction mixture was stirred at 50° C. for 16 hours. The reaction mixture was filtered through a sintered funnel. The filtrate was concentrated in a rotavapour and purified by 230-400 silica gel column chromatography using MeOH-DCM (1-3%) as the eluent to yield 2-[3-(Indan-2-yl-phenyl-amino)-propyl]-1,1-dimethyl-piperidinium iodide.

Yield: 51 mg (46.9%);
¹H-NMR (400 MHz, CDCl₃) δ 7.28 (s, 1H), 7.25 (s, 3H), 7.16 (t, J=3 Hz, 2H), 6.89-6.82 (m, 3H), 4.52 (t, J=7 Hz, 1H), 3.99 (d, J=13 Hz, 1H), 3.66-3.50 (m, 1H), 3.38-3.33 (m, 4H), 3.27-3.13 (m, 4H), 3.04-2.97 (m, 5H), 1.87-1.81 (m, 5H), 1.68-1.61 (m, 1H), 1.48-1.42 (m, 2H), 1.29-1.23 (m, 2H);
LCMS [M⁺]=363, RT=3.32 minutes.
UPLC: 98.11%, RT=3.11 minutes, λ₂₀₀ ₙₘ, Mobile phase: (i) 0.05% TFA in Water, (ii) Acetonitrile; Column: Zorbax® SB C18 (50×4.6 mm) 1.8μ

Example 8

General Procedure E

Preparation of 1,1-dimethyl-2-[((indan-2-yl)phenyl) amino)methyl]pyrrolidinium iodide

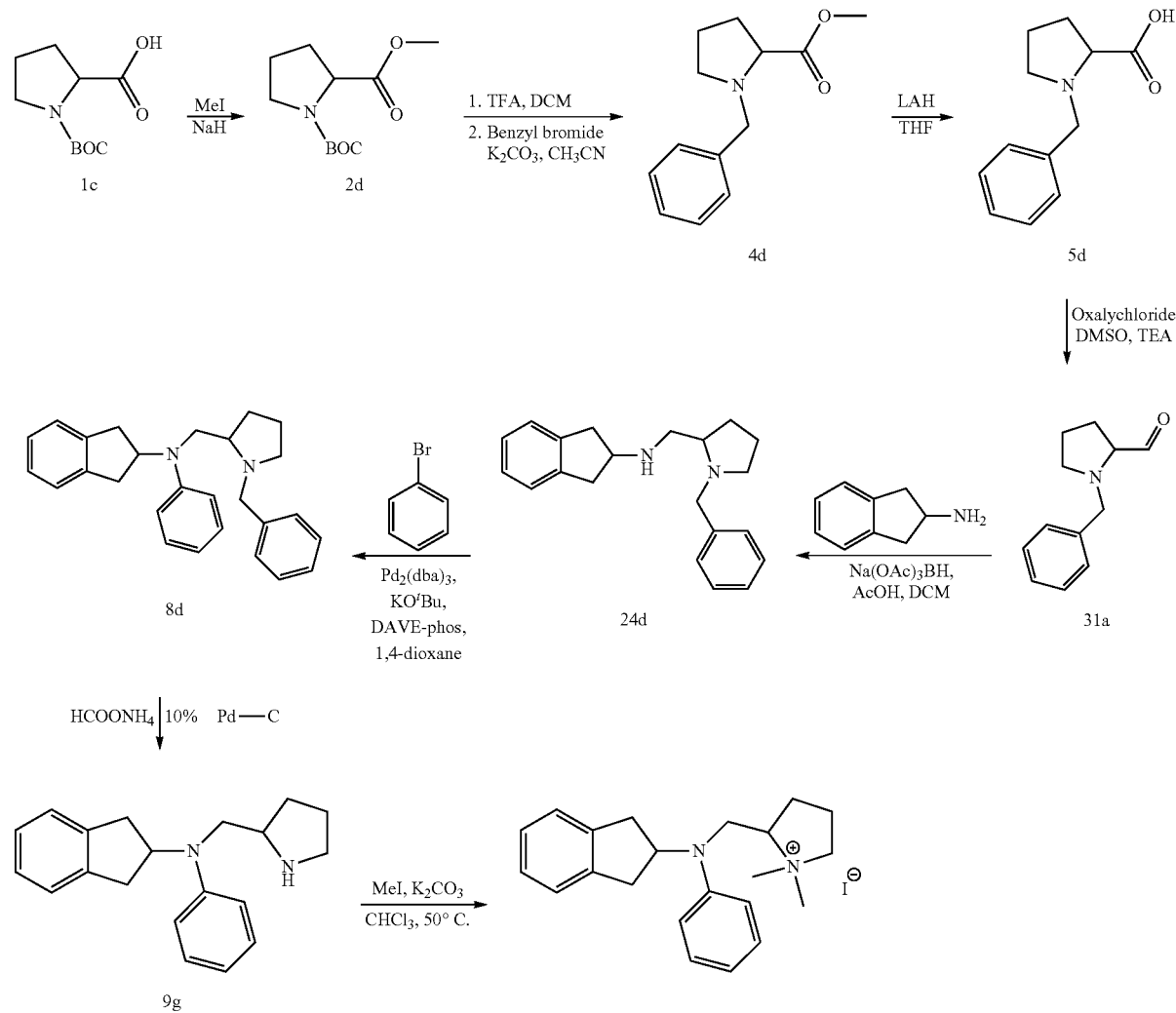

A: Pyrrolidine-1,2-dicarboxylic acid 1-tert-butyl ester 2-methyl ester

To a stirred solution of pyrrolidine-1,2-dicarboxylic acid 1-tert-butyl ester (5.0 g, 23.25 mmol) and methyl iodide (6.0 mL, 93.02 mmol) in DMF (25 mL) was added NaH (60% w/w, 2.3 g, 57.09 mmol) portion-wise at 0° C. The resulting mixture was allowed to stir at rt for 24 hours. The reaction mixture was poured into cold water and extracted with ethyl acetate. The organic layer was washed with water and brine. Drying over $Na_2SO_4$, filtering and concentration provided crude compound 2d.

Yield: 5.0 g (93.91%);
$^1$H-NMR (400 MHz, DMSO-$d_6$): δ 4.18-4.13 (m, 1H), 3.65 (s, 3H), 3.38-3.32 (m, 2H), 2.22-2.18 (m, 1H), 1.87-1.78 (m, 3H), 1.32 (s, 9H);
LCMS [M+H]=230.2, RT=3.28 minutes (Program P1, Column Z).

B: 1-Benzyl-pyrrolidine-2-carboxylic acid methyl ester

To a stirred solution of compound 2d (6.8 g, 29.69 mmol) in DCM (55 mL) was added TFA (15.2 mL, 203.94 mmol) drop-wise at ice-cold conditions. The resulting mixture was allowed to stir at rt for 4 hours. The reaction mixture was concentrated under reduced pressure, the crude material was dissolved in acetonitrile (100 mL) and the mixture was cooled to 0° C. $K_2CO_3$ (20.48 g, 148.47 mmol) was then added (pH was adjusted to basic) and the mixture stirred at 0° C. for 15 minutes. Benzyl bromide (5.2 mL, 44.54 mmol) was added and the resulting mixture was heated at reflux for 16 hours. The reaction mixture was filtered and the filtrate was concentrated. The residue was dissolved in ethyl acetate and the organic layer was washed with water and brine. Drying over $Na_2SO_4$, filtering, and concentrating provided crude compound 4d.

Yield: 3.0 g (46.11%);
$^1$H-NMR (400 MHz, DMSO-$d_6$): δ 7.32-7.21 (m, 5H), 3.85 (d, J=13 Hz, 1H), 3.58 (s, 3H), 3.50 (d, J=13 Hz, 1H), 3.28-3.24 (m, 1H), 2.86-2.81 (m, 1H), 2.38-2.32 (m, 1H), 2.08-2.03 (m, 1H), 1.84-1.69 (m, 3H);
LCMS [M+H]=219.6, RT=3.35 minutes (Program P1, Column X).

C: (1-Benzyl-pyrrolidin-2-yl)methanol

To a stirred suspension of LAH (1.03 g, 27.39 mmol) in THF (120 mL) was added a solution of compound 4d (3.0 g, 13.69 mmol) in THF (30 mL) at ice-cold conditions. The resulting mixture was allowed to stir at rt for 4 hours. The reaction mixture was quenched by adding brine solution and filtered through a Celite® pad. The filtrate was dried over $Na_2SO_4$, filtered and concentrated to get crude compound 5d.

Yield: 2.5 g (95.54%);
$^1$H-NMR (400 MHz, DMSO-$d_6$): δ 7.30-7.19 (m, 5H), 4.37 (t, J=5 Hz, 1H), 4.04 (d, J=13 Hz, 1H), 3.47-3.41 (m, 1H), 3.32 (d, J=13 Hz, 1H), 3.27-3.24 (m, 1H), 2.76-2.74 (m, 1H), 2.58-2.55 (m, 1H), 2.16-2.10 (m, 1H), 1.86-1.80 (m, 1H), 1.60-1.55 (m, 3H);
LCMS: [M+H]=192.0, RT=1.67 minutes (Program P1, Column Y).

D: 1-Benzylpyrrolidine-2-carboxaldehyde

To a stirred solution of DMSO (2.79 mL, 39.27 mmol) in DCM (120 mL) was added oxalyl chloride (1.69 mL, 19.63 mmol) drop-wise at −78° C. and the mixture stirred for 15 minutes. A solution of compound 5d (2.5 g, 13.08 mmol) in DCM (30 mL) was then slowly added and stirred at −78° C. for 1 hour. Triethyl amine (TEA; 9.1 mL, 65.44 mmol) was added to the reaction mixture and the reaction mixture was diluted with DCM. The organic layer was washed with water and brine. Drying over $Na_2SO_4$, filtering and concentrating provided crude compound 31a.

Yield: 2.59 g;
$^1$H-NMR (400 MHz, DMSO-$d_6$): δ 9.26 (d, J=4 Hz, 1H), 7.32-7.23 (m, 5H), 3.73 (d, J=13 Hz, 1H), 3.63 (d, J=13 Hz, 1H), 2.98-2.94 (m, 2H), 2.39-2.32 (m, 1H), 1.97-1.90 (m, 1H), 1.83-1.72 (m, 3H).

E: (1-Benzyl-pyrrolidin-2-ylmethyl)indan-2-yl-amine

To a stirred solution of compound 31a (1.6 g, 8.46 mmol) in DCM (30 mL) were added successively 2-aminoindane (1.12 g, 8.46 mmol), $Na(OAc)_3BH$ (5.38 g, 25.40 mmol) and acetic acid (0.5 mL) at 0° C. The resulting mixture was allowed to stir at rt for 16 hours. The reaction mixture was diluted with DCM and the organic layer was washed with saturated $NaHCO_3$ solution, water and brine, dried over $Na_2SO_4$, filtered and concentrated and the crude material was purified by Combiflash® eluting 8% ethyl acetate-hexane to provide sticky compound 24d.

Yield: 1.5 g (57.94%);
$^1$H-NMR (400 MHz, DMSO-$d_6$): δ 7.30-7.09 (m, 9H), 3.96 (d, J=13 Hz, 1H), 3.46-3.42 (m, 1H), 3.25 (d, J=13 Hz, 1H), 3.07-2.99 (m, 2H), 2.78-2.74 (m, 1H), 2.68-2.55 (m, 5H), 2.15-2.08 (m, 1H), 1.87-1.82 (m, 1H), 1.67-1.55 (m, 3H);
LCMS [M+H]=307.0, RT=3.23 minutes (Program P1, Column X).

F: (1-Benzylpyrrolidin-2-ylmethyl)indan-2-yl-phenylamine (Compound 33)

The stirred mixture of compound 24d (1.0 g, 3.26 mmol), bromobenzene (0.6 mL, 6.53 mmol), KO$^t$Bu (0.92 g, 8.16 mmol) and DavePhos (0.26 g, 0.65 mmol) in 1,4-dioxane (30 mL) was purged with nitrogen for 15 minutes. $Pd_2(dba)_3$ (0.3 g, 0.33 mmol) was then added and the resulting mixture was heated at 100° C. for 1 hour under microwave conditions. The reaction mixture was diluted with ethyl acetate and the organic layer was washed with water and brine. Drying over $Na_2SO_4$, filtering, concentrating, and Combiflash® chromatography eluting using 6% ethyl acetate-hexane provided sticky compound 8d.

Yield: 0.24 g (9.62%);
$^1$H-NMR (400 MHz, DMSO-$d_6$): δ 7.30-7.27 (m, 2H), 7.23-7.13 (m, 9H), 6.88-6.86 (m, 2H), 6.76-6.68 (m, 1H), 4.64-4.60 (m, 1H), 4.00 (d, J=13 Hz, 1H), 3.26-3.22 (m, 2H), 3.15-3.09 (m, 4H), 3.04-2.98 (m, 1H), 2.80-2.77 (m, 2H), 2.15-2.09 (m, 1H), 1.82-1.77 (m, 1H), 1.62-1.57 (m, 2H), 1.51-1.48 (m, 1H);
LCMS [M+H]=383.2, RT=2.69 minutes (Program P1, Column Y).

G: Indan-2-yl-phenylpyrrolidin-2-yl-methylamine (Compound 34)

The stirred mixture of compound 8d (0.7 g, 1.83 mmol) and $HCOONH_4$ (2.32 g, 36.79 mmol) in MeOH (30 mL) was purged with nitrogen for 15 minutes. Ten percent Pd—C (0.28 g) was added and the resulting mixture was heated at reflux for 6 hours. The reaction mixture was filtered through a Celite® pad and washed with methanol. The filtrate was concentrated and the residue was taken in ethyl acetate. The organic layer was washed with water and brine. Drying over $Na_2SO_4$, filtering, concentrating, and Combiflash® chromatography eluting with 10% methanol-DCM provided compound 9g.

Yield: 0.35 g (65.50%);

$^1$H-NMR (400 MHz, DMSO-$d_6$): δ 7.23-7.20 (m, 4H), 7.15-7.13 (m, 2H), 6.97 (d, J=8 Hz, 2H), 6.78 (t, J=7 Hz, 1H), 4.61-4.57 (m, 1H), 3.33-3.30 (m, 1H), 3.16-3.06 (m, 4H), 3.01-2.89 (m, 4H), 1.86-1.67 (m, 3H), 1.44-1.38 (m, 1H);

LCMS [M+H]=293.0, RT=2.90 minutes (Program P1, Column Y).

H: 1,1-Dimethyl-2-[((indan-2-yl)phenyl)amino)methyl]pyrrolidinium iodide

To a stirred solution of compound 9g (0.12 g, 0.41 mmol) in $CHCl_3$ (4 mL) were added successively $K_2CO_3$ (0.57 g, 4.1 mmol) and methyl iodide (0.3 mL, 4.1 mmol) The resulting mixture was heated at 50° C. for 40 hours in a sealed tube. The reaction mixture was filtered and washed with methanol. The filtrate was concentrated and the crude material was purified by Combiflash® chromatography eluting with 2.5% methanol-DCM to get a yellow solid which was triturated with pentane and ether to provide 2-[(indan-2-yl-phenyl-amino)-methyl]-1,1-dimethyl-pyrrolidinium iodide.

Yield: 0.056 g (30.48%);

$^1$H-NMR (400 MHz, DMSO-$d_6$): δ 7.32-7.28 (m, 2H), 7.20-7.10 (m, 6H), 6.96 (t, J=7 Hz, 1H), 4.43-4.38 (m, 1H), 3.79-3.74 (m, 1H), 3.60-3.54 (m, 2H), 3.52-3.46 (m, 2H), 3.16 (s, 3H), 3.09-2.99 (m, 4H), 2.92 (s, 3H), 2.18-2.15 (m, 1H), 1.97-1.90 (m, 3H);

LCMS [M$^+$]=321.2, RT=2.99 minutes;

UPLC: 97.43%, RT=4.44 minutes, $\lambda_{200\ nm}$, Mobile Phase (i) 0.05% HCOOH in water, (ii) acetonitrile; Column: Gemini® NX C18 (50×4.6 mm), 3µ.

Examples 9-35

Additional compounds listed in Table 2 were prepared in a similar manner, using the methods described for Examples 1 to 8 and in Schemes 1 to 27. Yields and $^1$H-NMR, LCMS, and HPLC characterization data for Examples 9 to 35 are provided immediately following Table 2.

Example 36

General Procedure F

Preparation of 1,1-diethyl-2-[2-((indan-2-yl)(phenyl)amino)ethyl]pyrrolidinium iodide

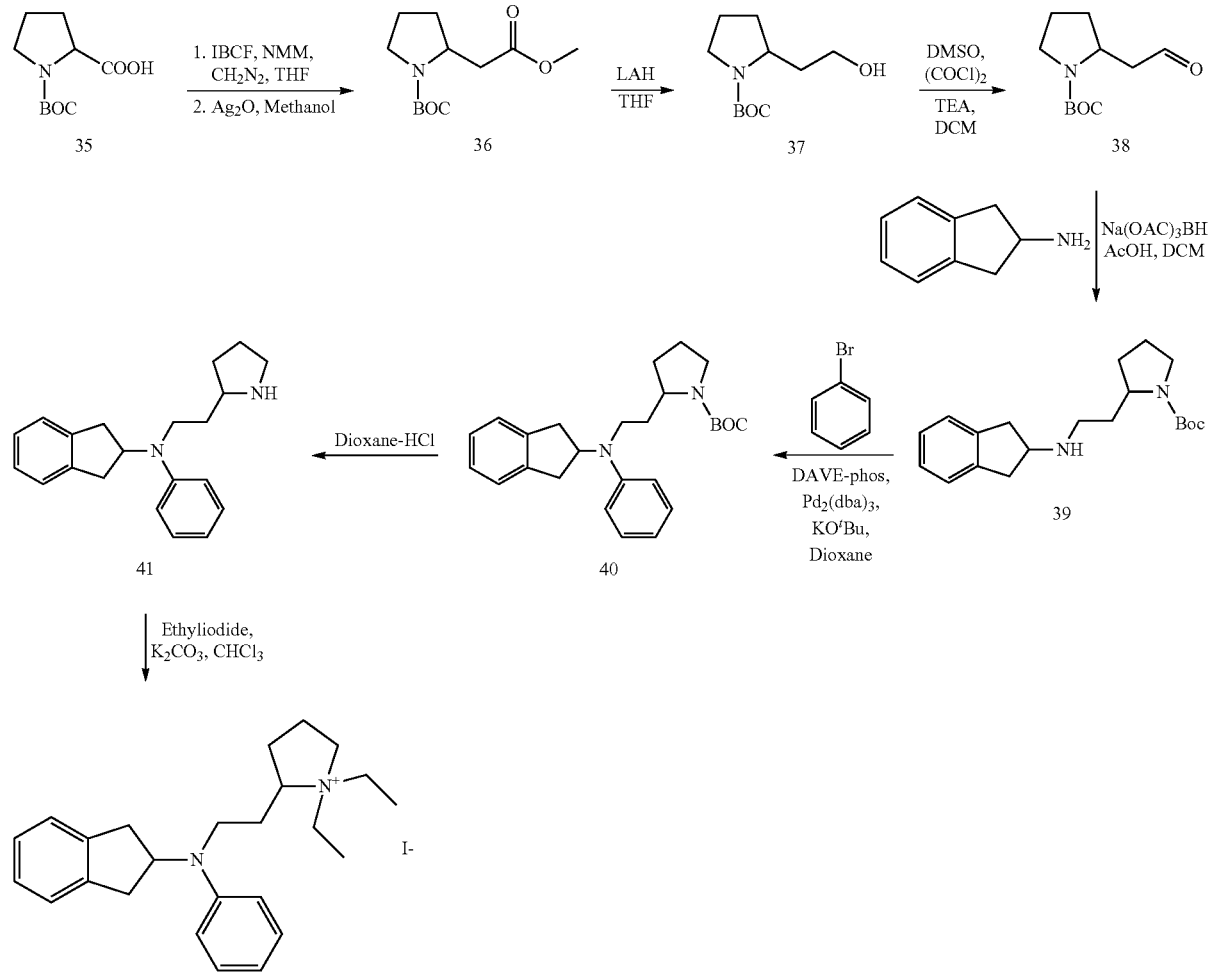

A:
2-Methoxycarbonylmethylpyrrolidine-1-carboxylic acid tert-butyl ester (Compound 36)

To a stirred solution of pyrrolidine-1,2-dicarboxylic acid 1-tert-butyl ester 35 (10 g, 46.46 mmol) in dry THF were added drop wise N-methyl morpholine (6.4 mL, 58.1 mmol) and isobutyl chloroformate (6.7 mL, 65.1 mmol) at −30° C. The reaction mixture was stirred at same temperature for one hour and diazomethane solution (prepared in situ) was added at −30° C. The resulting mixture was allowed to stir at rt overnight. Excess diazomethane was quenched with acetic acid (15 mL) and evaporated under reduced pressure. The residue was dissolved in ether and washed with water and brine. The organic layer was dried over anhydrous $Na_2SO_4$, filtered and evaporated. The residue was dissolved in methanol (100 mL) and $Ag_2O$ (5.5 g) was added portion-wise at ice-cold conditions, and then allowed to stir at rt for 2 hours. Chloroform was added, filtered through Celite® reagent and washed with methanol. The filtrate was concentrated and the crude material was purified by chromatography on silica-gel (230-400 mesh) eluting with 1-5% of ethyl acetate-hexane to get light yellow liquid compound 36.
Yield: 4.0 g (45%);
$^1$H-NMR (400 MHz, DMSO-$d_6$): δ 3.99-3.95 (m, 1H), 3.59 (s, 3H), 3.23-3.21 (m, 2H), 2.72-2.65 (m, 1H), 2.38-2.34 (m, 1H), 1.98-1.95 (m, 1H), 1.81-1.72 (m, 2H), 1.65-1.63 (m, 1H), 1.39 (s, 9H).

B: 2-(2-Hydroxyethyl)pyrrolidine-1-carboxylic acid tert-butyl ester (Compound 37)

To a stirred solution of LAH (0.94 g, 24.69 mmol) in dry THF (100 mL) was added solution of compound 36 (3.0 g 12.34 mmol) in THF (40 mL) at 0° C. and stirred at rt for 16 hours. The reaction mixture was quenched with brine solution and filtered through a Celite® bed. The organic layer was dried over anhydrous $Na_2SO_4$ and evaporated. The crude was purified by Combiflash® chromatography eluting with 2-3% of methanol-DCM to provide liquid compound 37.
Yield: 1.4 g (52.8%);
$^1$H-NMR (400 MHz, DMSO-$d_6$): δ 4.37 (t, J=5 Hz, 1H), 3.73-3.71 (m, 1H), 3.42-3.37 (m, 2H), 3.22-3.19 (m, 2H), 1.83-1.64 (m, 5H), 1.43-1.41 (m, 1H), 1.39 (s, 9H);
LCMS [M+H]=216.0, RT=2.83 minutes, (Program P1, Column Y).

C: 2-(2-Oxoethyl)pyrrolidine-1-carboxylic acid tert-butyl ester (Compound 38)
To a stirred solution of DMSO (2.08 mL, 29.30 mmol) in DCM (60 mL) was added oxalyl chloride (1.26 mL, 14.65 mmol) at −78° C. and stirred for 15 minutes. Then a solution of compound 37 (2.1 g, 9.76 mmol) in DCM (30 mL) was added at −78° C. and stirred at same temperature for 1 hour. TEA (4.9 mL, 48.83 mmol) was added and the reaction mixture was allowed to warm to rt. The reaction mixture was diluted with DCM and washed with water and brine. The organic layer was dried over anhydrous $Na_2SO_4$, filtered and evaporated to provide crude compound 38.
Yield: 2.3 g (crude).

D: 2-[2-((Indan-2-yl)amino)ethyl]pyrrolidine-1-carboxylic acid tert-butyl ester (Compound 39)

To a stirred solution of compound 38 (2.3 g, 10.80 mmol) in DCM (90 mL) were added successively 2-aminoindane (1.4 mL, 10.80 mmol), Na(OAC)$_3$BH (6.86 g, 32.39 mmol) and acetic acid (2 mL) at 0° C. The resulting mixture was allowed to stir at rt for 16 hours. The reaction mixture was diluted in DCM and washed with 1N NaOH, water and brine solution. The organic layer was dried over anhydrous $Na_2SO_4$, filtered and evaporated. The crude material was purified by Combiflash® chromatography eluting with 3-4% of methanol-DCM to provide compound 39.
Yield: 3.0 g (84.26%).

E: 2-[2-(((Indan-2-yl)phenyl)amino)-ethyl]pyrrolidine-1-carboxylic acid tert-butyl ester (Compound 40)

To a stirred solution of compound 39 (1.5 g, 4.54 mmol) in dioxane (22 mL) were added bromobenzene (1 mL, 9.09 mmol), DavePhos (0.36 g, 0.91 mmol), and KO$^t$Bu (1.28 g, 11.36 mmol) and purged with argon for 15 minutes. Then Pd$_2$(dba)$_3$ (0.42 g, 0.45 mmol) was added and the solution was again purged for 15 minutes. The reaction mixture was heated in a microwave for 1 hour at 100° C. The reaction mixture was diluted in ethyl acetate and washed with water and brine. The organic layer was dried over anhydrous $Na_2SO_4$, filtered and evaporated. The crude product was purified by Combiflash® chromatography eluting with 5-6% of ethyl acetate-hexane to provide compound 40.
Yield: 1.7 g (94.44%);
$^1$H-NMR (400 MHz, DMSO-$d_6$): δ 7.24-7.22 (m, 2H), 7.18-7.14 (m, 4H), 6.81 (d, J=8 Hz, 2H), 6.65 (t, J=7 Hz, 1H), 4.66-4.64 (m, 1H), 3.62-3.60 (m, 1H), 3.21-3.14 (m, 6H), 2.97-2.90 (m, 2H), 1.82-1.77 (m, 2H), 1.67-1.65 (m, 2H), 1.40-1.35 (m, 11H);
LCMS [M+H]=407.0, RT=2.53 minutes, (Program P1, Column Y).

F: 2-[2-(((Indan-2-yl)phenyl)amino)ethyl]pyrrolidine (Compound 41)

Dioxane-HCl (25 mL) was added to compound 40 (1 g, 2.46 mmol) at 0° C. and allowed to stir at rt for 4 hours. The reaction mixture was evaporated, diluted in ethyl acetate, and washed with sodium bicarbonate solution, water and brine. The organic layer was dried over anhydrous $Na_2SO_4$ and evaporated to provide crude compound 41.
Yield: 0.6 g (crude).
$^1$H-NMR (400 MHz, DMSO-$d_6$): δ 7.25-7.22 (m, 2H), 7.18-7.14 (m, 4H), 6.83 (d, J=8 Hz, 2H), 6.63 (t, J=7 Hz, 1H), 4.67-4.63 (m, 1H), 3.21-3.13 (m, 3H), 3.00-2.95 (m, 2H), 2.83-2.75 (m, 2H), 2.66-2.64 (m, 1H), 1.74-1.71 (m, 1H), 1.57-1.50 (m, 4H), 1.08-1.07 (m, 1H);
LCMS [M+H]=307.0, RT=3.01 minutes, (Program P1, Column Y).

G: 1,1-Diethyl-2-[2-((indan-2-yl)(phenyl)amino) ethyl]pyrrolidinium iodide

To a stirred solution of compound 41 (0.3 g, 0.98 mmol) in chloroform (6 mL) were added K$_2$CO$_3$ (0.68 g, 4.90 mmol) and ethyl iodide (0.75 mL, 9.8 mmol). The reaction mixture was heated at 50° C. for 16 hours in a sealed tube. The reaction mixture was filtered and evaporated. The crude product was purified by flash column chromatography eluting with 1-2% of methanol-DCM to provide a sticky compound. The compound was lyophilized and dried under high vacuum to get the desired compound.
Yield: 0.12 g (24.99%);
$^1$H-NMR (400 MHz, DMSO-$d_6$): δ 7.25-7.16 (m, 6H), 6.89 (d, J=8 Hz, 2H), 6.73 (t, J=7 Hz, 1H), 4.65-4.61 (m, 1H), 3.59-3.55 (m, 1H), 3.45-3.36 (m, 2H), 3.25-3.05 (m, 8H), 3.02-2.94 (m, 2H), 2.22-2.20 (m, 1H), 1.92-1.90 (m, 3H), 1.69-1.64 (m, 2H), 1.18-1.08 (m, 6H);
LCMS [M$^+$]=363.0, RT=3.07 minutes, (Program P1, Column Y);

UPLC: 98.00% (RT=4.97 minutes, $\lambda_{200\ nm}$, Mobile Phase A. 0.05% TFA in water, B. Acetonitrile; Column: Zorbax® SB-C18 (50×4.6 mm) 1.8μ).

Example 37

General Procedure G

Preparation of 1,1-dimethyl-2-[2-((indan-2-yl)(pyridine-2-yl)amino)ethyl]piperidinium iodide

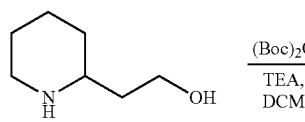
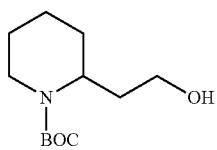
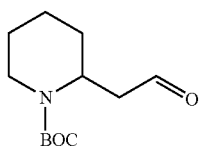

42

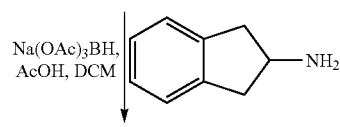

43

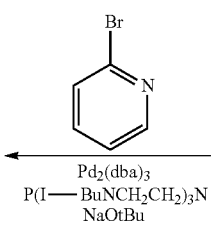
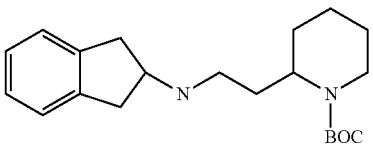
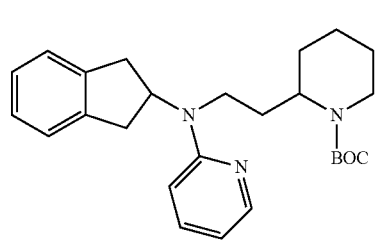

44

45

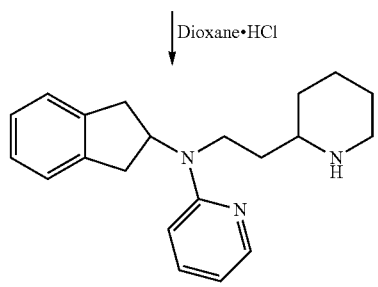
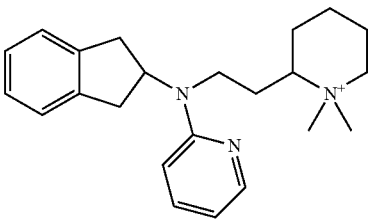

46

A. 2-(2-Hydroxyethyl)piperidine-1-carboxylic acid tert-butyl ester (Compound 42)

To a stirred solution of piperidine-2-ethanol (5 g, 38.69 mmol) in DCM (80 m:) was added TEA (6.5 mL, 46.43 mmol), followed by BOC anhydride (9.8 mL, 42.56 mmol) at 0° C. and the reaction mixture was stirred at rt for 16 hours. The reaction mixture was diluted with ethyl acetate and the organic layer was washed with water and brine solution then dried over anhydrous Na$_2$SO$_4$, filtered and concentrated to get crude compound 42.

Yield: 10 g (crude);

$^1$H-NMR (400 MHz, DMSO-d$_6$): δ 4.33 (t, J=5 Hz, 1H), 4.20-4.18 (m, 1H), 3.82-3.79 (m, 2H), 3.37-3.34 (m, 1H), 2.73 (t, J=13 Hz, 1H), 1.79-1.72 (m, 1H), 1.61-1.47 (m, 7H), 1.38 (s, 9H), 1.26-1.22 (m, 1H);

LCMS [M+H]=230.2, RT=2.95 minutes, (Program P1, Column Y).

B. 2-(2-Oxoethyl)piperidine-1-carboxylic acid tert-butyl ester (Compound 43)

To a stirred solution of DMSO (1.86 mL, 26.2 mmol) in DCM (60 mL) was added (COCl)$_2$ (1.13 mL, 13.1 mmol) at −78° C. and the reaction mixture was stirred at −78° C. for 15 minutes. Compound 42 (2 g, 8.733 mmol) in DCM (20 mL) was then added dropwise at −78° C. and the solution then stirred at same temperature for 1 hour. TEA (6.06 mL, 43.66 mmol) was then added and the reaction mixture was stirred at rt. The reaction mixture was diluted with DCM and the organic layer was washed with water and brine solution, dried over Na$_2$SO$_4$, filtered and concentrated to provide sticky crude compound 43.

Yield: 2.4 g (crude).

C. 2-[2-((Indan-2-yl)amino)ethyl]piperidine-1-carboxylic acid tert-butyl ester (Compound 44)

To a stirred solution of compound 43 (2.4 g, 10.57 mmol) in DCM (50 mL) were added successively 2-aminoindane (1.37 mL, 10.57 mmol), sodium triacetoxyborohydride (6.72 g, 31.72 mmol) and acetic acid (2 drops) at 0° C. The reaction mixture was stirred at rt for 16 hours. The reaction mixture was diluted with DCM and basified with 1N NaOH. The organic layer was washed with water and brine, dried over anhydrous $Na_2SO_4$, filtered and concentrated. The crude compound was purified by column chromatography (using 230-400 silica mesh) eluting with 4-5% methanol-DCM to provide the desired compound 44.

Yield: 1.6 g (44.4%);

$^1$H-NMR (400 MHz, DMSO-$d_6$): δ 7.18-7.13 (m, 2H), 7.11-7.08 (m, 2H), 4.19 (brs, 1H), 3.84-3.81 (m, 1H), 3.52-3.49 (m, 1H), 3.07-3.02 (m, 2H), 2.76-2.60 (m, 5H), 1.86-1.83 (m, 1H), 1.57-1.50 (m, 7H), 1.39 (s, 9H), 1.25-1.23 (m, 1H);

LCMS [M+H]=345.0, RT=3.04 minutes, (Program P1, Column Y).

D: 2-[2-((Indan-2-yl)(pyridin-2-yl)amino)ethyl]piperidine-1-carboxylic acid tert-butyl ester (Compound 45)

The stirred mixture of compound 44 (0.6 g, 1.74 mmol), 2-bromo-pyridine (0.17 mL, 1.74 mmol) and NaO$^t$Bu (0.23 g, 2.44 mmol) in toluene (20 mL) was purged with argon for 15 minutes. $Pd_2(dba)_3$ (0.08 g, 0.09 mmol) and P(i-BuNCH$_2$CH$_2$)$_3$N (0.12 mL, 0.35 mmol) were then added. The resulting mixture was again degassed with argon for 15 minutes and heated at 110° C. for 16 hours. The reaction mixture was diluted with ethyl acetate and washed with water and brine. The organic layer was dried over anhydrous sodium sulphate and concentrated under reduced pressure. The crude compound was purified by column chromatography (using 230-400 mesh silica gel) eluting with 1-2% of ethyl acetate-hexane to provide the desired compound 45.

Yield: 0.32 g (43.6%);

$^1$H-NMR (400 MHz, DMSO-$d_6$): δ 8.10-8.08 (m, 1H), 7.51-7.47 (m, 1H), 7.25-7.23 (m, 2H), 7.17-7.15 (m, 2H), 6.62 (d, J=9 Hz, 1H), 6.57-6.54 (m, 1H), 5.29-5.26 (m, 1H), 4.10-4.08 (m, 1H), 3.78-3.75 (m, 1H), 3.36-3.34 (m, 1H), 3.22-3.13 (m, 3H), 2.98-2.91 (m, 2H), 2.65-2.59 (m, 1H), 1.83-1.80 (m, 1H), 1.67-1.61 (m, 1H), 1.54-1.50 (m, 1H), 1.45-1.42 (m, 4H), 1.32 (s, 9H), 1.26-1.17 (m, 1H);

LCMS [M+H]=422.6, RT=3.18 minutes, (Program R1, Column X).

E. 2-[2-((Indan-2-yl)(pyridin-2-yl)amino)ethyl]piperidine (Compound 46)

Dioxane-HCl (10 mL) was added to compound 45 (0.35 g, 0.83 mmol) at 0° C. The reaction mixture was stirred at rt for 3 hours. The reaction mixture was dried under reduced pressure. The crude compound was dissolved in ethyl acetate and washed with saturated sodium bicarbonate, water and brine. The organic layer was dried over anhydrous sodium sulphate and concentrated to provide the desired compound 46.

Yield: 0.23 g (87%);

LCMS [M+H]=322.4, RT=2.25 minutes, (Program R1, Column Z).

F. 1,1-Dimethyl-2-[2-((indan-2-yl)(pyridine-2-yl)amino)ethyl]piperidinium iodide To a stirred solution of compound 46 (0.12 g, 0.37 mmol) in chloroform (5 mL) were added $K_2CO_3$ (0.257 g, 1.87 mmol) and methyl iodide (0.12 mL, 1.87 mmol). The resulting mixture was heated at 50° C. for 16 hours in a sealed tube. The reaction mixture was filtered and the filtrate was concentrated. The crude material was purified by column chromatography (using 230-400 mesh silica) eluting with 2-3% of methanol-DCM to provide the desired compound.

Yield: 0.08 g (44.96%);

$^1$H-NMR (400 MHz, DMSO-$d_6$): δ 8.11 (d, J=3 Hz, 1H), 7.52 (t, J=7 Hz, 1H), 7.27-7.25 (m, 2H), 7.19-7.17 (m, 2H), 6.74 (d, J=10 Hz, 1H), 6.63-6.60 (m, 1H), 5.17-5.10 (m, 1H), 3.46-3.43 (m, 3H), 3.28-3.25 (m, 2H), 3.20-3.13 (m, 2H), 3.07-2.99 (m, 5H), 2.85 (s, 3H), 2.12-2.09 (m, 1H), 1.92-1.89 (m, 1H), 1.82-1.76 (m, 1H), 1.70-1.67 (m, 2H), 1.60-1.50 (m, 2H), 1.40-1.37 (m, 1H);

LCMS [M$^+$]=350.4, RT=1.72 minutes (Program R1, Column Z)

UPLC: 99.57% (RT=2.70 minutes, $\lambda_{200\,nm}$, Mobile Phase A. 0.05% TFA in water, B. Acetonitrile; Column: Zorbax® XDB-C18 (4.6×50 mm), 1.8μ).

Example 38

General Procedure H

Preparation of 1,1-dimethyl-2-[2-((indan-2-yl)(pyrimidine-2-yl)amino)ethyl]piperidinium iodide

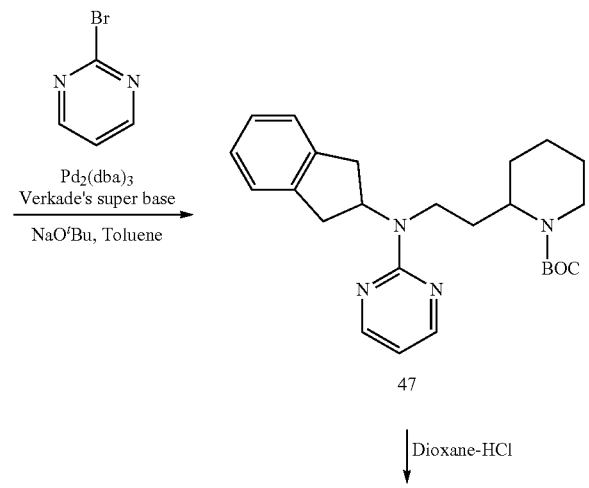

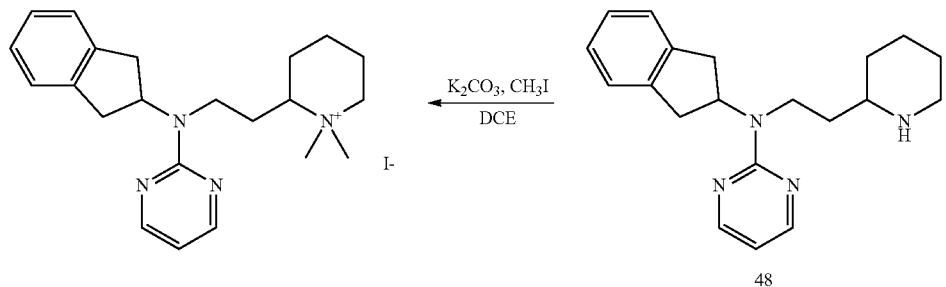

A. 2-[2-((Indan-2-yl)(pyrimidin-2-yl)amino)ethyl]piperidine-1-carboxylic acid tert-butyl ester (Compound 47)

To a stirred solution of compound 44 (1.2 g, 3.48 mmol) in dry toluene (35 mL) were added 2-bromo-pyrimidine (0.55 g, 3.48 mmol) and NaO'Bu (0.47 g, 4.88 mmol) and the solution was purged with argon for 30 minutes. $Pd_2(dba)_3$ (0.159 g, 0.17 mmol) and Verkade's super base (0.24 g, 0.70 mmol) were then added and the solution refluxed overnight. The reaction mixture was filtered through Celite® reagent and washed with ethyl acetate. The filtrate was washed with water and brine solution, dried over anhydrous $Na_2SO_4$, filtered and concentrated. The crude material was purified by Combiflash® chromatography eluting with 14-15% ethyl acetate-hexane to get compound 47.

Yield: 0.303 g (20.6%);

$^1$H-NMR (DMSO-d$_6$): δ 8.35 (d, J=5 Hz, 2H), 7.22 (s, 2H), 7.16-7.14 (m, 2H), 6.61 (t, J=5 Hz, 1H), 5.47-5.43 (m, 1H), 4.07 (s, 1H), 3.77-3.74 (m, 1H), 3.42-3.39 (m, 1H), 3.18-3.11 (m, 2H), 3.03-2.97 (m, 2H), 2.65 (t, J=12 Hz, 1H), 1.89-1.87 (m, 1H), 1.66-1.63 (m, 1H), 1.55-1.37 (m, 6H), 1.31 (s, 9H), 1.26-1.17 (m, 1H);

LCMS [M+H]=423.2, RT=2.62 minutes, (Program P1, Column Y).

B. 2-[2-((Indan-2-yl)(pyrimidin-2-yl)amino)ethyl]piperidine (Compound 48)

To compound 47 (0.303 g, 0.72 mmol) was added dioxane-HCl (20 mL) at ice-cold condition and the solution was stirred for 4 hours at rt. The solution was then concentrated under reduced pressure and dissolved in ethyl acetate. The organic layer was washed with saturated $NaHCO_3$ solution, water and brine, dried over anhydrous $Na_2SO_4$, filtered and concentrated under reduced pressure to provide sticky compound 48.

Yield: 0.21 g (90.83%);

$^1$H-NMR (400 MHz, DMSO-d$_6$): δ 8.34 (d, J=5 Hz, 2H), 7.22-7.21 (m, 2H), 7.16-7.14 (m, 2H), 6.59 (t, J=9 Hz, 1H), 5.37-5.34 (m, 1H), 4.07 (s, 1H), 3.77-3.74 (m, 1H), 3.55-3.53 (m, 2H), 3.16-3.01 (m, 4H), 2.9-2.88 (m, 1H), 1.53-1.45 (m, 5H), 1.35-1.23 (m, 3H);

LCMS [M+H]=322.8, RT=3.08 minutes, (Program P1, Column Y).

C. 1,1-Dimethyl-2-[2-((indan-2-yl)(pyrimidine-2-yl)amino)ethyl]piperidinium iodide To a stirred solution of compound 48 (0.21 g, 0.65 mmol) in $CHCl_3$ (5 mL) was added $K_2CO_3$ (0.45 g, 3.26 mmol) followed by addition of methyl iodide (0.2 mL, 3.26 mmol. The solution was stirred at 50° C. for 16 hours in a sealed tube. The reaction mixture was filtered through a sintered funnel and concentrated. The crude material was purified by column chromatography on neutral alumina eluting with 1-1.5% methanol-DCM to get the desired compound.

Yield: 0.16 g (51.34%);

$^1$H-NMR (400 MHz, DMSO-d$_6$): δ 8.39 (d, J=5 Hz, 2H), 7.25-7.24 (m, 2H), 7.18-7.16 (m, 2H), 6.68-6.66 (m, 1H), 5.45-5.41 (m, 1H), 3.55-3.51 (m, 2H), 3.46-3.42 (m, 1H), 3.26-3.23 (m, 2H), 3.12-3.05 (m, 7H), 2.86 (s, 3H), 2.20-2.17 (m, 1H), 1.93-1.36 (m, 7H);

LCMS [M$^+$]=351, RT=2.90 minutes, (Program P1, Column Y);

UPLC: 99.9% (RT=4.70 minutes, λ$_{220\ nm}$, Mobile Phase; A. 0.05% TFA in water, B. Acetonitrile; Column: Zorbax® SB-C18 (50×4.6 mm) 1.8μ).

Example 39

General procedure I

Preparation of 1,1-dimethyl-2-[2-((indan-2-yl)(thiazol-2-yl)amino)ethyl]piperidinium iodide

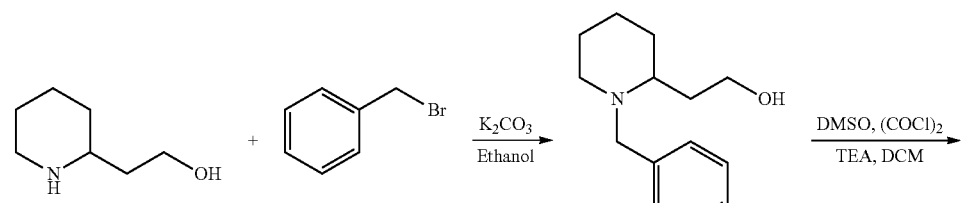

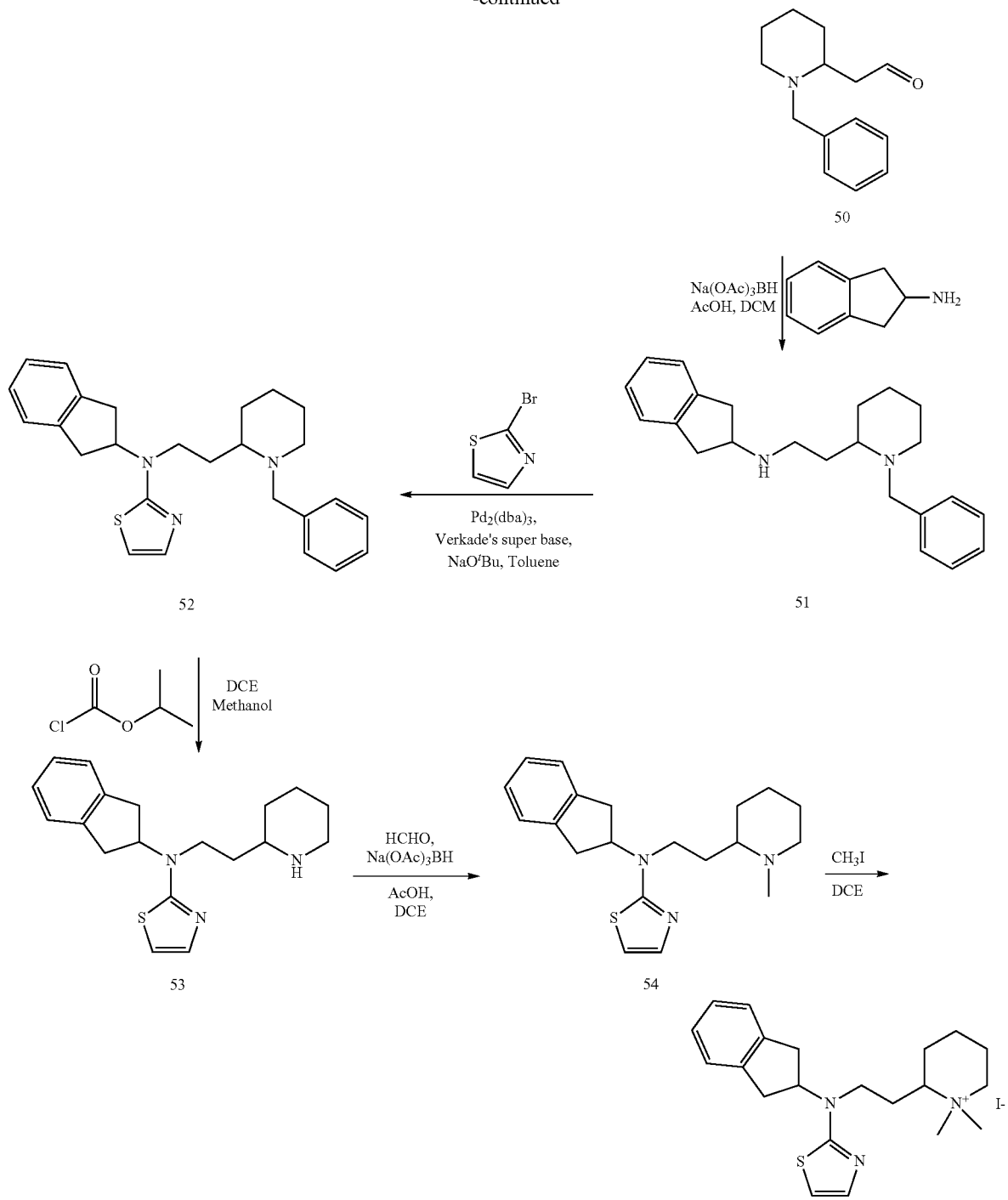

A. 2-(1-Benzylpiperidin-2-yl)ethanol (Compound 49)

To a stirred solution of piperdine-2-ethanol (20 g, 155 mmol) in ethanol (240 mL) was added $K_2CO_3$ (106 g, 775.1 mmol) followed by addition of benzyl bromide (18.4 mL, 155.04 mmol) at 0° C. The reaction mixture was stirred at rt overnight, filtered through a sintered funnel and concentrated. The crude material was dissolved in ethyl acetate, the organic layer was washed with water and brine, dried over anhydrous $Na_2SO_4$, filtered and concentrated to get liquid compound 49.

Yield: 25 g (73.65%);

$^1$H-NMR (400 MHz, DMSO-$d_6$): δ 7.31 (d, J=13 Hz, 4H), 7.24-7.19 (m, 1H), 4.41 (s, 1H), 3.88 (d, J=14 Hz, 1H), 3.54-3.41 (m, 2H), 3.31-3.23 (m, 1H), 2.62-2.58 (m, 1H), 2.45 (s, 1H), 2.06-2.01 (m, 1H), 1.83-1.76 (m, 1H), 1.66-1.57 (m, 3H), 1.42-1.26 (m, 4H);

LCMS [M+H]=220.4, RT=2.35 minutes, (Program P1, Column Y).

B. (1-Benzylpiperidin-2-yl)acetaldehyde (Compound 50)

To a stirred solution of DMSO (5.84 mL, 82.2 mmol) in dry DCM (220 mL) was added (COCl)$_2$ (3.55 mL, 41.1 mmol) at −78° C. and the mixture stirred at same temperature for 20 minutes. A solution of compound 49 (6 g, 27.4 mmol) in DCM (30 mL) was then added slowly and the reaction mixture was stirred at −78° C. for 1 hour. TEA (13.8 mL, 137 mmol) was added at −78° C. and the reaction mixture was stirred and allowed to come to rt. The reaction mixture was diluted with DCM and the organic layer was washed with water and brine, dried over anhydrous Na$_2$SO$_4$, filtered and concentrated to provide sticky compound 50.

Yield: 7.0 g (Crude);
$^1$H-NMR (400 MHz, DMSO-d$_6$): δ 9.76 (s, 1H), 7.43-7.21 (m, 5H), 3.81 (d, J=13 Hz, 1H), 3.24 (d, J=8 Hz, 1H), 3.06 (d, J=6 Hz, 1H), 2.92 (s, 1H), 2.71-2.62 (m, 2H), 2.58-2.49 (m, 3H), 2.13-2.03 (m, 1H), 1.79-1.59 (m, 3H), 1.44-1.35 (m, 4H), 1.23-1.16 (m, 1H).

C. 2-[1-Benzyl-2-((indan-2-yl)amino)ethyl]piperidine (Compound 51)

To a stirred solution of compound 50 (7 g, 32.2 mmol) in DCM (120 mL) were added successively 2-aminoindane (4.29 mL, 32.2 mmol), Na(OAc)$_3$BH (20.5 g, 96.7 mmol) and acetic acid (3 mL) at 0° C. The resulting mixture was allowed to stir at RT for 16 hours. The reaction mixture was diluted with DCM and basified by 1N NaOH solution. The organic layer was separated and washed with water and brine, dried over anhydrous Na$_2$SO$_4$, filtered and concentrated. The crude material was purified by Combiflash® chromatography eluting with 1-2% methanol-DCM to afford compound 51.

Yield: 6.6 g (61.37%);
$^1$H-NMR (400 MHz, DMSO-d$_6$): δ 7.29-7.0 (m, 9H), 3.91 (d, J=14 Hz, 1H), 3.48-3.46 (m, 1H), 3.21 (s, 1H), 3.18-3.12 (m, 1H), 3.05-2.99 (m, 2H), 2.64 (d, J=8 Hz, 1H), 2.62-2.55 (m, 5H), 2.38 (s, 1H), 2.01-1.95, (m, 1H), 1.78 (s, 1H), 1.74-1.70 (m, 1H), 1.67-1.60 (m, 3H), 1.41-1.27 (m, 6H);
LCMS [M+H]=334.8, RT=3.0 minutes, (Program P1, Column Y).

D. 2-[1-Benzyl-2-((indan-2-yl)(thiazol-2-yl)amino)ethyl]piperidine (Compound 52)

To a stirred solution of compound 51 (2 g, 5.98 mmol) in dry toluene (35 mL) were added 2-bromo-thiazole (0.53 mL, 5.98 mmol) and NaO$^t$Bu (0.805 g, 8.38 mmol) and the solution was degassed with argon for 30 minutes. Pd$_2$dba$_3$ (0.274 g, 0.30 mmol) and Verkade's super base (0.42 mL, 1.19 mmol) were then added and the resulting mixture was refluxed for 16 hours. The reaction mixture was filtered through a Celite® pad and was washed with ethyl acetate. The organic layer was washed with water and brine, dried over anhydrous Na$_2$SO$_4$, filtered and concentrated. The crude material was purified by Combiflash® chromatography eluting with 20-22% ethyl acetate-hexane to provide compound 52.

Yield: 0.688 g (27.42%);
$^1$H-NMR (DMSO-d$_6$): δ 7.29-7.20 (m, 9H), 7.12 (m, 1H), 6.73 (d, J=4 Hz, 1H), 4.79-4.75 (m, 1H), 3.82 (d, J=14 Hz, 1H), 3.40-3.37 (m, 1H), 3.35-3.25 (m, 2H), 3.23-3.07 (m, 3H), 2.67-2.61 (m, 1H), 2.5-2.49 (m, 1H), 2.32-2.26 (m, 1H), 2.22-1.98 (m, 1H), 1.97-1.95 (m, 1H), 1.93-1.82 (m, 3H), 1.73-1.51 (m, 4H);
LCMS [M+H]=418.1, RT=3.95 minutes, (Program P1, Column Y).

E. 2-[2-((Indan-2-yl)(thiazol-2-yl)amino)ethyl]piperidine (Compound 53)

To a stirred solution of compound 52 (0.688 g, 1.64 mmol) in DCE (15 mL) was added isobutyl chloroformate (0.53 mL, 4.94 mmol) at 0° C. and the solution was refluxed for 9.5 hours. Methanol (30 mL) was added and the mixture was allowed to stir at rt for 16 hours. The reaction mixture was concentrated under reduced pressure to provide compound 53.

Yield: 0.53 g (98.78%);
$^1$H-NMR (400 MHz, DMSO-d$_6$): δ 7.4-7.18 (m, 4H), 7.0 (d, J=4 Hz, 1H), 6.52-6.48 (m, 1H), 4.75 (s, 1H), 4.70-4.67 (m, 1H), 3.78 (s, 3H), 3.73-3.59 (m, 1H), 3.28-3.10 (m, 3H), 3.08-2.98 (m, 1H), 2.78-2.75 (m, 1H), 1.99-1.97 (m, 1H), 1.86-1.82 (m, 1H), 1.78-1.75 (m, 2H), 1.7-1.68 (m, 2H), 1.58-1.55 (m, 1H), 1.39-1.34 (m, 2H);
LCMS [M+H]=328, RT=3.08 minutes, (Program P1, Column X).

F. 2-[2-((Indan-2-yl)(thiazol-2-yl)amino)ethyl]-1-methylpiperidine (Compound 54)

To a stirred solution of compound 53 (0.53 g, 1.62 mmol) in DCE (25 mL) were added successively formaldehyde (35% solution in H$_2$O, 0.2 mL, 2.43 mmol), Na(OAc)$_3$BH (1.03 g, 4.86 mmol) and acetic acid (0.2 mL) at 0° C., and the solution was allowed to stir at rt for 16 hours. The reaction mixture was diluted with ethyl acetate and basified with 1N NaOH solution. The organic layer was separated and washed with water and brine, dried over anhydrous Na$_2$SO$_4$, filtered and concentrated. The crude material was purified by chromatography on neutral alumina eluting 1% methanol-DCM to get compound 54.

Yield: 0.25 g (45.25%);
$^1$H-NMR (400 MHz, DMSO-d$_6$): δ 7.26-7.24 (m, 2H), 7.18-7.15 (m, 2H), 7.13 (d, J=4 Hz, 1H), 6.74 (d, J=4 Hz, 1H), 4.80-4.76 (m, 1H), 3.35-3.31 (m, 1H), 3.31-3.20 (m, 3H), 3.12-3.06 (m, 2H), 2.67-2.64 (m, 1H), 2.03 (s, 3H), 1.87-1.84 (m, 1H), 1.75-1.69 (m, 2H), 1.61-1.55 (m, 2H), 1.45-1.38 (m, 1H), 1.35-1.32 (m, 2H), 1.23-1.11 (m, 3H);
LCMS [M+H]=342, RT=2.91 minutes, (Program P1, Column Y).

G. 1,1-Dimethyl-2-[2-((indan-2-yl)(thiazol-2-yl)amino)ethyl]piperidinium iodide To a stirred solution of compound 54 (0.25 g, 0.733 mmol) in DCE (5 mL) was added methyl iodide (0.2 mL, 2.93 mmol) and the reaction mixture was stirred at rt for 16 hours in a sealed tube. The reaction mixture was concentrated and the crude material purified by column chromatography on neutral alumina eluting with 1% methanol-DCM to provide a solid compound. The solid material crystallized from methanol-ether to provide the desired compound as an off white solid.

Yield: 0.146 g (41.24%);
$^1$H-NMR (400 MHz, DMSO-d$_6$): δ 7.28-7.22 (m, 2H), 7.19-7.16 (m, 3H), 6.83 (d, J=4 Hz, 1H), 3.39-3.32 (m, 3H), 3.2-3.08 (m, 6H), 3.01 (s, 3H), 2.84 (s, 3H), 2.32-2.21 (m, 1H), 1.86-1.78 (m, 2H), 1.67 (d, J=12 Hz, 2H), 1.52-1.49 (m, 2H), 1.38-1.35 (m, 1H);
LCMS [M$^+$]=356.2, RT=2.44 minutes, (Program R1, Column Z);

UPLC: 99.28% (RT=4.56 minutes, $\lambda_{260\ nm}$, Mobile Phase A. 0.05% TFA in water, B. Acetonitrile; Column: Zorbax® SB-C18 (4.6×50 mm) 1.8μ).

Example 40

General Procedure J

Preparation of 1,1-dimethyl-4-[2-((indan-2-yl)(2-methylphenyl)amino)ethyl]piperidinium bromide

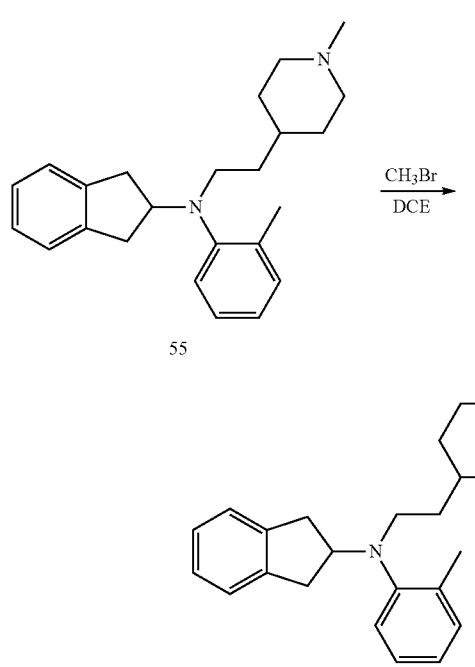

To a stirred solution of compound 55, which is prepared according to general procedure A1 for the preparation of compound 8 (except substituting compound 7e for compound 7 and 4-(2-hydroxyethyl)-1-methylpiperidine for compound 5, (1.2 g, 3.45 mmol) in DCE (20 mL) was added a solution of methyl bromide (25% solution in toluene, 5.23 mL, 13.79 mmol) and the reaction mixture was stirred at rt for 16 hours in a sealed tube. The reaction mixture was concentrated and the crude material was purified by chromatography on silica-gel (230-400 mesh) eluting with 10% methanol-DCM and then crystallized from methanol-ether to provide the desired compound.

Yield: 1.5 g (98.15%);

$^{1}$H-NMR (400 MHz, DMSO-d$_{6}$): δ 7.28 (d, J=8 Hz, 1H), 7.21 (t, J=8 Hz, 2H), 7.17-7.14 (m, 2H), 7.11-7.09 (m, 2H), 7.03 (t, J=7 Hz, 1H), 3.98-3.94 (m, 1H), 3.37-3.33 (m, 2H), 3.24-3.18 (m, 2H), 3.06 (s, 3H), 3.02-2.92 (m, 7H), 2.79 (dd, J=15, 8 Hz, 2H), 2.28 (s, 3H), 1.69-1.66 (m, 2H), 1.51-1.46 (m, 3H), 1.27-1.25 (m, 2H);

LCMS: [M$^{+}$]=363.2, RT=3.30 minutes, (Program P1, Column Y);

UPLC: 99.54% (RT=3.21 minutes, $\lambda_{200\ nm}$, Mobile Phase: A 0.05% TFA in water, B Acetonitrile; Column: Zorbax® SB C18 (4.6×50 mm) 1.8μ).

Example 41

General Procedure K

Preparation of 7-[2-((indan-2-yl)(2-methylpheny)amino)ethyl]-3-oxa-6-azaspiro[5.5]undecan-6-ium chloride

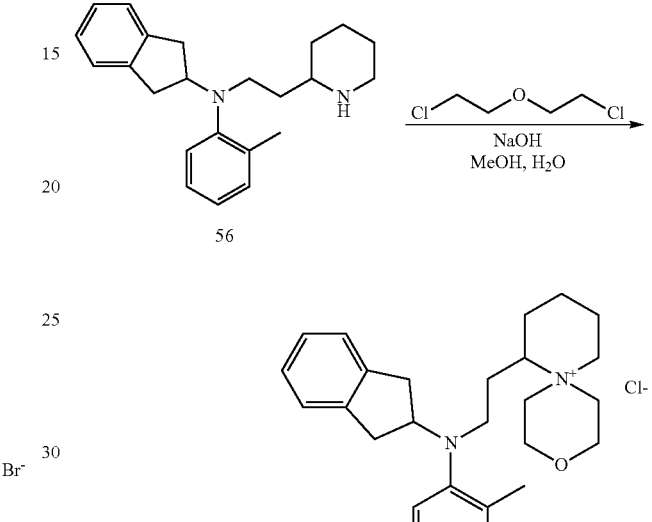

To a stirred solution of NaOH (78 mg, 1.95 mmol) in water (16 mL) was added 1-chloro-2-(2-chloro-ethoxy)ethane (0.3 mL, 2.6 mmol) and the solution was refluxed for 1 hour. Then a solution of compound 56 (435 mg, 1.3 mmol) in methanol (4-5 drops) and water (4 mL) was added and the resultant solution refluxed for 16 hours. 40% NaOH was added to the reaction mixture at ice salt conditions and extracted with chloroform. The solution was then dried over anhydrous Na$_{2}$SO$_{4}$, filtered and concentrated. The crude material was purified by column chromatography on neutral alumina eluting with 2-3% methanol-DCM to provide a solid. The solid material was triturated with dry ether and dried under vacuum to get the desired compound as a white solid.

Yield: 88 mg (15.35%);

$^{1}$H-NMR (400 MHz, DMSO-d$_{6}$): δ 7.33-7.31 (m, 1H), 7.26-7.21 (m, 4H), 7.19-7.10 (m, 2H), 7.07-7.03 (m, 1H), 4.06-4.02 (m, 1H), 3.96-3.90 (m, 1H), 3.84-3.73 (m, 3H), 3.59-3.49 (m, 5H), 3.12-3.10 (m, 2H), 3.02-2.95 (m, 3H), 2.92-2.81 (m, 3H), 2.30 (s, 3H), 1.97 (brs, 1H), 1.88 (brs, 1H), 1.71 (brs, 2H), 1.58-1.48 (m, 4H);

LCMS [M$^{+}$]=405, RT=3.32 minutes, (Program P1, Column Y);

UPLC: 98.59% (RT=5.47 minutes, $\lambda_{220\ nm}$, Mobile Phase A. 0.05% TFA in water, B. Acetonitrile; Column: Zorbax® XDB-C18 (4.6×50 mm) 1.8μ).

Example 42

General Procedure L

Preparation of 1,1-dimethyl-2-[2-((2,3-dihydrobenzo[b][1,4]dioxin-6-yl)(indan-2-yl)amino)ethyl]piperidinium iodide

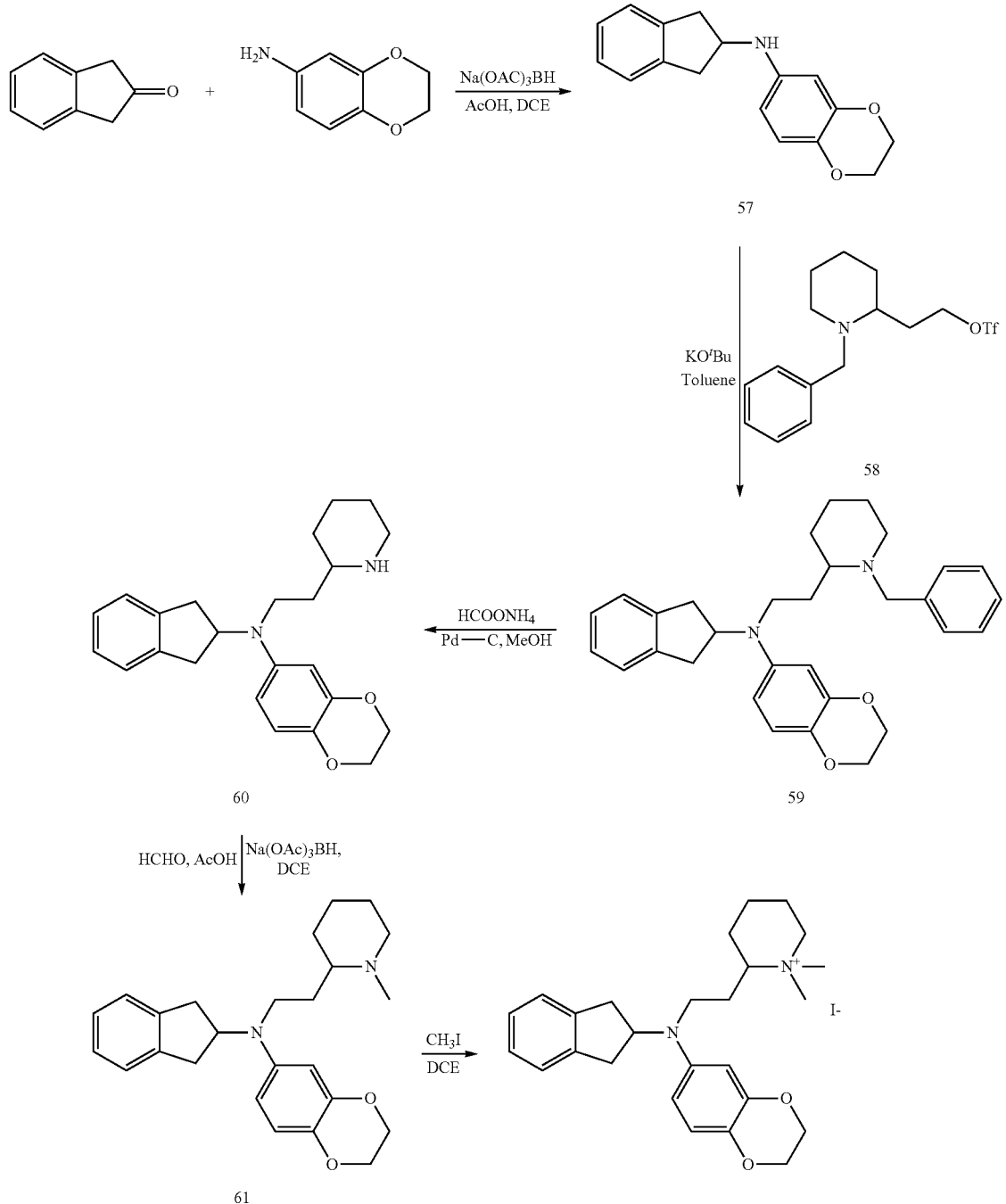

A. N-2,3-Dihydro-benzo[1,4]dioxin-6-yl-N-indan-2-ylamine (Compound 57)

To a stirred solution of 2-indanone (2 g, 15.1 mmol) in DCE (50 mL) were added 2,3-dihydro-benzo[1,4]dioxin-6-ylamine (2.28 g, 15.1 mmol), Na(OAc)$_3$BH (4.81 g, 22.6 mmol), AcOH (1.8 mL) successively at 0° C. and the mixture was stirred overnight at rt. The reaction mixture was dissolved in ethyl acetate and was washed with 1N NaOH, water and brine. The solution was dried over Na$_2$SO$_4$, filtered and concentrated. The crude material was purified by Combiflash® chromatography eluting with 9-10% ethyl acetate-hexane to get compound 57.

Yield: 3.9 g (96.5%);

$^1$H-NMR (400 MHz, DMSO-d$_6$): δ 7.21-7.11 (m, 4H), 6.60-6.56 (m, 1H), 6.14-6.11 (m, 2H), 5.41 (d, J=7 Hz, 1H), 4.16-4.02 (m, 6H), 3.32-3.21 (m, 2H), 2.77-2.71 (m, 2H);

LCMS [M+H]=268.2, RT=3.54 minutes, (Program P1, Column Y).

B. 2-[1-Benzyl-2-((2,3-dihydrobenzo[b][1,4]dioxin-6-yl)(indan-2-yl)amino)ethyl]piperidine (Compound 59)

To a stirred solution of compound 57 (1 g, 3.74 mmol) in dry toluene (25 mL) was added KO$^t$Bu (0.63 g, 5.61 mmol) at 0° C. and the solution was heated at 50° C. for 5 hours. A solution of trifluoromethanesulfonic acid 2-(1-benzyl-piperidin-2-yl)-ethyl ester (58) (1.4 g, 4.11 mmol) in dry toluene (5 mL) was then added at 0° C. and refluxed for 16 hours. TLC showed incomplete conversion of the starting material, hence another 0.5 eq of compound 58 was added and refluxed for 16 hours. The reaction mixture was diluted with ethyl acetate and the organic layer was washed with water and brine. The solution was dried over anhydrous Na$_2$SO$_4$, filtered and concentrated. The crude material was purified by Combiflash® chromatography eluting with 7-8% methanol-DCM to get compound 59.

Yield: 1.8 g (68.46%);
$^1$H-NMR (400 MHz, DMSO-d$_6$): δ 7.28-7.10 (m, 9H), 6.69-6.67 (m, 1H), 6.38 (m, 2H), 4.35-4.34 (m, 1H), 4.17-4.14 (m, 4H), 3.67-3.63 (m, 1H), 3.14-3.07 (m, 4H), 2.87-2.81 (m, 3H), 2.49-2.5 (m, 1H), 2.32-2.28 (m, 1H), 2.00-1.95 (m, 2H), 1.61-1.23 (m, 8H);
LCMS [M+H]=468.8, RT=4.37 minutes, (Program P1, Column Y).

C. 2-[2-((2,3-Dihydrobenzo[b][1,4]dioxin-6-yl)(indan-2-yl)amino)ethyl]piperidine (Compound 60)

To a stirred solution of compound 59 (1.55 g, 3.31 mmol) in methanol (30 mL) was added HCOONH$_4$ (2.08 g, 33.11 mmol) and the solution was purged with nitrogen for 30 minutes. 10% Pd—C (0.4 g) was then added and the solution was refluxed for 6 hours. The reaction mixture was filtered through Celite® reagent and the filtrate was concentrated. The residue was dissolved in ethyl acetate and washed with water and brine. The solution was dried over anhydrous Na$_2$SO$_4$, filtered and concentrated under reduced pressure to provide compound 60.

Yield: 0.98 g (78.2%);
$^1$H-NMR (400 MHz, DMSO-d$_6$): δ 7.20-7.11 (m, 4H), 6.74-6.71 (m, 1H), 6.47-6.46 (m, 2H), 4.33-4.29 (m, 1H), 4.20-4.15 (m, 4H), 3.16-3.11 (m, 3H), 3.07-3.01 (m, 2H), 2.88-2.81 (m, 3H), 2.78-2.71 (m, 1H), 1.75-1.67 (m, 4H), 1.48-1.37 (m, 2H), 1.37-1.34 (m, 1H), 1.23-1.17 (m, 1H);
LCMS [M+H]=469.2, RT=3.05 minutes, (Program P1, Column Y).

D. 2-[2-((2,3-Dihydrobenzo[b][1,4]dioxin-6-yl)(indan-2-yl)amino)ethyl]-1-methylpiperidine (Compound 61)

To a stirred solution of compound 60 (0.5 g, 1.32 mmol) in DCE (25 mL) were added formaldehyde (35% solution in H$_2$O, 0.17 mL, 1.98 mmol), Na(OAc)$_3$BH (0.84 g, 3.96 mmol) and AcOH (0.2 mL) successively at 0° C. and the mixture was stirred at rt for 16 hours. The reaction mixture was dissolved in ethyl acetate and basified with 1N NaOH. The organic layer was separated and washed with water and brine. The solution was dried over anhydrous Na$_2$SO$_4$, filtered and concentrated. The crude material was purified by Combiflash® chromatography eluting with 5-5.2% methanol-DCM to provide compound 61.

Yield: 0.25 g (48.2%);
$^1$H-NMR (400 MHz, DMSO-d$_6$): δ 7.21-7.19 (m, 2H), 7.13-7.11 (m, 2H), 6.71-6.69 (m, 1H), 6.41-6.37 (m, 2H), 4.36-4.33 (m, 1H), 4.19-4.14 (m, 4H), 3.14-3.01 (m, 4H), 2.84 (dd, J=16, 8 Hz, 2H), 2.67-2.64 (m, 1H), 1.97 (s, 3H), 1.91-1.86 (m, 1H), 1.78 (s, 1H), 1.58-1.55 (m, 1H), 1.50-1.33 (m, 5H), 1.20-1.11 (m, 2H);
LCMS [M+H]=393.2, RT=3.02 minutes, (Program P1, Column Y)

E. 1,1-Dimethyl-2-[2((2,3-dihydrobenzo[b][1,4]dioxin-6-yl)(indan-2-yl)amino)ethyl]piperidinium iodide To a stirred solution of compound 61 (0.25 g, 0.64 mmol) in DCE (3 mL) was added methyl iodide (0.15 mL, 2.55 mmol) and the mixture was stirred at rt for 40 hours in a sealed tube. The reaction mixture was concentrated and the crude material was purified by Combiflash® chromatography eluting with 6-7% methanol-DCM to provide a solid. The solid material was triturated with ether and filtered through a sintered funnel and dried under high vacuum to get the desired compound.

Yield: 0.185 g (54.39%);
$^1$H-NMR (400 MHz, DMSO-d$_6$): δ 7.20-7.19 (m, 2H), 7.14-7.12 (m, 2H), 6.75-6.73 (m, 1H), 6.50-6.49 (m, 2H), 4.34-4.30 (m, 1H), 4.19-4.17 (m, 4H), 3.43-3.40 (m, 1H), 3.15-3.05 (m, 6H), 3.03-2.8 (m, 8H), 1.96-1.94 (m, 1H), 1.85-1.76 (m, 2H), 1.69-1.65 (m, 2H), 1.54-1.51 (m, 1H), 1.39-1.34 (m, 2H);
LCMS [M$^+$]=407, RT=2.90 minutes, (Program P1, Column Y);
HPLC: 99.78% (RT=3.01 minutes, λ$_{220\ nm}$, Mobile Phase A. 10 mM ammonium acetate in water, B. Acetonitrile; Column: Gemini® NX-C18 (4.6×50 mm) 3μ).

Example 43

General Procedure M

Preparation of (R)-1,1-dimethyl-2-[2-((indan-2-yl)(2-methylphenyl)amino)ethyl]piperidinium bromide

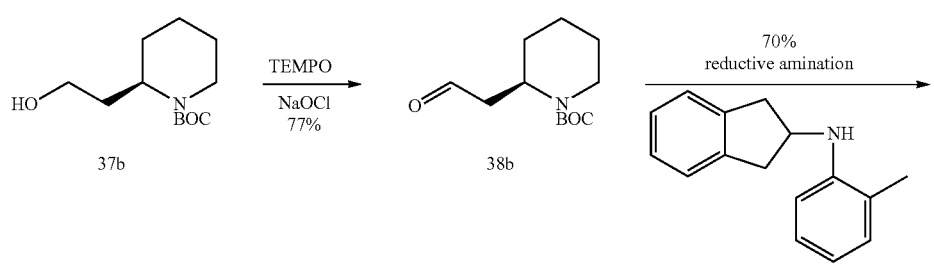

7e

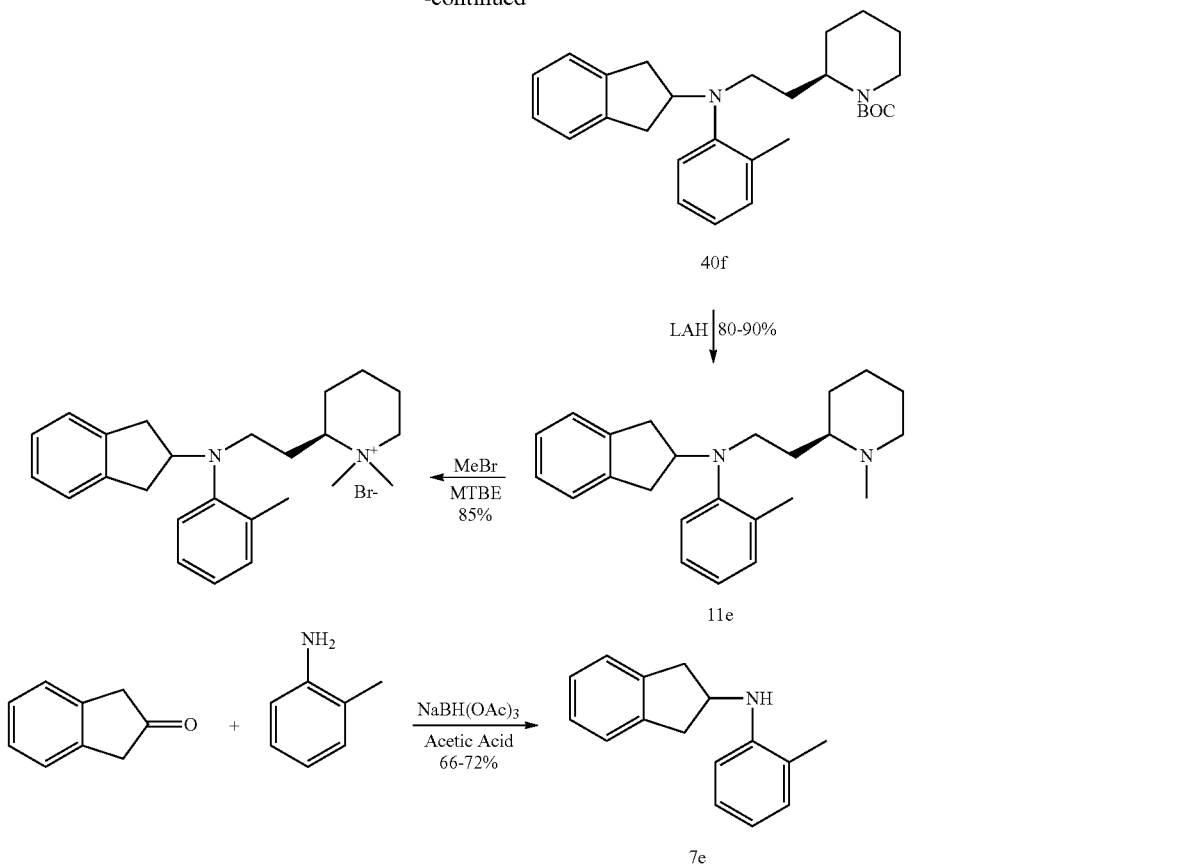

Alcohol 37b was synthesized as previously described (Tetrahedron 2007, 63, 3000-3005).

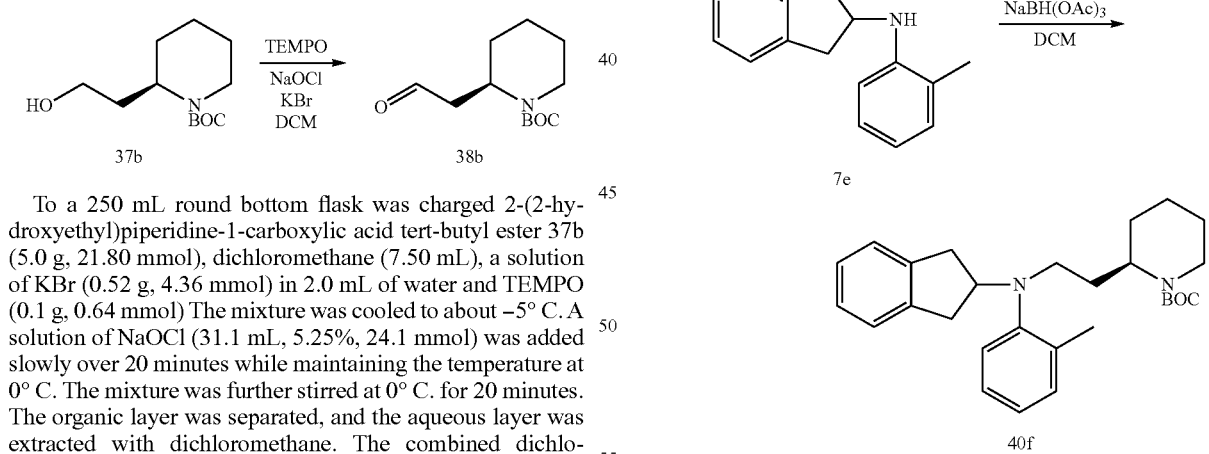

To a 250 mL round bottom flask was charged 2-(2-hydroxyethyl)piperidine-1-carboxylic acid tert-butyl ester 37b (5.0 g, 21.80 mmol), dichloromethane (7.50 mL), a solution of KBr (0.52 g, 4.36 mmol) in 2.0 mL of water and TEMPO (0.1 g, 0.64 mmol) The mixture was cooled to about −5° C. A solution of NaOCl (31.1 mL, 5.25%, 24.1 mmol) was added slowly over 20 minutes while maintaining the temperature at 0° C. The mixture was further stirred at 0° C. for 20 minutes. The organic layer was separated, and the aqueous layer was extracted with dichloromethane. The combined dichloromethane extract was washed with water (50 mL), followed by brine. After drying over MgSO$_4$, the mixture was filtered and concentrated. The crude was purified with silica gel column chromatography to give product 38b (4.1 g, 83%) as colorless oil.

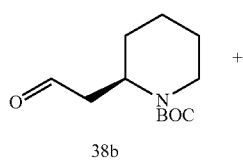

To a clean and dry 250 mL round bottom flask was charged sodium triacetoxyborohydride (5.59 g, 26.40 mmol), 4 Å molecular sieves (10.0 g), amine 7e (7.37 g, 33.00 mmol) and dichloromethane (20.0 mL). The mixture was stirred and cooled to about 0° C., and a solution of aldehyde 38b (5.0 g, 22.00 mmol) in 40 mL of dichloromethane was added. The mixture was then stirred further at 0° C. for about 1 hour and at ambient temperature for an additional 40 minutes. The reaction mixture was quenched with aqueous saturated NaHCO$_3$ (100 mL). After separation of organic layer, the mixture was extracted with dichloromethane. After drying over MgSO$_4$, the organic layer was concentrated. The crude product was purified by silica gel column chromatography to give product 40f (7.2 g, 75.3%) as colorless oil.

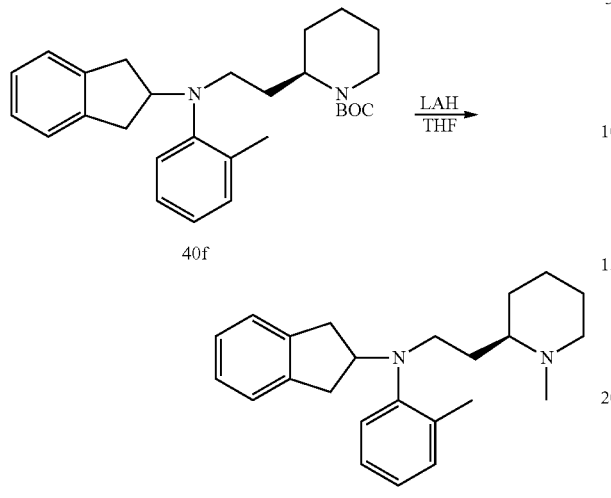

To a clean and dry 250 mL round bottom flask was charged lithium aluminum hydride (1.53 g, 40.27 mmol) and THF (30.0 mL). The mixture was heated to reflux. A solution of carbamate 40f (7.0 g, 16.11 mmol) in THF (40.0 mL) was added dropwise over 5 minutes. After refluxing for 15 h, the reaction mixture was cooled to 0° C., and water (1.55 mL) was added slowly and carefully, followed by THF (100 mL) and 15% NaOH (1.55 mL). After stirring the mixture at room temperature for 1.0 h, MgSO$_4$ was added, and the mixture was stirred further for 15 minutes. The mixture was filtered and concentrated to obtain the crude product, which was purified by silica gel column chromatography to afford product 11e (4.7 g, 84%) as pale yellow oil. Optical purity by chiral HPLC: 99.3% ee.

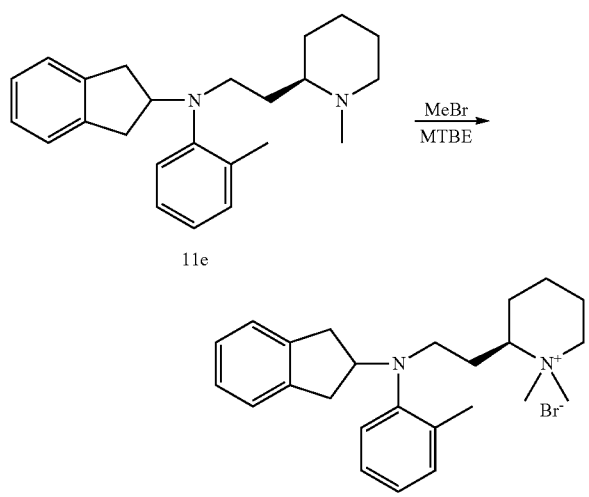

To a clean and dry 250 mL round bottom flask was charged diamine 11e (4.70 g, 13.49 mmol) and 1.07 M bromomethane in MTBE (126.0 mL, 134.8 mmol) After stirring at room temperature for 20 h, the reaction mixture was filtered. The solid cake was washed with MTBE to give the product (4.40 g, 73%) as white powder. Optical purity by chiral HPLC: 99.3% ee.

Example 44

General Procedure N

Preparation of (S)-1,1-dimethyl-2-[2-((indan-2-yl)(2-methylphenyl)amino)ethyl]piperidinium chloride

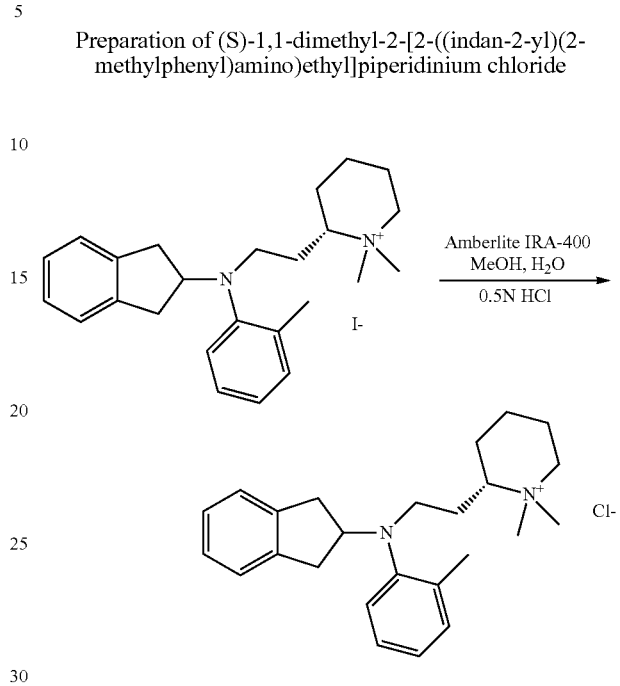

The compound of example 35 (0.185 g, 0.50 mmol) was dissolved in methanol:water (1:9, 20 mL) and was treated with Amberlite IRA-400 chloride form resin for 2 hours. The solution was filtered and washed with methanol. The filtrate was concentrated and the residue was treated with 0.5 N HCl (10 mL) for 30 minutes. The reaction mixture was concentrated and the residue was azeotroped with toluene, twice. The crude material was purified by Combiflash® chromatography (twice), eluting with 15% methanol-DCM to provide a sticky compound which showed a pH between 4 and 5. Then the compound was lyophilized over 16 hours. After lyophilization, the solid material was purified by Combiflash® chromatography again eluting with 15% methanol-DCM to provide a colorless sticky compound which showed a pH of 6. The sticky compound was lyophilized over 16 hours to provide the desired compound as a white solid.

Yield: 0.075 g (49.84%);

$^1$H-NMR (400 MHz, DMSO-d$_6$): δ 7.30 (d, J=8 Hz, 1H), 7.25-7.15 (m, 4H), 7.13-7.09 (m, 2H), 7.04 (t, J=7 Hz, 1H), 4.04-4.0 (m, 1H), 3.43 (d, J=12 Hz, 1H); 3.32-3.26 (m, 1H), 3.23-3.11 (m, 2H), 3.01-2.81 (m, 8H), 2.79 (s, 3H), 2.31 (s, 3H), 1.96-1.93 (m, 1H), 1.79-1.65 (m, 4H), 1.54-1.49 (m, 1H), 1.40-1.38 (m, 1H), 1.28-1.26 (m, 1H);

LCMS: [M$^+$]=363.2, RT=3.14 minutes, (Program P1, Column Y);

UPLC: 98.07% (RT=5.66 minutes, λ$_{200\ nm}$, Mobile Phase: A 0.05% TFA in water, B Acetonitrile; Column: Zorbax® SB-C18 (50×4.6 mm) 1.8μ).

Examples 45-52

Additional compounds listed in Table 2 were prepared in a similar manner, using the methods described for Examples 36 to 44 and in Schemes 1 to 27. Yields and $^1$H-NMR, LCMS, and HPLC characterization data for Examples 45-52 are provided immediately following Table 2.

TABLE 2

| Ex | Structure | Name | LC program, column | Synthetic Route |
|---|---|---|---|---|
| 1 | 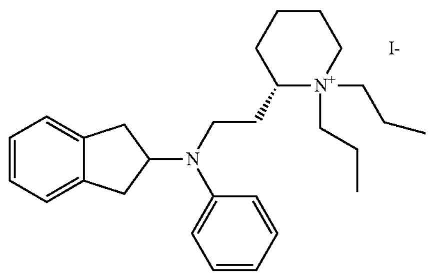 [SMILES: CCC[N+]1(CCC)CCCC[C@H]1CCN(c1ccccc1)C1Cc2ccccc2C1 ; [I-]] | (S)-1,1-dipropyl-2-[2-((indan-2-yl)(phenyl)amino)ethyl]piperidinium iodide | P1, Y | A1 or M |
| 2 | 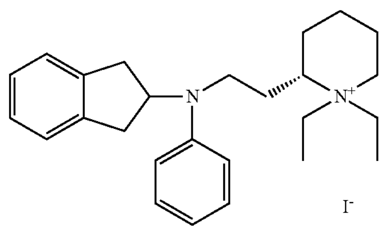 [SMILES: CC[N+]1(CC)CCCC[C@H]1CCN(c1ccccc1)C1Cc2ccccc2C1 ; [I-]] | (S)-1,1-diethyl-2-[2-((indan-2-yl)(phenyl)amino)ethyl]piperidinium iodide | P1, Y | A2 or M |
| 3 | 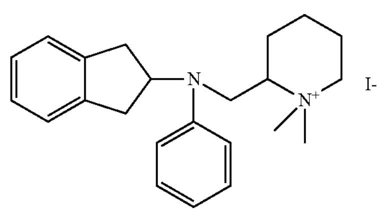 [SMILES: C[N+]1(C)CCCCC1CN(c1ccccc1)C1Cc2ccccc2C1 ; [I-]] | 1,1-dimethyl-2-[((indan-2-yl)(phenyl)amino)methyl]piperidinium iodide | P1, Y | B1 |
| 4 | 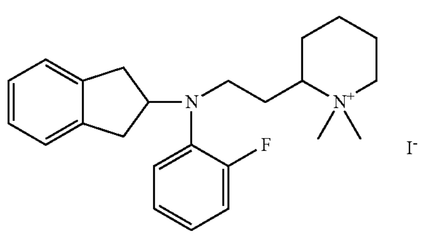 [SMILES: C[N+]1(C)CCCCC1CCN(c1ccccc1F)C1Cc2ccccc2C1 ; [I-]] | 1,1-dimethyl-2-[2-((2-fluorophenyl)(indan-2-yl)amino)ethyl]piperidinium iodide | R1, X | B2 |
| 5 | 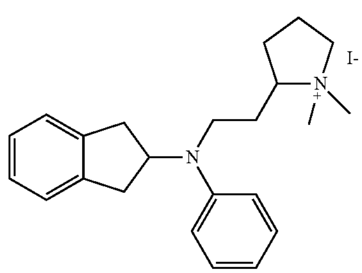 | 1,1-dimethyl-2-[2-((indan-2-yl)(phenyl)amino)ethyl]pyrrolidinium iodide | P1, Z | C |
| 7 | 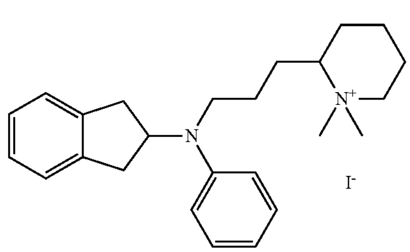 [SMILES: C[N+]1(C)CCCCC1CCCN(c1ccccc1)C1Cc2ccccc2C1 ; [I-]] | 1,1-dimethyl-2-[3-((indan-2-yl)(phenyl)amino)propyl]piperidinium iodide | P1, Y | D |

TABLE 2-continued

| Ex | Structure | Name | LC program, column | Synthetic Route |
|---|---|---|---|---|
| 8 | 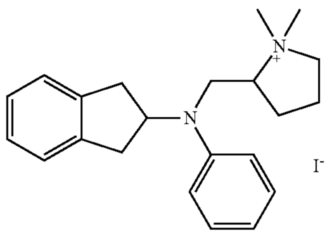 | 1,1-dimethyl-2-[((indan-2-yl)(phenyl)amino)methyl]pyrrolidinium iodide | P1, Y | E |
| 9 | 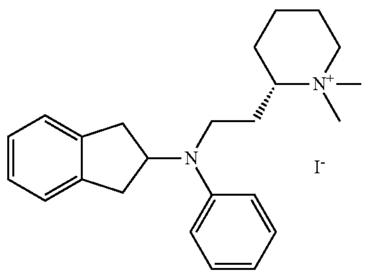 [SMILES: C[N+]1(C)CCCC[C@H]1CCN(c1ccccc1)C1Cc2ccccc2C1 ; [I-]] | (S)-1,1-dimethyl-2-[2-((indan-2-yl)(phenyl)amino)ethyl]piperidinium iodide | P1, X | A2 or M |
| 10 | 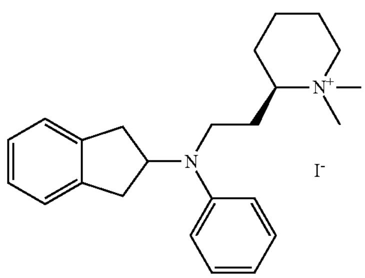 [SMILES: C[N+]1(C)CCCC[C@@H]1CCN(c1ccccc1)C1Cc2ccccc2C1 ; [I-]] | (R)-1,1-dimethyl-2-[2-((indan-2-yl)(phenyl)amino)ethyl]piperidinium iodide | P2, Y | A2 or M |
| 11 | 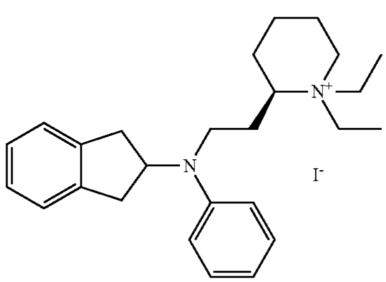 [SMILES: CC[N+]1(CC)CCCC[C@@H]1CCN(c1ccccc1)C1Cc2ccccc2C1 ; [I-]] | (R)-1,1-diethyl-2-[2-((indan-2-yl)(phenyl)amino)ethyl]piperidinium iodide | P1, Y | A2 or M |
| 12 | 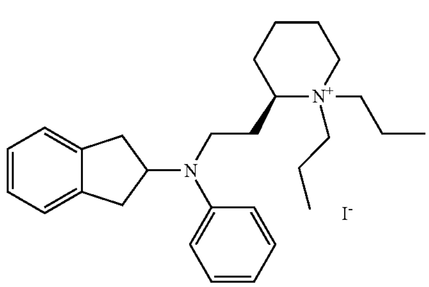 [SMILES: CCC[N+]1(CCC)CCCC[C@@H]1CCN(c1ccccc1)C1Cc2ccccc2C1 ; [I-]] | (R)-1,1-dipropyl-2-[2-((indan-2-yl)(phenyl)amino)ethyl]piperidinium iodide | P1, Y | A2 or M |

TABLE 2-continued

| Ex | Structure | Name | LC program, column | Synthetic Route |
|---|---|---|---|---|
| 13 | 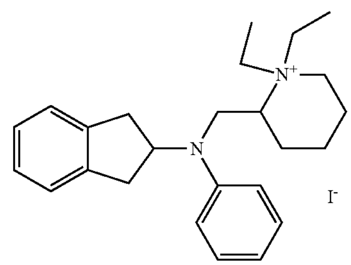 [SMILES: CC[N+]1(CC)CCCCC1CN(c1ccccc1)C1Cc2ccccc2C1 ; [I-]] | 1,1-diethyl-2-[((indan-2-yl)(phenyl)amino)methyl]piperidinium iodide | P1, Y | B1 |
| 14 | 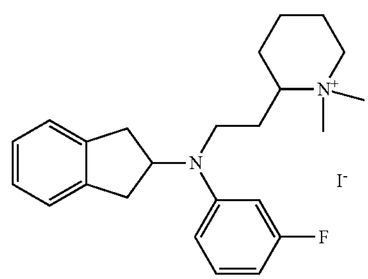 [SMILES: C[N+]1(C)CCCCC1CCN(c1cccc(F)c1)C1Cc2ccccc2C1 ; [I-]] | 1,1-dimethyl-2-[2-((3-fluorophenyl)(indan-2-yl)amino)ethyl]piperidinium iodide | R1, X | B2 |
| 15 | 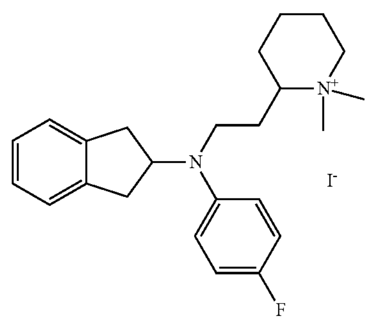 [SMILES: C[N+]1(C)CCCCC1CCN(c1ccc(F)cc1)C1Cc2ccccc2C1 ; [I-]] | 1,1-dimethyl-2-[2-((4-fluorophenyl)(indan-2-yl)amino)ethyl]piperidinium iodide | R1, X | B2 |
| 16 | 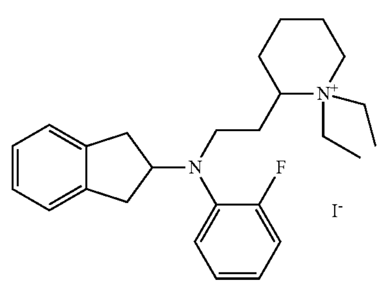 [SMILES: CC[N+]1(CC)CCCCC1CCN(c1ccccc1F)C1Cc2ccccc2C1 ; [I-]] | 1,1-diethyl-2-[2-((2-fluorophenyl)(indan-2-yl)amino)ethyl]piperidinium iodide | P1, Y | B2 |
| 17 | 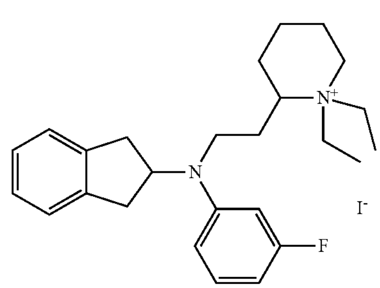 [SMILES: CC[N+]1(CC)CCCCC1CCN(c1cccc(F)c1)C1Cc2ccccc2C1 ; [I-]] | 1,1-diethyl-2-[2-((3-fluorophenyl)(indan-2-yl)amino)ethyl]piperidinium iodide | P1, Y | B2 |

TABLE 2-continued

| Ex | Structure | Name | LC program, column | Synthetic Route |
|---|---|---|---|---|
| 18 | 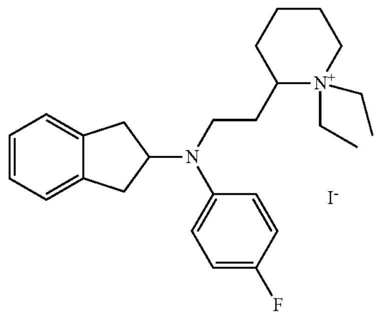 [SMILES: CC[N+]1(CC)CCCCC1CCN(c1ccc(F)cc1)C1Cc2ccccc2C1 ; [I-]] | 1,1-diethyl-2-[2-((4-fluorophenyl)(indan-2-yl)amino)ethyl] piperidinium iodide | P1, Y | B2 |
| 19 | 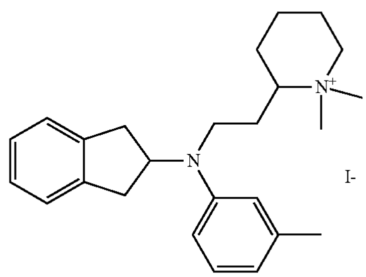 [SMILES: Cc1cccc(N(CCC2CCCC[N+]2(C)C)C2Cc3ccccc3C2)c1 ; [I-]] | 1,1-dimethyl-2-[2-((indan-2-yl)(3-methylphenyl)amino) ethyl]piperidinium iodide | P1, Y | B2 |
| 20 | 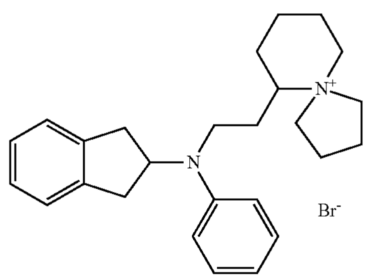 [SMILES: c1ccc(N(CCC2CCCC[N+]23CCCC3)C2Cc3ccccc3C2)cc1 ; [Br-]] | 6-[2-((indan-2-yl)(phenyl)amino) ethyl]-5-azoniaspiro[4.5] decane bromide | P1, Y | B2 |
| 21 | 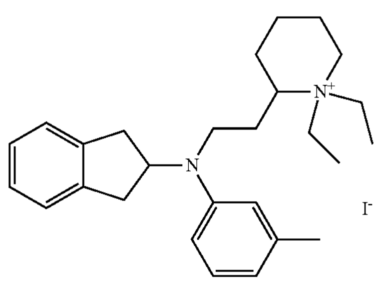 [SMILES: CC[N+]1(CC)CCCCC1CCN(c1cccc(C)c1)C1Cc2ccccc2C1 ; [I-]] | 1,1-diethyl-2-[2-((indan-2-yl)(3-methylphenyl)amino) ethyl]piperidinium iodide | P1, Y | B2 |
| 22 | 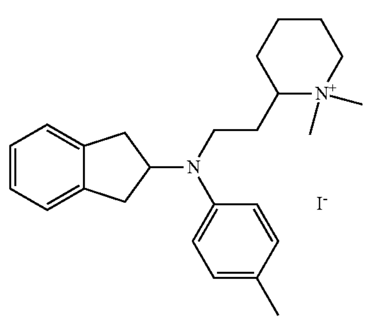 [SMILES: Cc1ccc(N(CCC2CCCC[N+]2(C)C)C2Cc3ccccc3C2)cc1 ; [I-]] | 1,1-dimethyl-2-[2-((indan-2-yl)(4-methylphenyl)amino) ethyl]piperidinium iodide | P1, Y | B2 |

TABLE 2-continued

| Ex | Structure | Name | LC program, column | Synthetic Route |
|---|---|---|---|---|
| 23 | 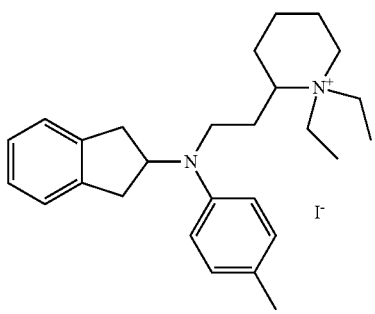 [SMILES: CC[N+]1(CC)CCCCC1CCN(c1ccc(C)cc1)C1Cc2ccccc2C1 ; [I-]] | 1,1-diethyl-2-[2-((indan-2-yl)(4-methylphenyl)amino)ethyl]piperidinium iodide | P1, Y | B2 |
| 24 | 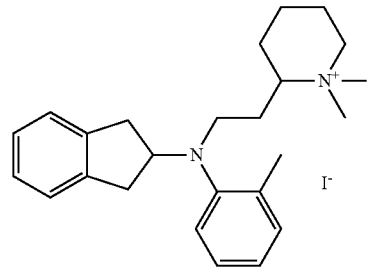 [SMILES: Cc1ccccc1N(CCC1CCCC[N+]1(C)C)C1Cc2ccccc2C1 ; [I-]] | 1,1-dimethyl-2-[2-((indan-2-yl)(2-methylphenyl)amino)ethyl]piperidinium iodide | P1, Z | B2 |
| 25 | 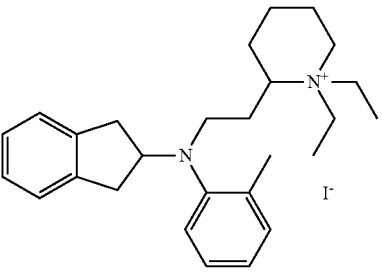 [SMILES: CC[N+]1(CC)CCCCC1CCN(c1ccccc1C)C1Cc2ccccc2C1 ; [I-]] | 1,1-diethyl-2-[2-((indan-2-yl)(2-methylphenyl)amino)ethyl]piperidinium iodide | P1, Y | B2 |
| 26 | 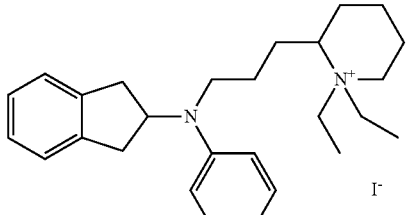 | 1,1-diethyl-2-[3-((indan-2-yl)(phenyl)amino)propyl]piperidinium iodide | P1, Y | D |
| 27 | 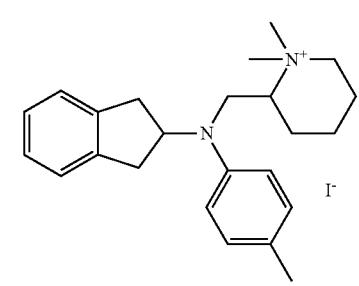 [SMILES: Cc1ccc(N(CC2CCCC[N+]2(C)C)C2Cc3ccccc3C2)cc1 ; [I-]] | 1,1-dimethyl-2-[((indan-2-yl)(4-methylphenyl)amino)methyl]piperidinium iodide | P1, X | B1 |

TABLE 2-continued

| Ex | Structure | Name | LC program, column | Synthetic Route |
|---|---|---|---|---|
| 28 | 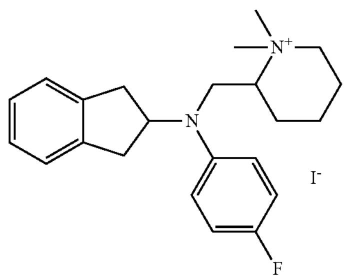 [SMILES: C[N+]1(C)CCCCC1CN(c1ccc(F)cc1)C1Cc2ccccc2C1 ; [I-]] | 1,1-dimethyl-2-[((4-fluorophenyl)(indan-2-yl)amino)methyl] piperidinium iodide | P1, Y | B1 |
| 29 | 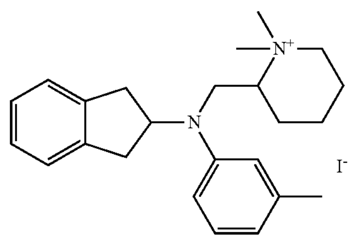 [SMILES: Cc1cccc(N(CC2CCCC[N+]2(C)C)C2Cc3ccccc3C2)c1 ; [I-]] | 1,1-dimethyl-2-[((indan-2-yl)(3-methylphenyl)amino) methyl]piperidinium iodide | P1, Y | B1 |
| 30 | 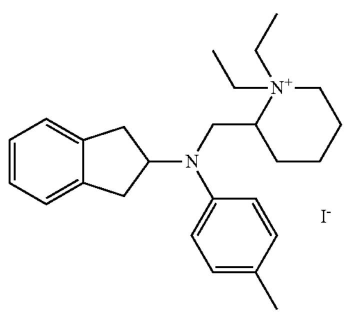 [SMILES: CC[N+]1(CC)CCCCC1CN(c1ccc(C)cc1)C1Cc2ccccc2C1 ; [I-]] | 1,1-diethyl-2-[((indan-2-yl)(4-methylphenyl)amino) methyl]piperidinium iodide | P1, Y | B1 |
| 31 | 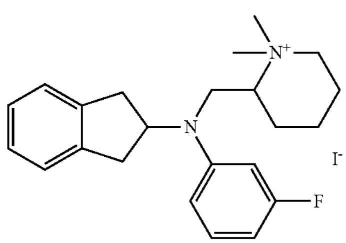 [SMILES: C[N+]1(C)CCCCC1CN(c1cccc(F)c1)C1Cc2ccccc2C1 ; [I-]] | 1,1-dimethyl-2-[((3-fluorophenyl)(indan-2-yl)amino)methyl] piperidinium iodide | P1, Y | B2 |
| 32 | 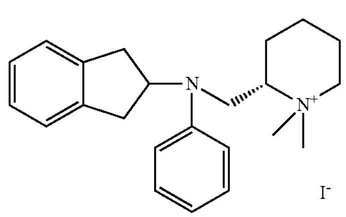 [SMILES: C[N+]1(C)CCCC[C@H]1CN(c1ccccc1)C1Cc2ccccc2C1 ; [I-]] | (S)-1,1-dimethyl-2-[((indan-2-yl)(phenyl)amino) methyl]piperidinium iodide | | B1 |
| 33 | 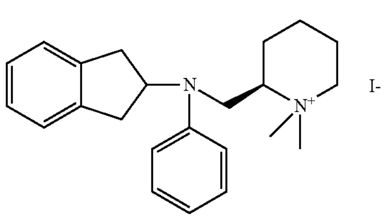 [SMILES: C[N+]1(C)CCCC[C@@H]1CN(c1ccccc1)C1Cc2ccccc2C1 ; [I-]] | (R)-1,1-dimethyl-2-[((indan-2-yl)(phenyl)amino) methyl]piperidinium iodide | | B1 |

TABLE 2-continued

| Ex | Structure | Name | LC program, column | Synthetic Route |
|---|---|---|---|---|
| 34 | 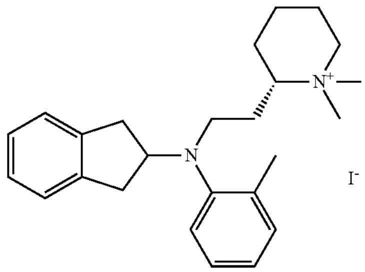 [SMILES: Cc1ccccc1N(CC[C@@H]1CCCC[N+]1(C)C)C1Cc2ccccc2C1 ; [I-]] | (S)-1,1-dimethyl-2-[2-((indan-2-yl)(2-methylphenyl)amino)ethyl]piperidinium iodide | | A2 or M |
| 35 | 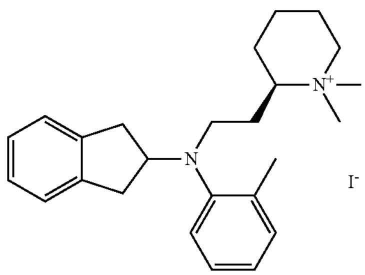 [SMILES: Cc1ccccc1N(CC[C@H]1CCCC[N+]1(C)C)C1Cc2ccccc2C1 ; [I-]] | (R)-1,1-dimethyl-2-[2-((indan-2-yl)(2-methylphenyl)amino)ethyl]piperidinium iodide | | A2 or M |
| 36 | 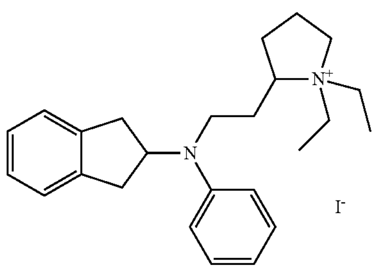 [SMILES: CC[N+]1(CC)CCCC1CCN(c1ccccc1)C1Cc2ccccc2C1 ; [I-]] | 1,1-diethyl-2-[2-((indan-2-yl)(phenyl)amino)ethyl]pyrrolidinium iodide | P1, Y | F |
| 37 | 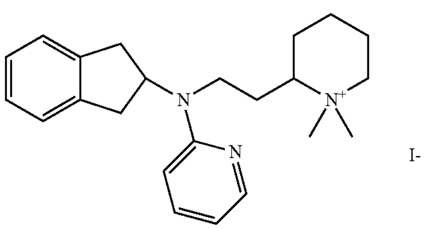 [SMILES: C[N+]1(C)CCCCC1CCN(c1ccccn1)C1Cc2ccccc2C1 ; [I-]] | 1,1-dimethyl-2-[2-((indan-2-yl)(pyridine-2-yl)amino)ethyl]piperidinium iodide | R1, Z | G |
| 38 | 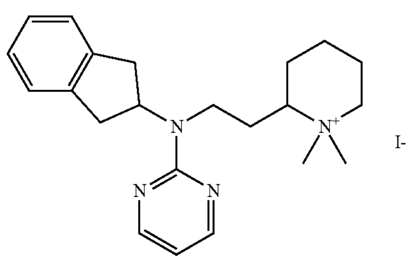 [SMILES: C[N+]1(C)CCCCC1CCN(c1ncccn1)C1Cc2ccccc2C1 ; [I-]] | 1,1-dimethyl-2-[2-((indan-2-yl)(pyrimidine-2-yl)amino)ethyl]piperidinium iodide | P1, Y | H |
| 39 | 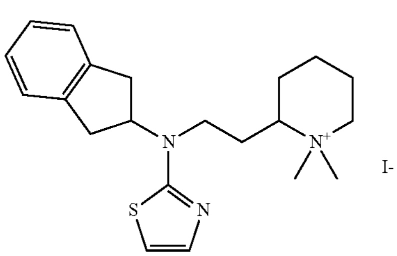 [SMILES: C[N+]1(C)CCCCC1CCN(c1nccs1)C1Cc2ccccc2C1 ; [I-]] | 1,1-dimethyl-2-[2-((indan-2-yl)(thiazol-2-yl)amino)ethyl]piperidinium iodide | R1, Z | I |

TABLE 2-continued

| Ex | Structure | Name | LC program, column | Synthetic Route |
|----|-----------|------|--------------------|-----------------|
| 40 | 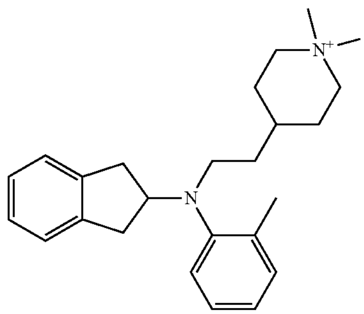 | 1,1-dimethyl-4-[2-((indan-2-yl)(2-methylphenyl)amino)ethyl]piperidinium bromide | P1, Y | J |
| 41 | 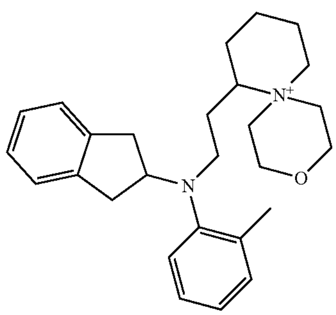 | 7-[2-((indan-2-yl)(2-methylpheny)amino)ethyl]-3-oxa-6-azaspiro[5.5]undecan-6-ium chloride | P1, Y | K |
| 42 | 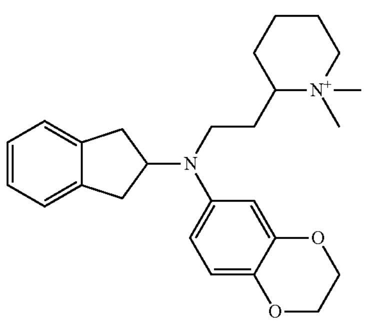 | 1,1-dimethyl-2-[2-((2,3-dihydrobenzo[b][1,4]dioxin-6-yl)(indan-2-yl)amino)ethyl]piperidinium iodide | P1, Y | L |
| 43 | 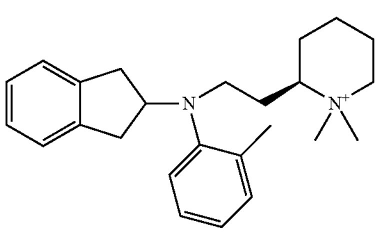 | (R)-1,1-dimethyl-2-[2-((indan-2-yl)(2-methylphenyl)amino)ethyl]piperidinium bromide | P1, X | M |
| 44 | 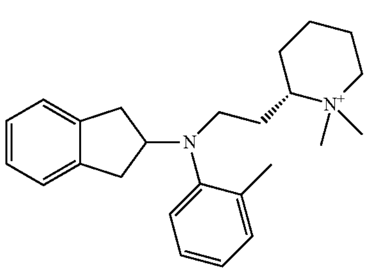 | (S)-1,1-dimethyl-2-[2-((indan-2-yl)(2-methylphenyl)amino)ethyl]piperidinium chloride | P1, Y | N |

TABLE 2-continued

| Ex | Structure | Name | LC program, column | Synthetic Route |
|---|---|---|---|---|
| 45 | 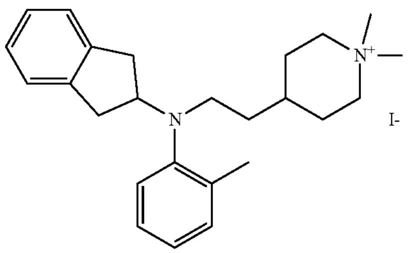 [SMILES: Cc1ccccc1N(CCC1CC[N+](C)(C)CC1)C1Cc2ccccc2C1 ; [I-]] | 1,1-dimethyl-4-[2-((indan-2-yl)(2-methylphenyl)amino)ethyl]piperidinium iodide | P1, Y | B1 |
| 46 | 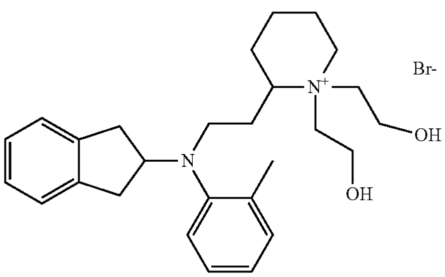 [SMILES: Cc1ccccc1N(CCC1CCCC[N+]1(CCO)CCO)C1Cc2ccccc2C1 ; [Br-]] | 1,1-bis(2-hydroxyethyl)-2-[2-((indan-2-yl)(2-methylphenyl)amino)ethyl]piperidinium bromide | P1, Y | B2 |
| 47 | 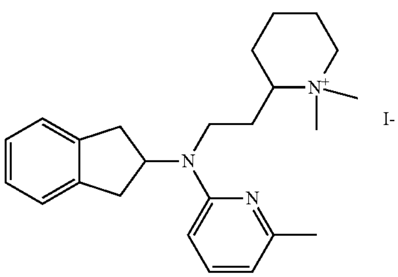 [SMILES: Cc1cccc(N(CCC2CCCC[N+]2(C)C)C2Cc3ccccc3C2)n1 ; [I-]] | 1,1-dimethyl-2-[2-((indan-2-yl)(6-methylpyridine-2-yl)amino)ethyl]piperidinium iodide | P1, Y | F |
| 48 | 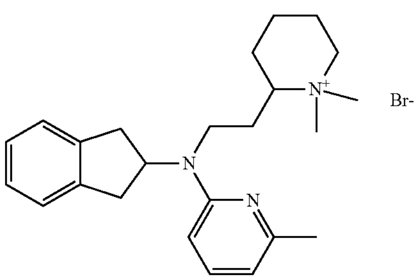 [SMILES: Cc1cccc(N(CCC2CCCC[N+]2(C)C)C2Cc3ccccc3C2)n1 ; [Br-]] | 1,1-dimethyl-2-[2-((indan-2-yl)(6-methylpyridine-2-yl)amino)ethyl]piperidinium bromide | P1, V | J |
| 49 | 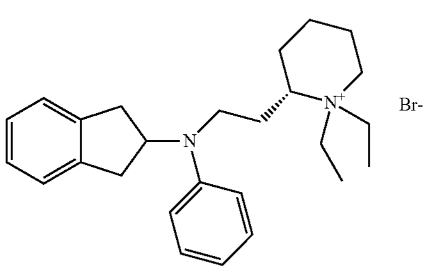 [SMILES: CC[N+]1(CC)CCCC[C@H]1CCN(c1ccccc1)C1Cc2ccccc2C1 ; [Br-]] | (S)-1,1-diethyl-2-[2-((indan-2-yl)(phenyl)amino)ethyl]piperidinium bromide | P1, Y | A2 or M |

TABLE 2-continued

| Ex | Structure | Name | LC program, column | Synthetic Route |
|---|---|---|---|---|
| 50 | 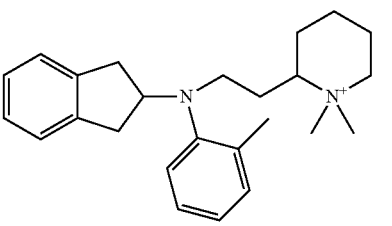 | 1,1-dimethyl-2-[2-((indan-2-yl)(2-methylphenyl)amino)ethyl]piperidinium chloride | P1, W | N |
| 51 | 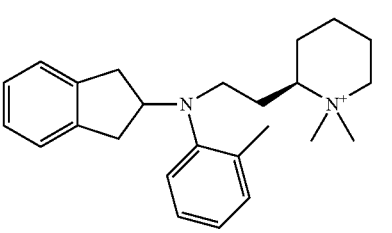 | (R)-1,1-dimethyl-2-[2-((indan-2-yl)(2-methylphenyl)amino)ethyl]piperidinium chloride | P1, V | N |
| 52 | 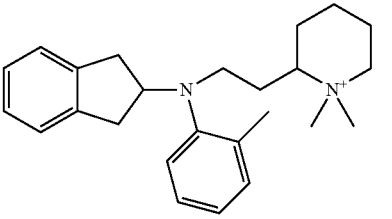 | 1,1-dimethyl-2-[2-((indan-2-yl)(2-methylphenyl)amino)ethyl]piperidinium bromide | P1, X | M |

Example 9

(S)-1,1-Dimethyl-2-[2-((indan-2-yl)(phenyl)amino)ethyl]piperidinium iodide

Yield: 0.25 g (66.48%);

$^1$H-NMR (400 MHz, DMSO-$d_6$): δ 7.25-7.16 (m, 6H), 6.87 (d, J=8 Hz, 2H), 6.72 (t, J=7 Hz, 1H), 4.67-4.64 (m, 1H), 3.44-3.41 (m, 1H), 3.27-3.15 (m, 6H), 3.02-2.92 (m, 5H), 2.82 (s, 3H), 2.02-1.98 (m, 1H), 1.85-1.77 (m, 2H), 1.69-1.65 (m, 2H), 1.55-1.52 (m, 1H), 1.42-1.33 (m, 2H);

LCMS: m/z=349.6 [M$^+$], RT=3.18 minutes;

HPLC: 98.41%, RT=2.73 minutes, $\lambda_{200\,nm}$, Mobile Phase (i) 0.05% TFA in water, (ii) acetonitrile; Column: Zorbax® SB-C18 (4.6×50 mm) 1.8μ.

Example 10

(R)-1,1-Dimethyl-2-[2-((indan-2-yl)(phenyl)amino)ethyl]piperidinium iodide

Yield: 0.1 g (33.35%);

$^1$H-NMR (400 MHz, DMSO-$d_6$): δ 7.25-7.16 (m, 6H), 6.87 (d, J=8 Hz, 2H), 6.72 (t, J=7 Hz, 1H), 4.67-4.64 (m, 1H), 3.45-3.42 (m, 1H), 3.28-3.15 (m, 6H), 3.02-2.93 (m, 5H), 2.82 (s, 3H), 2.02-1.99 (m, 1H), 1.85-1.77 (m, 2H), 1.69-1.66 (m, 2H), 1.55-1.52 (m, 1H), 1.42-1.36 (m, 2H);

LCMS: m/z=349.2 [M$^+$], RT=8.98 minutes;

HPLC: 96.78%, RT=2.73 minutes, $\lambda_{200\,nm}$, Mobile Phase (i) 0.05% TFA in water, (ii) acetonitrile; Column: Zorbax® SB-C18 (4.6×50 mm) 1.8μ.

Example 11

(R)-1,1-Diethyl-2-[2-((indan-2-yl)(phenyl)amino)ethyl]piperidinium iodide

Yield: 0.23 g (72.29%);

$^1$H-NMR (400 MHz, DMSO-$d_6$): δ 7.26-7.16 (m, 6H), 6.87 (d, J=8 Hz, 2H), 6.72 (t, J=7 Hz, 1H), 4.68-4.63 (m, 1H), 3.50-3.47 (m, 1H), 3.39-3.16 (m, 9H), 3.02-2.92 (m, 3H), 1.89-1.85 (m, 2H), 1.66-1.47 (m, 6H), 1.10 (t, J=7 Hz, 6H);

LCMS: m/z=377.0 [M$^+$], RT=3.35 minutes;

UPLC: 96.63%, RT=3.66 minutes, $\lambda_{200\,nm}$, Mobile Phase (i) 0.05% TFA in water, (ii) acetonitrile; Column: Zorbax® SB-C18 (4.6×50 mm) 1.8μ.

Example 12

(R)-1,1-Dipropyl-2-[2-((indan-2-yl)(phenyl)amino)ethyl]piperidinium iodide

Yield: 0.12 g (32.69%);

$^1$H-NMR (400 MHz, DMSO-$d_6$): δ 7.25-7.16 (m, 6H), 6.87 (d, J=8 Hz, 2H), 6.73 (t, J=7 Hz, 1H), 4.68-4.64 (m, 1H), 3.41-3.37 (m, 3H), 3.27-3.13 (m, 8H), 3.01-2.85 (m, 3H), 1.95-1.82 (m, 2H), 1.70-1.50 (m, 9H), 0.87 (t, J=7 Hz, 3H), 0.80 (t, J=7 Hz, 3H);

LCMS: m/z=405.0 [M$^+$], RT=3.54 minutes;

UPLC: 97.82%, RT=4.00 minutes, $\lambda_{200\,nm}$, Mobile Phase (i) 0.05% TFA in water, (ii) acetonitrile; Column: Zorbax® SB-C18 (4.6×50 mm) 1.8μ.

Example 13

1,1-Diethyl-2-[((indan-2-yl)(phenyl)amino)methyl] piperidinium iodide

Yield: 0.06 g (21.15%);
$^1$H-NMR (400 MHz, DMSO-d$_6$): δ 7.33 (t, J=8 Hz, 2H), 7.18-7.11 (m, 6H), 7.05 (t, J=7 Hz, 1H), 4.25 (t, J=8 Hz, 1H), 3.69-3.64 (m, 2H), 3.51-3.47 (m, 1H), 3.43-3.39 (m, 1H), 3.22-3.16 (m, 4H), 3.09-3.03 (m, 2H), 2.96-2.78 (m, 3H), 2.10-2.07 (m, 1H), 1.94-1.82 (m, 1H), 1.71-1.62 (m, 3H), 1.51-1.39 (m, 1H), 1.16 (t, J=7 Hz, 3H), 0.99 (t, J=7 Hz, 3H);
LCMS: m/z=363.1 [M$^+$], RT=3.37 minutes;
HPLC: 95.74%, RT=11.27 minutes, λ$_{200\ nm}$, Mobile Phase (i) acetonitrile, (ii) 0.05% TFA in water; Column: Atlantis® dC18 (150×4.6 mm) 5µ.

Example 14

1,1-Dimethyl-2-[2-((3-fluorophenyl)(indan-2-yl) amino)ethyl]piperidinium iodide

Yield: 63 mg (44.9%);
$^1$H-NMR (400 MHz, DMSO-d$_6$): δ 7.27-7.17 (m, 5H), 1.63 (t, J=8 Hz, 2H), 6.46 (t, J=8 Hz, 1H), 4.73-4.66 (m, 1H), 3.45-3.39 (m, 2H), 3.26-3.17 (m, 6H), 3.03-2.93 (m, 5H), 2.81 (s, 3H), 2.00-1.98 (m, 1H), 1.80 (t, J=15 Hz, 2H), 1.67 (d, J=13 Hz, 2H), 1.54-1.51 (m, 1H), 1.45-1.34 (m, 2H);
LCMS: m/z=367.2 [M$^+$], RT=2.66 minutes;
UPLC: 97.81%, RT=3.97 minutes, λ$_{200\ nm}$, Mobile phase: (i) 0.05% TFA in water, (ii) acetonitrile; Column: Zorbax® SB C18 (50×4.6 mm) 1.8µ.

Example 15

1,1-Dimethyl-2-[2-((4-fluorophenyl)(indan-2-yl) amino)ethyl]piperidinium iodide

Yield: 0.065 g (46%);
$^1$H-NMR (400 MHz, DMSO-d$_6$): δ 7.24-7.22 (m, 2H), 7.16-7.14 (m, 2H), 7.07 (t, J=9 Hz, 2H), 6.97-6.93 (m, 2H), 4.51-4.47 (m, 1H), 3.42 (d, J=13 Hz, 1H), 3.32-3.26 (m, 2H), 3.17-3.09 (m, 4H), 2.96-2.87 (m, 5H), 2.80 (s, 3H), 1.97 (brs, 1H), 1.81 (t, J=16 Hz, 2H), 1.67 (d, J=12 Hz, 2H), 1.55-1.51 (m, 1H), 1.39-1.37 (m, 2H);
LCMS: m/z=367.2 [M$^+$], RT=2.59 minutes;
HPLC: 98.57%, RT=4.01 minutes, λ$_{204\ nm}$, Mobile phase: (i) 10 mM NH$_4$OAc in water, (ii) acetonitrile; Column: Xbridge™ C18 (50×4.6 mm) 5µ.

Example 16

1,1-Diethyl-2-[2-((2-fluorophenyl)(indan-2-yl) amino)ethyl]piperidinium iodide

Yield: 119 mg (38.53%);
$^1$H-NMR (400 MHz, DMSO-d$_6$): δ 7.30 (t, J=16 Hz, 1H), 7.19-7.09 (m, 7H), 4.25-4.21 (m, 1H), 3.54-3.49 (m, 1H), 3.30 (s, 1H), 3.28-3.19 (m, 4H), 3.11-2.97 (m, 4H), 2.89-2.84 (m, 2H), 1.87-1.84 (m, 2H), 1.65 (brs, 4H), 1.49-1.47 (brs, 2H), 1.09-1.02 (m, 6H);
LCMS: m/z=395.4 [M$^+$], RT=3.25 minutes;
HPLC: 98.74%, RT=3.77 minutes, λ$_{200\ nm}$, Mobile phase: (i) 10 mM NH$_4$OAc in Water, (ii) acetonitrile; Column: Xbridge™ C18 (50×4.6 mm) 3µ.

Example 17

1,1-Diethyl-2-[2-((3-fluor-phenyl)(indan-2-yl) amino)ethyl]piperidinium iodide

Yield: 0.060 g (35.32%);
$^1$H-NMR (400 MHz, DMSO-d$_6$): δ 7.27-7.17 (m, 5H), 6.65-6.59 (m, 2H), 6.47 (t, J=9 Hz, 1H), 4.71-4.68 (m, 1H), 3.48-3.46 (m, 1H), 3.40-3.34 (m, 2H), 3.30-3.19 (m, 5H), 3.03-2.93 (m, 4H), 1.85 (m, 2H), 1.66-1.44 (m, 7H), 1.11 (t, J=6 Hz, 6H);
LCMS: m/z=395.4 [M$^+$], RT=3.25 minutes;
HPLC: 97.91%, RT=4.28 minutes, λ$_{200\ nm}$, Mobile phase: (i) 10 mM NH$_4$OAc in water, (ii) acetonitrile; Column: Xbridge™ C18 (50×4.6 mm) 5µ.

Example 18

1,1-Diethyl-2-[2-((4-fluorophenyl)(indan-2-yl) amino)ethyl]piperidinium iodide

Yield: 0.101 g (32%);
$^1$H-NMR (400 MHz, DMSO-d$_6$): δ 7.23 (brs, 2H), 7.17-7.14 (m, 2H), 7.07 (t, J=9 Hz, 2H), 6.95-6.92 (m, 2H), 4.51 (m, 1H), 3.55-3.45 (m, 1H), 3.31 (s, 1H), 3.29-3.23 (m, 2H), 3.19-3.11 (m, 5H), 3.01-2.91 (m, 4H), 1.85 (brs, 2H), 1.66-1.62 (m, 4H), 1.46 (brs, 2H), 1.11-1.06 (m, 6H);
LCMS: m/z=395.4 [M$^+$], RT=3.21 minutes;
HPLC: 99.51%, RT=3.71 minutes, λ$_{200\ nm}$, Mobile phase: (i) 10 mM NH$_4$OAc in water, (ii) acetonitrile; Column: Xbridge™ C18 (50×4.6 mm) 3µ.

Example 19

1,1-Dimethyl-2-[2-((indan-2-yl)(3-methylphenyl) amino)ethyl]piperidinium iodide

Yield: 0.053 g (40.47%);
$^1$H-NMR (400 MHz, DMSO-d$_6$): δ 7.24 (brs, 2H), 7.16 (t, J=3 Hz, 2H), 7.09 (t, J=8 Hz, 1H), 6.69-6.66 (m, 2H), 6.55 (d, J=7 Hz, 1H), 4.65-4.61 (m, 1H), 3.43 (d, J=12 Hz, 1H), 3.28-3.22 (m, 2H), 3.19-3.13 (dd, J=7, 16 Hz, 3H), 3.00-2.91 (m, 5H), 2.81 (s, 3H), 2.25 (s, 3H), 2.00 (brs, 1H), 1.81 (t, J=14 Hz, 2H), 1.67 (d, J=13 Hz, 2H), 1.54-1.51 (m, 2H), 1.39-1.36 (m, 2H);
LCMS: m/z=363.4 [M$^+$], RT=1.21 minutes;
HPLC: 95.71%, RT=3.79 minutes, λ$_{200\ nm}$, Mobile phase: (i) 10 mM NH$_4$OAc in water, (ii) acetonitrile; Column: Xbridge™ C18 (50×4.6 mm) 3µ.

Example 20

6-[2-((Indan-2-yl)(phenyl)amino)ethyl]-5-azoniaspiro[4.5]decane bromide

Yield: 0.020 g (11.72%);
$^1$H-NMR (400 MHz, DMSO-d$_6$): δ 7.25-7.16 (m, 6H), 6.88 (d, J=8 Hz, 2H), 6.72 (t, J=7 Hz, 1H), 4.67-4.64 (m, 1H), 3.59-3.57 (m, 1H), 3.50-3.39 (m, 1H), 3.31 (s, 1H), 3.26-3.17 (m, 7H), 3.00-2.96 (m, 2H), 1.99-1.72 (m, 10H), 1.49-1.44 (m, 3H);
LCMS: m/z=375 [M$^+$], RT=3.63 minutes;
UPLC: 99.64%, RT=3.62 minutes, λ$_{200\ nm}$, Mobile phase: (i) 0.05% TFA in water, (ii) acetonitrile; Column: Zorbax® SB C18 (50×4.6 mm) 1.8µ.

Example 21

1,1-Diethyl-2-[2-((indan-2-yl)(3-methylphenyl)amino)ethyl]piperidinium iodide

Yield: 0.194 g (47.38%);
$^1$H-NMR (400 MHz, DMSO-d$_6$): δ 7.25 (brs, 2H), 7.17 (t, J=3 Hz, 2H), 7.09 (t, J=8 Hz, 1H), 6.67 (d, J=8 Hz, 2H), 6.55 (d, J=7 Hz, 1H), 4.65-4.62 (m, 1H), 3.49-3.46 (m, 1H), 3.36-3.31 (m, 2H), 3.25-3.15 (m, 6H), 3.03-2.90 (m, 4H), 2.24 (s, 3H), 1.84 (brs, 2H), 1.66-1.58 (m, 4H), 1.46 (brs, 2H), 1.11-1.10 (m, 6H);
LCMS: m/z=391.2 [M$^+$], RT=3.95 minutes;
UPLC: 97.75%, RT=3.73 minutes, λ$_{200\ nm}$, Mobile phase: (i) 0.05% TFA in Water, (ii) acetonitrile; Column: Zorbax® SB C18 (50×4.6 mm) 1.8μ.

Example 22

1,1-Dimethyl-2-[2-((indan-2-yl)(4-methylphenyl)amino)ethyl]piperidinium iodide

Yield: 0.202 g (73.56%);
$^1$H-NMR (400 MHz, DMSO-d$_6$): δ 7.23-7.22 (m, 2H), 7.16-7.14 (m, 2H), 7.04 (d, J=8 Hz, 2H), 6.83 (d, J=8 Hz, 2H), 4.54-4.50 (m, 1H), 3.42 (d, J=13 Hz, 1H), 3.29-3.23 (m, 3H), 3.16-3.09 (m, 3H), 2.96-2.88 (m, 5H), 2.80 (s, 3H), 2.21 (s, 3H), 1.98 (brs, 1H), 1.84-1.73 (m, 2H), 1.67 (d, J=12 Hz, 2H), 1.53-1.47 (m, 1H), 1.39-1.36 (m, 2H);
LCMS: m/z=363.2 [M$^+$], RT=3.33 minutes;
UPLC: 99.25%, RT=3.38 minutes, λ$_{200\ nm}$, Mobile phase: (i) 0.05% TFA in water, (ii) acetonitrile; Column: Zorbax® SB C18 (50×4.6 mm) 1.8μ.

Example 23

1,1-Diethyl-2-[2-((indan-2-yl)(4-methylphenyl)amino)ethyl]piperidinium iodide

Yield: 0.318 mg (51.26%);
$^1$H-NMR (400 MHz, DMSO-d$_6$): δ 7.24-7.22 (m, 2H), 7.17-7.15 (m, 2H), 7.04 (d, J=8 Hz, 2H), 6.81 (d, J=8 Hz, 2H), 4.54-4.52 (m, 1H), 3.52-3.48 (m, 1H), 3.30-3.23 (m, 3H), 3.21-3.11 (m, 6H), 3.00-2.90 (m, 3H), 2.20 (s, 3H), 1.84 (brs, 2H), 1.65-1.59 (m, 4H), 1.45 (brs, 2H), 1.11-1.07 (m, 6H);
LCMS: m/z=391.2 [M$^+$], RT=3.28 minutes;
HPLC: 98.10%, RT=3.95 minutes, λ$_{200\ nm}$, Mobile phase: (i) 10 mM NH$_4$OAc in water, (ii) MeOH; Column: Xbridge™ C18 (50×4.6 mm) 5μ.

Example 24

1,1-Dimethyl-2-[2-((indan-2-yl)(2-methylphenyl)amino)ethyl]piperidinium iodide

Yield: 0.092 g (31.35%);
$^1$H-NMR (400 MHz, DMSO-d$_6$): δ 7.30 (d, J=8 Hz, 1H), 7.25-7.17 (m, 4H), 7.12-7.10 (m, 2H), 7.05 (t, J=7 Hz, 1H), 4.04-4.01 (m, 1H), 3.41 (d, J=13 Hz, 1H), 3.32-3.22 (m, 2H), 3.19-3.10 (m, 2H), 3.02-2.96 (m, 2H), 2.93-2.84 (m, 2H), 2.79 (s, 6H), 2.31 (s, 3H), 2.05-1.93 (m, 1H), 1.77 (d, J=14 Hz, 1H), 1.67 (d, J=10 Hz, 2H), 1.53-1.50 (m, 1H), 1.43-1.37 (m, 1H), 1.29-1.23 (m, 1H);
LCMS: m/z=363.1 [M$^+$], RT=2.85 minutes;
HPLC: 98.66%, RT=4.20 minutes, λ$_{210\ nm}$, Mobile phase: (i) 10 mM NH$_4$OAc in water, (ii) acetonitrile; Column: Xbridge™ C18 (50×4.6 mm) 5μ.

Example 25

1,1-Diethyl-2-[2-((indan-2-yl)(2-methylphenyl)amino)ethyl]piperidinium iodide

Yield: 0.140 g (30.15%);
$^1$H-NMR (400 MHz, DMSO-d$_6$): δ 7.31 (d, J=8 Hz, 1H), 7.25-7.23 (m, 1H), 7.20-7.17 (m, 3H), 7.12-7.10 (m, 2H), 7.05 (t, J=7 Hz, 1H), 4.02-3.98 (m, 1H), 3.50-3.47 (m, 1H), 3.25-3.17 (m, 6H), 3.02-2.93 (m, 3H), 2.87 (d, J=8 Hz, 2H), 2.84-2.80 (m, 1H), 2.30 (s, 3H), 1.84-1.79 (m, 2H), 1.69-1.62 (m, 4H), 1.49-1.43 (m, 2H), 1.04 (t, J=6 Hz, 3H), 0.89 (t, J=7 Hz, 3H);
LCMS: m/z=391.2 [M$^+$], RT=3.49 minutes;
HPLC: 99.51%, RT=8.11 minutes, λ$_{210\ nm}$, Mobile phase: (i) 10 mM NH$_4$OAc in water, (ii) acetonitrile; Column: XTerra® C18 (250×4.6 mm) 5μ.

Example 26

1,1-Diethyl-2-[3-((indan-2-yl)(phenyl)amino)propyl]piperidinium iodide

Yield: 58 mg (33%);
$^1$H-NMR (400 MHz, DMSO-d$_6$): δ 7.24-7.15 (m, 6H), 6.85 (d, J=8 Hz, 2H), 6.69 (t, J=7 Hz, 1H), 4.63 (t, J=7 Hz, 1H), 3.59-3.52 (m, 1H), 3.48-3.42 (m, 1H), 3.36-3.34 (m, 1H), 3.19-3.13 (m, 6H), 3.04-2.93 (m, 4H), 1.76-1.62 (m, 6H), 1.46-1.35 (m, 4H), 1.16 (t, J=7 Hz, 6H);
LCMS: m/z=391.2 [M+], RT=3.29 minutes;
UPLC: 99.47%, RT=3.27 minutes, λ$_{200\ nm}$, Mobile phase: (i) 0.05% TFA in Water (ii) Acetonitrile; Column: Zorbax® SB C18 (50×4.6 mm) 1.8μ.

Example 27

1,1-Dimethyl-2-[((indan-2-yl)(4-methylphenyl)amino)methyl]piperidinium iodide

Yield: 193 mg (32%);
$^1$H-NMR (400 MHz, DMSO-d$_6$): δ 7.18 (t, J=4 Hz, 2H), 7.14-7.10 (m, 4H), 7.02 (d, J=3 Hz, 2H), 7.01 (d, J=8 Hz, 2H), 4.33-4.29 (m, 1H), 3.77 (d, J=12 Hz, 1H), 3.38 (d, J=7 Hz, 2H), 3.20 (s, 1H), 3.16 (s, 3H), 2.99-2.92 (m, 8H), 2.24 (s, 3H), 1.97 (d, J=13 Hz, 1H), 1.72-1.63 (m, 4H), 1.39-1.23 (m, 1H);
LCMS: m/z=349 [M+], RT=1.40 minutes;
UPLC: 99.42%, RT=4.40 minutes, λ$_{200\ nm}$, Mobile phase: (i) 0.05% TFA in Water, (ii) Acetonitrile; Column: Zorbax® SB C18 (50×4.6 mm) 1.8μ.

Example 28

1,1-Dimethyl-2-[((4-fluorophenyl)(indan-2-yl)amino)methyl]piperidinium iodide

Yield: 164 mg (30%);
$^1$H-NMR (400 MHz, DMSO-d$_6$): δ 7.19-7.11 (m, 8H), 4.29-4.25 (m, 1H), 3.77 (d, J=11 Hz, 1H), 3.39-3.35 (m, 2H), 3.25-3.15 (m, 5H), 3.01-2.87 (m, 7H), 1.98 (d, J=14 Hz, 1H), 1.78-1.64 (m, 4H), 1.33-1.30 (m, 1H);
LCMS: m/z=353.2 [M+], RT=3.17 minutes;
UPLC: 99.87%, RT=3.19 minutes, λ$_{200\ nm}$, Mobile phase: (i) 0.05% Acetic acid in Water, (ii) Acetonitrile; Column: Gemini® NX C18 (50×4.6 mm) 3μ.

Example 29

1,1-Dimethyl-2-[((indan-2-yl)(3-methylphenyl) amino)methyl]piperidinium iodide Yield: 193 mg (42%);
$^1$H-NMR (400 MHz, DMSO-$d_6$): δ 7.23-7.13 (m, 5H), 6.86 (t, J=8 Hz, 2H), 6.72 (d, J=7 Hz, 1H), 4.46 (t, J=8 Hz, 1H), 3.82 (d, J=11 Hz, 1H), 3.42-3.37 (m, 2H), 3.25 (s, 1H), 3.19 (s, 3H), 3.03 (t, J=9 Hz, 2H), 2.98-2.95 (m, 5H), 2.26 (s, 3H), 1.95 (d, J=13 Hz, 1H), 1.76-1.65 (m, 4H), 1.35-1.31 (m, 1H);
LCMS: m/z=348.8 [M+], RT=3.34 minutes, (Mobile phase: ammonium acetate in water/acetonitrile; Column: X-Bridge);
UPLC: 99.85%, RT=3.19 minutes, $λ_{200\,nm}$, Mobile phase: (i) 0.05% Acetic acid in Water, (ii) Acetonitrile; Column: Gemini® NX C18 (50×4.6 mm) 3μ.

Example 30

1,1-Diethyl-2-[((indan-2-yl)(4-methylphenyl)amino) methyl]piperidinium iodide Yield: 90 mg (29%);
$^1$H-NMR (400 MHz, DMSO-$d_6$): δ 7.17-7.10 (m, 8H), 4.14-4.08 (m, 1H), 3.66-3.60 (m, 2H), 3.52-3.47 (m, 1H), 3.39-3.34 (m, 1H), 3.25-3.15 (m, 5H), 3.07-3.01 (m, 1H), 2.91-2.82 (m, 3H), 2.27 (s, 3H), 2.12 (d, J=14 Hz, 1H), 1.89-1.86 (m, 1H), 1.66 (brs, 3H), 1.43 (brs, 1H), 1.16 (t, J=8 Hz, 3H), 0.95 (t, J=7 Hz, 3H);
LCMS: m/z=377 [M+], RT=3.40 minutes;
HPLC: 95.06%, RT=6.08 minutes, $λ_{210\,nm}$, Mobile phase: (i) 10 mM NH$_4$OAc in Water, (ii) Acetonitrile; Column: XBridge® C18 (50×4.6 mm) 5μ.

Example 31

1,1-Dimethyl-2-[((3-fluorophenyl)(indan-2-yl) amino)methyl]piperidinium iodide Yield: 75 mg (25%);
$^1$H-NMR (400 MHz, DMSO-$d_6$): δ 7.28-7.16 (m, 5H), 6.79 (t, J=4 Hz, 2H), 6.64-6.60 (q, J=6 Hz, 1H), 4.58 (q, J=9 Hz, 1H), 3.86 (d, J=11 Hz, 1H), 3.47-3.41 (m, 4H), 3.21 (s, 3H), 3.13-3.02 (m, 4H), 3.00 (s, 3H), 1.88-1.70 (m, 5H), 1.35-1.32 (m, 1H);
LCMS: m/z=353 [M+], RT=3.09 minutes;
UPLC: 99.58%, RT=3.15 minutes, $λ_{200\,nm}$, Mobile phase: (i) 0.05% Acetic acid in Water, (ii) Acetonitrile; Column: Gemini® NX C18 (50×4.6 mm) 3μ.

Example 32

(S)-1,1-Dimethyl-2-[((indan-2-yl)(phenyl)amino) methyl]piperidinium iodide

Yield: 1 g (69.2%);
$^1$H-NMR (DMSO-$d_6$): δ 7.27 (t, J=8 Hz, 2H), 7.22-7.20 (m, 2H), 7.16-7.14 (m, 2H), 7.05 (d, J=8 Hz, 2H), 6.90 (t, J=7 Hz, 1H), 4.52-4.44 (m, 1H), 3.85 (d, J=12 Hz, 1H), 3.43-3.36 (m, 4H), 3.21 (s, 3H), 3.06 (d, J=8 Hz, 2H), 3.01-2.99 (m, 5H), 1.96-1.92 (m, 1H), 1.76-1.69 (m, 4H), 1.34-1.31 (m, 1H);
LCMS: m/z=335.4 [M+], RT=2.97 minutes;
UPLC: 98.93% (RT=3.13 minutes; $λ_{200\,nm}$, Mobile Phase A. 0.05% HCOOH in water, B. Acetonitrile; Column: Gemini NX C18 (50×4.6 mm) 3μ);
Specific rotation: [−9.3°] at ≈25° C. (0.60% solution in MeOH);
Chiral HPLC: 100% ee (RT=5.47 minutes; $λ_{254\,nm}$, Mobile Phase. Hexane:EtOH:DEA:TFA=60:40:0.1:0.1; Column: Chiralpak®-IC (4.6×250 mm) 5μ).

Example 33

(R)-1,1-Dimethyl-2-[((indan-2-yl)(phenyl)amino) methyl]piperidinium iodide

Yield: 0.62 g (78%);
$^1$H-NMR (DMSO-$d_6$): δ 7.27 (t, J=8 Hz, 2H), 7.22-7.20 (m, 2H), 7.16-7.14 (m, 2H), 7.05 (d, J=8 Hz, 2H), 6.90 (t, J=7 Hz, 1H), 4.52-4.44 (m, 1H), 3.84 (d, J=12 Hz, 1H), 3.43-3.35 (m, 4H), 3.19 (s, 3H), 3.06 (d, J=8 Hz, 2H), 3.01-2.99 (m, 5H), 1.96-1.92 (m, 1H), 1.76-1.69 (m, 4H), 1.34-1.31 (m, 1H);
LCMS: m/z=335.0 [M$^+$], RT=3.07 minutes;
UPLC: 99.83% (RT=3.13 minutes; $λ_{200\,nm}$, Mobile Phase A. 0.05% HCOOH in water, B. Acetonitrile; Column: Gemini NX C18 (50×4.6 mm) 3μ);
Specific rotation: [+9.3°] at ≈25° C. (0.60% solution in MeOH);
Chiral HPLC: 99.3% ee (RT=5.97 minutes; $λ_{254\,nm}$, Mobile Phase. Hexane:EtOH:DEA:TFA=60:40:0.1:0.1; Column: Chiralpak®-IC (4.6×250 mm) 5μ).

Example 34

(S)-1,1-Dimethyl-2-[2-((indan-2-yl)(2-methylphenyl)amino)ethyl]piperidinium iodide Yield: 0.193 g (39.9%);
$^1$H-NMR (DMSO-$d_6$): δ 7.31 (d, J=8 Hz, 1H), 7.25-7.17 (m, 4H), 7.13-7.10 (m, 2H), 7.05 (t, J=7 Hz, 1H), 4.05-4.00 (m, 1H), 3.43-3.40 (m, 1H), 3.26-3.12 (m, 3H), 3.02-2.93 (m, 2H), 2.90-2.82 (m, 5H), 2.79 (s, 3H), 2.31 (s, 3H), 1.99-1.95 (m, 1H), 1.79-1.66 (m, 4H), 1.53-1.50 (m, 1H), 1.40-1.37 (m, 1H), 1.29-1.23 (m, 1H);
LCMS: m/z=363.0 [M$^+$], RT=3.23 minutes;
HPLC: 99.11% (RT=4.28 minutes; $λ_{212\,nm}$, Mobile Phase A. 10 mM NH$_4$OAc in water, B. Acetonitrile; Column: Xbridge-C18 (50×4.6 mm) 5μ);
Specific rotation: [+13.5°] at ≈25° C. (0.599% solution in MeOH);
Chiral HPLC: 100% ee (RT=8.66 minutes; $λ_{212\,nm}$, Mobile Phase. Hexane:EtOH:DEA:TFA=70:30:0.1:0.1; Column: Chiralpak®-IC (4.6×250 mm) 5μ).

Example 35

(R)-1,1-Dimethyl-2-[2-((indan-2-yl)(2-methylphenyl)amino)ethyl]piperidinium iodide Yield: 0.4 g (41.9%);
$^1$H-NMR (DMSO-$d_6$): δ 7.31 (d, J=8 Hz, 1H), 7.25-7.17 (m, 4H), 7.13-7.10 (m, 2H), 7.05 (t, J=7 Hz, 1H), 4.05-4.00 (m, 1H), 3.43-3.40 (m, 1H), 3.26-3.12 (m, 3H), 3.02-2.96 (m, 2H), 2.91-2.84 (m, 5H), 2.79 (s, 3H), 2.31 (s, 3H), 1.99-1.95 (m, 1H), 1.79-1.66 (m, 4H), 1.53-1.50 (m, 1H), 1.40-1.37 (m, 1H), 1.29-1.24 (m, 1H);
LCMS: m/z=362.8 [M$^+$], RT=3.20 minutes;
UPLC: 98.82% (RT=4.86 minutes; $λ_{200\,nm}$, Mobile Phase A. 0.05% TFA in water, B. Acetonitrile; Column: Zorbax SB C18 (50×4.6 mm) 1.8μ);
Specific rotation: [−14.5°] at ≈25° C. (0.60% solution in MeOH);

Chiral HPLC: 98.5% ee (RT=12.79 minutes; $\lambda_{212\,nm}$, Mobile Phase. Hexane:EtOH:DEA:TFA=70:30:0.1:0.1; Column: Chiralpak®-IC (4.6×250 mm) 5μ).

Example 45

1,1-Dimethyl-4-[2-((indan-2-yl)(2-methylphenyl)amino)ethyl]piperidinium iodide

Yield: 0.081 g (13.9%);
$^1$H-NMR (DMSO-$d_6$): δ 7.29-7.27 (m, 1H), 7.23-7.19 (m, 2H), 7.16-7.14 (m, 2H), 7.10-7.08 (m, 2H), 7.04-7.01 (m, 1H), 3.98-3.94 (m, 1H), 3.36-3.31 (m, 2H), 3.23-3.17 (m, 2H), 3.05 (s, 3H), 3.01-2.90 (m, 7H), 2.82-2.76 (m, 2H), 2.28 (s, 3H), 1.69-1.66 (m, 2H), 1.50-1.45 (m, 3H), 1.26 (brs, 2H);
LCMS [M$^+$]=363, RT=3.38 minutes, (Program P1, Column Y);
UPLC: 99.47% (RT=5.02 minutes, $\lambda_{220\,nm}$, Mobile Phase A. 0.05% TFA, B. Acetonitrile; Column: Zorbax® XDB-C18 (4.6×50 mm) 1.8μ).

Example 46

1,1-Bis(2-hydroxyethyl)-2-[2-((indan-2-yl)(2-methylphenyl)amino)ethyl]piperidinium bromide Yield: 0.033 g (10%);
$^1$H-NMR (DMSO-$d_6$): δ 7.30-7.28 (m, 1H), 7.24-7.09 (m, 6H), 7.04 (t, J=7 Hz, 1H), 5.35-5.34 (m, 1H), 5.27-5.24 (m, 1H), 4.04-4.02 (m, 1H), 3.73-3.55 (m, 6H), 3.50 (s, 3H), 3.41-3.32 (m, 1H), 3.07-2.95 (m, 5H), 2.88-2.77 (m, 2H), 2.29 (s, 3H), 1.95 (brs, 1H), 1.86-1.83 (m, 2H), 1.64-1.61 (m, 3H), 1.46-1.36 (m, 2H);
LCMS [M$^+$]=423, RT=3.19 minutes, (Program P1, Column Y);
UPLC: 99.71% (RT=4.89 minutes, $\lambda_{220\,nm}$, Mobile Phase: A 0.05% TFA in water, B Acetonitrile; Column: Zorbax® SB-C18 (50×4.6 mm) 1.8μ).

Example 47

1,1-Dimethyl-2-[2-((indan-2-yl)(6-methylpyridine-2-yl)amino)ethyl]piperidinium iodide Yield: 0.15 g (36.20%);
$^1$H-NMR (DMSO-$d_6$): δ 7.40 (t, J=8 Hz, 1H), 7.26-7.25 (m, 2H), 7.18-7.16 (m, 2H), 6.54 (d, J=8 Hz, 1H), 6.48 (d, J=7 Hz, 1H), 5.12-5.05 (m, 1H), 3.46-3.41 (m, 3H), 3.28-3.22 (m, 2H), 3.19-3.13 (m, 2H), 3.05 (s, 3H), 3.02-2.98 (m, 2H), 2.86 (s, 3H), 2.29 (s, 3H), 2.17-2.13 (m, 1H), 1.97-1.93 (m, 1H), 1.83-1.77 (m, 1H), 1.70-1.67 (m, 2H), 1.61-1.55 (m, 1H), 1.51-1.37 (m, 2H);
LCMS [M$^+$]=364.2, RT=3.19 minutes, (Program P1, Column Y);
UPLC: 99.39% (RT=4.04 minutes, $\lambda_{220\,nm}$, Mobile Phase A. 0.05% TFA in water, B. Acetonitrile; Column: Zorbax® XDB-C18 (4.6×50 mm) 1.8μ).

Example 48

1,1-Dimethyl-2-[2-((indan-2-yl)(6-methylpyridine-2-yl)amino)ethyl]piperidinium bromide Yield: 0.057 g (18.8%);
$^1$H-NMR (DMSO-$d_6$): δ 7.40 (t, J=8 Hz, 1H), 7.26-7.25 (m, 2H), 7.19-7.16 (m, 2H), 6.54 (d, J=8 Hz, 1H), 6.48 (d, J=7 Hz, 1H), 5.10-5.06 (m, 1H), 3.46-3.42 (m, 3H), 3.26-3.22 (m, 2H), 3.19-3.13 (m, 2H), 3.05-2.98 (m, 5H), 2.86 (s, 3H), 2.29 (s, 3H), 2.17-2.13 (m, 1H), 1.97-1.93 (m, 1H), 1.83-1.77 (m, 1H), 1.70-1.57 (m, 3H), 1.47-1.37 (m, 2H);
LCMS: [M$^+$]=364.2, RT=3.04 minutes, (Program P1, Column V);
UPLC: 99.87% (RT=4.02 minutes, $\lambda_{200\,nm}$, Mobile Phase A. 0.05% TFA in water, B. Acetonitrile; Column: Zorbax® SB-C18 (4.6×50 mm) 1.8μ).

Example 49

(S)-1,1-Diethyl-2-[2-((indan-2-yl)(phenyl)amino)ethyl]piperidinium bromide

Yield: 2.9 g (25%);
$^1$H-NMR (DMSO-$d_6$): δ 7.25-7.16 (m, 6H), 6.87 (d, J=8 Hz, 2H), 6.72 (t, J=7 Hz, 1H), 4.67-4.63 (m, 1H), 3.52-3.47 (m, 1H), 3.40-3.34 (m, 1H), 3.28-3.16 (m, 8H), 3.04-2.92 (m, 3H), 1.88-1.86 (m, 2H), 1.67-1.47 (m, 6H), 1.10 (t, J=6 Hz, 6H);
LCMS [M$^+$]=377.0, RT=3.11 minutes, (Program P1, Column Y);
UPLC: 99.77% (RT=5.08 minutes, $\lambda_{200\,nm}$, Mobile Phase A. 0.05% TFA in water, B. Acetonitrile; Column: Zorbax® SB-C18 (50×4.6 mm) 1.8μ);
Chiral HPLC: 100% ee (RT=6.47 minutes, $\lambda_{257\,nm}$, Mobile Phase. MeOH:DEA:TFA=100:0.1:0.1, Column: Chiralpak®-IA (4.6×250 mm) 5μ);
Specific optical rotation: [−10.8°] at ≅25° C. (0.39% solution in CHCl$_3$)

Example 50

1,1-Dimethyl-2-[2-((indan-2-yl)(2-methylphenyl)amino)ethyl]piperidinium chloride Yield: 0.14 g (43%);
$^1$H-NMR (DMSO-$d_6$): δ 7.31 (d, J=8 Hz, 1H), 7.25-7.17 (m, 4H), 7.12-7.11 (m, 2H), 7.05 (t, J=7 Hz, 1H), 4.05-4.01 (m, 1H), 3.43 (d, J=12 Hz, 1H), 3.28-3.12 (m, 4H), 3.00-2.96 (m, 2H), 2.92-2.80 (m, 8H), 2.31 (s, 3H), 1.99-1.96 (m, 1H), 1.79-1.65 (m, 4H), 1.57-1.47 (m, 1H), 1.41-1.36 (m, 1H), 1.28-1.26 (m, 1H);
LCMS: [M$^+$]=363.2, RT=2.85 minutes, (Program P1, Column W);
UPLC: 99.29% (RT=5.80 minutes, $\lambda_{200\,nm}$, Mobile Phase: A 0.05% TFA in water, B. Acetonitrile; Column: Zorbax® SB-C18 (50×4.6 mm) 1.8μ).

Example 51

(R)-1,1-Dimethyl-2-[2-((indan-2-yl)(2-methylphenyl)amino)ethyl]piperidinium chloride Yield: 0.033 g (20%);
$^1$H-NMR (DMSO-$d_6$): δ 7.31 (d, J=8 Hz, 1H), 7.25-7.17 (m, 4H), 7.13-7.10 (m, 2H), 7.05 (t, J=7 Hz, 1H), 4.05-4.01 (m, 1H), 3.43 (d, J=12 Hz, 1H), 3.26-3.10 (m, 3H), 3.02-2.96 (m, 2H), 2.93-2.80 (m, 9H), 2.31 (s, 3H), 1.99-1.95 (m, 1H), 1.79-1.65 (m, 4H), 1.55-1.47 (m, 1H), 1.40-1.36 (m, 1H), 1.29-1.26 (m, 1H);
LCMS [M$^+$]=363, RT=3.53 minutes, (Program P1, Column V);
UPLC: 98.46% (RT=4.94 minutes, $\lambda_{200\,nm}$, Mobile Phase: A 0.05% HCOOH in water, B Acetonitrile; Column: Gemini® NX C18 (50×4.6 mm) 3μ).

Example 52

1,1-Dimethyl-2-[2-((indan-2-yl)(2-methylphenyl)amino)ethyl]piperidinium bromide

Yield: 0.215 g (42%);

$^1$H-NMR (DMSO-d$_6$): δ 7.31 (d, J=8 Hz, 1H), 7.25-7.17 (m, 4H), 7.12-7.10 (m, 2H), 7.05 (t, J=7 Hz, 1H), 4.05-4.01 (m, 1H), 3.42 (d, J=12 Hz, 1H), 3.26-3.12 (m, 3H), 3.02-2.96 (m, 2H), 2.91-2.79 (m, 9H), 2.31 (s, 3H), 1.99-1.95 (m, 1H), 1.79-1.65 (m, 4H), 1.57-1.47 (m, 1H), 1.43-1.36 (m, 1H), 1.29-1.26 (m, 1H);

LCMS: [M$^+$]=363.4, RT=1.83 minutes, (Program P1, Column V);

UPLC: 99.74% (RT=5.80 minutes, λ$_{200\ nm}$, Mobile Phase A. 0.05% TFA in water, B. Acetonitrile; Column: Zorbax® SB-C18 (50×4.6 mm) 1.8μ).

Example 53

In Vitro Assay for Effect of Compounds on Bladder Detrusor Muscle

This study was performed to determine the effects of test compounds on the contractile response of isolated detrusor muscle (Iravani & Zar, British Journal of Pharmacology 1994, 113:95-102).

Whole bladders were removed from euthanized female guinea pigs, longitudinal detrusor muscle strips were dissected from each bladder and were mounted in a conventional glass organ bath and perfused continuously with an oxygenated Krebs solution. Detrusor contractions were elicited in response to electrical field stimulation (EFS) and were recorded using isometric force transducers linked to a data acquisition software system. After an equilibration period, tissue strips were subjected to regular EFS for a period of 30 minutes or until stable baseline contractions were attained.

The test drugs (lidocaine or the compound of example 43, i.e., (R)-1,1-dimethyl-2-[2-((indan-2-yl)(2-methylphenyl)amino)ethyl]piperidinium bromide) were introduced into the organ bath at varying concentrations in order to construct cumulative concentration-response relationships for the inhibition of EFS-induced contractions.

Figure 1B:
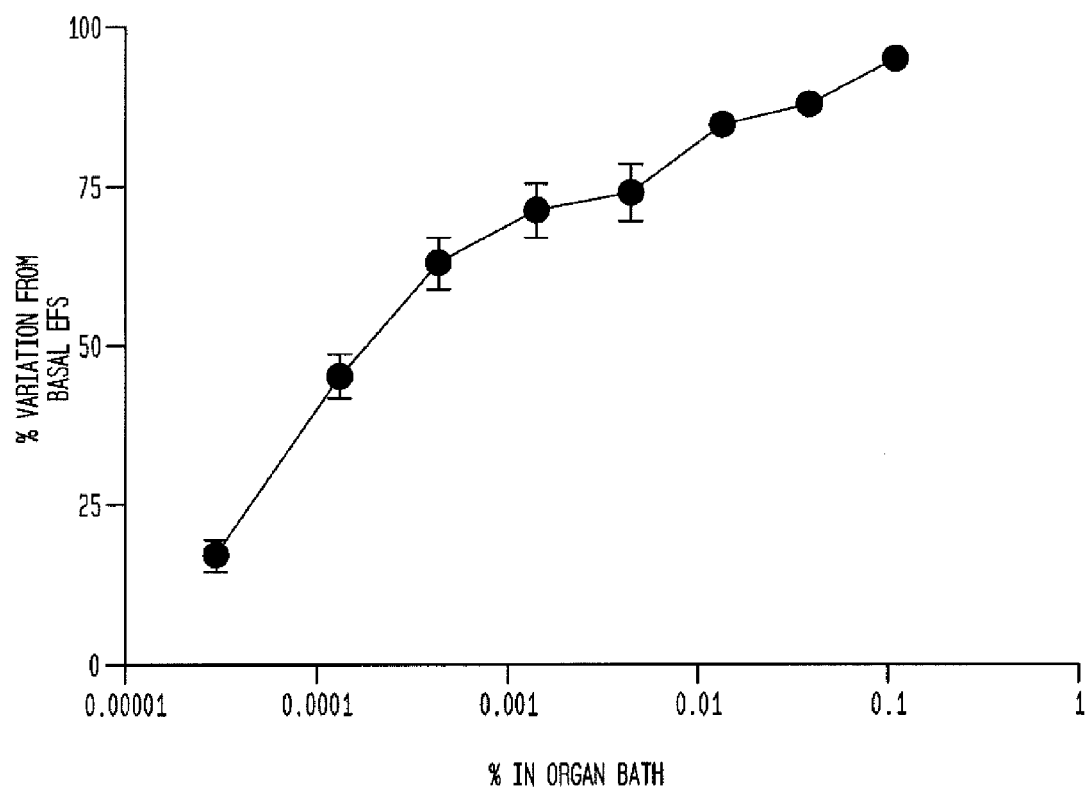

Both lidocaine and the compound of example 43 (EX43) produced concentration-dependent inhibitions of EFS-induced detrusor contractions. The compound of example 43 (IC$_{50}$~0.0001%) was about 10-fold more potent than lidocaine alone (IC$_{50}$~0.001%). See, FIGS. 1A and 1B.

Exposure of the detrusor tissue to a combination of lidocaine plus the compound of example 43 resulted in a concentration-inhibition relationship that suggested that the two drugs acted in an additive manner to inhibit the contractile response. The effects of lidocaine were more easily reversible than were those of the compound of example 43—thus washing out lidocaine (0.01%) from the organ bath, after attaining steady-state inhibition (~40%) resulted in recovery of EFS-induced contractile response to around 80% of predrug levels by 2 hours.

Figure 2A:
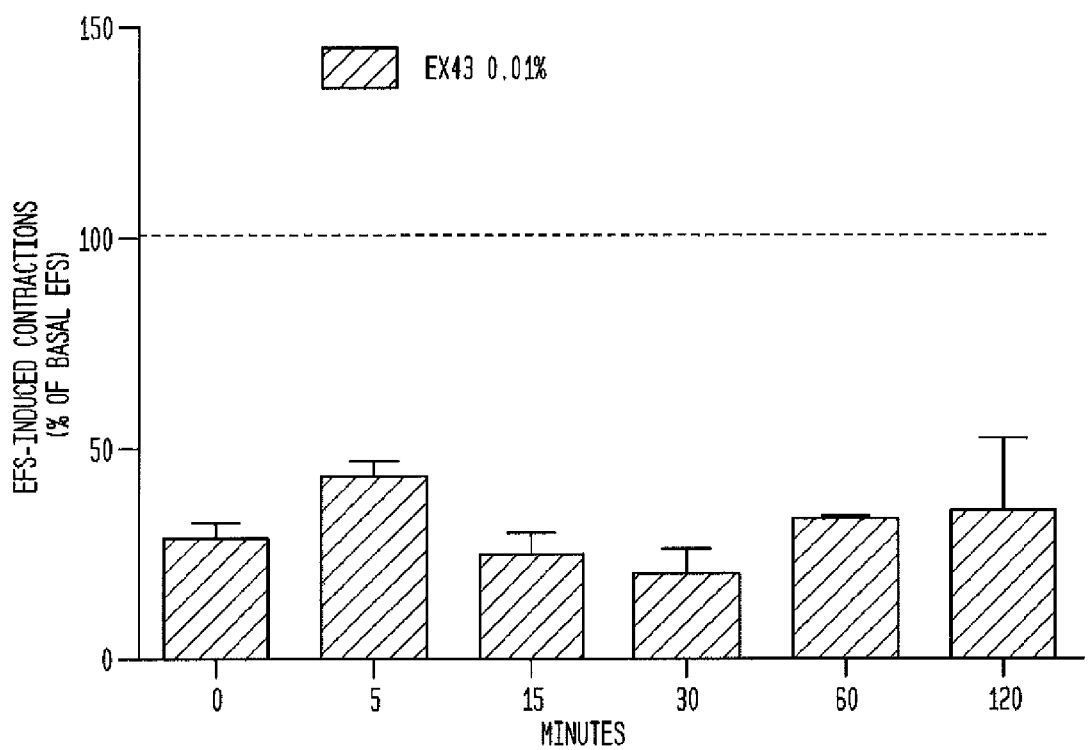
FIGS. 2A and 2B are bar graphs illustrating the potency and reversibility of the compound of example 43 (0.01%) alone and lidocaine (0.01%) alone, respectively, on the contractile response of isolated detrusor bladder muscle over a period of at least 2 hours.
Figure 2B:
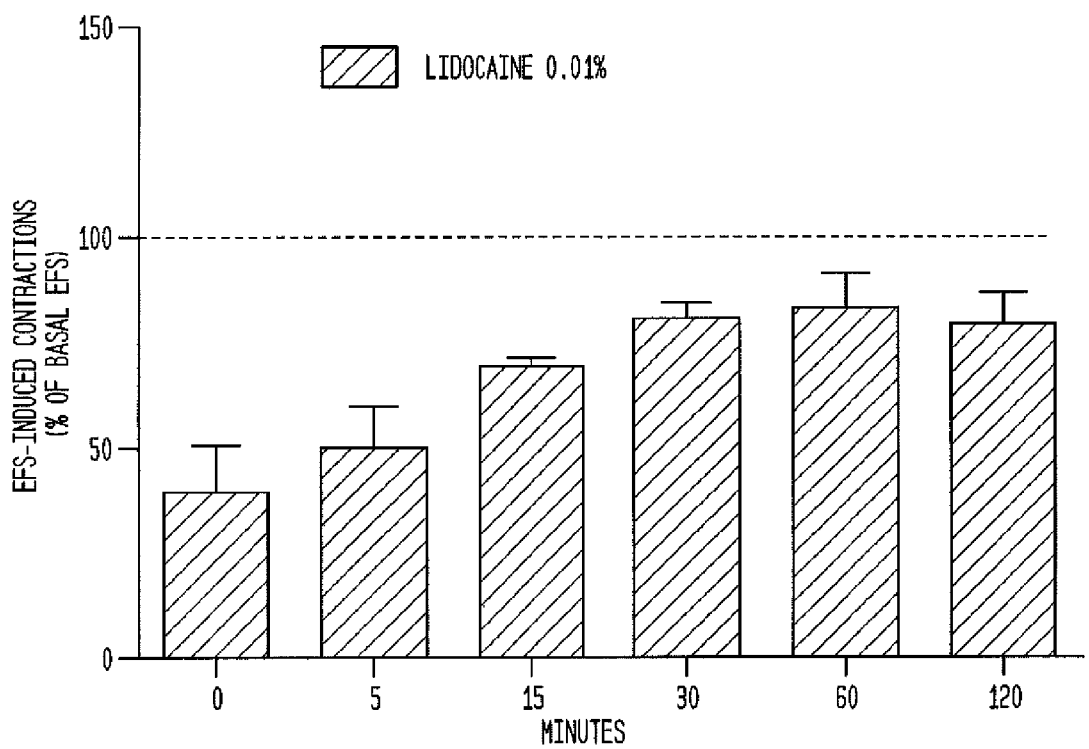

Similar experiments were performed with the compound of example 43 (0.01%) and, in this case, steady state inhibition of around 30-45% was maintained for at least 2 hours even though drug had been eliminated from the organ bath. See, FIGS. 2A and 2B. These data suggest that the compound of example 43 is not only capable of acting on the bladder detrusor muscle to inhibit contractility but that this effect is slow to reverse. The potency and slow reversibility of the effects of the compound of example 43 on bladder tissue may confer a considerable clinical advantage in the management of urinary dysfunction and bladder pain.

Example 54

In Vivo Assay of Bladder Function

This study was performed in order to assess the effects of compounds on various aspects of bladder function in conscious rats. See, Clouse, 2012, Urology 79(6):1410e1-1410e6.

Rats were prepared with indwelling polyethylene catheters positioned into the bladder through the dome and exteriorized at the scapular level. Intracysternal pressure was monitored by connecting the catheter to a commercial strain gauge via a T-connector that permitted the infusion of solutions and drugs. Cystometric recording commenced 48 hours after catheter implantation. Animals were continuously administered saline, with or without test compounds, through the catheter, at a rate of 2 mL/hr. Urine was collected and weighed using a force transducer and intravesical pressure was continually monitored in order to assess micturition amplitude, frequency and volume and bladder capacity. Saline perfusions were supplemented with test compounds in order to determine the effects on each of the above bladder function parameters.

The infusion of a solution of 0.3% of the compound of example 43, i.e., (R)-1,1-dimethyl-2-[2-((indan-2-yl)(2-methylphenyl)amino)ethyl]piperidinium bromide, produced an increase in bladder capacity and a decrease in micturition volume for a period of 2 hours after administration. An infusion of a combined solution of 0.3% (R)-1,1-dimethyl-2-[2-((indan-2-yl)(2-methylphenyl)amino)ethyl]piperidinium bromide with 2% lidocaine resulted in the suppression of micturition and a corresponding rise in intravesical pressure (FIG. 3). Compared to lidocaine, (R)-1,1-dimethyl-2-[2-((indan-2-yl)(2-methylphenyl)amino)ethyl]piperidinium iodide had a longer duration of action on micturition frequency. When both compounds were given together, the rate of micturition was decreased compared to the effects seen with either drug alone.

In summary, this example demonstrated that (R)-1,1-dimethyl-2-[2-((indan-2-yl)(2-methylphenyl)amino)ethyl]piperidinium bromide is capable of influencing bladder function. These results indicate that the compounds of the example will have therapeutic benefit to patients suffering from disease or pathological conditions that lead, directly or indirectly, to overactive bladder and/or painful bladder syndrome, irritable bowel syndrome or chemical sensitivities.

All publications cited in this specification, GenBank and NCBI database sequences referenced herein, and priority applications, i.e., U.S. Provisional Patent Application Nos. 61/683,518 and 61/718,062, are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method of treating interstitial cystitis, said method comprising administering to a patient in need thereof a therapeutically effective amount of a compound of formula (I) or (II):

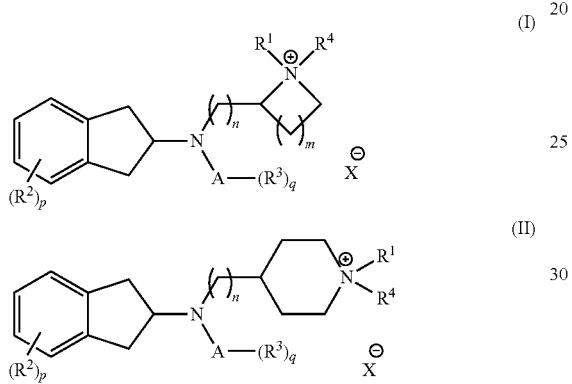

wherein:
A is phenyl or heteroaryl;
$R^1$ and $R^4$ are, independently, $C_1$ to $C_6$ alkyl or $CH_2CH_2OH$; or
$R^1$ and $R^4$ are joined to form a 4- or 6-membered carbocyclic or heterocyclic ring;
$R^2$ is independently selected from the group consisting of hydrogen, halogen, $NO_2$, OH, and $C_1$ to $C_6$ alkoxy;
$R^3$ is independently selected from the group consisting of hydrogen, halogen, CN, $NO_2$, $NH_2$, optionally substituted $C_1$ to $C_6$ alkyl, $C_2$ to $C_6$ alkenyl, $C_2$ to $C_6$ alkynyl, OH, $CF_3$, $OCF_3$, $SCF_3$, optionally substituted $C_1$ to $C_6$ alkoxy, $C_2$ to $C_6$ alkynyloxy, heterocyclyloxy, heteroaryloxy, optionally substituted $C_1$ to $C_6$ alkylthio, heteroarylthio, $C(O)O(C_1$ to $C_6$ alkyl), $C(O)(C_1$ to $C_6$ alkyl), C(O)(aryl), C(O)(heterocycle), $C(O)NH_2$, $C(O)NH(C_1$ to $C_6$ alkyl), C(O)NH(aryl), C(O)NH(heterocycle), C(O)NH(heteroaryl), C(O)N($C_1$ to $C_6$ alkyl)($C_1$ to $C_6$ alkyl), C(O)N(aryl)($C_1$ to $C_6$ alkyl), $C(S)NH_2$, optionally substituted aryl, heteroaryl, heterocycle, NHC(O)($C_1$ to $C_6$ alkyl), NHC(O)(aryl), NHC(O)(heteroaryl), NHC(O)O($C_1$ to $C_6$ alkyl), N($C_1$ to $C_6$ alkyl)C(O)($C_1$ to $C_6$ alkyl), N($C_1$ to $C_6$ alkyl)C(O)O($C_1$ to $C_6$ alkyl), $NHC(O)NH_2$, NHC(O)NH($C_1$ to $C_6$ alkyl), NHC(O)NH(heteroaryl), $NHSO_2(C_1$ to $C_6$ alkyl), $SO_2(C_1$ to $C_6$ alkyl), $SO_2NH_2$, $SO_2NH(C_1$ to $C_6$ alkyl), $SO_2NH(C_2$ to $C_6$ alkynyl), $SO_2N(C_1$ to $C_6$ alkyl)($C_1$ to $C_6$ alkyl), $SO_2NH$(heteroaryl), NH($C_1$ to $C_6$ alkyl), N($C_1$ to $C_6$ alkyl)($C_1$ to $C_6$ alkyl), N($C_1$ to $C_6$ alkyl)($C_2$ to $C_6$ alkenyl), and N($C_1$ to $C_6$ alkyl)(heterocycle); or q is 2 and two $R^3$ groups are joined to form an optionally substituted 6-membered aryl, optionally substituted 5- or 6-membered carbocyclic ring, or optionally substituted 5- or 6-membered heterocycle or heteroaryl containing 1 to 3 oxygen, nitrogen, or sulfur atoms and 4 or 5 carbon atoms;
m is 1 to 5;
n is 1 to 3;
p is 0 to 2;
q is 0 to 4; and
$X^-$ is a halogen ion, trifluoroacetate, sulfate, phosphate, acetate, fumarate, maleate, citrate, pyruvate, succinate, oxalate, bisulfate, malonate, xinafoate, ascorbate, oleate, nicotinate, saccharinate, adipate, formate, glycolate, L-lactate, D-lactate, aspartate, malate, L-tartrate, D-tartrate, stearate, 2-furoate, 3-furoate, napadisylate, edisylate, isethionate, D-mandelate, L-mandelate, propionate, tartarate, phthalate, hydrochlorate, hydrobromate, nitrate, methanesulfonate, ethanesulfonate, napthalenesulfonate, benzenesulfonate, toluenesulfonate, mesitylenesulfonate, camphorsulfonate or trifluoromethanesulfonate.

2. The method of claim 1, wherein said compound contains at least 1 chiral center.

3. The method of claim 1, wherein said compound is a mixture of enantiomers.

4. The method of claim 1, wherein said compound is an R-enantiomer.

5. The method of claim 1, wherein said compound is an S-enantiomer.

6. The method of claim 1, wherein said compound has the structure:

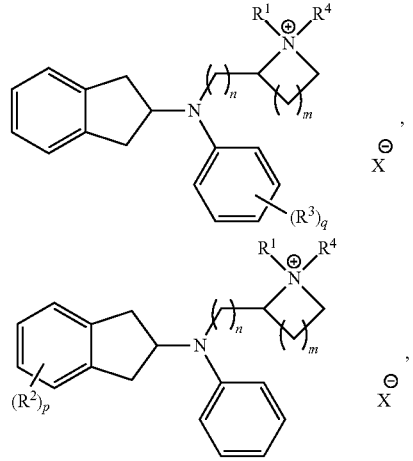

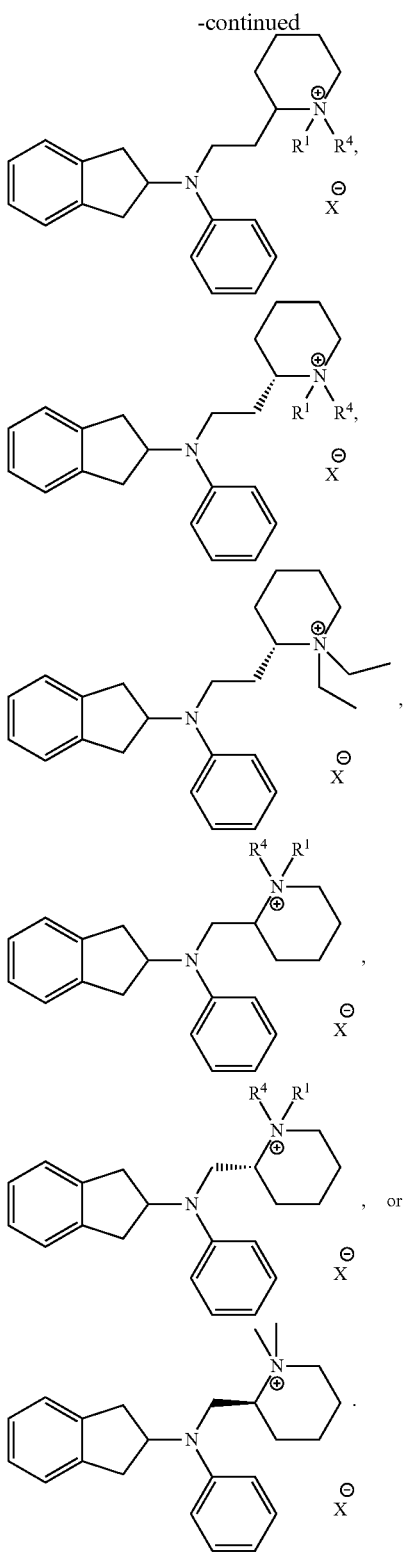

7. The method of claim 1, wherein said compound is selected from the group consisting of (S)-1,1-dimethyl-2-[2-((indan-2-yl)(phenyl)amino)ethyl]piperidinium iodide,
(R)-1,1-dimethyl-2-[2-((indan-2-yl)(phenyl)amino)ethyl]piperidinium iodide,
(S)-1,1-diethyl-2-[2-((indan-2-yl)(phenyl)amino)ethyl]piperidinium iodide,
(R)-1,1-diethyl-2-[2-((indan-2-yl)(phenyl)amino)ethyl]piperidinium iodide,
(S)-1,1-dipropyl-2-[2-((indan-2-yl)(phenyl)amino)ethyl]piperidinium iodide,
(R)-1,1-dipropyl-2-[2-((indan-2-yl)(phenyl)amino)ethyl]piperidinium iodide,
(S)-1,1-dimethyl-2-[((indan-2-yl)(phenyl)amino)methyl]piperidinium iodide,
(R)-1,1-dimethyl-2-[((indan-2-yl)(phenyl)amino)methyl]piperidinium iodide,
(S)-1,1-dimethyl-2-[2-((indan-2-yl)(2-methylphenyl)amino)ethyl]piperidinium iodide,
(R)-1,1-dimethyl-2-[2-((indan-2-yl)(2-methylphenyl)amino)ethyl]piperidinium iodide,
1,1-dimethyl-2-[((indan-2-yl)(phenyl)amino)methyl]piperidinium iodide,
1,1-dimethyl-2-[2-((indan-2-yl)(phenyl)amino)ethyl]pyrrolidinium iodide,
1,1-diethyl-2-[((indan-2-yl)(phenyl)amino)methyl]piperidinium iodide,
1,1-dimethyl-2-[2-((2-fluorophenyl)(indan-2-yl)amino)ethyl]piperidinium iodide,
1,1-dimethyl-2-[2-((3-fluorophenyl)(indan-2-yl)amino)ethyl]piperidinium iodide,
1,1-dimethyl-2-[2-((4-fluorophenyl)(indan-2-yl)amino)ethyl]piperidinium iodide,
1,1-diethyl-2-[2-((2-fluorophenyl)(indan-2-yl)amino)ethyl]piperidinium iodide,
1,1-diethyl-2-[2-((3-fluorophenyl)(indan-2-yl)amino)ethyl]piperidinium iodide,
1,1-diethyl-2-[2-((4-fluorophenyl)(indan-2-yl)amino)ethyl]piperidinium iodide,
1,1-dimethyl-2-[2-((indan-2-yl) (3-methylphenyl)amino)ethyl]piperidinium iodide,
1,1-diethyl-2-[2-((indan-2-yl) (3-methylphenyl)amino)ethyl]piperidinium iodide,
1,1-dimethyl-2-[2-((indan-2-yl) (4-methylphenyl)amino)ethyl]piperidinium iodide,
1,1-diethyl-2-[2-((indan-2-yl) (4-methylphenyl)amino)ethyl]piperidinium iodide,
1,1-dimethyl-2-[2-((indan-2-yl) (2-methylphenyl)amino)ethyl]piperidinium iodide,
1,1-diethyl-2-[2-((indan-2-yl) (2-methylphenyl)amino)ethyl]piperidinium iodide,
6-[2-((indan-2-yl) (phenyl)amino)ethyl]-5-azoniaspiro[4.5]decane bromide,
1,1-dimethyl-2-[3-((indan-2-yl) (phenyl)amino)propyl]piperidinium iodide,
1,1-diethyl-2-[3-((indan-2-yl) (phenyl)amino)propyl]piperidinium iodide,
1,1-dimethyl-2-[((indan-2-yl)(4-methylphenyl)amino)methyl]piperidinium iodide,
1,1-dimethyl-2-[((4-fluorophenyl)(indan-2-yl)amino)methyl]piperidinium iodide,
1,1-dimethyl-2-[((indan-2-yl) (3-methylphenyl)amino)methyl]piperidinium iodide,
1,1-diethyl-2-[((indan-2-yl)(4-methylphenyl)amino)methyl]piperidinium iodide,
1,1-dimethyl-2-[((3-fluorophenyl)(indan-2-yl)amino)methyl]piperidinium iodide,
1,1-dimethyl-2-[((indan-2-yl) (phenyl)amino)methyl]pyrrolidinium iodide,
1,1-diethyl-2-[2-((indan-2-yl) (phenyl)amino)ethyl]pyrrolidinium iodide, 1,1-dimethyl-2-[2-((indan-2-yl) (pyridine-2-yl)amino)ethyl]piperidinium iodide,
1,1-dimethyl-2-[2-((indan-2-yl) (pyrimidine-2-yl)amino)ethyl]piperidinium iodide,
1,1-dimethyl-2-[2-((indan-2-yl)(thiazol-2-yl)amino)ethyl]piperidinium iodide,
1,1-dimethyl-4-[2-((indan-2-yl) (2-methylphenyl)amino)ethyl]piperidinium bromide,
7-[2-((indan-2-yl) (2-methylpheny)amino)ethyl]-3-oxa-6-azaspiro[5.5]undecan-6-ium chloride,
1,1-dimethyl-2-[2-((2,3-dihydrobenzo[b][1,4]dioxin-6-yl)(indan-2-yl)amino)ethyl]piperidinium iodide,
(R)-1,1-dimethyl-2-[2-((indan-2-yl)(2-methylphenyl)amino)ethyl]piperidinium bromide,
(S)-1,1-dimethyl-2-[2-((indan-2-yl) (2-methylphenyl)amino)ethyl]piperidinium chloride,
1,1-dimethyl-4-[2-((indan-2-yl) (2-methylphenyl)amino)ethyl]piperidinium iodide,
1,1-bis(2-hydroxyethyl)-2-[2-((indan-2-yl)(2-methylphenyl)amino)ethyl]piperidinium bromide,
1,1-dimethyl-2-[2-((indan-2-yl)(6-methylpyridine-2-yl)amino)ethyl]piperidinium iodide,
1,1-dimethyl-2-[2-((indan-2-yl)(6-methylpyridine-2-yl)amino)ethyl]piperidinium bromide,
(S)-1,1-diethyl-2-[2-((indan-2-yl)(phenyl)amino)ethyl]piperidinium bromide,
1,1-dimethyl-2-[2-((indan-2-yl)(2-methylphenyl)amino)ethyl]piperidinium chloride,
(R)-1,1-dimethyl-2-[2-((indan-2-yl)(2-methylphenyl)amino)ethyl]piperidinium chloride, and
1,1-dimethyl-2-[2-((indan-2-yl)(2-methylphenyl)amino)ethyl]piperidinium bromide.

8. The method of claim 1, further comprising administering a therapeutically effective amount of a TRPV1 receptor activator.

9. The method of claim 8, wherein said TRPV1 receptor activator is selected from the group consisting of capsaicin, dihydrocapsaicin, nordihydrocapsaicin, lidocaine, articaine, procaine, tetracaine, mepivicaine, bupivicaine, eugenol, camphor, clotrimazole, N-arachidonoylvanillamine, anandamide, 2-aminoethoxydiphenyl borate, AM404, resiniferatoxin, phorbol 12-phenylacetate 13-acetate 20-homovanillate, olvanil, N-oleoyldopamine, N-arachidonyldopamine, 6'-iodoresiniferatoxin, a $C_{18}$ N-acylethanolamine, a lipoxygenase derivative, nonivamide, a fatty acyl amide of a tetrahydroisoquinoline inhibitor cysteine knot peptide, pipeline, N-[2-(3,4-dimethylbenzyl)-3-(pivaloyloxy)propyl]-2-[4-(2-aminoethoxy)-3-methoxyphenyl]acetamide, N-[2-(3,4-dimethylbenzyl)-3-(pivaloyloxy)propyl]-N'-(4-hydroxy-3-methoxybenzyl)thiourea, hydroxy-α-sanshool, 2-aminoethoxydiphenyl borate, 10-shogaol, oleylgingerol, oleylshogaol, N-(4-tert-butylbenzyl)-N'-(4-hydroxy-3-methoxybenzyl)thiourea, aprindine, benzocaine, butacaine, cocaine, dibucaine, encainide, mexiletine, oxetacaine, prilocaine, proparacaine, procainamide, n-acetylprocainamide, chloroprocaine, dyclonine, etidocaine, levobupivacaine, ropivacaine, cyclomethycaine, dimethocaine, propoxycaine, trimecaine, and sympocaine.

10. The method of claim 8, wherein said TRPV1 receptor activator and said compound of formula (I), formula (II), or a combination thereof are co-administered.

11. The method of claim 10, wherein the ratio of said TRPV1 receptor activator to said compound of formula (I), formula (II), or a combination thereof, is about 1:1 to about 10:1.

12. The method of claim 1, wherein said compound of formula (I) or (II), or combination thereof, is administered via direct instillation of said compound into the bladder or urothelium.

13. The method of claim 1, wherein said compound of formula (I) or (II), or combination thereof, is placed into said bladder or urothelium as an extended-release formulation.

14. The method of claim 1, wherein said compound of formula (I) or (II), or combination thereof, is injected directly into the urothelium.

15. The method of claim 1, wherein a combination of a compound of formula (I) and a compound of formula (II) is administered to the patient.

16. The method of claim 1, wherein the patient is a human.

* * * * *